(12) United States Patent
Nordvall

(10) Patent No.: US 11,352,332 B2
(45) Date of Patent: Jun. 7, 2022

(54) TRIAZINE DERIVATIVES FOR TREATING DISEASES RELATING TO NEUROTROPHINS

(71) Applicant: AlzeCure Pharma AB, Huddinge (SE)

(72) Inventor: Gunnar Nordvall, Rönninge (SE)

(73) Assignee: AlzeCure Pharma AB, Huddinge (SE)

( * ) Notice: Subject to any disclaimer, the term of this patent is extended or adjusted under 35 U.S.C. 154(b) by 0 days.

(21) Appl. No.: 16/975,437

(22) PCT Filed: Feb. 26, 2019

(86) PCT No.: PCT/GB2019/050523
§ 371 (c)(1),
(2) Date: Aug. 25, 2020

(87) PCT Pub. No.: WO2019/162702
PCT Pub. Date: Aug. 22, 2019

(65) Prior Publication Data
US 2020/0399230 A1 Dec. 24, 2020

(30) Foreign Application Priority Data
Feb. 26, 2018 (SE) .................................. 1850217-9
Jun. 28, 2018 (GB) .................................. 1810667

(51) Int. Cl.
| | | |
|---|---|---|
| *C07D 251/30* | (2006.01) |
| *A61K 31/53* | (2006.01) |
| *C07D 401/04* | (2006.01) |
| *C07D 403/10* | (2006.01) |
| *C07D 405/12* | (2006.01) |
| *C07D 409/04* | (2006.01) |
| *C07D 413/10* | (2006.01) |
| *C07D 417/04* | (2006.01) |

(52) U.S. Cl.
CPC ......... *C07D 251/30* (2013.01); *C07D 401/04* (2013.01); *C07D 403/10* (2013.01); *C07D 405/12* (2013.01); *C07D 409/04* (2013.01); *C07D 413/10* (2013.01); *C07D 417/04* (2013.01)

(58) Field of Classification Search
CPC .............................. C07D 251/30; A61K 31/53
USPC .......................................... 544/180; 514/241
See application file for complete search history.

(56) References Cited

U.S. PATENT DOCUMENTS

| | | |
|---|---|---|
| 3,933,814 A | 1/1976 | Haberkorn et al. |
| 3,948,893 A | 4/1976 | Aichinger et al. |
| 3,966,725 A | 6/1976 | Reisdorff et al. |
| 4,219,552 A | 8/1980 | Haberkorn et al. |
| 4,837,216 A | 6/1989 | Mehlhorn et al. |
| 4,874,860 A | 10/1989 | Gallenkamp et al. |
| 4,927,824 A | 5/1990 | Adler et al. |
| 4,933,341 A | 6/1990 | Lindner et al. |
| 5,519,133 A | 5/1996 | Crews, Jr. et al. |
| 5,604,180 A | 2/1997 | Crews, Jr. et al. |
| 5,679,791 A | 10/1997 | Crews, Jr. et al. |
| 5,726,126 A | 3/1998 | Crews, Jr. et al. |
| 6,465,460 B1 | 10/2002 | Hundley et al. |
| 9,399,037 B2 | 7/2016 | Greif |
| 2003/0186320 A1 | 10/2003 | Yu et al. |
| 2009/0181040 A1 | 7/2009 | Greif |
| 2020/0113910 A1 | 4/2020 | Nordvall et al. |
| 2021/0261513 A1 | 8/2021 | Nordvall et al. |
| 2021/0371402 A1 | 12/2021 | Nordvall et al. |

FOREIGN PATENT DOCUMENTS

| | | |
|---|---|---|
| AU | 619004 B2 | 1/1992 |
| CA | 1185974 A | 4/1985 |
| DE | 2246109 A1 | 3/1974 |
| DE | 2718799 A1 | 11/1978 |
| DE | 3314739 A1 | 10/1984 |
| DE | 3408768 A1 | 9/1985 |
| DE | 3516631 A1 | 11/1986 |
| DE | 3516632 A1 | 11/1986 |
| DE | 4000624 A1 | 7/1991 |
| DE | 19958388 A1 | 6/2001 |

(Continued)

OTHER PUBLICATIONS

Bailey et al., Tropomyosin receptor kinase inhibitors: an updated patent review for 2010-2016—Part I. Expert Opin Ther Pat. 2017;27(6):733-751.
International Search Report and Written Opinion for Application No. PCT/GB2019/050523, dated Apr. 10, 2019, 12 pages.
Bartus, On neurodegenerative diseases, models, and treatment strategies: lessons learned and lessons forgotten a generation following the cholinergic hypothesis. Exp Neurol. Jun. 2000;163(2):495-529.
Blurton-Jones et al., Neural stem cells improve cognition via BDNF in a transgenic model of Alzheimer disease. Proc Natl Acad Sci U S A. Aug. 11, 2009;106(32):13594-9.

(Continued)

*Primary Examiner* — Charanjit Aulakh
(74) *Attorney, Agent, or Firm* — McCarter & English, LLP; Steven G. Davis; Mei Bai

(57) ABSTRACT

There is provided herein a compound of formula (I) wherein $R^1$, $R^2$, n, X, Q, L, m, $R^3$ and p are as defined herein, which compounds are useful in the treatment of treatment of diseases characterised by impaired signalling of neurotrophins and/or other trophic factors, such as Alzheimer's disease and the like.

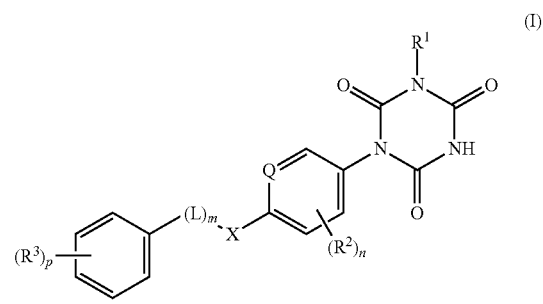

2 Claims, 1 Drawing Sheet

(56) References Cited

FOREIGN PATENT DOCUMENTS

| | | |
|---|---|---|
| EP | 0081142 A2 | 6/1983 |
| EP | 0279219 A1 | 8/1988 |
| EP | 0334135 A2 | 9/1989 |
| EP | 0339555 A2 | 11/1989 |
| EP | 0640600 A1 | 3/1995 |
| EP | 0745595 A1 | 12/1996 |
| EP | 1157991 A2 | 11/2001 |
| GB | 1571368 A | 7/1980 |
| SE | 402103 B | 6/1978 |
| WO | 2000/37084 A1 | 6/2000 |
| WO | 2001/10862 A2 | 2/2001 |
| WO | 2002/06277 A1 | 1/2002 |
| WO | 2002/13831 A1 | 2/2002 |
| WO | 2002/14288 A1 | 2/2002 |
| WO | 2003/011839 A1 | 2/2003 |
| WO | 2004/007499 A1 | 1/2004 |
| WO | 2008/019785 A2 | 2/2008 |
| WO | 2008/148008 A1 | 12/2008 |
| WO | 2015/107053 A1 | 7/2015 |
| WO | 2016/094682 A2 | 6/2016 |
| WO | 2018/115891 A1 | 6/2018 |

OTHER PUBLICATIONS

Boots et al., BDNF Val66Met predicts cognitive decline in the Wisconsin Registry for Alzheimer's Prevention. Neurology. May 30, 2017;88(22):2098-2106.

Calabrese et al., Modulation of neuroplastic molecules in selected brain regions after chronic administration of the novel antidepressant agomelatine. Psychopharmacology (Berl). May 2011;215(2):267-75.

Castren et al., Brain-derived neurotrophic factor in mood disorders and antidepressant treatments. Neurobiol Dis. Jan. 2017;97(Pt B):119-126.

Castren, Neurotrophins and Psychiatric Disorders. Neurotrophic Factors, Handbook of Experimental Pharmacology. Springer-Verlag Berlin, G.R. Lewin (Ed.). vol. 220, pp. 461-479, (2014).

Chaldakov, The metabotrophic NGF and BDNF: an emerging concept. Arch Ital Biol. Jun. 2011;149(2):257-63.

Gasparini et al., Potential roles of insulin and IGF-1 in Alzheimer's disease. Trends Neurosci. Aug. 2003;26(8):404-6.

Guo et al., A convenient one-pot synthesis of asymmetric 1,3,5-triazine-2,4,6-triones and its application towards a novel class of gonadotropin-releasing hormone receptor antagonists. Bioorg Med Chem Lett. Feb. 1, 2005;15(3):693-8.

Hoshaw et al., Central administration of IGF-I and BDNF leads to long-lasting antidepressant-like effects. Brain Res. Mar. 10, 2005;1037(1-2):204-8.

Li et al., Modulation of FGF receptor signaling as an intervention and potential therapy for myelin breakdown in Alzheimer's disease. Med Hypotheses. Apr. 2013;80(4):341-4.

Lim et al., BDNF Val66Met moderates memory impairment, hippocampal function and tau in preclinical autosomal dominant Alzheimer's disease. Brain. Oct. 2016;139(Pt 10):2766-2777.

Lucidi-Phillipi et al., TrkA activation is sufficient to rescue axotomized cholinergic neurons. Neuron. Mar. 1996;16(3):653-63.

Sen et al., Serum brain-derived neurotrophic factor, depression, and antidepressant medications: meta-analyses and implications. Biol Psychiatry. Sep. 15, 2008;64(6):527-32.

Shimizu et al., Alterations of serum levels of brain-derived neurotrophic factor (BDNF) in depressed patients with or without antidepressants. Biol Psychiatry. Jul. 1, 2003;54(1):70-5.

Suzuki et al., Identification of approved drugs that inhibit the binding of amyloid beta oligomers to ephrin type-B receptor 2. FEBS Open Bio. Apr. 1, 2016;6(5):461-8.

Yeo et al., A de novo mutation affecting human TrkB associated with severe obesity and developmental delay. Nat Neurosci. Nov. 2004;7(11):1187-9.

Belikov, The relationship between the chemical structure, properties of agents and their effect on the body. Pharmaceutical Chemistry. M.:MEDpress-inform. Chapter 2.6, pp. 27-29, (2007).

Gomazkov, Neurotrophins: The Therapeutic Potential and Concept of Minipeptides. Neurochemical Journal. 2012;6(3):163-172. Original Russian: Neirokhimiya. 2012;29(30):189-199.

Khamatova, Problem book on psychogenetics. Study Guide, Kazan. p. 139, (2005).

Mashkovsky, Medicaments, Moscow. Part 1, p. 8, (1993).

Russian Office Action for Application No. 2019120431/04(039889), dated Mar. 9, 2021, 24 pages.

Chen et al., Brain-derived neurotrophic factor accelerates gut motility in slow-transit constipation. Acta Physiol (Oxf). Nov. 2014;212(3):226-38.

Coulie et al., Recombinant human neurotrophic factors accelerate colonic transit and relieve constipation in humans. Gastroenterology. Jul. 2000;119(1):41-50.

Iihama et al., Regiospecific Syntheses of All Isomeric Nitrofluorenones and Nitrofluorenes by Transition Metal Catalyzed Cross-Coupling Reactions. Synthesis. 1989;1989(3):184-188.

Kim et al., PHarmacokinetics and Metabolism to Toltrazuil and Its Major Metabolites after Oral Administration in Broilers. J Poult Sci. 2013;50:257-261.

Paibir et al., High-performance liquid chromatographic analysis of phenobarbital and phenobarbital metabolites in human urine. J Chromatogr B Biomed Sci Appl. Mar. 28, 1997;691(1):111-7.

Senda et al., Uracil derivatives and related compounds. VII. Synthesis and anti-inflammatory activity of bucolome's compounds. (2). Yakugaku Zasshi. Feb. 1969;89(2):254-9.

STN RN 393524-33-9, 1, 3, 5-Triazine-2, 4, 6 (1H, 3H, 5H)-trione, 1-[4-(4-fluorophenoxy)phenyl]-3-methyl, 2 pages, Feb. 19, 2002.

The BDNF Study Group (Phase III), A controlled trial of recombinant methionyl human BDNF in ALS: The BDNF Study Group (Phase III). Neurology. Apr. 22, 1999;52(7):1427-33.

Tsoka et al., Effects of BNN27, a novel C17-spiroepoxy steroid derivative, on experimental retinal detachment-induced photoreceptor cell death. Sci Rep. Jul. 13, 2018;8(1):10661, 12 pages.

Wellmer et al., A double-blind placebo-controlled clinical trial of recombinant human brain-derived neurotrophic factor (rhBDNF) in diabetic polyneuropathy. J Peripher Nerv Syst. Dec. 2001;6(4):204-10.

Zhang et al., Roles of brain-derived neurotrophic factor/tropomyosin-related kinase B (BDNF/TrkB) signalling in Alzheimer's disease. J Clin Neurosci. Jul. 2012;19(7):946-9.

Damasio, Alzheimer's Disease and Related Dementias. Cecil Textbook of Medicine, 20th Edition, vol. 2. W.B. Saunders Company, Philadelphia, J.Claude Bennett (Ed.). pp. 1992-1996, (1996).

Ghilardi et al., Sustained blockade of neurotrophin receptors TrkA, TrkB and TrkC reduces non-malignant skeletal pain but not the maintenance of sensory and sympathetic nerve fibers. Bone. Feb. 2011;48(2):389-98.

Layzer, Section Five—Degenerative Diseases of the Nervous System. Cecil Textbook of Medicine, 20th Edition, vol. 2. W.B. Saunders Company, Philadelphia. J. Claude Bennett (Ed.). pp. 2050-2057, (1996).

U.S. Appl. No. 17/172,516, filed Feb. 10, 2021, Gunnar Nordvall.
U.S. Appl. No. 17/329,777, filed May 25, 2021, Gunnar Nordvall.

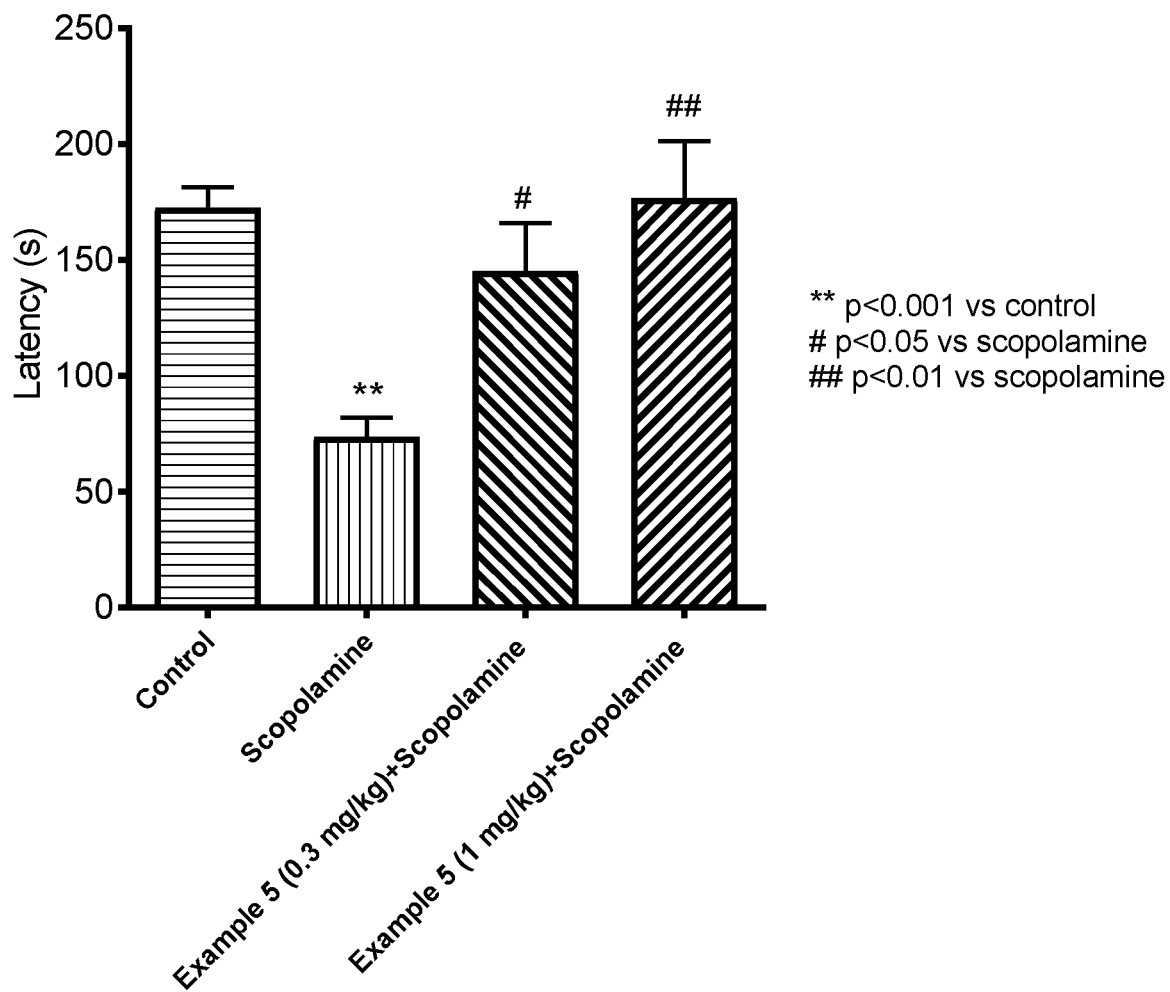

TRIAZINE DERIVATIVES FOR TREATING DISEASES RELATING TO NEUROTROPHINS

CROSS-REFERENCE TO RELATED APPLICATIONS

This application is a U.S. national stage filing, under 35 U.S.C. § 371(c), of International Application No. PCT/GB2019/050523, filed on Feb. 26, 2019, which claims priority to United Kingdom Patent Application No. 1810667.4, filed on Jun. 28, 2018, and Swedish Patent Application No. 1850217-9, filed on Feb. 26, 2018.

FIELD OF THE INVENTION

This invention relates to the pharmaceutical use of certain compounds in human medicine, to pharmaceutical compositions comprising such compounds, as well as to novel pharmaceutically-active compounds. In particular, the invention relates to the use of these compounds and compositions in methods for the treatment and/or prevention of diseases characterised by impaired signalling of neurotrophins and/or other trophic factors.

BACKGROUND OF THE INVENTION

The listing or discussion of an apparently prior-published document in this specification should not necessarily be taken as an acknowledgement that the document is part of the state of the art or is common general knowledge.

Nerve growth factor (NGF), Brain Derived Neurotrophic Factor (BDNF) and neurotrophin-3 (NT-3) and neurotrophin-4/5 all belong to the neurotrophin protein family. These hormones act through a class of receptor tyrosine kinases called tropomyosin-receptor kinase (Trk). Ligand binding to Trks initiates receptor dimerization and autophosphorylation of the kinase domain, which activates the kinase activity of the receptor. This results in further receptor phosphorylation at Tyr490, Tyr751 and Tyr785 of TrkA (or their equivalent residues in other Trk receptors). This phosphorylation leads to adaptor binding sites that couple the receptor to SHC adaptor protein 1 (SHC-1), phosphoinositide 3-kinase (PI3K) and phospholipase Cγ1 (PLCγ1). The coupling of adaptor proteins to the receptor initiates several different cellular events leading to e.g. neurite outgrowth and axonal elongation. These receptors, and their signalling pathways, play a pivotal role in many key processes in the brain e.g. hippocampal neurogenesis, synaptic plasticity, and long-term potentiation, a proposed mechanism underlying memory formation at the level of the synapse. Both NGF/TrkA and BDNF/TrkB-stimulated signalling is also necessary for the survival and morphogenesis of neurons.

In addition to activation of Trk-receptors by classical ligand binding, there are ligand independent events that can regulate neurotrophin signalling.

The balance between the activity of the receptor tyrosine kinase and the activity of tyrosine phosphatases intricately regulates the levels of phosphorylated receptor. Thus, protein tyrosine phosphatases such as PTP-1B or other phosphatases can increase neurotrophin signalling and regulate temporal and spatial activity of the Trk-receptor as well as receptor tyrosine kinases.

Also, adenosine and adenosine agonists can mediate phosphorylation of Trk-receptors, via a mechanism that requires the adenosine 2A (A2A) receptor. This phosphorylation of Trk-receptors is independent of ligand binding suggesting that modulation of Trk-receptor signalling can be accomplished by several different mechanisms.

Other key members of growth factor family are the fibroblast growth factors (FGF 1-23) and insulin growth factors (IGF 1-2). FGFs, through binding to their receptors (FGFR1, FGFR2, FGFR3, and FGFR4), play a key role in proliferation and differentiation processes of a wide variety of cells and tissues and thereby are involved in processes such as angiogenesis, wound healing, embryonic development and various endocrine-signalling pathways. IGF on the other hand, has a similar molecular structure to insulin, and binds to its receptor IGF-1R mediating effects on growth in childhood and continuing to have anabolic effects in adults. Both of these factors have also been implicated in the pathogenesis of neurodegenerative disorders of the central nervous system (CNS) such as Alzheimer's disease (Li J S et al., Med Hypotheses, 2013 April 80(4), 341-4 and Gasparini et al., Trends Neurosci. 2003 Aug. 26(8):404-6).

Synapse loss and a decrease in the hippocampal volume are pathological signatures of Alzheimer's disease in the brain and a number of studies suggest that synapse loss is the best neuroanatomical indicator of cognitive decline in the disease. Basal forebrain cholinergic neurons (BFCN) are a subpopulation of neurons that seem to be particularly vulnerable to the pathology of AD. Dysfunctional atrophy of these neurons, which in turn results in severe loss of cortical and hippocampal innervation, may be the source for the malfunction of the cholinergic system in AD (Bartus R T Exp Neurol 2000; 163:495-529). The severe cortical cholinergic deficits in the disease also include a loss of choline acetyltransferase (ChAT) and acetylcholinesterase (AChE) activity. The basal forebrain cholinergic system is dependent on NGF and cholinergic basal forebrain neurons are the major cell group that expresses the receptor for NGF, i.e. TrkA. Although the role of NGF in cholinergic neuronal survival and function is well established, studies have also shown neuroprotective/neurorestorative effects mediated by this system, e.g. that axotomized cholinergic projections in animals can be rescued by TrkA activation (Lucidi-Phillipi C A, Neuron., 1996, 16(3):653-663).

An early morphological change in the brain of AD-patients is a decreased hippocampal volume. BDNF/TrkB-stimulated signalling has previously been shown to be necessary for survival and morphogenesis of especially hippocampal neurons. Moreover, it is widely accepted that BDNF plays a critical role in neuronal plasticity and long-term potentiation (LTP). Indeed, a growing body of experimental evidence suggests that increased BDNF signalling could potentially improve cognition in AD. The transplantation of stem cells into the brain of a triple-transgenic mouse model of AD, that expresses amyloid and tau pathology, i.e. the major neuropathological hallmarks of AD, results in improved cognition (Blurton-Jones M, PNAS, 2009. 106(32): p. 13594-13599). This effect is mediated by BDNF as gain-of-function studies show that recombinant BDNF mimics the beneficial effects of neural stem cell (NSC) transplantation. Furthermore, loss-of-function studies show that depletion of NSC-derived BDNF fails to improve cognition or restore hippocampal synaptic density.

Given the potent neuroprotective and neurorestorative effects of the TrkA/NGF and TrkB/BDNF systems, small molecule positive modulators of neurotrophin signalling might be beneficial in treating a number of diseases with neurodegeneration including, but not limited to, Alzheimer's disease, Lewy body dementia, frontotemporal dementia, HIV dementia, Huntington's disease, amyotrophic lateral sclerosis and other motor neuron diseases, Rett syndrome, epilepsy, Parkinson's disease and other parkinsonian disorders. The modulators can also be used in the treatment of diseases where enhancement of nerve regeneration is beneficial, such as demyelinating diseases including, but not limited to, multiple sclerosis. The modulators could also be used for neuroprotection before or after an insult such as spinal cord injury, stroke, hypoxia, ischemia, brain injury including traumatic brain injury. Moreover, the important role of these neurotrophin systems in synaptic plasticity is thought to mediate learning and memory processes, and indicates that the modulators could also be used in disorders where cognitive function is impaired, including, but not limited to, mild cognitive impairment, dementia disorders (including dementia of mixed vascular and degenerative origin, presenile dementia, senile dementia and dementia associated with Parkinson's disease, progressive supranuclear palsy or corticobasal degeneration) and cognitive dysfunction in schizophrenia.

Recent data have also indicated that NGF/TrkA and BDNF/TrkB systems may operate as metabotrophins, that is, be involved in the maintenance of cardiometabolic homeostasis (glucose and lipid metabolism as well as energy balance, cardioprotection, and wound healing) (Chaldakov G, Arch Ital Biol. 2011 June 149(2):257-63). In fact, mutations in the genes encoding BDNF and its receptor TrkB have been shown to lead to severe obesity in humans (Yeo, G S. et al. Nat. Neurosci. 2004, 7, 1187-1189). Therefore, indications such as atherosclerosis, obesity, diabetes and metabolic syndrome could also benefit from NGF/TrkA and BDNF/TrkB directed therapies.

Another area of interest when it comes to neurotrophin signalling is neuropsychiatric disorders (Castrén E et al., Neurobiol Dis. 2016 Jul. 15, 30169-3). Studies have, for example, clearly demonstrated that depressed patients have reduced serum BDNF levels, which are restored after successful recovery (Shimizu et al., 2003, Sen et al., 2008). Moreover, several studies have demonstrated that chronic treatment with various antidepressant drugs increase BDNF mRNA and protein levels in the cerebral cortex and hippocampus (Calabrese et al., Psychopharmacology, 2011, 215, pp. 267-275). Also, local administration of BDNF into the brain has been shown to reduce depression-like behavior and mimic the effects of antidepressants (Hoshaw et al., Brain Res., 2005, 1037, pp. 204-208). Notably, the role for BDNF does not seem to be restricted to depression; it has also been implicated in other disorders, such as anxiety and schizophrenia (Castrén E., Handb. Exp. Pharmacol., 2014, 220, pp. 461-479). These data suggest that therapies targeting neurotrophin systems e.g. NGF/TrkA and BDNF/TrkB could have a therapeutic effect in several neuropsychiatric disorders, including, but not limited to, depression, schizophrenia and anxiety.

The finding that NGF and BDNF play important roles in neuronal homeostasis in combination with their neuroprotective and neurorestorative effect makes these pathways highly suitable as candidates for drug intervention for the treatment of diseases of the central nervous system and the peripheral nervous system. However, BDNF and NGF are themselves not ideal drug candidates due to their pharmacokinetic properties, the difficulties in administration and their limited ability to cross the blood-brain barrier. This has led to several attempts to identify peptides, cyclized peptides, peptide mimetics, small molecule agonist or selective modulators of NGF or BDNF. Several natural products such as gambogic amide (and analogues thereof), deoxygedunin and 7,8-dihydroxyflavone have been demonstrated to act as TrkA or TrkB agonists. Moreover, the tricyclic depressant amitriptyline has also been shown to be a TrkA and TrkB agonist. However, there is currently no specific TrkA or TrkB agonist that has reached the market. Therefore, there is an unmet need in the art for small molecule compounds that have the ability to stimulate or modulate TrkA and/or TrkB receptors, in combination with TrkC, FGFR1 and/or IGF1R and optionally other receptor tyrosine kinases for the treatment of both neurological and non-neurological disorders. There is still a need for compounds that have an improved potency and improved selectivity to TrkA and/or TrkB receptor.

BDNF production can be affected by a polymorphism within the BDNF gene (rs6265) causes a valine (Val) to methionine (Met) substitution at codon 66 (Val66Met). This polymorphism is found in approximately 30% of Caucasians and up to 70% in Asian populations. The presence of one or two Met alleles is associated with lower BDNF production in a subject. This lower BDNF production can lead to increased cognitive decline and decreased hippocampal volume.

A study by Boots et al (Neurology, 2017, 88, 1-9) demonstrated that subjects suffering sporadic Alzheimer's disease who carry the BDNF Met allele experience a steeper decline in episodic memory and executive function than non-carriers. Greater memory decline and decreased hippocampal function have also been observed in Val66Met patients with familial Alzheimer's disease (Lim et al., Brain, 2016, 139(10), 2766-2777). The same study also showed increased tau-protein and phosphorylated tau-protein in the cerebrospinal fluid in this patient group. The decline in memory in subjects with pre-clinical or clinical Alzheimer's disease was exacerbated by greater amyloid plaque burden, thus suggesting that it is possible to treat Alzheimer's disease at various stages of the disease by potentiating the effects of BDNF in patients with the Val66Met polymorphism. Such treatment may lead to neuroprotection and increased cognitive function.

In general therefore, there remains a need for alternative and/or more effective compounds that are useful in the treatment and/or prevention of diseases characterised by impaired signalling of neurotrophins and/or other trophic factors, and in particular neurodegenerative diseases such as Alzheimer's disease.

Toltrazuril (1-methyl-3-(3-methyl-4-{4-[(trifluoromethyl)sulfanyl]phenoxy}phenyl)-1,3,5-triazinane-2,4,6-trione; Baycox®) is a triazine-based antiprotozoal compounds that are used in veterinary medicine to treat coccidial infections, such as isosporiasis, toxoplasmosis, neosporosis, and equine protozoal meningoencephalitis.

A recent study by Suzuki et al. (FEBS Open Bio 2016, 6 461-468), reported that toltrazuril inhibits the binding of β-amyloid oligomers to ephrin type-B receptor 2 (EphB2; a receptor understood to play a role memory and learning functions) by 30%. However, due to a lack of selectivity at this receptor, it was not selected for further studies as a potential candidate compound for the treatment of Alzheimer's disease.

Other phenyl-1,3,5-triazine derivatives are disclosed for similar use in veterinary medicine in several old patent documents, such as U.S. Pat. No. 3,933,814, SE 402 103, DE 3 408 768 A1, EP 0 081 142 A2 and 279 219 A1. There is no suggestion that any of the compounds that are disclosed in any of these documents may be used to treat human patients per se and certainly not that the compounds may be useful in the treatment and/or prevention of diseases characterised by impaired signalling of neurotrophins and/or other trophic factors, such as Alzheimer's disease.

It has now surprisingly been found that certain 4-substituted phenyl-1,3,5-triazine derivatives are positive modulators of Trk receptors (including TrkA, TrkB and TrkC) and receptor tyrosine kinases such as IGF1R and/or FGFR1, and thus have properties rendering them useful for the treatment of diseases characterised by impaired signalling of neurotrophins and/or other trophic factors, such as Alzheimer's disease. As a result of their mode of action, the compounds are thought to be particularly suitable as therapeutic agents for use in disorders such as Alzheimer's disease, for example in patients having the Val66Met mutation in the brain-derived neurotrophic factor (BDNF) gene.

DETAILED DESCRIPTION OF THE INVENTION

According to the invention, there is provided a compound of formula I,

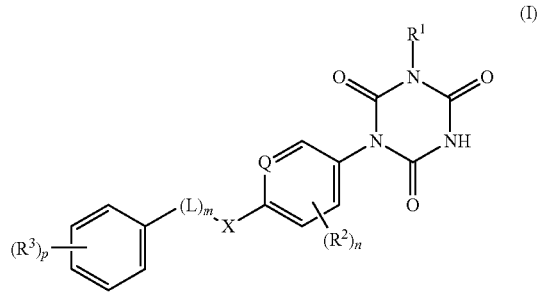

wherein:
$R^1$ represents methyl; phenyl, optionally substituted by one or more $G^1$ groups; or a 5- to 9-membered heteroaryl group, optionally substituted by one or more $G^2$ groups;

$G^1$ represents halo; phenyl, optionally substituted by one or more $G^{a1}$ groups; phenoxy, optionally substituted by one or more $G^{a2}$ groups; cyano; —N($R^{a1}$)$R^{a2}$; —C(O)N(R)$R^{a4}$, a 4- to 7-membered heterocyclyl ring, optionally substituted by one or more $G^{a3}$ groups; a 5- to 6-membered heteroaryl group, optionally substituted by one or more $G^{a4}$ groups; a $C_{1-4}$ alkyl group or a $C_{1-4}$ alkoxy group, which latter two groups are optionally substituted by one or more fluoro atoms; or any two $G^1$ groups may be joined together to form a 5- to 6-membered heterocyclyl ring, which may be optionally substituted by one or more $G^8$ groups;

$G^2$ represents halo; phenyl, optionally substituted by one or more $G^{a6}$ groups; phenoxy, optionally substituted by one or more $G^{a7}$ groups; cyano; —N($R^{a5}$)$R^{a6}$; —C(O)N($R^{a7}$)$R^{a8}$; a 4- to 7-membered heterocyclyl ring, optionally substituted by one or more $G^0$ groups; a $C_{1-4}$ alkyl group or a $C_{1-4}$ alkoxy group, which latter two groups are optionally substituted by one or more fluoro groups;

n represents 0, 1 or 2;

$R^2$ represents halo; cyano; —N($R^{a9}$)$R^{a10}$; a 4- to 7-membered heterocyclyl ring, optionally substituted by one or more $G^{a9}$ groups; or a phenyl group, optionally substituted by one or more $G^{a10}$ groups, which latter two groups (i.e. the optionally substituted 4- to 7-membered heterocyclyl ring and the optionally substituted phenyl group) are optionally linked to the relevant phenyl group in the compound of formula I via an O atom; or a $C_{1-6}$ alkyl group, a $C_{1-6}$ alkoxy group or a —S(O)$_q$$C_{1-6}$ alkyl group which latter three groups are optionally substituted by one or more fluoro, =O, hydroxy, $C_{1-2}$ alkoxy or —N($R^{a11}$)$R^{a12}$ groups, and/or are optionally substituted by a 4- to 7-membered heterocyclyl ring, optionally substituted by one or more $G^{a11}$ groups; or a phenyl group, optionally substituted by one or more $G^{a12}$ groups;

q represents 0, 1 or 2;
Q represents —N— or —CH—;
X represents —C($R^4$)$R^5$—, —O—, —S— or —N($R^6$)—;
m represents 0 or 1;
L represents —C($R^7$)$R^8$;
p represents 0 to 1;
$R^3$ represents halo; hydroxy; cyano; or $C_{1-4}$ alkyl or $C_{1-4}$ alkoxy, wherein each alkyl group or alkoxy group is optionally substituted by one or more fluoro groups;
$R^4$, $R^5$, $R^6$, $R^7$ and $R^8$ each independently represent H or $C_{1-2}$ alkyl;
$R^{a1}$, $R^{a2}$, $R^{a3}$, $R^{a4}$, $R^{a5}$, $R^{a6}$, $R^{a7}$, $R^{a8}$, $R^{a9}$, $R^{a10}$, $R^{a11}$ and $R^{a12}$ each independently represent H or $C_{1-3}$ alkyl; or
$R^{a1}$ and $R^{a2}$, $R^{a3}$ and $R^{a4}$, $R^{a5}$ and $R^{a6}$, $R^{a7}$ and $R^{a8}$, $R^{a9}$ and $R^{a10}$ and $R^{a11}$ and $R^{a12}$ may independently be joined together to form, together with the atom to which they are attached, a 4- to 7-membered heterocyclyl ring;
$G^{a1}$, $G^{a2}$, $G^{a4}$, $G^{a6}$, $G^{a7}$, $G^{a10}$ and $G^{a12}$ each independently represent $C_{1-2}$ alkyl or halo;
$G^{a3}$, $G^{a5}$, $G^{a8}$, $G^{a9}$ and $G^{a11}$ each independently represent $C_{1-2}$ alkyl, halo or =O;
and wherein an $R^2$ group may also be joined together with any one of $R^4$, $R^5$, $R^6$, $R^7$ or $R^8$ to form a 4- to 7-membered heterocyclyl ring, or a 5- to 6-membered heteroaryl ring, wherein said heterocyclyl or heteroaryl rings are optionally substituted by one or more substituents selected from $G^3$; and
$G^3$ represents halo, $C_{1-2}$ alkyl or $C_{1-2}$ alkoxy;
or a pharmaceutically acceptable salt thereof, for use in a method for the treatment and/or prevention of a disease characterised by impaired signalling of neurotrophins and/or other trophic factors.

Compounds of formula I that maybe mentioned include those in which $G^1$ represents halo; phenyl, optionally substituted by one or more $G^{a1}$ groups; phenoxy, optionally substituted by one or more $G^{a2}$ groups; cyano; —N($R^{a1}$)$R^{a2}$; —C(O)N($R^{a3}$)$R^{a4}$, a 4- to 7-membered heterocyclyl ring, optionally substituted by one or more $G^{a3}$ groups; a 5- to 6-membered heteroaryl group, optionally substituted by one or more $G^{a4}$ groups; a $C_{1-4}$ alkyl group or a $C_{1-4}$ alkoxy group, which latter two groups are optionally substituted by one or more fluoro atoms; or any two $G^1$ groups may be joined together to form a 5- to 6-membered heterocyclyl ring, which may be optionally substituted by one or more $G^a$ groups;
$G^{a1}$, $G^{a2}$ and $G^{a4}$ each independently represent methyl, ethyl, fluoro or chloro; and
$G^{a3}$ and $G^{a5}$ each independently represent methyl, ethyl, fluoro, chloro or =O.

Further compounds of formula I that may be mentioned include those in which $G^1$ represents halo; phenyl; phenoxy; cyano; —N($R^{a1}$)$R^{a2}$; a 4- to 7-membered heterocyclyl ring; a $C_{1-4}$ alkyl group or a $C_{1-4}$ alkoxy group, which latter two groups are optionally substituted by one or more fluoro atoms; or any two $G^1$ groups may be joined together to form a 5- to 6-membered heterocyclyl ring.

Compounds of formula I that may be mentioned include those in which $G^2$ represents halo; phenyl, optionally substituted by one or more $G^{a6}$ groups; phenoxy, optionally substituted by one or more $G^{a7}$ groups; cyano; —N($R^{a5}$)$R^{a6}$; —C(O)N($R^{a7}$)$R^{a8}$; a 4- to 7-membered heterocyclyl ring, optionally substituted by one or more $G^{a8}$ groups; a $C_{1-4}$ alkyl group or a C$_{1-4}$ alkoxy group, which latter two groups are optionally substituted by one or more fluoro groups;

G$^{a6}$, G$^{a7}$ and G$^{a4}$ each independently represent methyl, ethyl, fluoro or chloro; and G$^{a8}$ represents methyl, ethyl, fluoro, chloro or =O.

Further particular compounds of formula I that may be mentioned include those in which G$^2$ represents halo; phenyl; phenoxy; cyano; —N(R$^{a3}$)R$^{a4}$; a 4- to 7-membered heterocyclyl ring; a C$_{1-4}$ alkyl group or a C$_{1-4}$ alkoxy group, which latter two groups are optionally substituted by one or more fluoro groups.

Compounds of the invention that may be mentioned include those in which R$^2$ represents halo; cyano; —N(R$^{a9}$)R$^{a10}$; a 4- to 7-membered heterocyclyl ring, optionally substituted by one or more G$^{a9}$ groups; or a phenyl group, optionally substituted by one or more G$^{a10}$ groups, which latter two groups (i.e. the optionally substituted 4- to 7-membered heterocyclyl ring and the optionally substituted phenyl group) are optionally linked to the relevant phenyl group in the compound of formula I via an O atom; or a C$_{1-6}$ alkyl group, a C$_{1-6}$ alkoxy group or a —S(O)$_q$C$_{1-6}$ alkyl group which latter three groups are optionally substituted by one or more fluoro, =O, hydroxy, C$_{1-2}$ alkoxy or —N(R$^{a11}$)R$^{a12}$ groups, and/or are optionally substituted by a 4- to 7-membered heterocyclyl ring, optionally substituted by one or more G$^{a11}$ groups; or a phenyl group, optionally substituted by one or more G$^{a12}$ groups;

G$^{a9}$, and G$^{a11}$ each independently represent methyl, ethyl, fluoro or chloro or =O; and G$^{a10}$ and G$^{a12}$ each independently represent methyl, ethyl, fluoro, chloro.

q represents 0 or 2.

Compounds of the invention that may be mentioned include those in which R$^2$ represents halo; cyano; —N(R$^{a9}$)R$^{a10}$; a 4- to 7-membered heterocyclyl ring, optionally substituted by one or more G$^{a9}$ groups; or a phenyl group, optionally substituted by one or more G$^{a10}$ groups, which latter two groups (i.e. the optionally substituted 4- to 7-membered heterocyclyl ring and the optionally substituted phenyl group) are optionally linked to the relevant phenyl group in the compound of formula I via an O atom; or a C$_{1-6}$ alkyl group, or a C$_{1-6}$ alkoxy group, which latter two groups are optionally substituted by one or more fluoro, =O, hydroxy, C$_{1-2}$ alkoxy or —N(R$^{a11}$)R$^{a12}$ groups, and/or are optionally substituted by a 4- to 7-membered heterocyclyl ring, optionally substituted by one or more G$^{a11}$ groups; or a phenyl group, optionally substituted by one or more G$^{a12}$ groups; and G$^{a9}$, and G$^{a11}$ each independently represent methyl, ethyl, fluoro or chloro or =O; and G$^{a10}$ and G$^{a12}$ each independently represent methyl, ethyl, fluoro, chloro.

More particular compounds of formula I that may be mentioned include those in which R$^2$ represents halo; cyano; —N(R)R$^{a10}$; a 4- to 7-membered heterocyclyl ring or a phenyl group, which latter two groups are optionally linked to the relevant phenyl group in the compound of formula I via an O atom; or a C$_{1-6}$ alkyl group, a C$_{1-6}$ alkoxy group, which latter two groups are optionally substituted by one or more fluoro, =O, hydroxy, C$_{1-2}$ alkoxy or —N(R$^{a11}$)R$^{a12}$ groups, and/or are optionally substituted by a 4- to 7-membered heterocyclyl ring or a phenyl group.

Compounds of formula I that may be mentioned include those in which Q represents —CH—.

For the avoidance of doubt, when Q represents —CH—, the position may be substituted by an R$^2$ group as defined herein (i.e. Q may represent —CH— or —CR$^2$—).

Other compounds of formula I that may be mentioned include those in which Q represents —N—.

There is further provided a compound of formula I, wherein the compound of formula I is a compound of formula Ia,

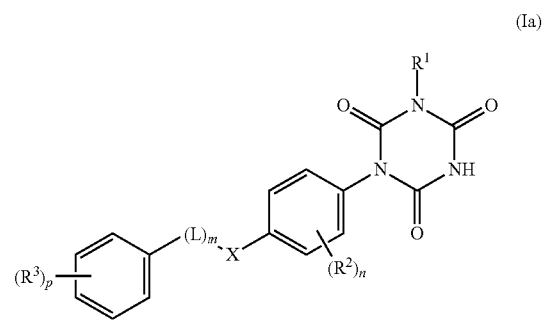

(Ia)

wherein:

R$^1$ represents methyl; phenyl, optionally substituted by one or more G$^1$ groups; or a 5- to 9-membered heteroaryl group, optionally substituted by one or more G$^2$ groups;

G$^1$ represents halo; phenyl; phenoxy; cyano; —N(R$^{a1}$)R$^{a2}$; a 4- to 7-membered heterocyclyl ring; a C$_{1-4}$ alkyl group or a C$_{1-4}$ alkoxy group, which latter two groups are optionally substituted by one or more fluoro atoms; or any two G$^1$ groups may be joined together to form a 5- to 6-membered heterocyclyl ring;

G$^2$ represents halo; phenyl; phenoxy; cyano; —N(R$^{a5}$)R$^{a6}$; a 4- to 7-membered heterocyclyl ring; a C$_{1-4}$ alkyl group or a C$_{1-4}$ alkoxy group, which latter two groups are optionally substituted by one or more fluoro groups;

n represents 0, 1 or 2;

R$^2$ represents halo; cyano; —N(R)R$^{a10}$; a 4- to 7-membered heterocyclyl ring or a phenyl group, which latter two groups are optionally linked to the relevant phenyl group in the compound of formula I via an O atom; a C$_{1-6}$ alkyl group or a C$_{1-6}$ alkoxy group, which latter two groups are optionally substituted by one or more fluoro, =O, hydroxy, C$_{1-2}$ alkoxy or —N(R$^{a11}$)R$^{a12}$ groups, and/or are optionally substituted by a 4- to 7-membered heterocyclyl ring, or a phenyl group;

X represents —C(R$^4$)R$^5$—, —O—, —S— or —N(R$^6$)—;

m represents 0 or 1;

L represents —C(R$^7$)R$^8$—;

p represents 0 to 1;

R$^3$ represents halo; hydroxy; cyano; or C$_{1-4}$ alkyl or C$_{1-4}$ alkoxy, wherein each alkyl group or alkoxy group is optionally substituted by one or more fluoro groups;

R$^4$, R$^5$, R$^6$, R$^7$ and R$^8$ each independently represent H or C$_{1-2}$ alkyl;

R$^{a1}$, R$^{a2}$, R$^{a5}$, R$^{a6}$, R$^{a9}$, R$^{a10}$, R$^{a11}$ and R$^{a12}$ each independently represent H or C$_{1-3}$ alkyl; or R$^{a1}$ and R$^{a2}$, R$^{a5}$ and R$^{a6}$, R$^{a9}$ and R$^{a10}$, and R$^{a11}$ and R$^{a12}$ may independently be joined together to form, together with the atom to which they are attached, a 4- to 7-membered heterocyclyl ring;

and wherein an R$^2$ group may also be joined together with any one of R$^4$, R$^5$, R$^6$, R$^7$ or R$^8$ to form a 4- to 7-membered (preferably 5- to 6-membered) heterocyclyl ring, or a 5- to 6-membered (preferably 5-membered) heteroaryl ring, wherein said heterocyclyl or heteroaryl rings are optionally substituted by one or more substituents selected from G$^3$; and $G^3$ represents halo, $C_{1-2}$ alkyl or $C_{1-2}$ alkoxy, or a pharmaceutically acceptable salt thereof, and optionally one or more pharmaceutically-acceptable excipient, such as an adjuvant, diluent or carrier.

Compounds of formula I, including compounds of formula Ia, that may also be mentioned include those in which:

$R^2$ represents halo; cyano; $-N(R^{a9})R^{a10}$; a 4- to 7-membered heterocyclyl ring or a phenyl group, which latter two groups are optionally linked to the relevant phenyl group in the compound of formula I via an O atom; a $C_{1-6}$ alkyl group or a $C_{1-6}$ alkoxy group, which latter two groups are optionally substituted by one or more fluoro, $=O$, hydroxy or $C_{1-2}$ alkoxy groups, and/or are optionally substituted by a 4- to 7-membered heterocyclyl ring, or a phenyl group; and $R^{a1}$, $R^{a2}$, $R^{a5}$, $R^{a6}$, $R^{a9}$ and $R^{a10}$ each independently represent H or $C_{1-3}$ alkyl;

or $R^{a1}$ and $R^{a2}$, $R^{a5}$ and $R^{a6}$, and $R^{a9}$ and $R^{a10}$ may independently be joined together to form, together with the atom to which they are attached, a 4- to 7-membered heterocyclyl ring, or a pharmaceutically acceptable salt thereof, for use in a method for the treatment and/or prevention of a disease characterised by impaired signalling of neurotrophins and/or other trophic factors.

For the avoidance of doubt, the skilled person will understand that where a particular group is depicted herein as being bound to a ring system via a floating bond (i.e. a bond not shown as being bound to a particular atom within the ring), the relevant group may be bound to any suitable atom within the relevant ring system (i.e. the ring within which the floating bond terminates).

The skilled person will understand that when an $R^2$ group is joined together with any one of $R^4$, $R^5$, $R^6$, $R^7$ or $R^8$ to form a 4- to 7-membered heterocyclic ring or a 5- to 6-membered heteroaryl ring, said ring will be fused to the benzene ring to which $R^2$ is attached (i.e. the heteroaryl or heterocyclyl ring in combination with the benzene ring constitutes an 8- to 11-membered (e.g. 9-membered) heteroaryl group).

There is further provided a compound of formula I, including a compound of formula Ia, as hereinbefore defined, or a pharmaceutically acceptable salt thereof, provided that, when $R^1$ represents methyl, m is 0, and:

(i) X represents O or S, then n and p do not both represent 0;

(ii) when X represents 0, and $R^2$ represents a single fluoro group in the 3-position relative to the triazine ring, then $R^3$ does not represent a single $-CF_3$ group in the 4-position relative to the point of attachment of the benzene ring;

$R^2$ represents two chloro groups in the 3- and 5-positions relative to the triazine ring, then $R^3$ does not represent a single $-OCF_3$ or cyano group in the 4-position relative to the point of attachment of the benzene ring;

$R^2$ represents a single chloro group in the 3-position relative to the triazine ring, then either (a) p does not represent 0 or, (b) when p represents 1, then $R^3$ does not represent a chloro group in the 4-position relative to the point of attachment of the benzene ring; and when n represents 0, then $R^3$ does not represent a single fluoro, chloro, $-CF_3$, cyano or methyl group in the 4-position, or a chloro group in the 3-position, relative to the point of attachment of the benzene ring; and (iii) when X represents S, and $R^2$ represents two chloro atoms in the 3- and 5-positions relative to the triazine ring, then $R^3$ does not represent a single ethyl group in the 2-position, a single ethoxy group in the 3- or in the 4-position, or a single chloro, bromo, cyano, $-CF_3$, or tert-butyl, group in the 4-position relative to the point of attachment of the benzene ring;

$R^2$ represents two methyl groups in the 3- and 5-positions relative to the triazine ring, then $R^3$ does not represent a single chloro or bromo group in the 4-position relative to the point of attachment of the benzene ring;

$R^2$ represents two methyl groups in the 2- and 5-positions relative to the triazine ring, then $R^3$ does not represent a single methyl or tert-butyl group in the 4-position relative to the point of attachment of the benzene ring; and n represents 0, then $R^3$ does not represent a single chloro, methyl, cyano or tert-butyl group in the 4-position relative to the point of attachment of the benzene ring.

There is further provided a compound of formula I, including a compound of formula Ia, as hereinbefore defined, or a pharmaceutically acceptable salt thereof, provided that, when $R^1$ represents methyl, m is 0, and:

(iv) X represents O or S, then n and p do not both represent 0;

(v) when X represents 0, and $R^2$ represents a single fluoro group in the 3-position relative to the triazine ring, then $R^3$ does not represent a single $-CF_3$ group in the 4-position relative to the point of attachment of the benzene ring;

$R^2$ represents two chloro groups in the 3- and 5-positions relative to the triazine ring, then $R^3$ does not represent a single $-OCF_3$ group in the 4-position relative to the point of attachment of the benzene ring;

$R^2$ represents a single chloro group in the 3-position relative to the triazine ring, then either (c) p does not represent 0 or, (d) when p represents 1, then $R^3$ does not represent a chloro group in the 4-position relative to the point of attachment of the benzene ring; and when n represents 0, then $R^3$ does not represent a single fluoro, chloro, $-CF_3$, cyano or methyl group in the 4-position, or a chloro group in the 3-position, relative to the point of attachment of the benzene ring; and (vi) when X represents S, and $R^2$ represents two chloro atoms in the 3- and 5-positions relative to the triazine ring, then $R^3$ does not represent a single ethyl group in the 2-position, a single ethoxy group in the 3- or in the 4-position, or a single chloro, bromo, cyano, $-CF_3$, or tert-butyl, group in the 4-position relative to the point of attachment of the benzene ring;

$R^2$ represents two methyl groups in the 3- and 5-positions relative to the triazine ring, then $R^3$ does not represent a single chloro or bromo group in the 4-position relative to the point of attachment of the benzene ring;

$R^2$ represents two methyl groups in the 2- and 5-positions relative to the triazine ring, then $R^3$ does not represent a single methyl or tert-butyl group in the 4-position relative to the point of attachment of the benzene ring; and n represents 0, then $R^3$ does not represent a single chloro, methyl, or tert-butyl group in the 4-position relative to the point of attachment of the benzene ring.

The skilled person will understand that, as used herein, references to the point of attachment of the benzene ring refer to the point of attachment of the benzene ring to which the relevant substituent is attached to the relevant essential structural feature defined in the compound of formula I. In the case of the benzene ring to which $R^3$ is attached, the point of attachment of the benzene ring refers to the atom through which it is attached to the X group, or, if present, the L group.

References to the position of an $R^2$ substituent relative to the triazine ring may be understood to refer to the position of the relevant substituent relative to the point of attachment of the benzene ring (i.e. the atom through which the benzene ring is attached) to the essential 1,3,5-triazine-2,4,6-trione ring in the compound of formula I.

Compounds of formula I, including compounds of formula Ia, (including pharmaceutically acceptable salts thereof) as defined in any of the definitions provided hereinbefore are referred to collectively hereinafter as "the compounds of the invention".

Compounds of formula I, including compounds of formula Ia, (i.e. the compounds of the invention) that may be mentioned include those in which, when $R^1$ represents methyl, then
(i) n and p do not both represent 0;
(ii) when X represents O, then
  $R^3$ does not represent a single fluoro, chloro, methyl, cyano, —$CF_3$, or —$OCF_3$ group in the 4-position, or a single chloro group in the 3-position, relative to the point of attachment of the benzene ring; or
  $R^2$ does not represent a single chloro group in the 3-position relative to the triazine ring;
(iii) when X represents S, then $R^3$ does not represent a single chloro, bromo, —$CF_3$, cyano, methyl, ethoxy, or tert-butyl group in the 4-position, a single ethoxy group in the 3-position, or a single ethyl group in the 2-position, relative to the point of attachment of the benzene ring, or a pharmaceutically acceptable salt thereof.

Certain compounds of the invention may be novel and/or not previously used in human medicine, thus, in a further embodiment of the invention, there is provided a compound of formula I, including a compound of formula Ia, as defined herein.

There is further provided a compound of formula I, including a compound of formula Ia, for use in human medicine and/or as a pharmaceutical.

For the avoidance of doubt, the skilled person will understand that references herein to compounds of particular aspects of the invention (such as any aspect of the invention referring to compounds of formula I as defined hereinbefore) will include references to all embodiments and particular features thereof, which embodiments and particular features may be taken in combination to form further embodiments and features of the invention.

Unless indicated otherwise, all technical and scientific terms used herein will have their common meaning as understood by one of ordinary skill in the art to which this invention pertains.

Pharmaceutically acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared using techniques known to those skilled in the art, such as by exchanging a counter-ion of a compound of the invention in the form of a salt with another counter-ion, for example using a suitable ion exchange resin.

Particular acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxy-benzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts, including HCl, HBr and HI salts and the like), sulphonate salts (e.g. benzenesulphonate, methyl-, bromo- or chloro-benzenesulphonate, xylenesulphonate, methanesulphonate, ethanesulphonate, propanesulphonate, hydroxy-ethanesulphonate, 1- or 2-naphthalenesulphonate or 1,5-naphthalene-disulphonate salts) or sulphate, pyrosulphate, bisulphate, sulphite, bisulphite, phosphate, monohydrogenphosphate, dihydrogenphosphate, metaphosphate, pyrophosphate or nitrate salts, and the like.

Particular base addition salts that may be mentioned include salts formed with alkali metals (such as Li, Na and K salts), alkaline earth metals (such as Mg and Ca salts), or other metals (such as Al and Zn salts) organic bases (such as benzathine, ethylenediamine, ethanolamine, diethanolamine, triethanolamine, tromethamine, procaine and lysine) and inorganic bases (such as ammonia and aluminium hydroxide). More particularly, base addition salts that may be mentioned include Mg, Ca and, most particularly, K and Na salts.

For the avoidance of doubt, compounds of the invention may exist as solids, and thus the scope of the invention includes all amorphous, crystalline and part crystalline forms thereof, and may also exist as oils. Where compounds of the invention exist in crystalline and part crystalline forms, such forms may include solvates, which are included in the scope of the invention.

For the avoidance of doubt, compounds of the invention may also exist in solution (i.e. in solution in a suitable solvent). For example, compounds of the invention may exist in aqueous solution, in which case compounds of the invention may exist in the form of hydrates thereof.

Compounds of the invention may contain double bonds and, unless otherwise indicated, may thus exist as E (entgegen) and Z (zusammen) geometric isomers about each individual double bond. Unless otherwise specified, all such isomers and mixtures thereof are included within the scope of the invention.

Compounds of the invention may also exhibit tautomerism. All tautomeric forms and mixtures thereof are included within the scope of the invention (particularly those of sufficient stability to allow for isolation thereof).

Compounds of the invention may also contain one or more asymmetric carbon atoms and may therefore exhibit optical and/or diastereoisomerism (i.e. existing in enantiomeric or diastereomeric forms). Diastereoisomers may be separated using conventional techniques, e.g. chromatography or fractional crystallisation. The various stereoisomers (i.e. enantiomers) may be isolated by separation of a racemic or other mixture of the compounds using conventional, e.g. fractional crystallisation or HPLC, techniques. Alternatively the desired enantiomer or diastereoisomer may be obtained from appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution; for example, with a homochiral acid followed by separation of the diastereomeric derivatives by conventional means such as chromatography), or by reaction with an appropriate chiral reagent or chiral catalyst, all of which methods and processes may be performed under conditions known to the skilled person. Unless otherwise specified, all stereoisomers and mixtures thereof are included within the scope of the invention.

Unless otherwise specified, $C_{1-z}$ alkyl groups, and the alkyl parts of $C_{1-z}$ alkoxy groups (where, in both cases, z is the upper limit of the range), defined herein may be straight-chain or, when there is a sufficient number (i.e. a minimum of two or three, as appropriate) of carbon atoms, be branched-chain, and/or cyclic (so forming a $C_{3-z}$ cycloalkyl group). When there is a sufficient number (i.e. a minimum of four) of carbon atoms, such groups may also be part cyclic (so forming a $C_{4-z}$ partial cycloalkyl group). For example, cycloalkyl groups that may be mentioned include cyclopropyl, cyclopentyl and cyclohexyl. Similarly, part cyclic alkyl groups (which may also be referred to as "part cycloalkyl" groups) that may be mentioned include cyclopropylmethyl. When there is a sufficient number of carbon atoms, such groups may also be multicyclic (e.g. bicyclic or tricyclic) and/or spirocyclic. For the avoidance of doubt, particular alkyl groups that may be mentioned include straight chain (i.e. not branched and/or cyclic) alkyl groups.

For the avoidance of doubt, alkyl and alkoxy as described herein may also act as linker groups (i.e. groups joining two or more parts of the compound as described), in which case such groups may be referred to as "alkylene", "oxyalkylene", etc.

For the avoidance of doubt, as used herein, references to heteroatoms will take their normal meaning as understood by one skilled in the art. Particular heteroatoms that may be mentioned include phosphorus, selenium, tellurium, silicon, boron, oxygen, nitrogen and sulfur (e.g. oxygen, nitrogen and sulfur, such as oxygen and nitrogen).

As used herein, the term "heterocyclyl" rings or groups may refer to non-aromatic monocyclic and polycyclic (e.g. bicyclic) heterocyclic rings or groups (which groups may, where containing a sufficient number of atoms, also be bridged) in which at least one (e.g. one to four) of the atoms in the ring system is other than carbon (i.e. a heteroatom), and in which the total number of atoms in the ring system is between as specified hereinbefore. Further, such heterocyclyl groups may be saturated, forming a heterocycloalkyl, or unsaturated containing one or more carbon-carbon or, where possible, carbon-heteroatom or heteroatom-heteroatom double and/or triple bonds, forming for example a $C_{2-z}$ (e.g. $C_{4-z}$) heterocycloalkenyl (where z is the upper limit of the range) or a $C_{7-z}$ heterocycloalkynyl group.

For the avoidance of doubt, the skilled person will understand that heterocyclyl groups that may form part of compounds of the invention are those that are chemically obtainable, as known to those skilled in the art. Various heterocyclyl groups will be well-known to those skilled in the art, such as 7-azabicyclo-[2.2.1]heptanyl, 6-azabicyclo [3.1.1]heptanyl, 6-azabicyclo[3.2.1]-octanyl, 8-azabicyclo [3.2.1]octanyl, aziridinyl, azetidinyl, 2,3-dihydroisothiazolyl, dihydropyranyl, dihydropyridinyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, isothiazolidinyl, morpholinyl, 7-oxabicyclo[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuryl, tetrahydropyridinyl (such as 1,2,3,4-tetrahydropyridinyl and 1,2,3,6-tetrahydropyridinyl), thietanyl, thiiranyl, thiolanyl, tetrahydrothiopyranyl, thiomorpholinyl, trithianyl (including 1,3,5-trithianyl), tropanyl and the like.

Substituents on heterocyclyl groups may, where appropriate, be located on any atom in the ring system including a heteroatom. Further, in the case where the substituent is another cyclic compound, then the cyclic compound may be attached through a single atom on the heterocyclyl group, forming a spirocyclic compound. The point of attachment of heterocyclyl groups may be via any suitable atom in the ring system, including (where appropriate) a further heteroatom (such as a nitrogen atom), or an atom on any fused carbocyclic ring that may be present as part of the ring system. Heterocyclyl groups may also be in the N- or S-oxidised forms, as known to those skilled in the art.

For the avoidance of doubt, any references to polycyclic (e.g. bicyclic or tricyclic) groups (for example when employed in the context of heterocyclyl or cycloalkyl groups (e.g. heterocyclyl)) as may be employed herein will refer to ring systems wherein at least two scissions would be required to convert such rings into a non-cyclic (i.e. straight or branched) chain, with the minimum number of such scissions corresponding to the number of rings defined (e.g. the term bicyclic may indicate that a minimum of two scissions would be required to convert the rings into a straight chain). For the avoidance of doubt, the term bicyclic (e.g. when employed in the context of alkyl groups) may refer to groups in which the second ring of a two-ring system is formed between two adjacent atoms of the first ring, to groups in which two non-adjacent atoms are linked by an alkyl (which, when linking two moieties, may be referred to as alkylene) group (optionally containing one or more heteroatoms), which later groups may be referred to as bridged, or to groups in which the second ring is attached to a single atom, which latter groups may be referred to as spiro compounds.

Particular heterocyclyl groups that may be mentioned include piperidinyl (e.g. piperidin-1-yl), octahydro-1H-isoindolyl (e.g. octahydro-1H-isoindol-2-yl), azetidinyl (e.g. azetidine-1-yl), oxetanyl (e.g. oxetan-3-yl), morpholinyl (e.g. morpholin-4-yl), piperazinyl (e.g. piperazin-1yl or piperazin-4-yl), azepanyl (e.g. azepan-1-yl), imidazolidinyl (e.g. imidazolidine-2-yl), pyrrolidinyl (e.g. pyrrolidine-1yl), and diazepanyl (e.g. 1,4-diazepan-1-yl).

As may be used herein, references to "heteroaryl" (with may also be referred to as heteroaromatic) rings or groups may refer to heteroaromatic groups containing one or more heteroatoms (such as one or more heteroatoms selected from oxygen, nitrogen and/or sulfur). Such heteroaryl groups may comprise one, two, or three rings, of which at least one is aromatic (which aromatic ring(s) may or may not contain the one or more heteroatom). Substituents on heteroaryl/heteroaromatic groups may, where appropriate, be located on any suitable atom in the ring system, including a heteroatom (e.g. on a suitable N atom).

The point of attachment of heteroaryl/heteroaromatic groups may be via any atom in the ring system including (where appropriate) a heteroatom. Bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocycly ring.

For the avoidance of doubt, the skilled person will understand that heteroaryl groups that may form part of compounds of the invention are those that are chemically obtainable, as known to those skilled in the art. Various heteroaryl groups will be well-known to those skilled in the art, such as pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, imidazothiazolyl, thienothiophenyl, pyrimidinyl, furopyridinyl, indolyl, azaindolyl, pyrazinyl, pyrazolopyrimidinyl, indazolyl, pyrimidinyl, quinolinyl, isoquinolinyl, quinazolinyl, benzofuranyl, benzothiophenyl, benzoimidazolyl, benzoxazolyl, benzothiazolyl, benzotriazolyl and purinyl.

For the avoidance of doubt, the oxides of heteroaryl/heteroaromatic groups are also embraced within the scope of the invention (e.g. the N-oxide).

As stated above, heteroaryl includes polycyclic (e.g. bicyclic) groups in which one ring is aromatic (and the other may or may not be aromatic). Hence, other heteroaryl groups that may be mentioned include groups such as benzo[1,3]dioxolyl, benzo[1,4]dioxinyl, dihydrobenzo[d]isothiazole, 3,4-dihydrobenz[1,4]oxazinyl, dihydrobenzothiophenyl, indolinyl, 5H,6H,7H-pyrrolo[1,2-b]pyrimidinyl, 1,2,3,4-tetrahydroquinolinyl, thiochromanyl and the like.

Aromatic groups may be depicted as cyclic groups comprising therein a suitable number of double bonds to allow for aromaticity.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. compounds of the invention in which one or more hydrogen atoms are replaced by the hydrogen isotope deuterium.

For the avoidance of doubt, in cases in which the identity of two or more substituents in a compound of the invention may be the same, the actual identities of the respective substituents are not in any way interdependent. For example, in the situation in which two or more halo groups are present, those groups may be the same or different (e.g. two chloro groups or a fluoro and a chloro group). Similarly, where two or more alkyl groups are present, the groups in question may be the same or different in terms of their number of carbon atoms and/or whether they are linear branched or otherwise.

Also for the avoidance of doubt, when a term such as "4- to 7-membered" is employed herein, this will be understood by the skilled person to mean 4-, 5-, 6- and 7-membered, inclusively. Unless otherwise stated, the same reasoning will apply to other such terms used herein.

Further for the avoidance of doubt, when it is specified that a substituent is itself optionally substituted by one or more substituents (e.g. phenyl optionally substituted by one or more groups independently selected from halo), these substituents where possible may be positioned on the same or different atoms. Such optional substituents may be present in any suitable number thereof (e.g. the relevant group may be substituted with one or more such substituents, such as one such substituent).

For the avoidance of doubt, where groups are referred to herein as being optionally substituted it is specifically contemplated that such optional substituents may be not present (i.e. references to such optional substituents may be removed), in which case the optionally substituted group may be referred to as being unsubstituted.

For the avoidance of doubt, the skilled person will appreciate that compounds of the invention that are the subject of this invention include those that are obtainable, i.e. those that may be prepared in a stable form. That is, compounds of the invention include those that are sufficiently robust to survive isolation, e.g. from a reaction mixture, to a useful degree of purity.

Compounds of the invention that may be mentioned include those in which:

$R^1$ does not represent methyl, that is $R^1$ represents phenyl, optionally substituted by one or more $G^1$ groups; or a 5- to 9-membered heteroaryl group, optionally substituted by one or more $G^2$ groups;

n and p do not both represent 0; or n does not represent 2, that is n represents 0 or 1;

Compounds of the invention that may be mentioned include those in which $R^1$ represents phenyl, optionally substituted by one or more $G^1$ groups.

Compounds of the invention that may be mentioned include those in which, when $R^1$ represents phenyl, the optional $G^1$ substituent is one or more (preferably one) of:
  halo (e.g. fluoro or chloro),
  phenoxy,
  $N(R^{a1})R^{a2}$, in which $R^{a1}$ and $R^{a2}$ each represent H or $C_{1-2}$ alkyl or are preferably joined together to form a 6-membered heterocyclyl group, such as a morpholin-4-yl group;
  $C_{1-4}$ alkyl, which latter group is optionally substituted with one or more fluoro groups or $C_{1-2}$ alkoxy groups, and/or
  $C_{1-2}$ alkoxy, which latter group is optionally substituted with one or more fluoro groups.

Compounds of the invention that may be mentioned include those in which, when $R^1$ represents phenyl, the optional $G^1$ substituent is one or more (preferably one) of:
  halo (e.g. fluoro or chloro),
  phenoxy,
  $N(R^{a1})R^{a2}$, in which $R^{a1}$ and $R^{a2}$ each represent H or $C_{1-2}$ alkyl or are preferably joined together to form a 6-membered heterocyclyl group, such as a morpholin-4-yl group;
  —$C(O)N(R^{a3})R^{a4}$, in which $R^{a3}$ and $R^{a4}$ each represent H or $C_{1-2}$ alkyl or are joined together to form a 4- to 6-membered (e.g. 4-membered) heterocyclyl group,
  $C_{1-4}$ alkyl, which latter group is optionally substituted with one or more fluoro groups or $C_{1-2}$ alkoxy groups, and/or
  $C_{1-2}$ alkoxy, which latter group is optionally substituted with one or more fluoro groups.

Compounds of the invention that may be mentioned include those in which, when $R^1$ represents phenyl, the optional $G^1$ substituent is one or more (preferably one) of:

halo (e.g. fluoro or chloro),
phenoxy,
  a 5- to 6-membered heteroaryl group, which group is optionally substituted by one or more (preferably one) methyl group;
  $N(R^{a1})R^{a2}$, in which $R^{a1}$ and $R^{a2}$ each represent H or $C_{1-2}$ alkyl or are preferably joined together to form a 6-membered heterocyclyl group, such as a morpholin-4-yl group;
  $C_{1-4}$ alkyl, which latter group is optionally substituted with one or more fluoro groups or $C_{1-2}$ alkoxy groups, and/or
  $C_{1-2}$ alkoxy, which latter group is optionally substituted with one or more fluoro groups.

Compounds of the invention that may be mentioned include those in which, when R represents phenyl, the optional $G^1$ substituent is one or more (preferably one) of:
halo (e.g. fluoro or chloro),
phenoxy,
  a 5-membered heteroaryl group selected from pyrrolyl, imidazolyl, pyrazolyl, thiophenyl and furanyl, each of which may optionally be substituted by one or more (e.g. one) methyl groups. Preferably, the 5-membered heteroaryl group is selected from pyrrolyl, pyrazolyl and, particularly, imidazolyl (e.g. 4-methylimidazol-1-yl).
  $N(R^{a1})R^{a2}$, in which $R^{a1}$ and $R^{a2}$ each represent H or $C_{1-2}$ alkyl or are preferably joined together to form a 6-membered heterocyclyl group, such as a morpholin-4-yl group;
  —$C(O)N(R^{a3})R^{a4}$, in which $R^{a3}$ and $R^{a4}$ each represent H or $C_{1-2}$ alkyl, and preferably both $R^{a3}$ and $R^{a4}$ both represent methyl,
  $C_{1-4}$ alkyl, which latter group is optionally substituted with one or more fluoro groups or $C_{1-2}$ alkoxy groups, and/or
  $C_{1-2}$ alkoxy, which latter group is optionally substituted with one or more fluoro groups.

Compounds of the invention that may be mentioned include those in which, when R represents phenyl, two $G^1$ groups are present and are joined together to form a 5-membered heterocyclyl ring, such as a dioxolanyl ring.

Compounds of the invention that may be mentioned include those in which:
  $R^1$ represents a pyridinyl, a pyrazolyl, an indolyl, a thiazolyl, a benzofuranyl, or a thiophenyl, group, optionally substituted by one or more $G^2$ groups;
  the optional $G^2$ substituent is one or more (preferably one) phenyl, halo, $C_{1-2}$ alkyl or $C_{1-2}$ alkoxy groups, which latter two groups are optionally substituted with one or more fluoro groups.

Compounds of the invention that may be mentioned include those in which n is 0.

Compounds of the invention that may be mentioned include those in which n is 2 or, preferably, 1.

Compounds of the invention that may be mentioned include those in which $R^2$ represents halo; cyano; —$N(R^{a9})R^{a10}$; a 4- to 7-membered heterocyclyl ring or a phenyl group, which latter two groups are optionally linked to the relevant phenyl group in the compound of formula I via an O atom; a $C_{1-6}$ alkyl group or a $C_{1-6}$ alkoxy group, which latter two groups are optionally substituted by one or more fluoro, =O, —$N(R^1)R^{12}$ or $C_{1-2}$ alkoxy groups, and/or are optionally substituted by a 4- to 7-membered heterocyclyl ring or a phenyl group.

Compounds of the invention that may be mentioned include those in which $R^2$ represents a $C_{1-6}$ alkyl group or a $C_{1-6}$ alkoxy group, which groups are optionally substituted by one or more =O or —$N(R^{a11})R^{a12}$ groups.

Particular compounds of the invention that may be mentioned are those wherein, when present, $R^{a11}$ and $R^{a12}$ are not joined together.

Compounds of the invention that may be mentioned include those in which $R^2$ represents halo; cyano; —$N(R^{a9})R^{a10}$; a 4- to 7-membered heterocyclyl ring or a phenyl group, which latter two groups are optionally linked to the relevant phenyl group in the compound of formula I via an O atom; a $C_{1-6}$ alkyl group, a $C_{1-6}$ alkoxy group or a —$S(O)_q C_{1-6}$ alkyl group which latter three groups are optionally substituted by one or more fluoro, =O, —$N(R^{a11})R^{a12}$ or $C_{1-2}$ alkoxy groups, and/or are optionally substituted by a phenyl group or a 4- to 7-membered heterocyclyl ring, which 4- to 7-membered heterocyclyl ring may be optionally substituted by one or more (preferably one) methyl, ethyl, fluoro, chloro or, preferably, =O group; and
q represents 0 or 2.

Compounds of the invention that may be mentioned include those in which $R^2$ represents halo; cyano; —$N(R^{a9})R^{a10}$; a 4- to 7-membered heterocyclyl ring or a phenyl group, which latter two groups are optionally linked to the relevant phenyl group in the compound of formula I via an O atom; a $C_{1-6}$ alkyl group or a $C_{1-6}$ alkoxy group, which latter two groups are optionally substituted by one or more fluoro, =O, —$N(R^{a11})R^{a12}$ or $C_{1-2}$ alkoxy groups, and/or are optionally substituted by a phenyl group or a 4- to 7-membered heterocyclyl ring, which 4- to 7-membered heterocyclyl ring may be optionally substituted by one or more (preferably one) methyl, ethyl, fluoro, chloro or, preferably, =O group.

Compounds of the invention that may be mentioned include those in which $R^2$ represents halo; cyano; —$N(R^{a9})R^{a10}$; a 4- to 7-membered heterocyclyl ring or a phenyl group, which latter two groups are optionally linked to the relevant phenyl group in the compound of formula I via an O atom; a $C_{1-6}$ alkyl group or a $C_{1-6}$ alkoxy group, which latter two groups are optionally substituted by one or more fluoro or $C_{1-2}$ alkoxy groups, and/or are optionally substituted by a 4- to 7-membered heterocyclyl ring or a phenyl group.

Compounds of the invention that may be mentioned include those in which, when n is 1 or 2, $R^2$ represents one or more of:
  halo (e.g. bromo or chloro);
  cyano;
  linear, branched or cyclic, $C_{1-6}$ alkyl, optionally substituted with one or more fluoro, =O, —$N(R^{a11})R^{a12}$ or $C_{1-2}$ alkoxy groups;
  linear, branched or cyclic, $C_{1-6}$ alkoxy (which group is, for the avoidance of doubt, attached to the phenyl ring in a compound of formula I via the oxygen atom, and the alkyl part of which is optionally branched and/or cyclic), optionally substituted with one or more fluoro, =O, —$N(R^{a11})R^{a12}$ or $C_{1-2}$ alkoxy groups, a phenyl group, a 4- or 5-membered heterocyclyl group (e.g. oxetanyl or oxolanyl).

Compounds of the invention that may be mentioned include those in which, when n is 1 or 2, $R^2$ represents one or more of:
  halo (e.g. bromo or chloro);
  cyano;
  linear branched or cyclic $SC_{1-6}$ alkyl, optionally substituted by one or more one or more fluoro, =O, —$N(R^{a11})R^{a12}$ or $C_{1-2}$ alkoxy groups;

linear branched or cyclic $SO_2C_{1-6}$ alkyl, optionally substituted by one or more one or more fluoro, $=\!O$, $-\!N(R^{a11})R^{a12}$ or $C_{1-2}$ alkoxy groups;

linear, branched or cyclic, $C_{1-6}$ alkyl, optionally substituted with one or more fluoro, $=\!O$, $-\!N(R^{a11})R^{a12}$ or $C_{1-2}$ alkoxy groups;

linear, branched or cyclic, $C_{1-6}$ alkoxy (which group is, for the avoidance of doubt, attached to the phenyl ring in a compound of formula I via the oxygen atom, and the alkyl part of which is optionally branched and/or cyclic), optionally substituted with one or more fluoro, $=\!O$, $-\!N(R^{a11})R^{a12}$ or $C_{1-2}$ alkoxy groups, a phenyl group, or a 4- or 5-membered heterocyclyl group, (e.g. oxetanyl, oxolanyl or imidazolidinone), which 4- or 5-membered heterocyclyl group is optionally substituted by one (e.g. one) or more fluoro, methyl or $=\!O$ groups.

Particular compounds of the invention that may be mentioned include those in which, when n is 1 or 2, $R^2$ represents:

linear, branched or cyclic, $C_{1-6}$ alkyl, optionally substituted with one or more $=\!O$ or $-\!N(R^{a11})R^{a12}$ groups;

linear, branched or cyclic, $C_{1-6}$ alkoxy (which group is, for the avoidance of doubt, attached to the phenyl ring in a compound of formula I via the oxygen atom, and the alkyl part of which is optionally branched and/or cyclic), optionally substituted with one or more $=\!O$ or $-\!N(R^{a11})R^{a12}$ groups.

Particular compounds of the invention that may be mentioned are those wherein, when present, $R^{a11}$ and $R^{a12}$ are not joined together.

Compounds of the invention that may be mentioned include those in which, when n is 1 or 2, $R^2$ represents one or more of:

halo (e.g. bromo or chloro);

cyano;

linear, branched or cyclic, $C_{1-6}$ alkyl, optionally substituted with one or more fluoro groups, $C_{1-2}$ alkoxy groups;

linear, branched or cyclic, $C_{1-6}$ alkoxy (which group is, for the avoidance of doubt, attached to the phenyl ring in a compound of formula I via the oxygen atom, and the alkyl part of which is optionally branched and/or cyclic), optionally substituted with one or more fluoro groups, $C_{1-2}$ alkoxy groups, a phenyl group, a 4- or 5-membered heterocyclyl group (e.g. oxetanyl or oxolanyl).

Compounds of the invention that may be mentioned include those in which, when n is 1 or 2, $R^2$ represents one or more of:

halo (e.g. bromo or chloro);

cyano;

linear, branched or cyclic, $C_{1-6}$ alkyl, optionally substituted with one or more fluoro groups, $C_{1-2}$ alkoxy groups;

linear, branched or cyclic, $C_{1-6}$ alkoxy (which group is, for the avoidance of doubt, attached to the phenyl ring in a compound of formula I via the oxygen atom, and the alkyl part of which is optionally branched and/or cyclic), optionally substituted with one or more fluoro groups, $C_{1-2}$ alkoxy groups, a phenyl group or a 4- or 5-membered heterocyclyl group (e.g. oxetanyl, oxolanyl or imidazolidinone), which 4- or 5-membered heterocyclyl group is optionally substituted by one or more fluoro, methyl or $=\!O$ groups.

Compounds of the invention that may be mentioned include those in which, when n is 1 or 2, $R^2$ represents one or more of:

halo (e.g. bromo or chloro);

cyano;

$-\!SC_{1-3}$ alkyl (e.g. SMe);

$-\!S(O)_2C_{1-3}$ alkyl (e.g. $SO_2Me$)

linear, branched or cyclic, $C_{1-6}$ alkyl, optionally substituted with one or more fluoro groups, $C_{1-2}$ alkoxy groups;

linear, branched or cyclic, $C_{1-6}$ alkoxy (which group is, for the avoidance of doubt, attached to the phenyl ring in a compound of formula I via the oxygen atom, and the alkyl part of which is optionally branched and/or cyclic), optionally substituted with one or more fluoro groups, $C_{1-2}$ alkoxy groups, a phenyl group or a 4- or 5-membered heterocyclyl group (e.g. oxetanyl, oxolanyl or imidazolidinone), which 4- or 5-membered heterocyclyl group is optionally substituted by one or more fluoro, methyl or $=\!O$ groups.

Compounds of the invention that may be mentioned include those in which m is 1.

Compounds of the invention that may be mentioned include those in which, when m is 1:

$R^7$ and $R^8$ independently represent H or methyl;

X represents $-\!C(R^4)R^5\!-\!$, $-\!N(R^6)\!-\!$, $-\!S\!-\!$ or, more preferably $-\!O\!-\!$.

Compounds of the invention that may be mentioned include those in which, when m is 0 and X represents $-\!N(R^6)\!-\!$, $R^6$ represents methyl or, preferably, H; or $R^6$ may be joined together with an $R^2$ group to form a 5-membered heteroaryl ring (e.g. indolyl or indazolyl), which ring is optionally substituted by one or more halo or $C_{1-2}$ alkyl substituent.

Compounds of the invention that may be mentioned include those in which, when m is 1 and X represents O and L represents $-\!C(R^7)R^8\!-\!$;

$R^8$ represents H;

$R^7$ is joined together with $R^2$ to form, e.g. together along with adjacent carbon atoms on the benzene ring to which $R^2$ is attached in a compound of formula I, a 5-membered heterocyclyl ring (e.g. a dioxolanyl ring).

Compounds of the invention that may be mentioned include those in which X represents $-\!C(R^4)R^5\!-\!$, $-\!O\!-\!$ or $-\!N(R^6)\!-\!$.

Compounds of the invention that may be mentioned include those in which m is 0.

Compounds of the invention that may be mentioned include those in which, when m is 0, X represents $-\!S\!-\!$ or, more preferably, $-\!O\!-\!$.

Compounds of the invention that may be mentioned include those in which p is 0.

Compounds of the invention that may be mentioned include those in which, when p is 1, $R^3$ represents:

cyano;

halo (e.g. fluoro or, preferably, chloro);

$C_{1-2}$ alkoxy, optionally substituted with one or more fluoro groups; or linear, branched or cyclic, $C_{1-3}$ alkyl, optionally substituted with one or more fluoro groups.

Compounds of the invention that may be mentioned include those in which $R^1$ represents phenyl, optionally substituted by a fluoro, a chloro, a methyl, a methoxy, a trifluoromethyl, or a trifluoromethoxy substituent in the 3- or the 4-position relative to the point of attachment of the benzene ring.

Compounds of the invention that may be mentioned include those in which $R^1$ represents a pyridinyl (e.g. pyridin-2-yl), an indolyl (e.g. indol-4-yl or indol-5-yl), a thiazolyl (e.g. 1,3-thiazol-5-yl), a benzofuranyl (e.g. benzofuran-5-yl, benzofuran-4-yl or benzolfuran-7-yl), or a thiophenyl (e.g. thiophen-2-yl), group, which thiophenyl group is optionally substituted by a methyl group (e.g. in the 5-position), or a pyrazolyl group, which pyrazolyl group is optionally substituted by one or more (e.g. one) phenyl group (e.g. 1-phenylpyrazol-4-yl).

Compounds of the invention that may be mentioned include those in which $R^1$ represents a pyridinyl (e.g. pyridin-2-yl), an indolyl (e.g. indol-4-yl or indol-5-yl), a thiazolyl (e.g. 1,3-thiazol-5-yl), a benzofuranyl (e.g. benzofuran-5-yl), or a thiophenyl (e.g. thiophen-2-yl), group, which thiophenyl group is optionally substituted by a methyl group (e.g. in the 5-position).

Compounds of the invention that may be mentioned include those in which $R^1$ represents methyl or, preferably, phenyl optionally substituted by one methyl, methoxy, fluoro or chloro group (e.g. phenyl (i.e. unsubstituted), 3- or 4-methylphenyl, 2-,3- or 4-methoxyphenyl, 3- or 4-chlorophenyl or 4-fluorophenyl), benzofuran-yl (e.g. benzofuran-5-yl, benzofuran-4-yl or benzofuran-7-yl), indolyl (e.g. indol-4-yl or indol-5-yl) benzodioxyl (e.g. 1,3-benzodiox-5-yl), thiophenyl optionally substituted by one or more methyl group (e.g. 5-methylthiophen-2-yl) or pyrazoylyl optionally substituted by one or more phenyl group (e.g. 1-phenylpyrazol-4-yl).

Compounds of the invention that may be mentioned include those in which $R^1$ represents methyl or, preferably, phenyl optionally substituted by one methyl, methoxy, fluoro or chloro group (e.g. phenyl (i.e. unsubstituted), 3- or 4-methylphenyl, 2-,3- or 4-methoxyphenyl, 3- or 4-chlorophenyl or 4-fluorophenyl), benzofuran-yl (e.g. benzofuran-5-yl), indolyl (e.g. indol-4-yl or indol-5-yl) benzodioxyl (e.g. 1,3-benzodiox-5-yl), thiophenyl optionally substituted by one or more methyl group (e.g. 5-methylthiophen-2-yl) or pyrazoylyl optionally substituted by one or more phenyl group (e.g. 1-phenylpyrazol-4-yl).

More particular compounds of the invention that may be mentioned include those in which $R^1$ represents phenyl, 3-methylphenyl, 4-methylphenyl, 3-chlorophenyl, 4-chlorophenyl, 3-methoxyphenyl, 4-methoxyphenyl or 5-methylthiophen-2-yl.

Compounds of the invention that may be mentioned include those in which, when n is 2, $R^2$ represents one or more substituents selected from $C_{1-2}$ alkyl and $C_{1-2}$ alkoxy, both of which are optionally substituted with one or more fluoro groups.

Compounds of the invention that may be mentioned include those in which, when n is 2, the $R^2$ groups are located at the 2- and 5-positions, relative to the triazine ring. In particular compounds that may be mentioned, n is 2, the $R^2$ groups are positioned at the 2- and 5-positions, relative to the triazine ring, and each $R^2$ represents methyl.

Compounds of the invention that may be mentioned include those in which n is 1.

Compounds of the invention that may be mentioned include those in which, when n is 1, $R^2$ represents bromo, linear or branched $C_{1-4}$ alkyl (e.g. methylorethyl), optionally substituted with one or more fluoro, =O or $—N(R^{a11})R^{a12}$ groups; or $C_{1-5}$ alkoxy (e.g. methoxy or ethoxy), optionally substituted with one or more fluoro, =O or $—N(R^{a11})R^{a12}$ groups, a 4- to 7-membered (e.g. 4- to 5-membered) heterocyclyl ring (forming, for example, an oxetanylmethoxy group e.g. an oxetan-3-ylmethoxy group) or $C_{1-2}$ alkoxy groups (forming, for example, a methoxyethoxy group).

Particular compounds of the invention that may be mentioned include those in which, when n is 1, $R^2$ represents linear or branched $C_{1-4}$ alkyl (e.g. methyl or ethyl), optionally substituted with one or more =O or $—N(R^{a11})R^{12}$ groups; or $C_{1-5}$ alkoxy (e.g. methoxy or ethoxy), optionally substituted with one or more =O or $—N(R^{a11})R^{12}$ groups.

Particular $—N(R^{a11})R^{a12}$ groups that may be mentioned include —N(H)methyl, —N(H)ethyl, —N(methyl)$_2$, —N(ethyl)$_2$, —N(n-propyl)$_2$. Preferably, when present, the $—N(R^{a7})R^{a8}$ group is —N(methyl)$_2$ (i.e. —N(Me)$_2$ or —N(CH$_3$)$_2$).

Particular compounds of the invention that may be mentioned are those wherein, when present, $R^{a11}$ and $R^{a12}$ are not joined together.

Compounds of the invention that may be mentioned include those in which, when n is 1, $R^2$ represents bromo, linear or branched $C_{1-4}$ alkyl (e.g. methyl), optionally substituted with one or more fluoro groups; or $C_{1-5}$ alkoxy (e.g. methoxy, ethoxy, isopropoxy, cyclopentoxy), optionally substituted with one or more fluoro groups, a 4- to 7-membered (e.g. 4- to 5-membered) heterocyclyl ring (forming, for example, an oxetanylmethoxy group e.g. an oxetan-3-ylmethoxy group) or $C_{1-2}$ alkoxy groups (forming, for example, a methoxyethoxy group).

Compounds of the invention that may be mentioned include those in which, when n is 1 the $R^2$ group is located at the 2- or, preferably, the 3-position, relative to the triazine ring.

Compounds of the invention that may be mentioned include those in which $R^2$ is joined to $R^6$ to form a pyrrole ring (i.e. forming, together with the benzene ring to which $R^2$ is attached, an indole group), said pyrrole ring (or indole group) being preferably substituted at the 3-position by a methyl group, and m represents 0.

Particular compounds of the invention that may be mentioned include those in which, n is 1, $R^2$ is located at the 3-position relative to the triazine ring, and $R^2$ represents methyl, methoxy, 2-methoxyethoxy, —OCH$_2$C(O)N(CH$_3$)$_2$ or —CH$_2$C(O)N(CH$_3$)$_2$.

In particular, compounds of the invention that may be mentioned include those in which, n is 1, $R^2$ is located at the 3-position relative to the triazine ring, and $R^2$ represents —OCH$_2$C(O)N(CH$_3$)$_2$ or —CH$_2$C(O)N(CH$_3$)$_2$.

Particular compounds of the invention that may be mentioned include those in which, n is 1, $R^2$ is located at the 3-position relative to the triazine ring, and $R^2$ represents methyl, methoxy or 2-methoxyethoxy.

Compounds of the invention that may be mentioned include those in which X represents O.

Compounds of the invention that may be mentioned include those in which, when p is 1, $R^3$ represents $C_{1-2}$ alkyl or $C_{1-2}$ alkoxy, optionally substituted with one or more fluoro groups.

Compounds of the invention that may be mentioned include those in which m is 0 and/or p is 0.

Compounds of the invention that may be mentioned include those in which p is 0, or p is 1 and $R^3$ represents methyl. In such compounds $R^3$ may preferably be in the 2-position relative to the point of attachment of the benzene ring.

Compounds of the invention that may be mentioned include those in which:

$R^1$ represents phenyl optionally substituted by one methyl, methoxy, fluoro or chloro group (e.g. phenyl (i.e. unsubstituted), 3- or 4-methylphenyl, 2-,3- or 4-methoxyphenyl, 3- or 4-chlorophenyl or 4-fluorophenyl), benzofuran-yl (e.g. benzofuran-5-yl, benzofuran-4-yl or benzofuran-7-yl), indolyl (e.g. indol-4-yl or indol-5-yl) benzodioxyl (e.g. 1,3-benzodiox-5-yl), thiophenyl optionally substituted by one or more methyl group (e.g. 5-methylthiophen-2-yl) or pyrazoylyl optionally substituted by one or more phenyl group (e.g. 1-phenylpyrazol-4-yl);

n represents 1 and $R^2$ represents bromo, linear or branched $C_{1-4}$ alkyl (e.g. ethyl, or, preferably, methyl), optionally substituted with one or more fluoro, =O or —N($R^{a11}$)$R^{a12}$ groups; or $C_{1-5}$ alkoxy (e.g. methoxy or ethoxy), optionally substituted with one or more fluoro, =O or —N($R^{a11}$)$R^{a12}$ groups, a 4- to 7-membered (e.g. 4- to 5-membered) heterocyclyl ring (forming, for example, an oxetanylmethoxy group e.g. an oxetan-3-ylmethoxy group) or $C_{1-2}$ alkoxy groups (forming, for example, a methoxyethoxy group); or n represents 2 and each $R^2$ represents $C_{1-2}$ alkyl (e.g. methyl) or $C_{1-2}$ alkoxy (e.g. methoxy), both of which are optionally substituted with one or more fluoro groups;

Q represents —CH—;

X represents —S—, or, preferably, —O—;

m represents 0; and p represents 0 or p represents 1 and $R^3$ represents methyl (in such compounds, the methyl group is preferably in the 2-position relative to the point of attachment of the benzene ring.).

Further compounds of the invention that may be mentioned include those in which:

$R^1$ represents phenyl optionally substituted by one methyl, methoxy, fluoro or chloro group (e.g. phenyl (i.e. unsubstituted), 3- or 4-methylphenyl, 2-,3- or 4-methoxyphenyl, 3- or 4-chlorophenyl or 4-fluorophenyl), benzofuran-yl (e.g. benzofuran-5-yl, benzofuran-4-yl or benzofuran-7-yl), indolyl (e.g. indol-4-yl or indol-5-yl) benzodioxyl (e.g. 1,3-benzodiox-5-yl), thiophenyl optionally substituted by one or more methyl group (e.g. 5-methylthiophen-2-yl) or pyrazoylyl optionally substituted by one or more phenyl group (e.g. 1-phenylpyrazol-4-yl);

n is 1, $R^2$ is located at the 3-position relative to the triazine ring, and $R^2$ represents methyl, methoxy or 2-methoxyethoxy;

Q represents —CH—;

X represents —O—;

m represents 0; and p represents 0 or p represents 1 and $R^3$ represents methyl (in such compounds, the methyl group is preferably in the 2-position relative to the point of attachment of the benzene ring).

Other compounds of the invention that may be mentioned include those in which:

$R^1$ represents methyl or, preferably, phenyl optionally substituted by one methyl, methoxy, fluoro or chloro group (e.g. phenyl (i.e. unsubstituted), 3- or 4-methylphenyl, 2-,3- or 4-methoxyphenyl, 3- or 4-chlorophenyl or 4-fluorophenyl), benzofuran-yl (e.g. benzofuran-5-yl), indolyl (e.g. indol-4-yl or indol-5-yl) benzodioxyl (e.g. 1,3-benzodiox-5-yl), thiophenyl optionally substituted by one or more methyl group (e.g. 5-methylthiophen-2-yl) or pyrazoylyl optionally substituted by one or more phenyl group (e.g. 1-phenylpyrazol-4-yl);

$R^2$ is joined to $R^6$ to form a pyrrole ring (i.e. forming, together with the benzene ring to which $R^2$ is attached, an indole group), said pyrrole ring (or indole group) being preferably substituted at the 3-position by a methyl group;

m represents 0;

Q represents —CH—; and p represents 1 or, preferably, 0;

Other compounds of the invention that may be mentioned include those in which:

$R^1$ represents methyl;

n represents 1;

$R^2$ represents bromo, linear or branched $C_{1-4}$ alkyl, optionally substituted with one or more fluoro groups; or $C_{1-5}$ alkoxy, optionally substituted with one or more fluoro groups, a 4- to 7-membered heterocyclyl ring or $C_{1-2}$ alkoxy groups; and p represents 0 or 1 (preferably 0).

Other compounds of the invention that may be mentioned include those in which:

$R^1$ represents methyl;

n represents 1 and $R^2$ is preferably located in the 2, or, more preferably the 3-position relative to the point of attachment of the benzene ring;

$R^2$ represents bromo, linear or branched $C_{1-4}$ alkyl, optionally substituted with one or more fluoro groups; or $C_{1-5}$ alkoxy, optionally substituted with one or more fluoro groups, a 4- to 7-membered heterocyclyl ring or $C_{1-2}$ alkoxy groups; and p represents 0 or 1 (preferably 0).

Other compounds of the invention that may be mentioned include those in which:

$R^1$ represents methyl;

n represents 1 or 2;

$R^2$ represents bromo, linear or branched $C_{1-4}$ alkyl, optionally substituted with one or more fluoro groups; or $C_{1-5}$ alkoxy, optionally substituted with one or more fluoro groups, a 4- to 7-membered heterocyclyl ring or $C_{1-2}$ alkoxy groups; and p represents 0.

Other compounds of the invention that may be mentioned include those in which:

$R^1$ represents methyl;

n represents 1 and $R^2$ represents bromo, linear or branched $C_{1-4}$ alkyl (e.g. ethyl, or, preferably, methyl), optionally substituted with one or more fluoro, =O or —N($R^{a11}$)$R^{a12}$ groups; or $C_{1-5}$ alkoxy (e.g. methoxy or ethoxy), optionally substituted with one or more fluoro, =O or —N($R^{a11}$)$R^{a12}$ groups, a 4- to 7-membered (e.g. 4- to 5-membered) heterocyclyl ring (forming, for example, an oxetanylmethoxy group e.g. an oxetan-3-ylmethoxy group) or $C_{1-2}$ alkoxy groups (forming, for example, a methoxyethoxy group);

Q represents —CH—;

X represents —S—, or, preferably —O—;

m represents 0;

p represents 0 or p represents 1 and $R^3$ represents methyl (in such compounds, the methyl group is preferably in the 2-position relative to the point of attachment of the benzene ring.).

Further compounds of the invention that may be mentioned include those in which:

$R^1$ represents methyl;

n is 1, $R^2$ is located at the 3-position relative to the triazine ring, and $R^2$ represents methyl, methoxy or 2-methoxyethoxy;

Q represents —CH—;

X represents —O—;

m represents 0; and p represents 0 or p represents 1 and $R^3$ represents methyl (in such compounds, the methyl group is preferably in the 2-position relative to the point of attachment of the benzene ring.) (preferably p represents 0).

Particular compounds of the invention that may be mentioned include those compounds as described in the examples provided herein, and pharmaceutically acceptable salts thereof. For the avoidance of doubt, where such compounds of the invention include compounds in a particular salt form, compounds of the invention include those compounds in non-salt form and in the form of any pharmaceutically acceptable salt thereof (which may include the salt form present in such examples).

More particular compounds of the invention that may be mentioned include those described in Examples 5, 9, 11, 16, 24, 27, 35, 40, 41, 43, 45, 46, 47, 48, 49, 50, 51, 52, 54, 56, 57, 58, 59, 60, 61, 62, 66, 68, 69 72 and 73. Yet more particular compounds of the invention that may be mentioned include those described in Examples 5, 11, 41, 56, 57, 58, 59, 60, 61, 62, 66, 69, 72 and 73.

Medical Uses

As indicated herein, the compounds of the invention, and therefore compositions and kits comprising the same, are useful as pharmaceuticals.

Although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the active compounds to which they are metabolised) may therefore be described as "prodrugs" of compounds of the invention.

As used herein, references to prodrugs will include compounds that form a compound of the invention, in an experimentally-detectable amount, within a predetermined time, following enteral (e.g. oral) or parenteral administration. All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the active compounds of the invention to which they are metabolised), may also be described as "prodrugs".

For the avoidance of doubt, compounds of the invention are therefore useful because they possess pharmacological activity, and/or are metabolised in the body following oral or parenteral administration to form compounds that possess pharmacological activity.

As described herein, compounds of the invention may be particularly useful in the treatment of diseases characterised by impaired signalling of neurotrophins and/or other trophic factors. Due to their mode of action, the compounds of the invention may have particular utility in the treatment of such diseases in patients with the Val66Met mutation in the BDNF gene.

The compounds of the invention may also have particular utility in the treatment of diseases characterised by impaired signalling of neurotrophins and/or other trophic factors in patients having other genetic variations, including deletions, that directly or indirectly affect the BDNF gene. For example, the compounds of the invention may have particular utility in treating diseases in patients having the rs12291063 minor C allele, which is known to be associated with lower BDNF expression, and/or in patients having the deletions associated with WAGR syndrome, such as the deletions in chromosome 11.

Accordingly, in particular embodiments of the invention, there is provided the compounds of the invention for use in the treatment of the diseases described herein in a patient having the Val66Met mutation in the BDNF gene, and/or in a patient having the rs12291063 minor C allele, and/or in a patient having the genetic deletions associated with WAGR syndrome.

The skilled person will understand that trophic factors refer to a class of molecules that promote the growth and maintenance of cellular tissues. Neurotrophins may be understood to refer to a class of molecules associated with promoting the growth and survival of neurons, which are also referred to as neurotrophic factors. Examples of neurotrophins include NGF, BDNF, NT3 and NT4/5. Other trophic factors include insulin-like growth factor (IGF-1), fibroblast growth factors (FGFs), hepatocyte growth factor (HGF) and glial cell line-derived neurotrophic factors such as glial cell-derived neurotrophic factor (GDNF), Neurturin (NRTN), artemin (ARTN) and persephin (PSPN).

As used herein, the phrase diseases characterised by impaired signalling of neurotrophins and other trophic factors may be understood to indicate diseases and disorders that involve reduced signalling of trophic factors, such as those listed above. Such disorders may be treated through the positive modulation of neurotrophin receptors, such as TrKA, TrKB and TrkC and/or their signalling, and receptor tyrosine kinases such as FGFR1 and IGF1R and/or their signalling and/or the positive modulation of other trophic factor receptors.

The Val66Met mutation in the BDNF gene refers to a common single-nucleotide polymorphism in the brain-derived neurotrophic factor (BDNF) gene, resulting in a methionine (Met) substitution for valine (Val) at codon 66 (Val66Met).

The skilled person will understand that references to the treatment of a particular condition (or, similarly, to treating that condition) will take their normal meanings in the field of medicine. In particular, the terms may refer to achieving a reduction in the severity and/or frequency of occurrence of one or more clinical symptom associated with the condition, as adjudged by a physician attending a patient having or being susceptible to such symptoms. For example, in the case of Alzheimer's disease, the term may refer to achieving an improvement in cognition in the patient being treated.

As used herein, the term prevention (and, similarly, preventing) will include references to the prophylaxis of the disease or disorder (and vice versa). As such, references to prevention may also be references to prophylaxis, and vice versa. In particular, such terms may refer to achieving a reduction (for example, at least a 10% reduction, such as at least a 20%, 30% or 40% reduction, e.g. at least a 50% reduction) in the likelihood of the patient (or healthy subject) developing the condition (which may be understood as meaning that the condition of the patient changes such that patient is diagnosed by a physician as having, e.g. requiring treatment for, the relevant disease or disorder).

As used herein, references to a patient (or to patients) will refer to a living subject being treated, including mammalian (e.g. human) patients. In particular, a "pharmaceutical composition" is intended to refer to a composition that is intended to for use to treat human patients in human medicine. Similarly, compounds or compositions for use as pharmaceuticals are intended to be used in the treatment of human patients. In this respect, and in general, references to a patient will refer to human patients.

For the avoidance of doubt, the skilled person will understand that such treatment or prevention will be performed in a patient (or subject) in need thereof. The need of a patient (or subject) for such treatment or prevention may be assessed by those skilled the art using routine techniques.

As used herein, the terms disease and disorder (and, similarly, the terms condition, illness, medical problem, and the like) may be used interchangeably.

Compounds of the invention are modulators of neurotrophin receptors, such as TrkA, TrkB, TrkC and/or their signalling and receptor tyrosine kinases, such as FGFR1 and IGF1R and/or their signalling. The compounds are believed to have an improved potency for the modulation of neurotrophin receptors, such as TrkA, TrkB, TrkC and/or their signalling and receptor tyrosine kinases, such as FGFR1 and IGF1R and/or their signalling. It is believed that the compounds of the invention would have a reduced potential for side effects associated with conventional agonists for TrkA and TrkB.

Another indication includes setting in which there is a goal for enhancing plasticity of the nervous system, such as during rehabilitation or acquisition of a new learned physical or intellectual skill. Moreover, it also includes facilitation of neuronal or non-neuronal or stem cell survival or promoting neural function by treating a neural or non-neuronal or stem cell with a compound of the invention having the ability to have a positive modulatory effect, either directly or indirectly, on the signalling mediated by the TrkA, TrkB and TrkC receptors, optionally in combination with a modulatory effect, either directly or indirectly, on the signalling mediated by receptor tyrosine kinases such as IGF1R and/or FGFR1 receptor.

The invention relates to the compounds of the invention and pharmaceutically acceptable salts thereof, as defined above, for use in therapy. Without being bound to theory regarding the mode of action of the compounds defined above, it is believed that the compounds can be used for treatment and/or prevention of the diseases mentioned herein.

In particular embodiments, the diseases that may be treated by compounds of the invention include Alzheimer's disease, depression, Parkinson's disease, other Parkinsonian disorders and/or other tauopathies, Lewy body dementia, multiple sclerosis, Huntington's disease, mild cognitive impairment, brain injuries (including traumatic brain injuries), stroke, other dementia disorders, motoneurone diseases, Pick disease, spinal chord injury, hypoxic ischemia injury, cognitive dysfunction, coronary artery disease, obesity, metabolic syndrome, diabetes, Charcot-Marie-Tooth disease, diabetic neuropathy, tissue regeneration, diabetes-induced osteoporosis, motor function, nerve injury, hearing loss (including genetic or acquired hearing loss), blindness, posterior eye diseases, anterior eye diseases, dry eye disease, neurotrophic keratitis, glaucoma, high intraocular pressure (IOP), retinitis pigmentosa, post-traumatic stress disorders, WAGR syndrome, Prader-Willi syndrome, diseases of the olfactory tract, olfactory decline, olfactory dysfunction, anxiety, fragile X syndrome, congenital central hypoventilation syndrome, obsessive-compulsive disorder, generalized anxiety disorder, eating disorders, bipolar disorder, chronic fatigue syndrome, neuromyelitis optica, Rett syndrome, Friedrich's ataxia and obstructive sleep apnea-hypopnea syndrome.

In particular embodiments, the diseases that may be treated by compounds of the invention include Alzheimer's disease, depression, Parkinson's disease, other Parkinsonian disorders and/or other tauopathies, Lewy body dementia, multiple sclerosis, Huntington's disease, mild cognitive impairment, brain injuries (including traumatic brain injuries), stroke, other dementia disorders, motoneurone diseases, Pick disease, spinal chord injury, hypoxic ischemia injury, cognitive dysfunction, coronary artery disease, obesity, metabolic syndrome, diabetes, Charcot-Marie-Tooth disease, diabetic neuropathy, tissue regeneration, motor function, nerve injury, hearing loss, blindness, posterior eye diseases, dry eye disease, neurotrophic keratitis, glaucoma, high intraocular pressure (IOP), retinitis pigmentosa, post-traumatic stress disorders, WAGR syndrome, diseases of the olfactory tract, olfactory decline, olfactory dysfunction, anxiety, fragile X syndrome, congenital central hypoventilation syndrome, obsessive-compulsive disorder, generalized anxiety disorder, eating disorders, bipolar disorder, chronic fatigue syndrome, neuromyelitis optica, Rett syndrome, Friedrich's ataxia and obstructive sleep apnea-hypopnea syndrome.

As used herein, the phrase "other Parkinsonian disorders" may be understood to refer to disorders that have symptoms similar to Parkinson's disease, such as bradykinesia, tremors and postural instability. Examples of such disorders include progressive supranuclear palsy (PSP), multiple system atrophy (MSA), and corticobasal degeneration (CBD).

The phrase "other tauopathies" may be understood to refer to neurodegenerative diseases other than Alzheimer's disease that are associated with the pathological misfolding of tau protein in the brain. Examples of such disorders include primary age-related tauopathy, progressive supranuclear palsy, Pick's disease, corticobasal degeneration and post-encephalitic parkinsonism. The skilled person will understand that certain disorders such as progressive supranuclear palsy may be described as both a Parkinsonian disorder and a tauopathy.

The phrase "other dementia disorders" may be understood to include vascular dementia, mixed vascular dementia, incident dementia, post-operative dementia, presenile dementia, dementia associated with Parkinson's disease and dementia due to HIV infection. Progressive supranuclear palsy and corticobasal degeneration may also be classed as dementia disorders.

Motoneurone diseases include amyotrophic lateral sclerosis (ALS), hereditary spastic paraplegia (HSP), primary lateral sclerosis (PLS), progressive muscular atrophy (PMA), progressive bulbar palsy (PBP) and pseudobulbar palsy.

Cognitive dysfunction may be understood to refer to reduced cognitive abilities in a patient including reduced ability in learning, memory loss, perception, and problem solving. Cognitive dysfunction is associated with a range of conditions, such as Alzheimer's disease, Parkinson's disease, progressive supranuclear palsy, corticobasal degeneration and schizophrenia. Accordingly, in particular embodiments, the compounds of the invention may be used in the treatment of cognitive dysfunction in Alzheimer's disease, Parkinson's disease, progressive supranuclear palsy, corticobasal degeneration or schizophrenia. Cognitive dysfunction also includes post-operative cognitive dysfunction and impaired cognition associated with preterm delivery.

Similarly, in other particular embodiments, the compounds of the invention may be used in improving cognition in a patient with Alzheimer's disease, Parkinson's disease, progressive supranuclear palsy, corticobasal degeneration or schizophrenia. As used herein, the phrase "improving cognition" may be understood to indicate enhancing a patient's learning, memory, perception, and/or problem-solving ability. Improving cognition may also refer to slowing or arresting the rate of decline in cognition in a patient suffering from cognitive dysfunction (e.g. associated with the disorders listed above).

Cognitive function may be assessed using standard tests known to the person skilled in the art. Examples of such tests include the Alzheimer's Disease Assessment Scale-Cognitive subscale test (ADAS-COG) the Mini-Mental State Examination (MMSE), the Clinical Dementia Rating (CDR) the Clinical Dementia Rating-Sum of Boxes (CDR-SB), the Alzheimer's Disease Cooperative Study-Preclinical Alzheimer Cognitive Composite (ADCS-PACC) and the Repeatable Battery for the Assessment of Neuropsychological Status (RBANS) test.

As used herein, "eating disorders" may be understood to include hyperphagia, anorexia nervosa, restricting anorexia nervosa and bulimia nervosa.

In accordance with a further aspect of the invention, there is provided the compounds of the invention, or a pharmaceutically acceptable salt thereof, for use in treatment and/or prevention of one or more disease selected from the group comprising or containing Alzheimer's disease, Lewy body dementia, frontotemporal dementia, HIV dementia, Huntington's disease, amyotrophic lateral sclerosis and other motor neuron diseases, Rett syndrome, epilepsy, Parkinson's disease and other parkinsonian disorders, disorders in which enhancement of nerve regeneration is beneficial, such as demyelinating diseases including multiple sclerosis, spinal cord injury, stroke, hypoxia, ischemia, brain injury including traumatic brain injury, mild cognitive impairment, dementia disorders (including dementia of mixed vascular and degenerative origin, presenile dementia, senile dementia and dementia associated with Parkinson's disease, progressive supranuclear palsy or corticobasal degeneration) and cognitive dysfunction in schizophrenia, obesity, diabetes and metabolic syndrome, diabetic neuropathy including Charcot Marie Tooth and its variants, nerve transplantation and its complications, diabetes induced osteoporosis, motor neuron disease, peripheral nerve injury, genetic or acquired or traumatic hearing loss, blindness and posterior eye diseases, anterior eye diseases, depression, obesity, metabolic syndrome, pain, depression, schizophrenia and anxiety.

In accordance with a further aspect of the invention, there is provided the compounds of the invention, or a pharmaceutically acceptable salt thereof, for use in treatment and/or prevention of one or more disease selected from the group comprising or containing Alzheimer's disease, Lewy body dementia, frontotemporal dementia, HIV dementia, Huntington's disease, amyotrophic lateral sclerosis and other motor neuron diseases, Rett syndrome, epilepsy, Parkinson's disease and other parkinsonian disorders, disorders in which enhancement of nerve regeneration is beneficial, such as demyelinating diseases including multiple sclerosis, spinal cord injury, stroke, hypoxia, ischemia, brain injury including traumatic brain injury, mild cognitive impairment, dementia disorders (including dementia of mixed vascular and degenerative origin, presenile dementia, senile dementia and dementia associated with Parkinson's disease, progressive supranuclear palsy or corticobasal degeneration) and cognitive dysfunction in schizophrenia, obesity, diabetes and metabolic syndrome, diabetic neuropathy including Charcot Marie Tooth and its variants, nerve transplantation and its complications, motor neuron disease, peripheral nerve injury, genetic or acquired or traumatic hearing loss, blindness and posterior eye diseases, depression, obesity, metabolic syndrome, pain, depression, schizophrenia and anxiety.

In more particular embodiments, the disease characterised by impaired signalling of neurotrophins and/or other trophic factors is selected from the group consisting of Alzheimer's disease, Parkinson's disease, other Parkinsonian diseases, other tauopathies, Lewy body dementia, motorneuron disease, Pick disease, obesity, metabolic syndrome, diabetes and Rett syndrome. The treatment of this group of disorders may be particularly effective in patients having the Val66Met mutation in the BDNF gene.

In yet more particular embodiments, the disease characterised by impaired signalling of neurotrophins and/or other trophic factors is selected from the group consisting of Alzheimer's disease, Parkinson's disease, Cognitive dysfunction, depression and Rett Syndrome.

A further embodiment of the invention relates to a compound of the invention, or a pharmaceutically acceptable salt thereof, for use in treatment and/or prevention of Alzheimer's disease, Lewy body dementia, frontotemporal dementia, HIV dementia, Huntington's disease, amyotrophic lateral sclerosis and other motor neuron diseases, Rett syndrome, epilepsy, Parkinson's disease and/or other Parkinsonian disorders.

A further embodiment of the invention relates to a compound of the invention, or a pharmaceutically acceptable salt thereof, for use in treatment and/or prevention of Alzheimer's disease, Parkinson's disease, Cognitive dysfunction in Schizophrenia, Rett's Syndrome and/or depression.

A further embodiment of the invention relates to a compound of the invention, or a pharmaceutically acceptable salt thereof, for use in treatment and/or prevention of Alzheimer's disease.

A further embodiment of the invention relates to a compound of the invention, or a pharmaceutically acceptable salt thereof, for use in treatment and/or prevention of depression.

A further embodiment of the invention relates to a compound of the invention, or a pharmaceutically acceptable salt thereof, for use in treatment and/or prevention of a disease where enhancement of nerve regeneration is beneficial, such as demyelinating diseases.

A further embodiment of the invention relates to a compound of the invention, or a pharmaceutically acceptable salt thereof, for use in treatment and/or prevention of multiple sclerosis.

A further embodiment of the invention relates to a compound of the invention, or a pharmaceutically acceptable salt thereof, for use in treatment and/or prevention of Rett syndrome.

A further embodiment of the invention relates to a compound of the invention, or a pharmaceutically acceptable salt thereof, for use in treatment and/or prevention spinal cord injury, stroke, hypoxia, ischemia and/or brain injury including traumatic brain injury.

A further embodiment of the invention relates to a compound of the invention, or a pharmaceutically acceptable salt thereof, for use in the treatment and/or prevention of mild cognitive impairment, dementia disorders (including dementia of mixed vascular and degenerative origin, presenile dementia, senile dementia and dementia associated with Parkinson's disease, progressive supranuclear palsy, corticobasal degeneration, post-operative dementia) and/or cognitive dysfunction in schizophrenia.

A further embodiment of the invention relates to a compound of the invention, or a pharmaceutically acceptable salt thereof, for use in the treatment and/or prevention of atherosclerosis, obesity, diabetes and metabolic syndrome, diabetic neuropathy including Charcot Marie Tooth and its variants, nerve transplantation and its complications, diabetes induced osteoporosis, motor neuron disease, peripheral nerve injury, genetic or acquired or traumatic hearing loss, blindness and posterior eye diseases, depression, obesity, metabolic syndrome, WAGR syndrome, Prader-Willi syndrome and/or pain.

A further embodiment of the invention relates to a compound of the invention, or a pharmaceutically acceptable salt thereof, for use in the treatment and/or prevention of atherosclerosis, obesity, diabetes and metabolic syndrome, diabetic neuropathy including Charcot Marie Tooth and its variants, nerve transplantation and its complications, motor neuron disease, peripheral nerve injury, genetic or acquired or traumatic hearing loss, blindness and posterior eye diseases, depression, obesity, metabolic syndrome and/or pain.

A further embodiment of the invention relates to a compound of the invention, or a pharmaceutically acceptable salt thereof, for use in the treatment and/or prevention of depression, schizophrenia and/or anxiety.

A further embodiment of the invention relates to a compound of the invention for use in the treatment and/or prevention of a disease selected from the group consisting of Alzheimer's disease, Parkinson's disease, another Parkinsonian disease, another tauopathy, Lewy body dementia, motorneuron disease, Pick disease, obesity, metabolic syndrome, diabetes and Rett syndrome.

A further embodiment of the invention relates to a compound of the invention for use in the treatment and/or prevention of a disease selected from the group consisting of Alzheimer's disease, Parkinson's disease, another Parkinsonian disease, another tauopathy, Lewy body dementia, motorneuron disease, Pick disease, obesity, metabolic syndrome, diabetes and Rett syndrome, posterior eye diseases and cognitive dysfunction.

Another embodiment relates to a use of a compound of the invention, or a pharmaceutically acceptable salt thereof, for the treatment and/or prevention of a disease in which modulators of neurotrophin receptors, such as TrkA, TrkB, TrkC and/or their signalling and receptor tyrosine kinases, such as FGFR1 and IGF1R and/or their signalling are beneficial, such as for the treatment and/or prevention of both non-neurological and neurological diseases, including one or more of the conditions mentioned hereinbefore.

The invention further relates to the use of a compound of the invention in a method of treating, preventing or reducing the risk of a disease in which modulators of neurotrophin receptors, such as TrkA, TrkB, TrkC and/or their signalling and receptor tyrosine kinases, such as FGFR1 and IGF1R and/or their signalling, are beneficial, such as in the treatment and/or prevention of both non-neurological and neurological diseases.

One embodiment relates to the use of a compound of the invention (for example in the manufacture of a pharmaceutical medicament) for use in a method of treating, preventing or reducing the risk of, one or more disease mentioned hereinbefore, which comprises administering to a mammal, such as a human, in need thereof, a therapeutically effective amount of a compound of the invention, or a pharmaceutically acceptable salt thereof.

Another embodiment relates to such a use of a compound of the invention in a method of treating, preventing or reducing the risk of Alzheimer's disease, Lewy body dementia, frontotemporal dementia, HIV dementia, Huntington's disease, amyotrophic lateral sclerosis and other motor neuron diseases, Rett syndrome, epilepsy, Parkinson's disease and/or other parkinsonian disorders.

A further embodiment relates to such a use of a compound of the invention in a method of treating, preventing or reducing the risk of Alzheimer's disease, Parkinson's disease, Cognitive dysfunction in Schizophrenia, Rett's Syndrome and/or Depression.

A further embodiment relates to such a use of a compound of the invention in a method of treating, preventing or reducing the risk of a disease where enhancement of nerve regeneration is beneficial such as demyelinating diseases, such as multiple sclerosis.

A further embodiment relates to such a use of a compound of the invention in a method of treating, preventing or reducing the risk of spinal cord injury, stroke, hypoxia, ischemia and/or brain injury including traumatic brain injury.

Another embodiment relates to such a use of a compound of the invention in a method of treating, preventing or reducing the risk of mild cognitive impairment, dementia disorders (including dementia of mixed vascular and degenerative origin, presenile dementia, senile dementia and dementia associated with Parkinson's disease, progressive supranuclear palsy or corticobasal degeneration) and/or cognitive dysfunction in schizophrenia.

A further embodiment relates to such a use of a compound of the invention in a method of treating, obesity, diabetes and metabolic syndrome, diabetic neuropathy including Charcot Mae Tooth and its variants, nerve transplantation and its complications, diabetes induced osteoporosis, motor neuron disease, peripheral nerve injury, genetic or acquired or traumatic hearing loss, blindness and posterior eye diseases, depression, obesity, metabolic syndrome and/or pain.

A further embodiment relates to such a use of a compound of the invention in a method of treating, obesity, diabetes and metabolic syndrome, diabetic neuropathy including Charcot Marie Tooth and its variants, nerve transplantation and its complications, motor neuron disease, peripheral nerve injury, genetic or acquired or traumatic hearing loss, blindness and posterior eye diseases, depression, obesity, metabolic syndrome and/or pain.

Yet another embodiment relates to such a use of a compound of the invention in a method of treating, preventing or reducing the risk of depression, schizophrenia and/or anxiety.

Pharmaceutical Compositions

As described herein, compounds of the invention are useful as pharmaceuticals. Such compounds may be administered alone or may be administered by way of known pharmaceutical compositions/formulations.

In a further aspect of the invention, there is provided a pharmaceutical composition comprising a compound of the invention, as defined herein, or a pharmaceutically-acceptable salt thereof, and a pharmaceutically-acceptable excipient, such as a pharmaceutically-acceptable adjuvant diluent or carrier.

In a further aspect of the invention, there is provided a pharmaceutical composition comprising a compound of the invention, or a pharmaceutically-acceptable salt thereof, and a pharmaceutically-acceptable excipient, such as a pharmaceutically-acceptable adjuvant, diluent or carrier, for use in the treatment of a disease characterised by impaired signalling of neurotrophins and/or other trophic factors (including the various diseases and disorders listed herein), optionally in a patient with the Val66Met mutation in the BDNF gene.

As used herein, the term pharmaceutically-acceptable excipients includes references to vehicles, adjuvants, carriers, diluents, pH adjusting and buffering agents, tonicity adjusting agents, stabilizers, wetting agents and the like. In particular, such excipients may include adjuvants, diluents or carriers.

The skilled person will understand that compounds of the invention may act systemically and/or locally (i.e. at a particular site), and may therefore be administered accordingly using suitable techniques known to those skilled in the art.

The skilled person will understand that compounds and compositions as described herein will normally be administered orally, intravenously, subcutaneously, buccally, rectally, dermally, nasally, tracheally, bronchially, sublingually, intranasally, topically (including topical administration to the eyes), by any other parenteral route or via inhalation, in a pharmaceutically acceptable dosage form.

Conventional procedures for the selection and preparation of suitable pharmaceutical formulations are described in, for example, "Pharmaceuticals—The Science of Dosage Form Designs", M. E. Aulton, Churchill Livingstone, 1988. For preparing pharmaceutical compositions from the compounds of the invention, inert, pharmaceutically acceptable carriers can be either solid or liquid. Solid form preparations include powders, tablets, dispersible granules, capsules, cachets, and suppositories.

Pharmaceutical compositions as described herein will include formulations in the form of tablets, capsules or elixirs for oral administration, suppositories for rectal administration, sterile solutions or suspensions for parenteral or intramuscular administration, and the like. Alternatively, particularly where such compounds of the invention act locally, pharmaceutical compositions may be formulated for topical administration. In particular, compounds may be formulated for local delivery to the CNS, for example in the form of artificial cerebrospinal fluid (CSF).

Thus, in particular embodiments, the pharmaceutical composition is provided in a pharmaceutically acceptable dosage form, including tablets or capsules, liquid forms to be taken orally or by injection, suppositories, creams, gels, foams, inhalants (e.g. to be applied intranasally), or forms suitable for topical administration. For the avoidance of doubt, in such embodiments, compounds of the invention may be present as a solid (e.g. a solid dispersion), liquid (e.g. in solution) or in other forms, such as in the form of micelles.

Thus, compounds, of the present invention, and compositions comprising the same, may be administered orally, parenteral, buccal, vaginal, rectal, inhalation, insufflation, sublingually, intramuscularly, subcutaneously, topically (including topical administration to the eyes), intranasally, intraperitoneally, intrathoracically, intravenously, epidurally, intrathecally, intracerebroventriculary and by injection into the joints.

Depending on the mode of administration, pharmaceutical compositions will preferably comprise from 0.05 to 99% wt (percent by weight), more preferably from 0.05 to 80% wt, still more preferably from 0.10 to 70% wt, and even more preferably from 0.10 to 50% wt, of a compounds of the invention (calculated as a non-salt form), all percentages by weight being based on total composition.

Depending on e.g. potency and physical characteristics of the compound of the invention (i.e. active ingredient), pharmaceutical formulations that may be mentioned include those in which the active ingredient is present in an amount that is at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in uses or methods of the invention.

More, particularly, the skilled person will understand that compounds of the invention may be administered (for example, as formulations as described hereinbefore) at varying doses, with suitable doses being readily determined by one of skill in the art. Oral, pulmonary and topical dosages (and subcutaneous dosages, although these dosages may be relatively lower) may range from between about 0.01 µg/kg of body weight per day (µg/kg/day) to about 200 µg/kg/day, preferably about 0.01 to about 10 µg/kg/day, and more preferably about 0.1 to about 5.0 µg/kg/day. For example, when administered orally, treatment with such compounds may comprise administration of a formulations typically containing between about 0.01 µg to about 2000 mg, for example between about 0.1 µg to about 500 mg, or between 1 µg to about 100 mg (e.g. about 20 µg to about 80 mg), of the active ingredient(s). When administered intravenously, the most preferred doses will range from about 0.001 to about 10 µg/kg/hour during constant rate infusion. Advantageously, treatment may comprise administration of such compounds and compositions in a single daily dose, or the total daily dosage may be administered in divided doses of two, three or four times daily (e.g. twice daily with reference to the doses described herein, such as a dose of 25 mg, 50 mg, 100 mg or 200 mg twice daily).

For the avoidance of doubt, the skilled person (e.g. the physician) will be able to determine the actual dosage which will be most suitable for an individual patient, which is likely to vary with the route of administration, the type of formulation, the type and severity of the condition that is to be treated, other medication the patient may be taking, as well as the species, age, weight, size, sex, diet, renal function, hepatic function, general physical condition, genetic factors and response of the particular patient to be treated. Although the above-mentioned dosages are exemplary of the average case, there can, of course, be individual instances where higher or lower dosage ranges are merited, and such doses are within the scope of the invention.

Thus, in a further aspect of the invention, there is provided a use of a pharmaceutical composition, as defined above, in therapy, or for the treatment and/or prevention of a disease in which modulators of neurotrophin receptors, such as TrkA, TrkB, TrkC and/or their signalling and receptor tyrosine kinases, such as FGFR1 and IGF1R and/or their signalling, are beneficial, such as in the treatment and/or prevention of both non-neurological and neurological diseases mentioned hereinbefore.

Combinations and Kits-of-Parts

The treatment and/or prevention of diseases of the nervous system and related pathology defined herein may be applied as a sole therapy or may involve, in addition to the compound of the invention, conjoint treatment with conventional therapy of value in treating one or more disease conditions referred to herein. Such conventional therapy may include one or more agents such as acetyl cholinesterase inhibitors, anti-inflammatory agents, cognitive and/or memory enhancing agents, atypical antipsychotic agents, dopamine agonists and/or L-DOPA.

Such conjoint treatment and/or prevention may be achieved by way of the simultaneous, sequential or separate dosing of the individual compounds of the invention or additional agents of the treatment and/or prevention. Such combination products employ the compounds, or pharmaceutically acceptable salts thereof, of the invention.

Accordingly, the skilled person will understand that treatment with compounds of the invention may further comprise (i.e. be combined with) further treatment(s) or preventative methods for the same condition. In particular, treatment with compounds of the invention may be combined with means for the treatment of diseases characterised by impaired signalling of neurotrophins and/or other trophic factors (such as Alzheimer's disease, Parkinson's disease, cognitive dysfunction and depression as described herein, e.g. Alzheimer's disease) such as treatment with one or more other therapeutic agent that is useful in the in the treatment the various diseases characterised by impaired signalling of neurotrophins and/or other trophic factors described herein, and/or one or more physical method used in the treatment (such as treatment through surgery), as known to those skilled in the art.

As described herein, compounds of the invention may also be combined with one or more other (i.e. different) therapeutic agents (i.e. agents that are not compounds of the invention) that are useful in the treatment and/or prevention of diseases characterised by impaired signalling of neurotrophins and/or other trophic factors. Such combination products that provide for the administration of a compound of the invention in conjunction with one or more other therapeutic agent may be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the one or more other therapeutic agent).

Thus, according to a further aspect of the invention, there is provided a combination product comprising:
(I) a compound of the invention as hereinbefore defined, or a pharmaceutically acceptable salt thereof; and
(II) one or more other therapeutic agent that is useful in the treatment or prevention of a disease characterised by impaired signalling of neurotrophins and/or other trophic factors,
wherein each of components (I) and (II) is formulated in admixture, optionally with a pharmaceutically-acceptable excipient, such as a pharmaceutically-acceptable adjuvant diluent or carrier.

Accordingly to a further aspect of the invention there is provided a pharmaceutical composition comprising a compound of the invention as hereinbefore defined, or a pharmaceutically acceptable salt thereof, one or more other therapeutic agent that is useful in the treatment or prevention of a disease characterised by impaired signalling of neurotrophins and/or other trophic factors, formulated together in admixture, optionally with a pharmaceutically-acceptable excipient, such as a pharmaceutically-acceptable adjuvant diluent or carrier.

According to a further aspect of the invention, there is provided a kit-of-parts comprising:
(a) a pharmaceutical composition comprising a compound of the invention as hereinbefore defined, or a pharmaceutically acceptable salt thereof, formulated in admixture, optionally with a pharmaceutically-acceptable excipient, such as a pharmaceutically-acceptable adjuvant diluent or carrier; and
(b) a pharmaceutical composition comprising one or more other therapeutic agent that is useful in the treatment or prevention of a disease characterised by impaired signalling of neurotrophins and/or other trophic factors, formulated in admixture, optionally with a pharmaceutically-acceptable excipient, such as a pharmaceutically-acceptable adjuvant diluent or carrier,
which components (a) and (b) are each provided in a form that is suitable for administration in conjunction with the other.

With respect to the kits-of-parts as described herein, by "administration in conjunction with" (and similarly "administered in conjunction with") we include that respective formulations are administered, sequentially, separately or simultaneously, as part of a medical intervention directed towards treatment of the relevant condition.

Thus, in relation to the present invention, the term "administration in conjunction with" (and similarly "administered in conjunction with") includes that the two active ingredients are administered (optionally repeatedly) either together, or sufficiently closely in time, to enable a beneficial effect for the patient, that is greater, over the course of the treatment and/or prevention of the relevant condition, than if either agent is administered (optionally repeatedly) alone, in the absence of the other component, over the same course of treatment and/or prevention. Determination of whether a combination provides a greater beneficial effect in respect of, and over the course of, treatment or prevention of a particular condition will depend upon the condition to be treated or prevented, but may be achieved routinely by the skilled person.

Further, in the context of the present invention, the term "in conjunction with" includes that one or other of the two formulations may be administered (optionally repeatedly) prior to, after, and/or at the same time as, administration of the other component. When used in this context, the terms "administered simultaneously" and "administered at the same time as" includes instances where the individual doses of the compound of the invention and the additional compound for the treatment of a disease characterised by impaired signalling of neurotrophins and/or other trophic factors, or pharmaceutically acceptable salts thereof, are administered within 48 hours (e.g. within 24 hours, 12 hours, 6 hours, 3 hours, 2 hours, 1 hour, 45 minutes, 30 minutes, 20 minutes or 10 minutes) of each other.

Other therapeutic agents useful in the treatment or prevention of diseases characterised by impaired signalling of neurotrophins and/or other trophic factors will be well-known to those skilled in the art. For example, such other therapeutic agents may include: acetyl cholinesterase inhibitors, anti-inflammatory agents, cognitive enhancing agents, memory enhancing agents, and atypical antipsychotic agents, anti-depressive agents, anti-Alzheimer agents, beta-secretase inhibitors, gamma-secretase modulators, agents modifying tau function, amyloid-beta production inhibitors, antibodies directed at amyloid-beta, antibodies directed at tau, antibodies directed at alpha-synuclein, anti-Parkinson agents, anti-diabetic agents, anti-multiple sclerosis agents, anti-obesity agents, agents used for treatment of auditory dysfunction, agents used for treatment of ocular disease, agents used for the treatment of olfactory dysfunction, agents used for the treatment of gustatory dysfunction, anti-huntington agents, anti-Rett syndrome agents, anti-stroke agents. Particular therapeutic agents that may be mentioned include acetyl cholinesterase inhibitors, anti-Alzheimer agents, anti-Parkinson agents, cognitive enhancing agents, antibodies directed at amyloid-beta, antibodies directed at tau, antibodies directed at alpha-synuclein, beta-secretase inhibitors, gamma-secretase modulators, NGF, BDNF, NT-3; NT-4/5, IGF-1, FGF, GDNF, CTNF and/or HGF.

Preparation of Compositions

Pharmaceutical compositions/formulations, combination products and kits as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically-acceptable excipient.

In further aspects of the invention, there is provided a process for the preparation of a combination product or kit-of-parts as hereinbefore defined, which process comprises bringing into association a compound of the invention, as hereinbefore defined, with the other therapeutic agent that is useful in the treatment of the relevant disease or disorder, and at least one pharmaceutically-acceptable excipient.

As used herein, references to bringing into association will mean that the two components are rendered suitable for administration in conjunction with each other.

Thus, in relation to the process for the preparation of a kit-of-parts as hereinbefore defined, by bringing the two components "into association with" each other, we include that the two components of the kit-of-parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

Preparation of Compounds of the Invention

Compounds of the invention as described herein may be prepared either as a free base or as a pharmaceutically acceptable salt in accordance with techniques that are well known to those skilled in the art, such as those described in the examples provided hereinafter.

According to a further aspect of the invention there is provided a process for the preparation of a compound of the invention, which comprises the step of reaction of a compound of formula II,

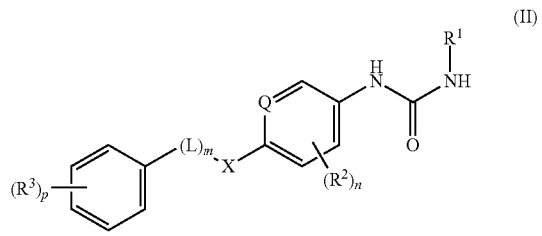

wherein $R^1$, $R^2$, n, X, Q, L, m, $R^3$ and p are as hereinbefore defined, with a suitable isocyanate (e.g. methoxycarbonyl isocyante, chlorocarbonyl isocyanate or, preferably, ethoxycarbonyl isocyanate).

This reaction may be performed for example:

(a) in a sealed microwave vial in a suitable solvent (such as toluene or bromobenzene), at a suitable reaction temperature (e.g. between room temperature and reflux temperature); or (b) by first treating the compound of formula II with a suitable base, such as sodium hydride, at a suitable reaction temperature (e.g. between 0° C. and room temperature) for between about 1 and about 60 minutes in a suitable solvent, such as DMF, followed by the addition of the ethoxycarbonyl isocyanate at approximately the same, with stirring, for a suitable time, such as between about 1 and about 60 minutes.

Compounds of formula II may be obtained by reacting a compound of formula III,

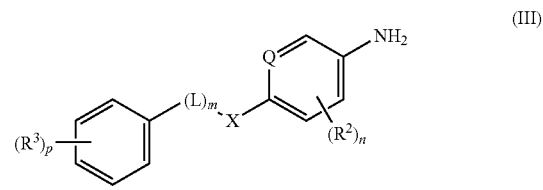

wherein $R^2$, n, X, Q, L, m, $R^3$ and p are as hereinbefore defined, with either:

(a) a compound of formula IV, $$R^1\text{—}N\text{=}C\text{=}O \qquad (IV)$$

wherein $R^1$ is as hereinbefore defined; or (b) a compound of formula V, $$R^1\text{—}N(H)C(O)Cl \qquad (V)$$

wherein $R^1$ is as hereinbefore defined, for example (in both cases) in the presence of a suitable base, such as TEA, in a suitable solvent, such as DCM, THF or, pyridine, at a suitable reaction temperature (for example between room temperature and reflux temperature).

Compounds of formula II may alternatively be obtained by reacting a compound of formula VI,

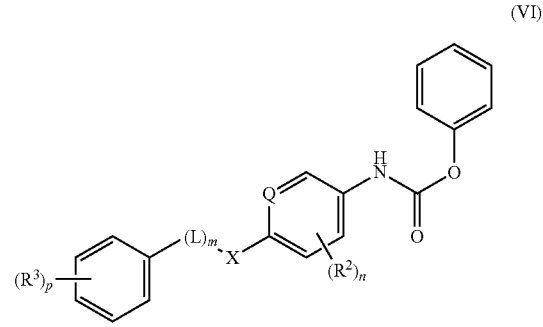

wherein $R^2$, n, X, Q, L, m, $R^3$ and p are as hereinbefore defined, with an amine of formula VII, $$R^1\text{—}NH_2 \qquad (VII)$$

wherein $R^1$ is as hereinbefore defined, for example in the presence of a suitable base, such as TEA, in a suitable solvent, such as THF, and at a suitable reaction temperature (e.g. between room temperature and reflux temperature).

Compounds of formula II may alternatively be prepared by reacting a compound of formula III as hereinbefore defined with triphosgene or phosgene in the presence of a suitable base, such as $NaHCO_3$ or TEA, in a suitable solvent, such as DCM, and at a suitable reaction temperature (e.g. between 0° C. and room temperature). After a suitable period of time, such as between about 1 and about 6 hours, a compound of formula VII may be added, together with an additional amount of a suitable (e.g. the above-mentioned) base, which reaction mixture is then allowed to react at a suitable temperature, such as room temperature, for a suitable period of time, such as between about 1 and about 24 hours. Alternatively, the sequence of this reaction may be altered by first reacting a compound of formula IV with triphosgene or phosgene, followed by the addition of the compound of formula VII, under substantially the same reaction conditions as described above.

Compounds of formula III may be obtained by reducing a compound of formula VIII,

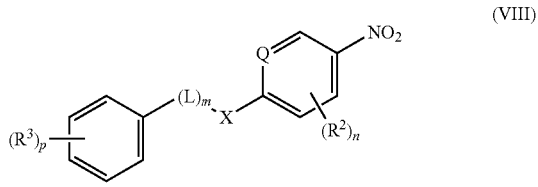

wherein $R^2$, n, X, Q, L, m, $R^3$ and p are as hereinbefore defined, in the presence of a suitable reducing agent such as $SnCl_2.2H_2O$, for example in the presence of HCl, or using Pd/C in the presence of $H_2(g)$. This reaction may be performed in a suitable solvent, such as ethanol, and at a suitable temperature (for example between room temperature and reflux temperature).

In a further embodiment of the invention, there is provided a process for the preparation of a compound of the invention, which comprises the step of reacting a compound of formula IX

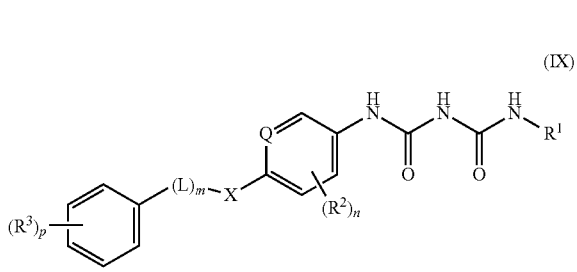

wherein $R^1$, $R^2$, n, X, Q, L, m, $R^3$ and p are as hereinbefore defined, with a compound of formula X,

wherein $LG^1$ and $LG^2$ represent suitable leaving groups independently selected from chloro, methoxy, ethoxy and 1-imidazolyl (particular compounds of formula X that may be mentioned include diethylcarbonate), in the presence of a suitable solvent, such as ethanol and optionally a suitable base, such as sodium ethoxide or methoxide.

Compounds of formula IX may be obtained by reacting a compound of formula (X),

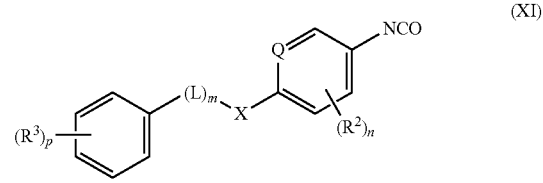

wherein $R^2$, n, X, Q, L, m, $R^3$ and p are as hereinbefore defined, with a compound of formula (XII),

wherein $R^1$ is as defined herein above, in the presence of a suitable solvent, such as dichloromethane or tetrahydrofuran and, optionally a suitable base, such as triethylamine.

Compounds of formula XI may be obtained by reacting a compound of formula III with triphosgene or phosgene.

In a further embodiment of the invention, there is provided a process for the preparation of a compound of the invention, which comprises the step of reacting a compound of formula XIII,

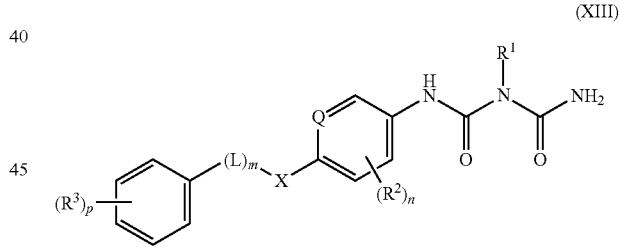

wherein $R^1$, $R^2$, n, X, Q, L, m, $R^3$ and p are as hereinbefore defined, with a compound of formula X, as defined herein, such as diethyl carbonate, in the presence of a suitable solvent, such as ethanol and, optionally, a suitable base, such as sodium ethoxide.

Compounds of formula XIII may be obtained by reacting a compound of formula II with phosgene or triphosgene in the presence of a suitable solvent, and optionally a suitable base, followed by the addition of ammonia to the reaction mixture.

In a further embodiment of the invention, there is provided a process for the preparation of a compound of the invention, which comprises the step of reacting a compound of formula XIV,

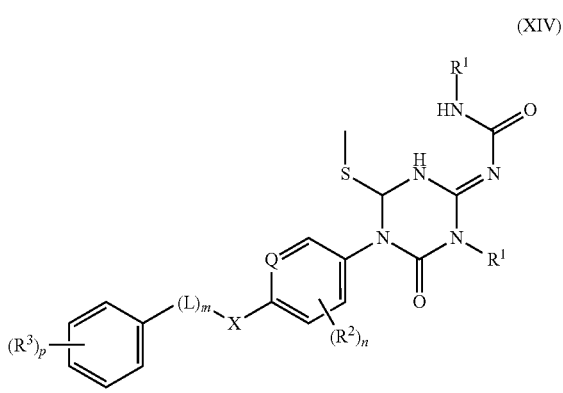

(XIV)

wherein $R^1$, $R^2$, n, X, Q, L, m, $R^3$ and p are as hereinbefore defined, particularly wherein $R^1$ represents an aryl or heteroaryl group as defined herein (more particularly wherein $R^1$ represents phenyl), in the presence of an aqueous acid (such as HCl (e.g. 2M HCl)) and optionally an organic co-solvent (e.g. 1,4-dioxane), and at a suitable temperature (for example at between room temperature and reflux temperature).

Compounds of formula XIV may be obtained by reacting a compound of formula XV,

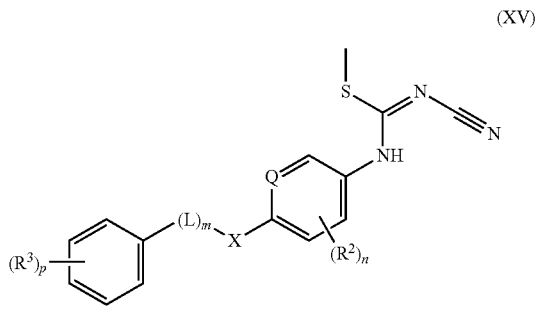

(XV)

wherein $R^2$, n, X, Q, L, m, $R^3$ and p are as hereinbefore defined, with an excess (e.g. 2 equivalents) of a compound of formula XVI,

$R^1$—N=C=O     (XVI)

wherein $R^1$ is as hereinbefore defined, particularly wherein $R^1$ represents an aryl or heteroaryl group as defined herein (more particularly wherein $R^1$ represents phenyl), in the presence of a suitable base (e.g. triethylamine) and a suitable solvent (e.g. acetonitrile), and at a suitable temperature (e.g., room temperature).

Compounds of formula XIV may be obtained by reacting a compound of formula III as defined herein, with dimethyl cyanocarbonimidodithioate in the presence of a suitable solvent (e.g. ethanol) at a suitable temperature (e.g. reflux temperature) for a suitable period of time (for example an extended period of time, such as more than 5 days (e.g. more than 10 days).

Compounds of formulae IV, V, VI, VII, VIII, X, XII and XVI are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "Comprehensive Organic Synthesis" by B. M. Trost and I. Fleming, Pergamon Press, 1991. Further references that may be employed include "Heterocyclic Chemistry" by J. A. Joule, K. Mills and G. F. Smith, 3$^{rd}$ edition, published by Chapman & Hall, "Comprehensive Heterocyclic Chemistry II" by A. R. Katritzky, C. W. Rees and E. F. V. Scriven, Pergamon Press, 1996 and "Science of Synthesis", Volumes 9-17 (Hetarenes and Related Ring Systems), Georg Thieme Verlag, 2006.

The skilled person will understand that the substituents as defined herein, and substituents thereon, may be modified one or more times, after or during the processes described above for the preparation of compounds of the invention by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. The precursor groups can be changed to a different such group, or to the groups defined in formula I, at any time during the reaction sequence. The skilled person may also refer to "Comprehensive Organic Functional Group Transformations" by A. R. Katritzky, O. Meth-Cohn and C. W. Rees, Pergamon Press, 1995 and/or "Comprehensive Organic Transformations" by R. C. Larock, Wiley-VCH, 1999.

Compounds of the invention may be isolated from their reaction mixtures and, if necessary, purified using conventional techniques as known to those skilled in the art. Thus, processes for preparation of compounds of the invention as described herein may include, as a final step, isolation and optionally purification of the compound of the invention.

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be applied and removed in accordance with techniques that are well-known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "Protective Groups in Organic Synthesis", 3rd edition, T. W. Greene & P. G. M. Wutz, Wiley-Interscience (1999), the contents of which are incorporated herein by reference.

When used herein in relation to a specific value (such as an amount), the term "about" (or similar terms, such as "approximately") will be understood as indicating that such values may vary by up to 10% (particularly, up to 5%, such as up to 1%) of the value defined. It is contemplated that, at each instance, such terms may be replaced with the notation "±10%", or the like (or by indicating a variance of a specific amount calculated based on the relevant value). It is also contemplated that, at each instance, such terms may be deleted.

Compounds of the invention may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, compounds of the invention may have the advantage that they are more efficacious and/or exhibit advantageous properties in vivo.

BRIEF DESCRIPTION OF THE FIGURE

FIG. 1 shows the results of the passive avoidance task described in the biological examples. The graph demonstrates that administering the compound of Example 5 to mice treated with scopolamine improves cognitive function, as illustrated by the increased retention latency within the bright area.

EXAMPLES

The present invention will be further described by reference to the following examples, which are not intended to limit the scope of the invention.

Experimental Procedures

Starting materials and intermediates used in the synthesis of compounds described herein are commercially available or can be prepared by the methods described herein or by methods known in the art.

Experiments were generally carried out under inert atmosphere (nitrogen or argon), particularly in cases where oxygen- or moisture-sensitive reagents or intermediates were used.

Mass spectrometry data are reported from liquid chromatography-mass spectrometry (LC-MS) using electrospray ionization. Chemical shifts for NMR data are expressed in parts per million (ppm, δ) referenced to residual peaks from the deuterated solvent used.

For syntheses referencing general procedures, reaction conditions (such as length of reaction or temperature) may vary. In general, reactions were followed by thin layer chromatography or LC-MS, and subjected to work-up when appropriate. Purifications may vary between experiments: in general, solvents and the solvent ratios used for eluents/gradients were chosen to provide an appropriate R and/or retention time.

General Methods:

All solvents were of analytical grade and commercially available anhydrous solvents were routinely used for reactions. Starting materials used were available from commercial sources or prepared according to literature procedures, Room temperature refers to 20-25° C. Solvent mixture compositions are given as volume percentages or volume ratios.

MW heating was performed in a standard MW reactor producing continuous irradiation at 2450 MHz. It is understood that MWs can be used for the heating of reaction mixtures.

Thin layer chromatography (TLC) was performed on Merck TLC-plates (Silica gel 60 $F_{254}$) and spots were UV visualized. TLC was generally used to monitor reaction progression and solvents used were for example: ethyl acetate or acetonitrile or DCM with 1-10% of MeOH, ethyl acetate with 0-95% hexane. Straight phase flash column chromatography ("flash chromatography"/"column chromatography") was manually performed on Merck Silica gel 60 (0.040-0.063 mm) or basic aluminum oxide or neutral aluminum oxide, or automatically using ISCO Combiflash® Companion™ system using RediSep™ normal-phase flash columns ("Combiflash") using the solvent system indicated.

NMR spectra was recorded on a 400 MHz NMR spectrometer (Bruker 400 MHz Avance-III) fitted with a probe of suitable configuration. Spectra were recorded at ambient temperature unless otherwise stated. Chemical fields are given in ppm down- and upfield from TMS (0.00 ppm). The following reference signals were used in $^1$H-NMR: TMS δ 0.00, or residual solvent signal of DMSO-d6 δ 2.49, CDCL3 δ 7.25 (unless otherwise indicated). Resonance multiplicities are denoted s, d, t, q, m, dd, tt, dt br and app for singlet, doublet, triplet, quartet, doublet of doublet, triplet of triplet, doublet of triplet, multiplet, broad and apparent, respectively. In some cases only diagnostic signals are reported.

High pressure liquid chromatography (HPLC) was performed on a reversed phase (RP) column. A gradient was applied using for example mobile phase A (5 mM Ammonium acetate+0.1% Formic acid in water) and B (0.1% Formic acid in Acetonitrile) or A (0.1% NH3 in water) and B (0.1% NH3 in acetonitrile) or A (10 mM Ammonium acetate in water) and B (Acetonitrile).

Reversed phase columns used were for example: BEH C18 (50*2.1 mm), 1.7 μm; X-Bridge C18 (50*4.6 mm), 3.5 μm; X-Bridge/YMCC18 (150*4.6 mm), 5 μm; BEH C18 (50*2.1 mm), 1.7 μm; X-Bridge C8 (250*19) mm, 5 μm. The flowrate used was for example 0.55 ml/min or 1.00 ml/min Mass spectrometry (MS) analysis were performed in positive and/or negative ion mode using electrospray ionization (ESI+/−).

Preparative HPLC chromatography was run on a Waters e2695 Separation Module with a PDA Detector. Column; X-BRIDGE C18, 150*4.6 mm, 5 μm or X-Bridge C18 (250*19 mm) 5 μm or GEMINI C18 (250*21.2 mm) 5 μm.

A gradient was applied using for example mobile phase A (0.1% $NH_3$ in water) and B (0.1% NH3 in acetonitrile); A (0.1% TFA in water) and B (Acetonitrile); A (5 mM ammonium bicarbonate+0.05% ammonia in water) and B (Acetonitrile); A (5 mM ammonium bicarbonate) and B (acetonitrile) for LC-separation at a flow rate 1 ml/min.

High pressure liquid chromatography (HPLC) was performed on a straight phase column. A linear gradient or isocratic flow was applied using for example phase A (Hexane) and B (XX)

Compounds have been named using CDD vault from Collaborative Drug Discovery Inc. Burlingame Calif., USA or ChemDoodle 8.1.0 from iChemLabs LLC, USA or ACD/ChemSketch 2012 (14.01) from Advanced Chemistry Development (ACD/labs) Ontario, Canada. In case of inconsistency between a name of a compound and the structural formula of the same compound, it is the structural formula that is decisive for the molecular structure of the compound.

In the event that there is a discrepancy between nomenclature and any compounds depicted graphically, then it is the latter that presides (unless contradicted by any experimental details that may be given or unless it is clear from the context).

Intermediate 1

1-(4-phenoxyphenyl)-3-phenylurea

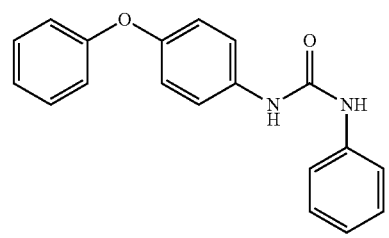 [SMILES: O=C(Nc1ccccc1)Nc1ccc(Oc2ccccc2)cc1]

Phenyl isocyanate (0.115 g, 0.00097 mol) was added to a solution of 4-phenoxyaniline (commercially available, 0.150 g, 0.00081 mol) in pyridine under N₂ (g). The reaction mixture was heated to 90° C. for 1 hour. The reaction mixture was diluted with water (50 ml) and extracted with ethyl acetate (3×40 ml). The combined organic layers were washed with brine (30 ml), dried over sodium sulfate and evaporated under reduced pressure to obtain crude product. The crude product was purified on silica gel (100-200 mesh) using 50% ethyl acetate in hexane as an eluent to obtain 0.200 g (81% yield) of the title compound.

$^1$H NMR (400 MHz, DMSO-d$_6$) δ ppm 6.93-7.04 (m, 5H) 7.09 (m, 1H) 7.28 (m, 2H) 7.37 (m, 2H) 7.47 (m, 4H) 8.67 (m, 2H); MS (ES+) m/z 305 [M+H]$^+$ Intermediate 2

1-(4-methoxyphenyl)-3-(4-phenoxyphenyl)urea

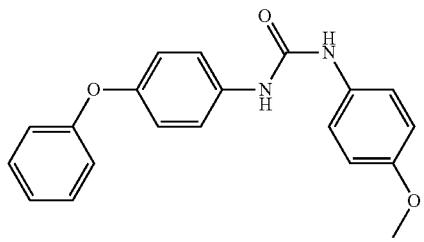 [SMILES: COc1ccc(NC(=O)Nc2ccc(Oc3ccccc3)cc2)cc1]

To a solution of phenyl (4-phenoxyphenyl)carbamate (commercially available, 0.300 g, 0.00091 mol) in THF (3.0 mL), TEA (0.273 g, 0.0019 mol) and 4-Methoxy Aniline (0.145 g, 0.0011 mol) were added at 0° C. under N₂ (g). The reaction mixture was heated at 70° C. 16 h. The reaction mixture was quenched with ice-water (30 ml) and extracted with Ethyl Acetate (3×40 ml). The combined organic layers were washed with brine (50 ml). The Organic layer was dried over sodium sulfate and evaporated under reduced pressure to obtain crude product. The crude product was purified on column chromatography using 45% Ethyl acetate in Hexane as a mobile phase and 60-120 silica as stationary phase to yield 0.214 g (77% yield) of the title compound. $^1$H NMR (400 MHz, DMSO-d$_6$) δ ppm 3.72 (s, 3H) 6.91-6.83 (m, 2H) 7.02-6.91 (m, 4H) 7.09 (app tt, 1H) 7.42-7.30 (m, 4H) 7.50-7.43 (m, 2H) 8.45 (s, 1H) 8.59 (s, 1H); MS (ES+) m/z 335 [M+H]$^+$ Intermediate 3

1-(3-cyanophenyl)-3-(4-phenoxyphenyl)urea

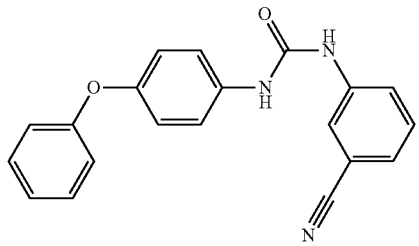 [SMILES: N#Cc1cccc(NC(=O)Nc2ccc(Oc3ccccc3)cc2)c1]

TEA (0.273 g, 0.0019 mol) was added dropwise to phenyl (4-phenoxyphenyl)carbamate (commercially available, 0.30 g, 0.00098 mol) followed by 3-amino-benzonitrile (0.139 g, 0.0011 mol) in THF (3.00 mL) under N₂ (g) at 0° C. The reaction mixture was stirred at 70° C. for 16 h. The reaction mixture was quenched with ice-water (20 ml) and product was extracted with Ethyl Acetate (3×20 ml). The combined organic layers were washed with brine (20 ml), over sodium sulfate and evaporated under reduced pressure to obtain the crude product. The crude product was purified on column chromatography using 30% ethyl acetate in hexane as a mobile phase and 60-120 silica as stationary phase to yield 0.139 g (46% yield) of the title compound. $^1$H NMR (400 MHz, DMSO-d$_6$) δ ppm 6.92-7.05 (m, 4H) 7.10 (app tt, 1H) 7.32-7.46 (m, 3H) 7.44-7.54 (m, 3H) 7.68 (app ddd, 1H) 7.98 (app t, 1H) 8.86 (s, 1H) 9.01 (s, 1H).

Intermediate 4

1-(3-methoxyphenyl)-3-(4-phenoxyphenyl)urea

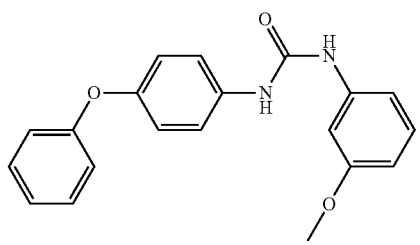 [SMILES: COc1cccc(NC(=O)Nc2ccc(Oc3ccccc3)cc2)c1]

m-Anisidine (0.145 g, 0.00170 mol) and TEA (0.273 g, 0.00196 mol) were added to a solution of phenyl-(4-phenoxyphenyl)carbamate (commercially available, 0.300 g, 0.00098 mol) in THF (3.0 mL) under stirring at 0° C. under N2 (g). The reaction mixture was stirred at 70° C. for 16 h. The reaction mixture was quenched with ice-water (50 ml) and extracted with ethyl acetate (3×40 ml). The combined organic layers were washed with brine (30 ml), dried over sodium sulfate and evaporated under reduced pressure to obtain crude product. The crude product was purified by column chromatography using 55% ethyl acetate in hexane as a mobile phase and 60-120 silica as stationary phase to yield 0.200 g (66% yield) of the title compound. $^1$H NMR (400 MHz, DMSO-d6) δ ppm 3.73 (s, 3H) 6.55 (m, 1H) 6.81-7.03 (m, 5H) 7.09 (app tt, 1H) 7.13-7.22 (m, 2H) 7.32-7.42 (m, 2H) 7.42-7.51 (m, 2H) 8.66 (app s, 2H); MS (ES+) m/z 335 [M+H]$^+$ Intermediate 5

1-(3-methyl-4-phenoxyphenyl)-3-phenylurea

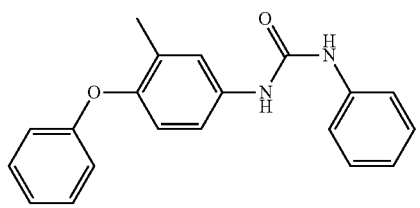 [SMILES: Cc1cc(NC(=O)Nc2ccccc2)ccc1Oc1ccccc1]

Phenyl isocyanate (6.53 g, 0.0548 mol) was added to a solution of 3-methyl-4-phenoxyaniline (commercially available, 8.40 g, 0.0390 mol) and TEA (11.76 mL, 0.084 mol) in DCM at 0° C. The reaction mixture was stirred at 25° C. for 16 h. The solid produced was filtered off and wash with n-pentane (20 ml) to yield 8.4 g (67% yield) of the title compound. This material was used in the next step without further purification. $^1$H NMR (400 MHz, DMSO-d6) δ ppm 2.12 (s, 3H) 6.81-6.91 (m, 3H) 6.88-7.08 (m, 3H) 7.24-7.38 (m, 4H) 7.40-7.50 (m, 3H) 8.64 (app d, 2H); MS (ES+) m/z 319 [M+H]$^+$ Intermediate 6

4-(benzyloxy)aniline

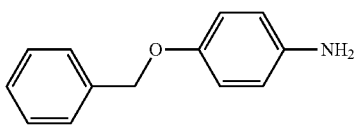 [SMILES: Nc1ccc(OCc2ccccc2)cc1]

In a 30 ml seal tube previously equipped with a magnetic stirrer and nitrogen balloon Potassium tert-butoxide (0.76 mg, 0.0068 mol) was added portion wise to a solution of 4-aminophenol (0.50 g, 0.0045 mol) in DMF (5.0 mL) at 0° C. After stirring for 1 h, benzylbromde (0.860 g, 0.005 mol) was added portion wise. The reaction mixture was allowed to come at 25° C. than heated at 120° C. for 16 hours. The reaction mixture was quenched with water (50 ml) and extracted with ethyl acetate (3×40 ml). The combine organic layers were washed with brine (30 ml), dried over sodium sulfate and evaporated under reduced pressure to obtain the crude product. The crude product was purified on silica gel (60-120 mesh) using 30% ethyl acetate in hexane as an eluent to obtained 0.400 g (44% yield) of the pure title product.

MS (ES+) m/z 200 [M+H]$^+$

Intermediate 7

1-[4-(benzyloxy)phenyl]-3-phenylurea

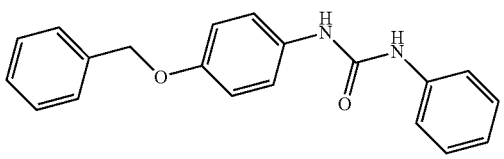 [SMILES: O=C(Nc1ccccc1)Nc1ccc(OCc2ccccc2)cc1]

Phenylisocyanate (0.286 g, 0.0024 mol) was added to a solution of 4-(benzyloxy)aniline (Intermediate 6, 0.400 g, 0.0020) and TEA (0.404 ml, 0.0040 mol) in DCM (4.00 ml) at 0° C. The resulting reaction mixture was allowed to come to 25° C. and stirred at 25° C. for 2 hrs. The solvent was evaporated under reduce pressure to obtain 0.450 g (71% yield) of the title compound. This material was used without further purification in the next step. $^1$H NMR (400 MHz, DMSO-d$_6$) δ ppm 5.06 (s, 2H) 6.95 (app dd, 3H) 7.22-7.33 (m, 3H) 7.34 (app dd, 3H) 7.41 (app dt, 5H) 8.58 (s, 1H), 8.47 (s, 1H); MS (ES+) m/z 319 [M+H]$^+$ Intermediate 8

1-[4-(4-chlorophenoxy)phenyl]-3-phenylurea

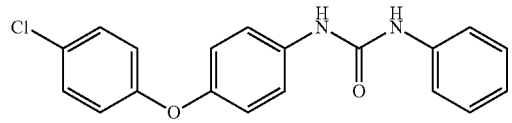 [SMILES: O=C(Nc1ccccc1)Nc1ccc(Oc2ccc(Cl)cc2)cc1]

Phenyl isocyanate (0.140 g, 0.00110 mol) was added to a solution of 4-(4-chlorophenoxy)aniline (commercially available, 0.200 g, 0.00091 mol) and TEA (0.255 ml, 0.00180 mol) in DCM (4.00 mL) under stirring at 0° C. The resulting reaction mixture was allowed to reach 25° C. and stirred for 16 h. The solid formed was filtered off and washed with n-pentane (3×15 ml) to yield 0.310 g of title compound. This solid was used in the next step without further purification. $^1$H NMR (400 MHz, DMSO-d$_6$) δ ppm 6.99 (m, 5H) 7.28 (m, 3H), 7.36-7.54 (m, 5H), 8.66 (s, 1H) 8.71 (s, 1H); MS (ES+) m/z 339 [M+H]$^+$ Intermediate 9

4-(4-aminophenoxy)benzonitrile

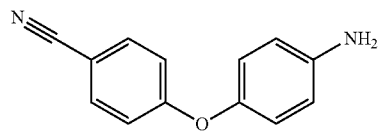 [SMILES: N#Cc1ccc(Oc2ccc(N)cc2)cc1]

Potassium tert-butoxide (1.02 g, 0.0091 mol) was added portion wise to the solution of 4-aminophenol (0.500 g, 0.0015 mol) in DMF (5.00 mL) at 0° C. under N$_2$ (g). After 1 hour, 4-bromobenzonitrile (0.830 g, 0.0045 mol) was added portion wise and the reaction mixture was stirred at 120° C. for 16 hours. The reaction mixture was quenched with ice-water (50 ml) and product was extracted with Ethyl Acetate (3×40 ml). The combined organic layer was washed with brine (30 ml). The organic layer was dried over sodium sulfate and evaporated under reduced pressure to obtain crude product. The crude product was purified on column chromatography using 100% Ethyl acetate in hexane as a mobile phase and 60-120 silica to yield 0.350 g (36% yield) of the title compound. $^1$H NMR (400 MHz, DMSO-d$_6$) δ ppm 5.12 (s, 2H) 6.57-6.65 (m, 2H) 6.79-6.86 (m, 2H) 6.94-7.00 (m, 2H) 7.73-7.80 (m, 2H).

Intermediate 10

1-[4-(4-cyanophenoxy)phenyl]-3-phenylurea

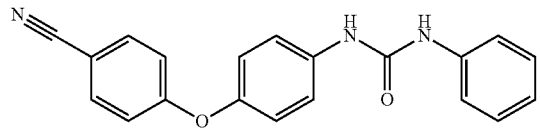 [SMILES: N#Cc1ccc(Oc2ccc(NC(=O)Nc3ccccc3)cc2)cc1]

Phenyl isocyanate was added to a solution of 4-(4-aminophenoxy)benzonitrile (Intermediate 9, 0.150 g, 0.00071 mol) and TEA (0.100 ml, 0.00071 mol) in DCM (5.00 mL) at 0° C. The reaction mixture was stirred at 25° C. for 16 h. The solvent was evaporated and the reaction mixture was quenched with water (25 ml) and was extracted with Ethyl Acetate (3×30 ml). The combined organic layer was washed with brine (30 ml). The organic layer was dried over sodium sulfate and evaporated under reduce pressure to obtain a crude product. The crude product was purified on column chromatography using 40% ethyl acetate in hexane as a mobile phase and 60-120 silica as stationary phase to yield 0.250 g of the title compound that was used in the next step without further purification. MS (ES+) m/z 330 [M+H]$^+$ Intermediate 11

1-(48-methoxy-4-phenoxyphenyl)-3-phenylurea

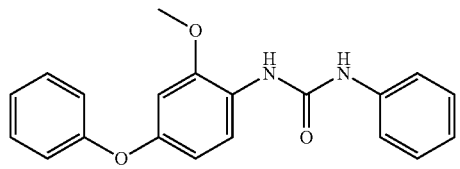 [SMILES: COc1cc(Oc2ccccc2)ccc1NC(=O)Nc1ccccc1]

2-methoxy-4-phenoxyaniline (commercially available, 0.250 g, 0.0011 mol) was added to TEA (0.234 mL, 0.0023 mol) in DCM (2.5 mL) and the mixture was cooled to 0° C. To the mixture phenyl isocyanate (0.179 g, 0.0015 mol) was added and the reaction mixture was stirred at 25° C. for 16 h. The solid material produced was filtered off and washed with n-pentane (5 ml) to yield 0.300 g (77% yield) of the title compound. This was used in the next step without further purification. $^1$H NMR (400 MHz, DMSO-d6) δ ppm 3.86 (s, 3H) 6.56 (app dd, 1H) 6.81 (app d, 1H) 6.92-7.02 (m, 3H) 7.09 (app ft, 1H) 7.23-7.33 (m, 2H) 7.32-7.42 (m, 2H) 7.41-7.49 (m, 2H) 8.08 (app d, 1H) 8.19 (s, 1H) 9.26 (s, 1H); MS (ES+) m/z 335 [M+H]$^+$ Intermediate 12

1-(4-Morpholinophenyl)-3-(4-phenoxyphenyl)urea

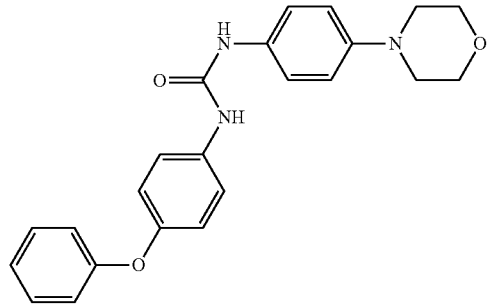 [SMILES: O=C(Nc1ccc(Oc2ccccc2)cc1)Nc1ccc(N2CCOCC2)cc1]

4-(4-isocyanatophenyl)morpholine (commercially available, 0.500 g, 0.0024 mol) was added to a solution of 4-phenoxyaniline (commercially available, 0.340 g, 0.0018 mol) and TEA (0.380 g, 0.0037 mol) in DCM (5.0 mL) at 0° C. The reaction mixture was allowed to come to 25° C. and stirred for 16 h. The reaction mixture was quenched with ice-water (50 ml) and product extracted with DCM (3×40 ml). The combined organic layers were washed with brine (30 ml), dried over sodium sulfate and evaporated under reduced pressure to obtain the crude product. The crude product was purified on silica gel (100-200 mesh) using 1.5% methanol in dichloromethane as an eluent to obtain 0.080 g (11% yield) of the title compound. MS (ES+) m/z 390 [M+H]$^+$ Intermediate 13

1-(3-methoxy-4-phenoxyphenyl)-3-phenylurea

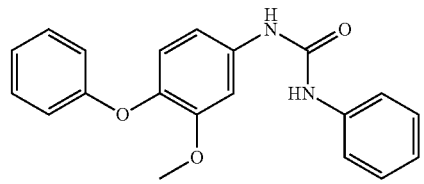 [SMILES: COc1cc(NC(=O)Nc2ccccc2)ccc1Oc1ccccc1]

In a 50 ml RBF previously equipped with a magnetic stirrer phenyl isocyanate (0.297 g, 0.0024 mol) was added to a solution of 3-methoxy-4-phenoxyaniline (commercially available, 0.450 g, 0.0020 mol) and TEA (0.406 mL, 0.0040 mol) in DCM (4.50 mL) at 0° C. The resulting reaction mixture was allowed to reach 25° C. and stirred for 2 h. The solvent was evaporated under reduce pressure to obtain 0.500 g of crude product. This was used in the next step without further purification. $^1$H NMR (400 MHz, DMSO-d6) δ ppm 3.72 (s, 3H) 6.76-6.85 (m, 2H) 6.91-7.06 (m, 4H) 7.29 (app ddt, 4H) 7.46 (app ddd, 3H) 8.69 (s, 1H) 8.77 (s, 1H).

Intermediate 14

1-(3-cyano-4-phenoxyphenyl)-3-phenylurea

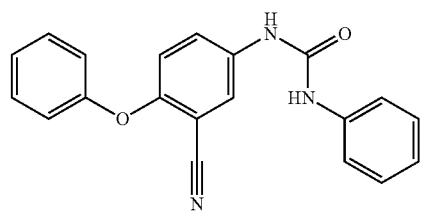 [SMILES: N#Cc1cc(NC(=O)Nc2ccccc2)ccc1Oc1ccccc1]

Phenyl isocyanate (0.373 g, 0.0017 mol) was added to a solution of 5-amino-2-phenoxybenzonitrile (commercially available, 0.600 g, 0.0015 mol) and TEA (0.521 ml, 0.0023 mol) in DCM (6.00 mL) at 0° C. The reaction mixture was stirred at 25° C. for 16 h. The solid produced was filtered to obtain the solid. The obtained solid was stirred in n-pentane (10 ml) for 15 min and the n-pentane was filtered off to yield 0.330 g (35% yield) of the solid title compound. $^1$H NMR (400 MHz, DMSO-d$_6$) δ ppm 7.00 (app t, 1H) 7.12-7.01 (m, 2H) 7.10 (app t, 1H) 7.17-7.26 (m, 1H) 7.25-7.34 (m, 2H) 7.39-7.50 (m, 4H) 7.66 (app dd, 1H) 8.01 (app d, 1H), 8.80 (s, 1H) 8.96 (s, 1H); MS (ES+) m/z 330 [M+H]$^+$

Intermediate 15

1-methoxy-4-methyl-2-nitro-5-phenoxybenzene

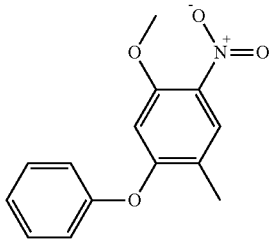

To a solution of taken Phenol (0.200 g, 0.0021 mol) in DMF (2.0 mL) in a seal tube flask, NaH (0.056 g, 0.0023 mol) was added portion wise at 0° C. under $N_2$ (g). The reaction mixture was stirred for 1 hour. 1-fluoro-5-methoxy-2-methyl-4-nitrobenzene (0.432 g, 0.0023 mol) was added portion wise and the reaction mixture was stirred at 120° C. for 5 h. The reaction mixture was quenched with ice-water (15 ml) and extracted with Diethyl ether (3×20 ml). The combined organic layers was washed with brine (30 ml). Organic layer was dried over sodium sulfate and evaporated under reduced pressure to obtain crude product. The crude product was purified on combi flash chromatography by using 20% Ethyl acetate in Hexane as a mobile phase and 60-120 silica to yield 0.550 g of the title compound. $^1$H NMR (400 MHz, DMSO-$d_6$) δ ppm 2.18 (s, 3H) 2.74 (s, 3H) 6.63-6.76 (m, 1H) 6.95 (app dt, 2H) 6.98-7.11 (m, 3H) 8.47 (s, 1H).

Intermediate 16

2-methoxy-5-methyl-4-phenoxyaniline

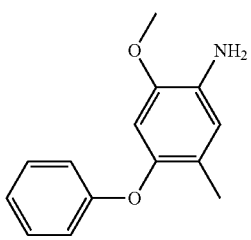 [SMILES: COc1cc(Oc2ccccc2)c(C)cc1N]

1-methoxy-4-methyl-2-nitro-5-phenoxybenzene (Intermediate 15, 0.540 g, 0.00208 mol) and $SnCl_2.2H_2O$ (1.870 g, 0.0833 mol) were dissolved in Ethanol (5.40 mL) and cooled to 0° C. 35% HCl (0.540 mL) was added and the reaction mixture was stirred at 50° C. for 5 h. The reaction mixture was diluted with ethyl acetate (50 ml) and basified with 30% aqueous ammonia solution to maintain pH 7-8. The precipitate was filtered through a celite pad and washed with ethyl acetate (3×5 ml). The filtrate was washed with $H_2O$ (3×40 ml) and brine (40 ml). Organic layer was dried over sodium sulfate and evaporated under reduce pressured to obtain 0.450 g of the title compound which was used without further purification in the next step. $^1$H NMR (400 MHz, DMSO-$d_6$) δ ppm 1.91 (s, 3H) 3.71 (s, 3H) 4.59 (s, 2H) 6.52 (app d, 2H) 6.72-6.81 (m, 2H) 6.92-7.01 (m, 1H) 7.23-7.33 (m, 2H).

Intermediate 17

1-(2-methoxy-5-methyl-4-phenoxyphenyl)-3-phenylurea

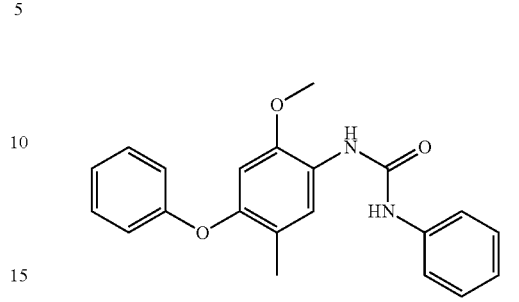

2-methoxy-5-methyl-4-phenoxyaniline (Intermediate 16, 0.440 g, 0.00191 mol) and TEA (0.400 mL, 0.00287 mol) were dissolved in DCM (4.50 mL) cooled to 0° C. Phenyl isocyanate (0.251 g, 0.00211 mol) was added and the resulting reaction mixture was stirred at 25° C. for 16 h. The solid produced was filtered off and filtered to obtain the solid. The obtained solid was stirred with n-pentane (15 ml) for 15 min and the n-pentane was filtered off to yield 0.285 g (43% yield) of the solid title compound which was used in the next step without further purification. $^1$H NMR (400 MHz, DMSO-$d_6$) δ ppm 2.04 (s, 3H) 3.81 (s, 3H) 6.72 (s, 1H) 6.80-6.88 (m, 2H) 7.00 (app dt, 2H) 7.24-7.38 (m, 4H) 7.42-7.50 (m, 2H) 8.07 (s, 1H) 8.19 (s, 1H) 9.28 (s, 1H).

Intermediate 18

1-methoxy-3-methyl-5-nitro-2-phenoxybenzene

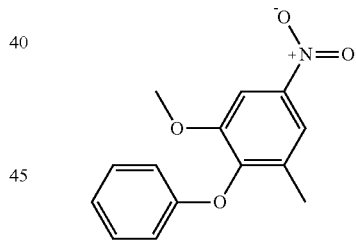

2-methoxy-6-methyl-4-nitrophenol (0.230 g, 0.0012 mol) and phenyl boronic acid (0.336 g, 0.0027 mol) were dissolved in DCM (11.9 mL) with 4 Å molecular sieves (11.5 g) at 25° C. under $N_2$ (g). The reaction mixture was cooled to 0° C. and TEA (0.881 mL, 0.0062) was added followed by the addition of calcium acetate (0.228 g, 0.0012 mol). The reaction mixture was stirred for 6 h at 0° C. then allowed to come to 25° C. and stirred for 16 h. The reaction mixture was filtered through a celite pad and washed with DCM (2×40 ml). The filtrate was washed with water (2×15 ml) followed by the washing with brine (20 ml), dried over sodium sulfate and evaporated under reduced pressure to obtained the crude product. The crude product was purified on silica gel (60-120 mesh) using 10% ethyl acetate in hexane as an eluent to obtained 0.340 g of the title compound. $^1$H NMR (400 MHz, DMSO-$d_6$) δ ppm 2.21 (s, 3H) 3.81 (s, 3H) 6.76-6.83 (m, 2H) 6.97-7.09 (m, 1H) 7.32-7.26 (m, 2H) 7.82 (d, 1H) 7.93 (dd, 1H).

Intermediate 19

3-methoxy-5-methyl-4-phenoxyaniline

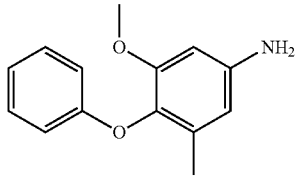 [SMILES: COc1cc(N)cc(C)c1Oc1ccccc1]

HCl (35%) (0.34 mL) was added drop wise under stirring to a solution of 1-methoxy-3-methyl-5-nitro-2-phenoxybenzene (Intermediate 18, 0.340 g, 0.0013 mol) and $SnCl_2.2H_2O$ (1.18 g, 0.0052 mol) in ethanol at 0° C. under $N_2$ (g). The reaction mixture was allowed to come to 25° C. and then heated at 50° C. for 4 h. The reaction mixture was allowed to cool to room temperature and diluted with ethyl acetate (50 ml) and basified using ammonia solution up to pH 7-8. The product was extracted in ethyl acetate (2×30 ml). The combine organic layer was washed with brine (50 ml), dried over sodium sulfate and evaporated under reduce pressure to obtained 0.290 g (97% yield) of the title compound. $^1$H NMR (400 MHz, DMSO-$d_6$) δ ppm 1.91 (s, 3H) 3.59 (s, 3H) 6.05 (d, 1H) 6.20 (d, 1H) 6.66-6.81 (m, 2H) 6.91 (m, 1H) 7.18-7.30 (m, 2H); MS (ES+) m/z 230 [M+H]$^+$

Intermediate 20

1-(3-methoxy-5-methyl-4-phenoxyphenyl)-3-phenylurea

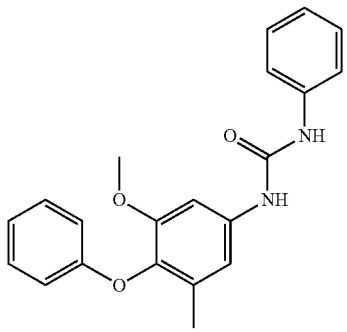 [SMILES: COc1cc(NC(=O)Nc2ccccc2)cc(C)c1Oc1ccccc1]

In a 10 ml seal tube previously equipped with a magnetic stirrer and nitrogen balloon, phenyl isocyanate (0.190 ml, 0.00099 mol) was added drop wise to a solution of 3-methoxy-5-methyl-4-phenoxyaniline (Intermediate 19, 0.190 g, 0.00082 mol) and TEA (0.232 mL, 0.0016 mol) in DCM (2.0 mL) at 0° C. The reaction mixture was allowed to reach 25° C. and stirred for 16 h. The reaction mixture was concentrated under reduced pressure to obtained crude product. The crude product was purified on combi flash using 50% ethyl acetate in hexane as an eluent to yield 0.100 g (34% yield) of the title compound. $^1$H NMR (400 MHz, DMSO-$d_6$) δ ppm 2.04 (s, 3H) 3.67 (s, 3H) 6.69-6.78 (m, 2H) 6.86-7.02 (m, 3H) 7.22-7.33 (m, 5H) 7.42-7.50 (m, 2H) 8.71 (app d, 2H); MS (ES+) m/z 349 [M+H]$^+$

Intermediate 21

2-(cyclopentyloxy)-4-nitro-1-phenoxybenzene

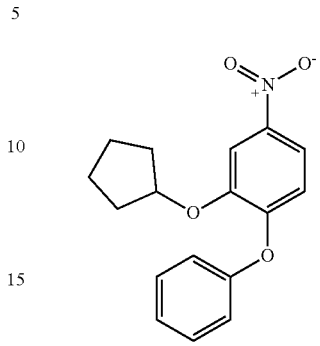

Phenol (0.325 g, 0.0034 mol) dissolved in DMF (9.00 mL), in a 30 ml seal tube previously equipped with a magnetic stirrer and nitrogen balloon, was cooled to 0° C. NaH (0.113 g, 0.0047 mol) was added portion wise and stirred for 1 h. 1-bromo-2-(cyclopentyloxy)-4-nitrobenzene (commercially available, 0.900 g, 0.0031 mol) was added portion wise and the reaction mixture was stirred at 120° C. for 16 h. The reaction mixture was quenched with ice-water (50 ml) and extracted with ethyl acetate (3×40 ml). The combined organic layers were washed with brine (30 ml). Organic layer was dried over sodium sulfate and evaporated under reduced pressure. The crude product was purified on column chromatography using 20% ethyl acetate in hexane as a mobile phase and 60-120 silica to yield 0.550 g (59% yield) of the title product. $^1$H NMR (400 MHz, DMSO-$d_6$) δ ppm 1.59-1.75 (m, 4H) 1.79-2.05 (m, 4H) 4.80-4.90 (m, 1H) 6.93-7.09 (m, 3H) 7.10-7.21 (m, 1H) 7.31-7.42 (m, 2H) 7.81-7.91 (m, 2H).

Intermediate 22

3-(cyclopentyloxy)-4-phenoxyaniline

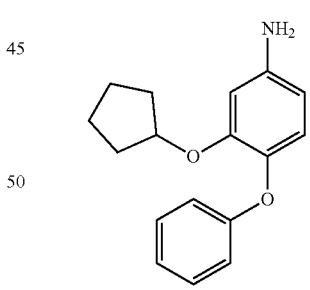

2-(cyclopentyloxy)-4-nitro-1-phenoxybenzene (Intermediate 21, 0.500 g, 0.0016 mol) $SnCl_2.2H_2$ (1.50 g, 0.0066 mol) were dissolved in ethanol (5.0 mL) and cooled to 0° C. HCl (35%, 0.50 mL) was added and the reaction mixture was stirred at 50° C. for 5 h. The reaction mixture was diluted with ethyl acetate (20 ml) and basified with 30% aqueous ammonia solution to maintain pH 7-8. The obtained solid was filtered and discarded. The filtrate was washed with $H_2O$ (3×15 ml) and brine (20 ml). Organic layer was dried over sodium sulfate and evaporated under reduced pressure to yield 0.480 g of the title compound which was used without further purification in the next step.

Intermediate 23

1-[3-(cyclopentyloxy)-4-phenoxyphenyl]-3-methyl-urea

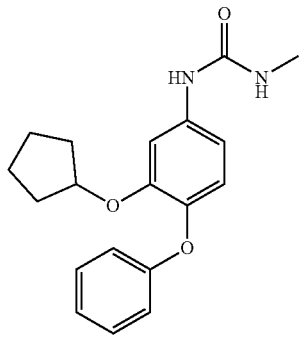 [SMILES: CNC(=O)Nc1ccc(Oc2ccccc2)c(OC2CCCC2)c1]

3-(cyclopentyloxy)-4-phenoxyaniline (Intermediate 22, 0.240 g, 0.00089 mol) and TEA (0.135 ml, 0.00130 mol) were dissolved in DCM (2.50 mL) and to 0° C. N-Methyl formyl chloride (0.099 g, 0.00100 mol) was added and the resulting reaction mixture was stirred at 25° C. for 16 h. The solvent was evaporated and the reaction mixture was quenched with water (10 ml) and product was extracted with ethyl acetate (3×30 ml). The combined organic layer was washed with brine (30 ml). Organic layer was dried over sodium sulfate and evaporated under reduced pressure to obtain crude product. The crude product was purified on Combi flash chromatography using 1% MeOH in DCM as a mobile phase and 60-120 silica as stationary phase to yield 0.180 g (62% yield) of the title compound. MS (ES+) m/z 327 [M+H]$^+$

Intermediate 24

1-(3-ethoxy-4-phenoxyphenyl)-3-phenylurea

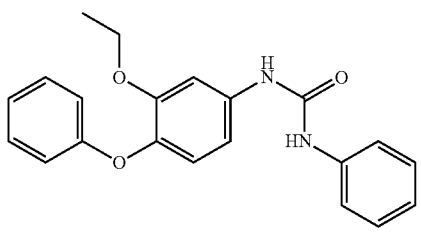 [SMILES: CCOc1cc(NC(=O)Nc2ccccc2)ccc1Oc1ccccc1]

In a 30 ml seal tube previously equipped with a magnetic stirrer and nitrogen balloon, phenyl isocyanate (0.226 mL, 0.0019 mol) was added drop wise to the solution of 3-ethoxy-4-phenoxyaniline (0.400 g, 0.0017 mol) and TEA (0.489 mL, 0.0034 mol) in DCM (4.0 mL) at 0° C. The reaction mixture was allowed to slowly reach 25° C. and stirred for 16 h. The solvent was evaporated under reduced pressure to obtain the crude product. The crude product was purified on silica gel (60-120 mesh) using 30% ethyl acetate in hexane as an eluent to obtain 0.230 g (38% yield) of the title compound. H NMR (400 MHz, DMSO-d6) δ ppm 1.16 (t, 3H) 3.94-4.04 (m, 2H) 6.79-6.86 (m, 1H) 6.87-7.01 (m, 1H) 7.11-7.20 (m, 1H) 7.24-7.34 (m, 4H) 7.39-7.50 (m, 6H) 8.62-8.69 (m, 1H) 8.72 (s, 1H); MS (ES+) m/z 349 [M+H]$^+$

Intermediate 25

3-(5-nitro-2-phenoxyphenoxy)tetrahydrofuran

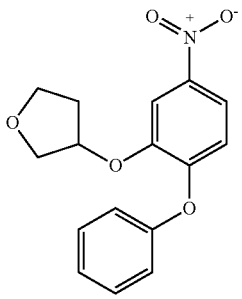

In a 30 ml seal tube flask previously equipped with a magnetic stirrer and nitrogen balloon, NaH (0.109 g, 0.0045 mol) was added portion wise to a solution of Phenol (0.391 g, 0.0041 mol) in DMF (12 mL) at 0° C. and stirred for 1 h. 3-(2-bromo-5-nitrophenoxy)tetrahydrofuran (commercially available, 1.200 g, 0.0041 mol) was added portion wise and the reaction mixture was stirred at 120° C. for 16 h. The reaction mixture was quenched with ice-water (50 ml) and product extracted with ethyl acetate (3×40 ml). The combined organic layers were washed with brine (30 ml). The organic layer was dried over sodium sulfate and evaporated under reduced pressure to obtain crude product. The crude product was purified on column chromatography using 20% Ethyl acetate in hexane as a mobile phase on 60-120 silica to yield 0.900 g (76% yield) of the title compound. $^1$H NMR (400 MHz, DMSO-d6) δ ppm 1.91 (m, 1H) 2.19 (m, 1H) 3.56-3.66 (m, 1H) 3.68-3.79 (m, 2H) 3.85-3.95 (m, 1H) 5.25 (m, 1H) 7.01-7.12 (m, 3H) 7.16-7.23 (m, 1H) 7.38-7.48 (m, 2H) 7.85-7.94 (m, 2H).

Intermediate 26

4-phenoxy-3-(tetrahydrofuran-3-yloxy)aniline

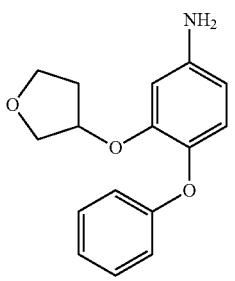 [SMILES: Nc1ccc(Oc2ccccc2)c(OC2CCOC2)c1]

in a u ml I-previously-equipped with a magnetic stirrer 35% HCl in water (0.30 mL) was added to a solution of 3-(5-nitro-2-phenoxyphenoxy)tetrahydrofuran (Intermediate 25, 0.90 g, 0.0029 mol) and SnCl$_2$.2H$_2$O (2.69 g, 0.0011 mol) in ethanol (20 mL) at 0° C. The reaction mixture was stirred at 50° C. for 5 h. The reaction mixture was diluted with ethyl acetate (50 ml) and basified with 30% aqueous ammonia solution to maintain pH 7-8. The precipitate was filtered through a celite pad and washed with ethyl acetate (3×5 ml). The filtrate was washed with water (3×40 ml) followed by washing with brine (40 ml), dried over sodium sulfate and evaporated under reduced pressure to yield 0.750 g (85% yield) the title compound that was used without further purification in the next step. ¹H NMR (400 MHz, DMSO-d6) δ 1.70-1.82 (m, 1H) 1.94-2.08 (m, 1H) 3.39-3.51 (m, 1H) 3.55-3.83 (m, 2H) 3.80-3.95 (m, 1H) 5.04 (s, 1H) 6.17 (dd, 1H) 6.32 (d, 1H) 6.75 (m, 3H) 6.82-6.98 (m, 1H) 7.11-7.29 (m, 2H).

Intermediate 27

1-[4-Phenoxy-3-(tetrahydrofur-3-yloxy)phenyl]-3-phenylurea

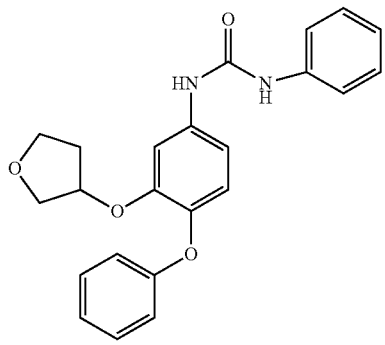 [SMILES: O=C(Nc1ccccc1)Nc1ccc(Oc2ccccc2)c(OC2CCOC2)c1]

In a 50 ml RBF previously equipped with a magnetic stirrer phenyl isocyanate (0.144 g, 0.0011 mol) was added to a solution of 4-phenoxy-3-(tetrahydrofuran-3-yloxy)aniline (Intermediate 26

Intermediate 28

1-(3-methyl-4-phenoxyphenyl)-3-pyridin-2-ylurea

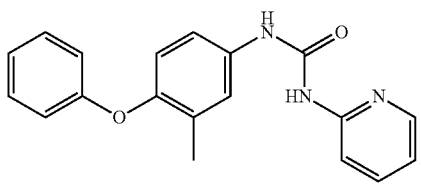 [SMILES: Cc1cc(NC(=O)Nc2ccccn2)ccc1Oc1ccccc1]

In a 50 ml RBF previously equipped with a magnetic stirrer was taken 3-methyl-4-phenoxyaniline (commercially available, 0.500 g, 0.0025 mol) and NaHCO₃ (0.63 g, 0.0075 mol) were added to DCM (5.0 mL) and cooled to 0° C. To the mixture, triphosgene (0.491 g, 0.0016 mol) was added and the resulting reaction mixture was stirred at 0° C. for 4 h. 2-amino pyridine (0.236 g, 0.0025 mol) and NaHCO₃ (0.63 g, 0.0075 mol) were added to the reaction mixture. The resulting reaction mixture was stirred at 25° C. for 16 h. The solvent was evaporated and the reaction mixture was quenched with water (25 ml) and product was extracted with DCM (3×30 ml). The combined organic layer was washed with brine (30 ml). The organic layer was dried over sodium sulfate and evaporated under reduced pressure to obtain a crude product. The crude product was purified by using 0.02% ammonia as a modifier and water:acetonitrile (0-100% gradient system) as a mobile phase in preparative HPLC purification to yield 0.4 g (50% yield) of the title compound. ¹H NMR (400 MHz, DMSO-d6) δ ppm 2.13 (s, 3H) 6.84-6.93 (m, 4H) 6.99-7.07 (m, 3H) 7.31-7.48 (m, 3H) 7.77 (m, 1H) 8.29 (m, 1H) 9.47 (s, 1H) 10.50 (s, 1H); MS (ES+) m/z 320 [M+H]⁺

Intermediate 29

1-phenyl-3-(1-phenyl-1H-indazol-5-yl)urea

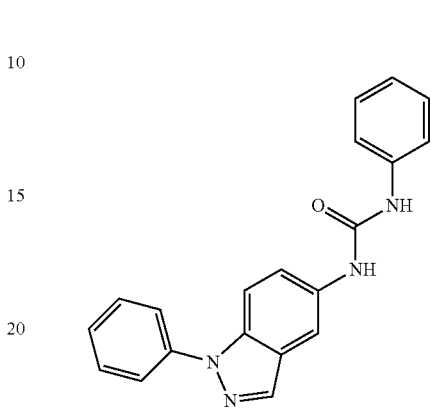

Phenyl isocyanate was added to a solution of 1-phenyl-1H-indazol-5-amine (commercially available, 0.187 g, 0.0008 mol) and TEA (0.240 mL, 0.0017 mol) in DCM (1.80 mL) at 0° C. The resulting reaction mixture was allowed to reach 25° C. and stirred for 16 h. The solvent was evaporated under reduced pressure to obtain a crude product. The crude product was purified on silica gel (60-120 mesh) using 2% ethyl acetate in hexane as an eluent to yield 0.150 g (92% yield) of the title compound. H NMR (400 MHz, DMSO-d6) δ ppm 6.98 (m, 1H) 7.25-7.34 (m, 2H), 7.35-7.46 (m, 1H) 7.48 (m, 3H) 7.55-7.65 (m, 2H) 7.74-7.85 (m, 3H) 8.07 (d, 1H) 8.32 (d, 1H) 8.67 (s, 1H) 8.79 (s, 1H); MS (ES+) m/z 329 [M+H]⁺

Intermediate 30

1-(3-ethoxy-4-phenoxyphenyl)-3-methylurea

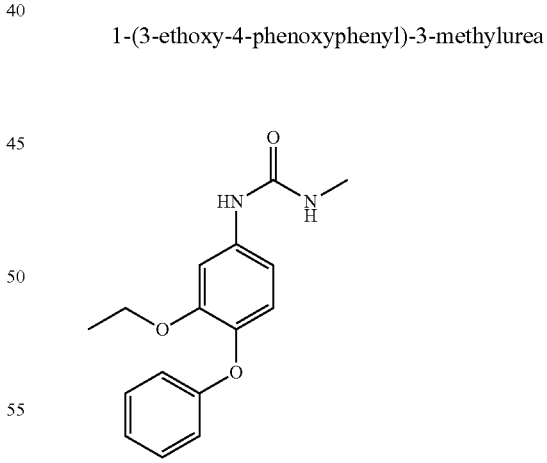

In a 30 ml seal tube previously equipped with a magnetic stirrer and nitrogen balloon, methylaminoformyl chloride (0.090 g, 0.00095 mol) was added drop wise to a solution of 3-ethoxy-4-phenoxyaniline (0.20 g, 0.00087 mol) and TEA (0.244 mL, 0.0017 mol) in DCM (2.0 ml) at 0° C. The reaction mixture was allowed to reach 25° C. and stirred for 16 h. The solvent was evaporated under reduced pressure to obtain a crude product. The crude product was purified on silica gel (60-120 mesh) using 3% methanol in dichloromethane as an eluent to yield 0.093 g (37% yield) of the title compound. H NMR (400 MHz, DMSO-d6) δ ppm 1.13 (m, 3H) 2.62 (s, 3H) 3.94 (m, 2H) 6.76-7.02 (m, 4H) 7.03-7.15 (m, 2H) 7.23-7.32 (m, 2H) 7.36 (s, 1H) 8.46 (s, 1H); MS (ES+) m/z 287 [M+H]+

Intermediate 31

1-methyl-3-[4-phenoxy-3-(tetrahydrofuran-3-yloxy)phenyl]urea

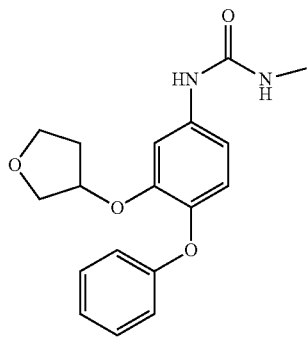 [SMILES: CNC(=O)Nc1ccc(Oc2ccccc2)c(OC2CCOC2)c1]

Methylaminoformyl chloride (0.075 g, 0.0008 mol) was added to a solution of 4-phenoxy-3-(tetrahydrofuran-3-yloxy)aniline (Intermediate 26, 0.200 g, 0.0007 mol) and TEA (0.115 mL, 0.0011 mol) in DCM (2.0 mL) at 0° C. The reaction mixture was allowed to reach 25° C. and stirred for 16 h. The reaction mixture was quenched with water (25 ml) and extracted with ethyl acetate (3×30 ml). The combined organic layers were washed with brine (30 ml), dried over sodium sulfate and evaporated under reduced pressure to obtain the crude product. The crude product was purified on silica gel (60-120 mesh) using 90% ethyl acetate in hexane as an eluent to yield 0.120 g (66% yield) of the title compound. $^1$H NMR (400 MHz, DMSO-d6) δ ppm 1.78 (m, 1H) 2.05 (m, 1H) 2.63 (s, 3H) 3.48 (m, 1H) 3.56 (m, 1H) 3.64 (m, 1H) 3.79 (m, 1H) 4.87 (m, 1H) 6.80 (m, 2H) 6.90 (m, 2H) 6.92-7.02 (m, 2H) 7.23-7.32 (m, 2H) 7.35 (s, 1H) 8.56 (s, 1H).

Intermediate 32

1-[3-(Cyclopentyloxy)-4-phenoxyphenyl]-3-phenylurea

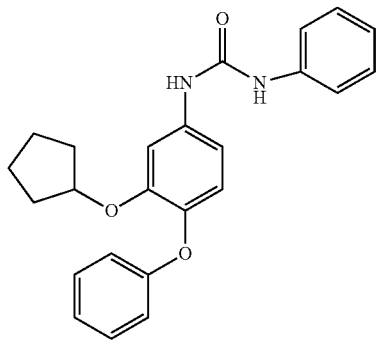 [SMILES: O=C(Nc1ccccc1)Nc1ccc(Oc2ccccc2)c(OC2CCCC2)c1]

Phenyl isocyanate (0.126 g, 0.0010 mol) was added to a solution of 3-(cyclopentyloxy)-4-phenoxyaniline (Intermediate 22, 0.240 g, 0.0008 mol) and TEA (0.135 mL, 0.0013 mol) in DCM (2.50 mL) at 0° C. The resulting reaction mixture was stirred at 25° C. for 16 h. The solvent was evaporated and the reaction mixture was quenched with water (25 ml) and product extracted with ethyl acetate (3×30 ml). The combined organic layers were washed with brine (30 ml). The organic layer was dried over sodium sulfate and evaporated under reduced pressure to obtain the crude product. The crude product was purified on combi flash chromatography by using 5% MeOH in DCM as a mobile phase and 60-120 silica as stationary phase to yield 0.125 g (58% yield) of the title compound.

Intermediate 33

3-[(2-bromo-5-nitrophenoxy)methyl]oxetane

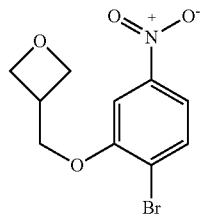

In RB flask previously equipped with a magnetic stirrer and nitrogen balloon, DEAD (1.298 g, 0.0064 mol) was added drop wise to a solution of 2-bromo-5-nitrophenol (0.700 g, 0.0032 mol), oxetan-3-ylmethanol (0.310 g, 0.0035 mol) and triphenyl phosphine (1.685 g, 0.0062 mol) in THF (7.0 mL) at 0° C. The reaction mixture was stirred at 25° C. for 16 h. The reaction mixture was evaporated under reduced pressure to obtain the crude product. The crude product was purified on column chromatography on 100-200 silica by using 15% ethyl acetate in hexane as a mobile phase to yield 1.3 g (quantitative yield) of the title compound that was directly used in the next step. $^1$H NMR (400 MHz, DMSO-d6) δ ppm 3.39-3.52 (m, 1H) 4.39-4.44 (m, 2H) 4.45-4.52 (m, 2H) 4.67-4.75 (m, 2H) 7.72-7.80 (m, 1H) 7.89-7.95 (m, 2H).

Intermediate 34

3-[(5-nitro-2-phenoxyphenoxy)methyl]oxetane

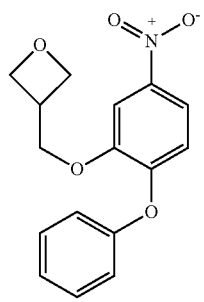

In a 30 ml seal tube flask previously equipped with a magnetic stirrer and nitrogen balloon, NaH (0.030 g, 0.0012 mol) was added portion wise to the solution of Phenol (0.119 g, 0.0012 mol) in DMF (2.80 mL) at 0° C. After stirring for 1 h, 3-[(2-bromo-5-nitrophenoxy)methyl]oxetane (Intermediate 33, 0.280 g, 0.0009 mol) was added portion wise and the reaction mixture was stirred at 120° C. for 16 h. The reaction mixture was quenched with ice-water (50 ml) and extracted with ethyl acetate (3×40 ml). The combined organic layers were washed with brine (30 ml). The organic layer was dried over sodium sulfate and evaporated under reduced pressure to obtain crude product. The crude product was purified on column chromatography by 15% ethyl acetate in hexane as a mobile phase and 60-120 silica as the stationary phase to yield 0.160 g (62% yield) of the title compound. $^1$H NMR (400 MHz, DMSO-d6) δ ppm 3.29 (m, 1H) 4.25 (m, 2H) 4.36 (m, 2H) 4.60-4.41 (m, 2H) 6.99-7.07 (m, 2H) 7.09-7.24 (m, 2H) 7.36-7.46 (m, 2H) 7.87-7.96 (m, 1H) 7.99 (d, 1H).

Intermediate 35

3-(oxetan-3-ylmethoxy)-4-phenoxyaniline

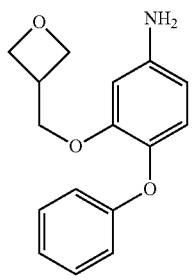 [SMILES: Nc1ccc(Oc2ccccc2)c(OCC2COC2)c1]

10% Pd/C (0.042 g) was added to a solution of 3-[(5-nitro-2-phenoxyphenoxy)methyl]oxetane (Intermediate 34, 0.160 g, 0.0005 mol) in methanol (1.60 mL) at 25° C. The resulting reaction mixture was stirred for 16 h under a hydrogen balloon. The reaction mixture was filtered through a celite bed, which was washed with MeOH (3×10 ml). The filtrate was evaporated under reduced pressure to obtain 0.100 g (66% yield) of the title compound. $^1$H NMR (400 MHz, DMSO-d6) δ ppm 3.14 (m, 1H) 3.98-4.11 (m, 4H) 4.35-4.46 (m, 2H) 5.06 (s, 2H) 6.18 (dd, J=8.4, 2.4 Hz, 1H) 6.38 (d, J=2.5 Hz, 1H) 6.71-6.81 (m, 3H) 6.93 (m, 1H) 7.19-7.28 (m, 2H); MS (ES+) m/z 272 [M+H]$^+$ Intermediate 36

1-methyl-3-[3-(oxetan-3-ylmethoxy)-4-phenoxyphenyl]urea

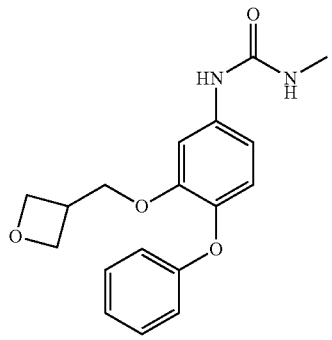 [SMILES: CNC(=O)Nc1ccc(Oc2ccccc2)c(OCC2COC2)c1]

Methylaminoformyl chloride (0.041 g, 0.00043 mol) was added to a solution of 3-(oxetan-3-ylmethoxy)-4-phenoxyaniline (Intermediate 35, 0.041 g, 0.00037 mol) and TEA (0.103 ml, 0.0007 mol) in DCM (1.0 mL) at 0° C. The reaction mixture was stirred at 25° C. for 16 h. The solvent was evaporated under reduced pressure to obtain the crude product. The crude product was purified on chromatography by using 0-5% MeOH in DCM (gradient) as a mobile phase and 60-120 silica as stationary phase to produce 0.120 g of the title compound in quantitative yield. $^1$H NMR (400 MHz, DMSO-d6) δ ppm 2.65 (d, 1H) 3.19-3.03 (m, 2H) 4.15-4.04 (m, 3H) 4.43 (m, 2H) 5.75 (m, 2H) 6.04 (s, 1H) 6.78 (m, 2H) 7.02-6.86 (m, 3H) 7.27 (m, 2H) 7.41 (s, 1H) 8.62 (s, 1H); MS (ES+) m/z 329 [M+H]$^+$ Intermediate 37

1-{3-[(3-Oxetanyl)methoxy]-4-phenoxyphenyl}-3-phenylurea

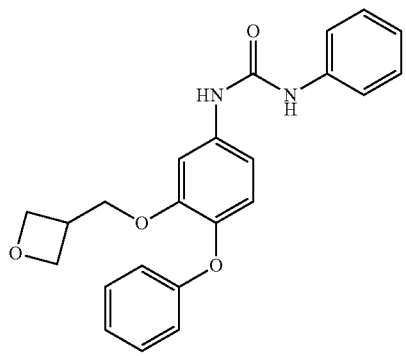 [SMILES: O=C(Nc1ccccc1)Nc1ccc(Oc2ccccc2)c(OCC2COC2)c1]

Phenyl isocyanate (0.283 mL, 0.0025 mol)) was added to a solution of 3-(oxetan-3-ylmethoxy)-4-phenoxyaniline (Intermediate 35, 0.640 g, 0.0023 mol) and TEA (0.662 mL, 0.0047 mol) in DCM (6.4 mL) under stirring at 0° C. The reaction mixture was stirred at 25° C. for 16 h. The solvent was evaporated under reduced pressure to obtain the crude product. The crude product was purified on column chromatography by using 70% ethyl acetate in hexane as a mobile phase and 60-120 silica as stationary phase to produce 0.840 g of the title compound in quantitative yield. $^1$H NMR (400 MHz, DMSO-d6) δ ppm 3.17 (m, 1H) 4.11 (m, 4H) 4.44 (m, 2H) 6.78-6.85 (m, 2H) 6.87-7.08 (m, 4H) 7.29-7.39 (m, 4H) 7.41-7.50 (m, 3H) 8.68 (s, 1H) 8.75 (s, 1H); MS (ES+) m/z 391 [M+H]$^+$ Intermediate 38

4-nitro-1-phenoxy-2-(propan-2-yloxy)benzene

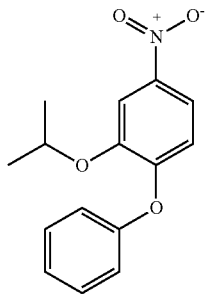

NaH (0.153 g, 0.0063 mol) was added portion wise to a solution of Phenol (0.119 g, 0.0012 mol) stirred in DMF (8.30 mL) under N$_2$ (g) and cooled at 0° C. After 1 h stirring, 1-Bromo-2-isopropoxy-4-nitrobenzene (commercially available, 0.830 g, 0.0031 mol) was added portion wise and the reaction mixture was heated at 120° C. for 16 h. The reaction mixture was quenched with ice-water (50 ml) and extracted with ethyl acetate (3×40 ml). The combined organic layers were washed with brine (30 ml), dried over sodium sulfate and the solvent was evaporated under reduced pressure. The crude product was purified on silica gel (60-120 mesh) using 20% ethyl acetate in hexane as an eluent to obtain 0.638 g (79% yield) of the title compound. $^1$H NMR (400 MHz, DMSO-d6) δ ppm 1.23 (d, 6H) 4.79 (m, 1H) 6.98-7.13 (m, 2H) 7.12-7.25 (m, 1H) 7.28-7.38 (m, 1H) 7.37-7.47 (m, 2H) 7.81-7.94 (m, 2H).

Intermediate 39

4-phenoxy-3-(propan-2-yloxy)aniline

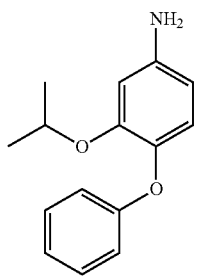 [SMILES: CC(C)Oc1cc(N)ccc1Oc1ccccc1]

35% HCl (0.6 mL) was added to a solution of 4-nitro-1-phenoxy-2-(propan-2-yloxy)benzene (Intermediate 38, 0.638 g, 0.0024 mol) and SnCl$_2$.2H$_2$O (2.490 g, 0.0098 mol) in ethanol (6 mL) at 0° C. The reaction mixture was allowed to slowly reach 25° C. and then heated at 50° C. for 3 h. The reaction mixture was diluted with ethyl acetate (50 ml) and basified with 30% aqueous ammonia to maintained pH 7-8. The precipitate was filter through celite pad and washed with ethyl acetate (2×10 ml). The filtrate was washed with water (3×40 ml) followed by the washing with brine (40 ml), dried over sodium sulfate and the solvent evaporated under reduce pressure to obtain 0.510 g (76% yield) of the title compound. $^1$H NMR (400 MHz, DMSO-d6) δ ppm 1.25 (m, 6H) 4.40 (m, 1H) 4.95 (s 2H) 6.00-6.19 (m, 1H) 6.35 (d, 1H) 6.69-6.81 (m, 1H) 6.82-6.99 (m, 1H) 6.99-7.19 (m, 2H) 7.19-7.28 (m, 2H); MS (ES+) m/z 244 [M+H]$^+$ Intermediate 40

1-methyl-3-[4-phenoxy-3-(propan-2-yloxy)phenyl]urea

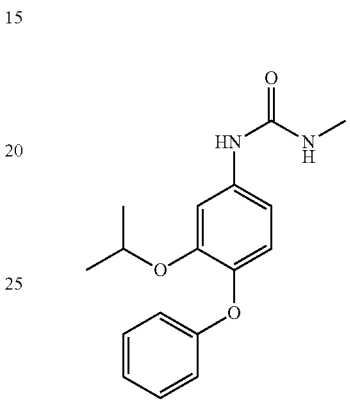

Methylaminoformyl chloride (0.074 ml, 0.0008 mol) was added to a solution of 4-phenoxy-3-(propan-2-yloxy)aniline (Intermediate 39, 0.200 g, 0.0007 mol) and TEA (0.205 mL, 0.0014 mol) in DCM (2 mL) under stirring at 0° C. The reaction mixture was stirred at 25° C. for 16 h. The solvent was evaporated under reduced pressure to obtain crude product. The crude product was purified on silica gel (60-120 mesh) using 2% methanol in dichloromethane as an eluent to obtain 0.103 g (41% yield) of the title compound. $^1$H NMR (400 MHz, DMSO-d6) δ ppm 1.13-1.32 (m, 6H) 4.35-4.55 (m, 1H) 2.61 (s, 3H) 6.75-7.02 (m, 4H) 7.02-7.15 (m, 2H) 7.27 (m, 2H) 7.37 (s, 1H) 8.53 (s, 1H); MS (ES+) m/z 301 [M+H]$^+$ Intermediate 41

1-[4-phenoxy-3-(propan-2-yloxy)phenyl]-3-phenylurea

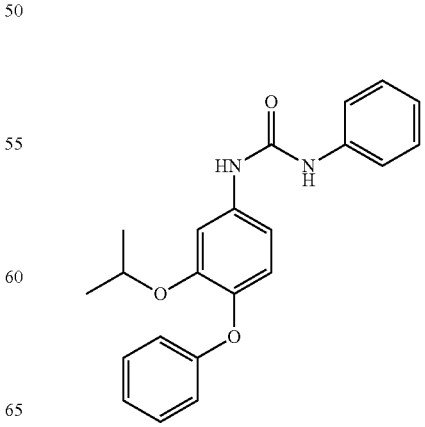

Phenyl isocyanate (0.143 mL, 0.0012 mol) was added to a solution of 4-phenoxy-3-(propan-2-yloxy)aniline (Intermediate 39, 0.300 g, 0.0010 mol) and TEA (0.307 mL, 0.0021 mol) in DCM (3 mL) under stirring at 0° C. The reaction mixture was allowed to reach 25° C. and stirred for 16 h. The solvent was evaporated under reduced pressure. The crude product was purified on silica gel (60-120 mesh) using 2% methanol in dichloromethane as an eluent to yield 0.103 g (53% yield) of the title compound. $^1$H NMR (400 MHz, DMSO-d6) δ ppm 1.20-1.37 (m, 6H) 4.51 (m, 1H) 6.76-6.92 (m, 1H) 6.89-7.05 (m, 3H) 7.11-7.19 (m, 1H) 7.24-7.33 (m, 4H) 7.40-7.50 (m, 4H), 8.60-8.73 (brs, 2H); MS (ES+) m/z 363 [M+H]$^+$ Intermediate 42

2-(2-methoxyethoxy)-4-nitro-1-phenoxybenzene

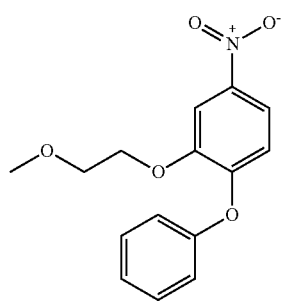

In a 30 ml seal tube previously equipped with a magnetic stirrer and nitrogen balloon, NaH (0.109 g, 0.0045 mol) was added portion wise to a solution of Phenol (0.224 g, 0.0022 mol) in DMF (6.3 mL) cooled at 0° C. After 1 h, 1-bromo-2-(2-methoxyethoxy)-4-nitrobenzene (commercially available, 0.630 g, 0.0022 mol) was added portion wise and the reaction mixture was heated at 120° C. for 16 h. The reaction mixture was quenched with ice-water (50 ml) and extracted with ethyl acetate (3×40 ml). The combined organic layers were washed with brine (30 ml), dried over sodium sulfate and evaporated under reduced pressure to obtain the crude product. The crude product was purified on silica gel (60-120 mesh) using 10% ethyl acetate in hexane as an eluent to yield 0.450 g (68% yield) of the title compound.

$^1$H NMR (400 MHz, DMSO-d6) δ 3.35 (s, 3H) 3.70-3.77 (m, 2H) 4.32-4.39 (m, 2H) 7.76 (m, 3H) 7.85-7.94 (m, 5H).

Intermediate 43

3-(2-methoxyethoxy)-4-phenoxyaniline

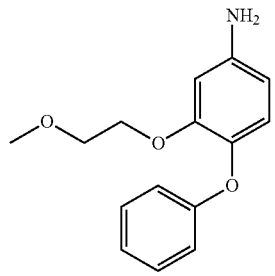 [SMILES: COCCOc1cc(N)ccc1Oc1ccccc1]

35% HCl$_{(aq)}$ (0.30 mL) and water (0.1 mL) were added to a solution of 2-(2-methoxyethoxy)-4-nitro-1-phenoxybenzene (Intermediate 42, 0.450 g, 0.0015 mol) and SnCl$_2$.2H$_2$O (1.400 g, 0.0062 mol) in ethanol under stirring at 0° C. The reaction mixture was allowed to reach 25° C. and then heated at 50° C. for 3 h. The reaction mixture was diluted with ethyl acetate (50 ml) and basified with 30% aqueous ammonia to maintain pH 7-8. The precipitate was filter through celite pad and washed with ethyl acetate (2×10 ml). The filtrate was washed with water (3×40 ml) and brine (40 ml), dried over sodium sulfate and evaporated under reduced pressure to obtain 0.310 g (77% yield) of the title compound which was used directly in the next step without further purification. $^1$H NMR (400 MHz, DMSO-d6) δ ppm 3.13 (s, 3H) 3.41-3.48 (m, 2H) 3.86-3.97 (m, 2H) 5.04 (s, 2H) 6.16 (m, 1H) 6.36 (d, 1H) 6.70-6.81 (m, 3H) 6.83-6.98 (m, 1H) 7.20-7.29 (m, 2H); MS (ES+) m/z 260 [M+H]$^+$ Intermediate 44

1-[3-(2-methoxyethoxy-4-phenoxyphenyl]-3-methylurea

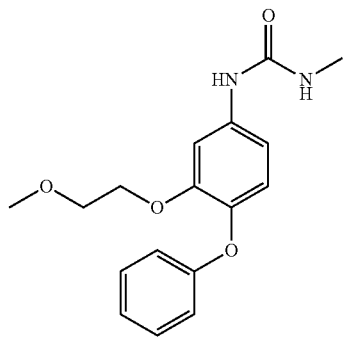

Methylaminoformyl chloride (0.056 g, 0.0006 mol) was added to a solution of 3-(2-methoxyethoxy)-4-phenoxyaniline (Intermediate 43, 0.180 g, 0.0005 mol) and TEA (0.130 mL, 0.0010 mol) in DCM (1.30 mL) at 0° C. The reaction mixture was stirred at 25° C. for 16 h. The solvent was evaporated under reduced pressure and the crude product was purified on silica gel (60-120 mesh) using 50% ethyl acetate in hexane as an eluent to 0.063 g (28% yield) of the title compound. $^1$H NMR (400 MHz, DMSO-d6)) δ ppm 2.62-2.66 (m, 3H) 3.15 (s, 3H) 3.44-3.50 (m, 2H) 3.95-4.05 (m, 2H) 6.01 (m, 1H) 6.77-6.84 (m, 2H) 6.86-6.94 (m, 2H) 6.95-7.01 (m, 1H) 7.23-7.31 (m, 2H) 7.36 (s, 1H) 8.52 (s, 1H); MS (ES+) m/z 317 [M+H]$^+$

Intermediate 45

1-[3-(2-methoxyethoxy)-4-phenoxyphenyl]-3-phenylurea

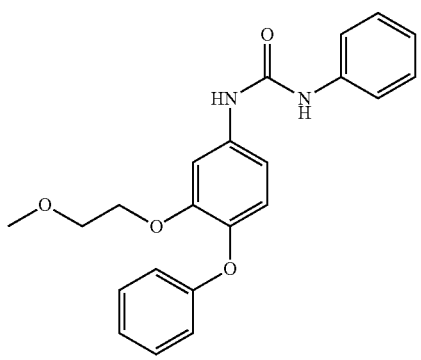 [SMILES: COCCOc1cc(NC(=O)Nc2ccccc2)ccc1Oc1ccccc1]

Phenyl isocyanate (0.090 g, 0.0007 mol) was added to a solution of 3-(2-methoxyethoxy)-4-phenoxyaniline (Intermediate 43, 0.180 g, 0.0006 mol) and TEA (0.140 mL, 0.0010 mol) in DCM (2.0 mL) under stirring at 0° C. The reaction mixture was stirred at 25° C. for 16 h. The solvent was evaporated and the reaction mixture was quenched with water (25 ml) and extracted with ethyl acetate (3×30 ml). The combined organic layers were washed with brine (30 ml). The organic layer was dried over sodium sulfate and evaporated under reduced pressure to obtain crude product. The crude product was purified on silica gel (60-120 mesh) using 50% ethyl acetate in hexane as an eluent to obtain 0.135 g (51% yield) of the title compound. $^1$H NMR (400 MHz, DMSO-d6) δ ppm 3.13 (s, 3H) 3.43-3.52 (m, 2H) 4.00-4.09 (m, 2H) 6.79-6.87 (m, 2H) 6.90-7.03 (m, 4H) 7.20-7.35 (m, 4H) 7.39-7.50 (m, 3H) 8.67 (s, 1H), 8.72 (s, 1H); MS (ES+) m/z 379 [M+H]$^+$

Intermediate 46

2-(benzyloxy)-4-nitro-1-phenoxybenzene

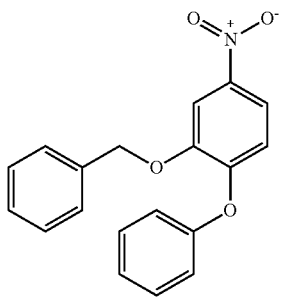

In a 30 ml seal tube previously equipped with a magnetic stirrer and nitrogen balloon, NaH (0.046 g, 1.95 mmol) was added portion wise to a solution of Phenol (0.183 g, 1.95 mmol) in DMF (6.0 mL) cooled at 0° C. After 1 hour, benzyl 2-bromo-5-nitrophenyl ether (commercially available, 0.600 g, 1.95 mmol) was added portion wise and the reaction mixture was heated at 120° C. for 16 h. The reaction mixture was quenched with ice-water (50 ml) and extracted with ethyl acetate (3×40 ml). The combined organic layers were washed with brine (30 ml), dried over sodium sulfate and evaporated under reduced pressure. The crude product was purified on silica gel (60-120 mesh) using 20% ethyl acetate in hexane as an eluent to obtained 0.386 g (82% yield) of the title compound. $^1$H NMR (400 MHz, DMSO-d6) δ ppm 5.29 (s, 2H) 7.03-7.14 (m, 3H) 7.22 (m, 1H) 7.27-7.40 (m, 5H) 7.39-7.48 (m, 2H) 7.90 (m, 1H) 8.05 (m, 1H); MS (ES+) m/z 322 [M+H]$^+$

Intermediate 47

3-(benzyloxy)-4-phenoxyaniline

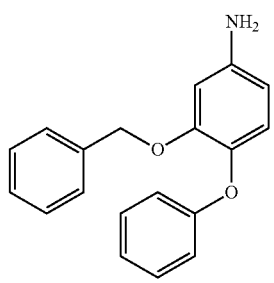 [SMILES: Nc1ccc(Oc2ccccc2)c(OCc2ccccc2)c1]

35% HCl$_{(aq)}$ (0.35 ml) was added to a solution of 2-(benzyloxy)-4-nitro-1-phenoxybenzene (Intermediate 46, 0.386 g, 1.2012 mmol) and SnCl$_2$.2H$_2$O (0.854 g, 3.788 mmol) in ethanol under stirring at 0° C. The reaction mixture was heated at 50° C. for 5 h. The reaction mixture was diluted with ethyl acetate (50 ml) and basified with 30% aqueous ammonia to maintain pH 7-8. The mixture was filtered through celite pad and washed with ethyl acetate (3×5 ml). The filtrate was washed with water (3×40 ml) and with brine (40 ml), dried over sodium sulfate and evaporated under reduced pressure to obtain 0.330 g of the title compound in quantitative yield. $^1$H NMR (400 MHz, DMSO-d6) δ ppm 5.06 (s, 2H) 5.15 (s, 2H) 6.18 (m, 1H) 6.43 (m, 1H) 6.56-6.70 (m, 1H) 6.72-6.88 (m, 2H) 6.85-7.00 (m, 1H) 7.08-7.21 (m, 2H) 7.21-7.31 (m, 3H) 7.31-7.51 (m, 2H); MS (ES+) m/z 292 [M+H]$^+$

Intermediate 48

1-[3-(benzyloxy)-4-phenoxyphenyl]-3-methylurea

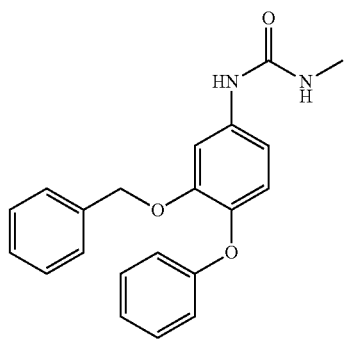 [SMILES: CNC(=O)Nc1ccc(Oc2ccccc2)c(OCc2ccccc2)c1]

Methylaminoformyl chloride (0.036 g, 0.386 mmol) was added to a solution of 3-(benzyloxy)-4-phenoxyaniline (Intermediate 47, 0.125 g, 0.429 mmol) and TEA (0.060 mL, 0.429 mmol) in DCM (2.0 mL) under stirring at 0° C. The reaction mixture was stirred at 25° C. for 16 h. The reaction mixture was quenched with water (20 ml) and extracted with DCM (3×30 ml). The combined organic layers were washed with brine (30 ml), dried over sodium sulfate and evaporated under reduced pressure. The crude product was purified on silica gel (60-120 mesh) using 100% ethyl acetate as an eluent to obtained 0.100 g (67% yield) of the title compound. $^1$H NMR (400 MHz, DMSO-d6) δ ppm 3.97 (s, 3H) 5.05 (s, 2H) 6.17 (m, 1H) 6.42 (m, 1H) 6.73-6.84 (m, 3H) 6.91-7.00 (m, 1H) 7.08-7.17 (m, 2H) 7.19-7.32 (m, 5H) 7.62 (s, 1H) 8.56 (s, 1H); MS (ES+) m/z 349 [M+H]$^+$ Intermediate 49

1-methyl-3-(1-phenyl-1H-indazol-5-yl)urea

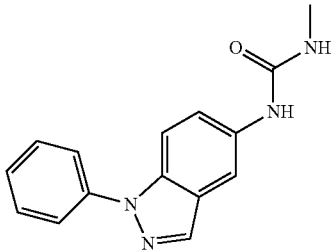 [SMILES: CNC(=O)Nc1ccc2c(cnn2-c2ccccc2)c1]

Methylaminoformyl chloride (0.100 g, 0.0010 mol) was added to a stirred solution of 1-phenyl-1H-indazol-5-amine (commercially available, 0.187 g, 0.0008 mol) and TEA (0.240 ml, 0.0017 mol) in DCM (1.80 mL) at 0° C. The reaction mixture was stirred at 25° C. for 16 h. The solvent was evaporated under reduced pressure. The crude product was purified on silica gel (60-120 mesh) using 50% ethyl acetate in hexane as an eluent to yield 0.085 g (35% yield) of the title compound. $^1$H NMR (400 MHz, DMSO-d6) δ 2.66 (s, 3H) 6.00 (m, 1H) 7.32-7.41 (m, 2H) 7.53-7.61 (m, 2H) 7.73-7.78 (m, 3H) 8.00 (s, 1H) 8.26 (s, 1H) 8.61 (s, 1H).

Intermediate 50

1-(3-methoxy-5-methyl-4-phenoxyphenyl)-3-methylurea

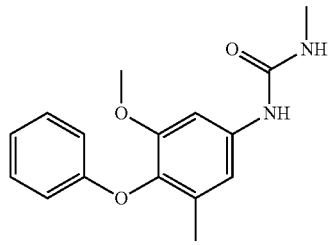 [SMILES: CNC(=O)Nc1cc(C)c(Oc2ccccc2)c(OC)c1]

In a 10 ml seal tube flask previously equipped with a magnetic stirrer and nitrogen balloon, methylaminoformyl chloride (0.048 ml, 0.0052 mol) was added portion wise to a solution of 3-methoxy-5-methyl-4-phenoxyaniline (Intermediate 19, 0.100 g, 0.00043 mol) and TEA (0.122 mL, 0.00087 mol) in DCM (1.0 mL) at 0° C. The reaction mixture was stirred for 16 hours at 25° C. The reaction mixture was concentrate under reduced pressure to obtain the crude product. The crude product was purified on silica gel using 10% methanol in dichloromethane as an eluent to 0.080 g (66% yield) of the title compound. $^1$H NMR (400 MHz, DMSO-d6) δ ppm 2.00 (s, 3H) 3.18 (s, 3H) 3.63 (s, 3H) 6.05 (s, 1H) 6.68-6.75 (m, 1H) 6.82 (m, 2H) 6.94 (m, 2H) 7.18-7.30 (m, 2H) 8.57 (s, 1H); MS (ES+) m/z 287 [M+H]$^+$ Intermediate 51

2-methoxy-3-methyl-1-nitro-4-phenoxybenzene

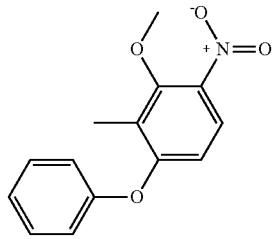

In a 30 ml seal tube previously equipped with a magnetic stirrer and nitrogen balloon, NaH (0.273 g, 0.0113 mol) was added portion wise to a solution of Phenol (0.588 g, 0.0062 mol) in DMF (14.0 mL) cooled at 0° C. After 1 hour, 1-bromo-3-methoxy-2-methyl-4-nitrobenzene (commercially available, 1.40 g, 0.0056 mol) was added portion wise and then the reaction mixture was heated at 120° C. for 16 h. The reaction mixture was quenched with ice-water (50 ml) and extracted with ethyl acetate (3×40 ml). The combined organic layers were washed with brine (30 ml), dried over sodium sulfate and evaporated under reduce pressure to obtain crude product. The crude product was purified on silica gel (60-120 mesh) using 5% ethyl acetate in hexane as an eluent to yield 0.815 g (55% yield) of the title compound. $^1$H NMR (400 MHz, DMSO-d6) δ ppm 2.26 (s, 3H) 3.87 (s, 3H) 7.20-7.07 (m, 2H) 7.34-7.21 (m, 1H) 7.52-7.42 (m, 2H) 7.81 (m, 1H) 7.93 (d, 1H).

Intermediate 52

2-methoxy-3-methyl-4-phenoxyaniline

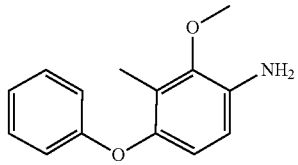 [SMILES: COc1c(N)ccc(Oc2ccccc2)c1C]

35% HCl$_{(aq)}$ (0.80 mL) was added to a solution of 2-methoxy-3-methyl-1-nitro-4-phenoxybenzene (Intermediate 51, 0.815 g, 0.0031 mol) and SnCl$_2$.2H$_2$O (2.83 g, 0.0120 mol) in ethanol (10.0 mL) under stirring at 0° C. The resulting reaction mixture was heated at 50° C. for 3 h. The reaction mixture was diluted with ethyl acetate (50 ml) and basified with 30% aqueous ammonia to maintain pH 7-8. The mixture was filtered through a celite pad and washed with ethyl acetate (2×5 ml). The filtrate were washed with water (3×40 ml) followed by washing with brine (40 ml), dried over sodium sulfate and evaporated under reduced pressure to yield 0.715 g of the title compound. MS (ES+) m/z 230 [M+H]+

Intermediate 53

1-(2-methoxy-3-methyl-4-phenoxyphenyl)-3-phenylurea

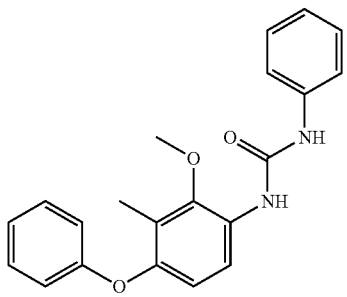 [SMILES: COc1c(NC(=O)Nc2ccccc2)ccc(Oc2ccccc2)c1C]

Phenyl isocyanate (0.446 g, 0.0037 mol) was added to a solution of 2-methoxy-3-methyl-4-phenoxyaniline (Intermediate 52, 0.715 g, 0.0031 mol) and TEA (0.875 mL, 0.0062 mol) in DCM (7.10 mL) under stirring at 0° C. The resulting reaction mixture was stirred at 25° C. for 16 h. The reaction mixture was quenched with water (25 ml) and extracted with ethyl acetate (3×30 ml). The combined organic layers were washed with brine (30 ml), dried over sodium sulfate and evaporated under reduced pressure to yield 0.394 g (36% yield) of the title compound. $^1$H NMR (400 MHz, DMSO-d6) δ ppm 2.09 (s, 3H) 3.75 (s, 3H) 6.73 (d, 1H) 6.86 (m, 2H) 6.97 (m, 1H) 7.05 (m, 1H) 7.25-7.38 (m, 4H) 7.47 (m, 2H) 8.04 (d, 1H) 8.33 (s, 1H) 9.30 (s, 1H); MS (ES+) m/z 349 [M+H]+

Intermediate 54

1-[3-methyl-4-(phenylsulfanyl)phenyl]-3-phenylurea

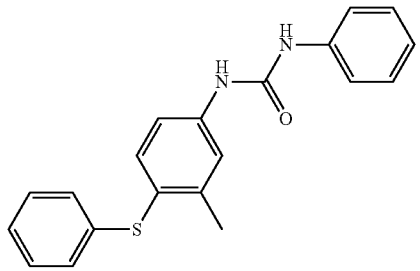 [SMILES: Cc1cc(NC(=O)Nc2ccccc2)ccc1Sc1ccccc1]

Phenyl isocyanate (1.05 g, 0.0088 mol) was added to a solution of 3-methyl-4-(phenylsulfanyl)aniline (commercially available, 1.74 g, 0.0080 mol) and TEA (2.27 mL, 0.0161 mol) in DCM (17.4 mL) under stirring at 0° C. The reaction mixture was stirred at 25° C. for 16 h. The solvent was evaporated and the reaction mixture was quenched with water (25 ml) and extracted with Ethyl Acetate (3×30 ml). The combined organic layers were washed with brine (25 ml). The organic layer was dried over sodium sulfate and evaporated under reduced pressure to obtain the crude product. The crude product was purified on column chromatography by using 15% ethyl acetate in hexane as a mobile phase and 100-200 silica as stationary phase to yield 1.10 g (40% yield) of the title compound. $^1$H NMR (400 MHz, DMSO-d6) δ ppm 2.29 (s, 3H) 6.93-7.08 (m, 3H) 7.12-7.21 (m, 1H) 7.26-7.36 (m, 4H) 7.38 (m, 2H) 7.41-7.53 (m, 3H) 8.74 (s, 1H) 8.83 (s, 1H); MS (ES+) m/z 335 [M+H]+

Intermediate 55

3-methyl-5-nitro-1-phenyl-1H-indole

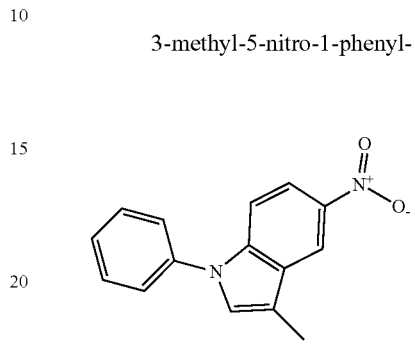

To a solution of 3-methyl-5-nitro-1H-indole (commercially available, 0.500 g, 0.0028 mol) in 1,4-dioxane (5.0 mL) was added dry cesium carbonate (2.770 g, 0.0085 mol) followed by the addition of Iodobenzene (0.753 g, 0.0036 mol) at 0° C. After 10 minutes of degassing with argon gas, X-phos (0.270 g, 0.00056 mol) and Pd(OAc)$_2$ (0.063 g, 0.00028 mol) were added under argon atmosphere. The reaction mixture was heated at 110° C. for 16 h under argon atmosphere. The reaction mixture was quenched with ice-water (30 ml) and extracted with ethyl acetate (3×25 ml). The combined organic layers were washed with brine (20 ml), dried over sodium sulfate and concentrated under reduce pressure to obtain crude product. The crude product was purified on silica gel (60-120 mesh) using 2% ethyl acetate in hexane as an eluent to yield 0.430 g (56% yield) of the title compound. $^1$H NMR (400 MHz, DMSO-d6) δ ppm 2.33 (s, 3H) 7.40-7.50 (m, 2H) 7.58-7.80 (4H) 8.02-8.11 (m, 2H) 8.60 (d, 1H); MS (ES+) m/z 253 [M+H]+

Intermediate 56

3-methyl-1-phenyl-1H-indol-5-amine

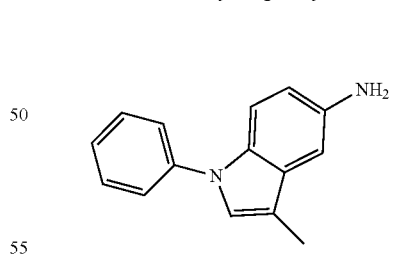

To a solution of 3-methyl-5-nitro-1-phenyl-1H-indole (Intermediate 55, 0.430 g, 0.0017 mol) in ethanol (4.30 mL) SnCl$_2$.2H$_2$O (1.538 g, 0.0068 mol) was added followed by the addition of 35% HCl (0.430 mL) at 0° C. The reaction mixture was heated at 50° C. for 5 h. The reaction mixture was diluted with ethyl acetate (40 ml) and basified with 30% ammonia aqueous solution. The precipitated was filtered and washed with ethyl acetate (3×25 ml). The combined organic layer was washed with water (3×20 ml) and brine (20 ml), dried over sodium sulfate and the solvent was evaporated under reduced pressure. The crude product was purified on basic alumina oxide using 40% ethyl acetate in hexane as an eluent to yield 0.200 g (55% yield) of the title compound. MS (ES+) m/z 223 [M+H]+

Intermediate 57

1-(3-methyl-1-phenyl-1H-indol-5-yl)-3-phenylurea

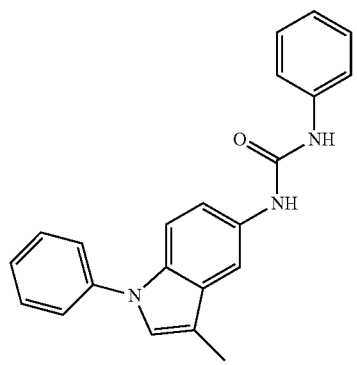 [SMILES: Cc1cn(-c2ccccc2)c2ccc(NC(=O)Nc3ccccc3)cc12]

To a solution of 3-methyl-1-phenyl-1H-indol-5-amine (Intermediate 56, 0.200 g, 0.0009 mol) in DCM (3.00 mL), sodium bicarbonate (0.23 g, 0.0027 mol) was added followed by addition of Triphosgene (0.176 g, 0.00059 mol) at 0° C. under nitrogen atmosphere. After stirring for 4 h at 0° C., aniline (0.092 g, 0.00099 mol) and sodium bicarbonate (0.23 g, 0.0027 mol) were added at 0° C. under nitrogen atmosphere. The resulting reaction mixture was allowed reach 25° C. and stirred for 16 hours. The reaction mixture was quenched with water (25 ml) and extracted with dichloromethane (3×30 ml). The combined organic layer was washed with brine (30 ml), dried over sodium sulfate and the solvent evaporated under reduced pressure to yield 0.310 g (quantitative yield) of the title compound that was used in the next step without further purification. $^1$H NMR (400 MHz, DMSO-d6) δ ppm 2.29 (s, 3H) 6.91-7.01 (m, 1H) 7.11-7.16 (m, 1H), 7.23-7.37 (m, 3H), 7.42-7.51 (m, 4H) 7.53-7.58 (m, 3H) 7.68-7.81 (m, 2H) 8.61 (s, 1H) 8.69 (s, 1H); MS (ES+) m/z 342 [M+H]+

Intermediate 58

1-benzyl-3-methyl-5-nitro-1H-indole

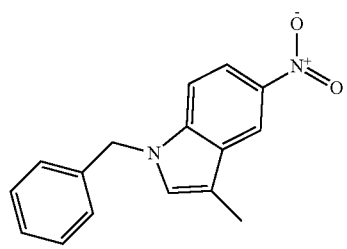

To a solution of 3-methyl-5-nitro-1H-indole (commercially available, 1.00 g, 0.0056 mol) in DMF (10.0 mL) was added potassium tert-butoxide (0.764 g, 0.0068 mol) at 0° C. After 20 min of stirring at 0° C., benzylbromide (0.970 g, 0.0056 mol) was added dropwise and the reaction mixture was allowed to slowly reach 25° C. and stirred for 18 h under nitrogen atmosphere. The reaction mixture was quenched with ice-water (50 ml) and extracted with ethyl acetate (3×40 ml). The combined organic layer was washed with brine (30 ml), dried over sodium sulfate and the solvent evaporated under reduced pressure. The crude product was purified using flash chromatography on silica gel (60-120 mesh) using 10% ethyl acetate in hexane as eluent to yield 0.935 g (62% yield) of the title compound. $^1$H-NMR (400 MHz, DMSO-d$_6$): δ ppm 2.33 (s, 3H). 5.46 (s, 2H), 7.35-7.20 (m, 5H), 7.53 (s, 1H), 7.65 (d, 1H), 8.00 (dd, 1H), 8.50 (d, 1H). MS (ES+) m/z 267 [M+H]+

Intermediate 59

1-benzyl-3-methyl-1H-indol-5-amine

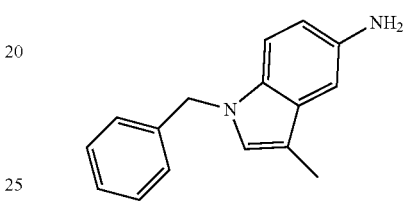

To a solution of 1-benzyl-3-methyl-5-nitro-1H-indole (Intermediate 58, 0.0081 mol) in ethanol (9.30 mL) was added SnCl$_2$.2H$_2$O (3.151 g, 0.0326 mol) followed by the addition of 35% HCl (0.930 mL) at 0° C. The reaction mixture was heated at 50° C. for 5 h. The reaction mixture was diluted with ethyl acetate (50 ml) and basified with 30% ammonia aqueous solution. The precipitated was filtered off and washed with ethyl acetate (3×5 ml). The combined organic layer was washed with water (3×40 ml) followed by the washing with brine (40 ml), dried over sodium sulfate and the solvent evaporated under reduce pressure. The crude product was purified on flash chromatography with basic alumina oxide using 50% ethyl acetate in hexane as an eluent to obtained 0.630 g (71% yield) of the title compound. $^1$H-NMR (400 MHz, DMSO-d$_6$): δ ppm 2.11 (s, 3H) 4.45 (s, 2H) 5.71 (s, 2H) 6.44 (d, 1H) 6.59 (s, 1H) 7.07-6.99 (m, 2H) 7.10-7.13 (m, 2H) 7.18-7.28 (m, 3H); MS (ES+) m/z 237 [M+H]+

Intermediate 60

1-(1-benzyl-3-methyl-1H-indol-5-yl)-3-phenylurea

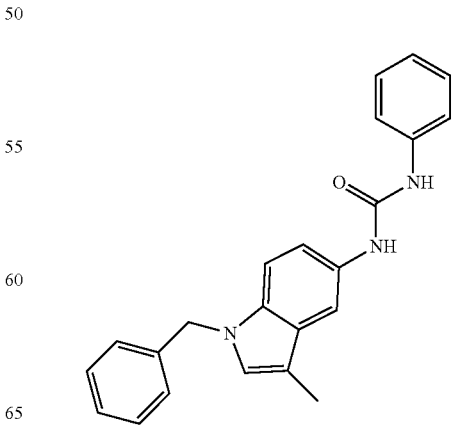

To a solution of 1-benzyl-3-methyl-1H-indol-5-amine (Intermediate 59, 0.300 g, 0.0012 mol) in DCM (3.00 mL) was added TEA (0.356 mL, 0.0025 mol) followed by the addition of phenyl isocyanate (0.166 g, 0.0013 mol) to 0° C. under nitrogen atmosphere. The reaction mixture was allowed to reach at 25° C. and stirred for 16 h. The solid obtained was filtered off and retained. The obtained solid was stirred in n-pentane (10 mL) for 15 min. The solid was filtered of and washed with n-pentane (5 mL) to obtain 0.425 g (94% yield) of the solid title compound. The compound was used in the next step without further purification. $^1$H NMR (400 MHz, DMSO-d6) δ ppm 2.25 (s, 3H) 5.31 (s, 2H) 6.91-6.99 (m, 1H) 7.02 (dd, 1H) 7.16-7.19 (m, 2H) 7.20-7.32 (m, 7H) 7.45 (app d, 2H) 7.67 (d, 1H) 8.43 (s, 1H) 8.56 (s, 1H); MS (ES+) m/z 356 [M+H]$^+$ Intermediate 61

1-methyl-3-(3-methyl-1-phenyl-1H-indol-5-yl)urea

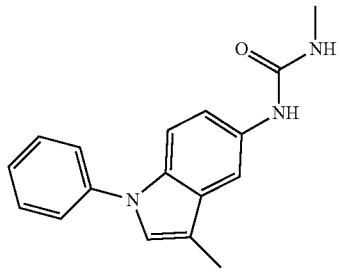 [SMILES: CNC(=O)Nc1ccc2c(c1)c(C)cn2-c1ccccc1]

To a solution of 3-methyl-1-phenyl-1H-indol-5-amine (Intermediate 56, 0.150 g, 0.00067 mol) in DCM (1.50 ml) was added sodium bicarbonate (0.172 g, 0.0020 mol) followed by addition of triphosgene (0.132 g, 0.00044 mol) at 0° C. under nitrogen atmosphere. After stirring for 4 h at 0° C., 33% methylamine solution in EtOH (0.069 mL, 0.00074 mol) and sodium bicarbonate (0.172 g, 0.0020 mol) were added. The reaction mixture was allowed to reach at 25° C. and stirred for 16 h. The reaction mixture was quenched with water (15 ml) and extracted with dichloromethane (3×20 ml). The combined organic layer was washed with brine (15 ml), dried over sodium sulfate and the solvent was evaporated under reduce pressure to yield 0.070 g (37% yield) of the title compound that was used in the next step without further purification. MS (ES+) m/z 280 [M+H]$^+$ Intermediate 62

1-(1-benzyl-3-methyl-1H-indol-5-yl)-3-methylurea

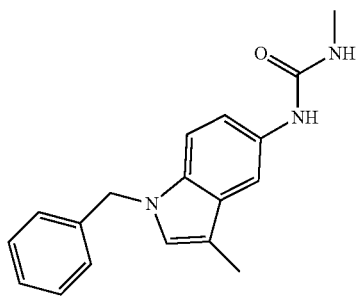 [SMILES: CNC(=O)Nc1ccc2c(c1)c(C)cn2Cc1ccccc1]

To a solution of 1-benzyl-3-methyl-1H-indol-5-amine (Intermediate 59, 0.480 g, 0.0020 mol) in DCM (4.80 mL) cooled to 0° C. and under N$_2$(g), TEA (0.410 mL, 0.0040 mol) was added under stirring followed by addition of N-methylformyl chloride (0.187 g, 0.0020 mol). The reaction mixture was allowed to reach 25° C. and stirred for 16 h.

The solid precipitates were filtered off and washed with n-pentane (10 ml) to yield 0.230 g (38%) of the title compound. The crude product was used in the next step without further purification. MS (ES+) m/z 294 [M+H]+

Intermediate 63

1-(3-chloro-4-phenoxyphenyl)-3-phenylurea

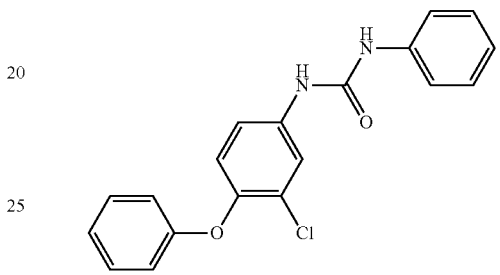

A solution of 3-chloro-4-phenoxyaniline (commercially available, 1.2 g, 0.0054 mol) and TEA (1.53 ml, 0.0109 mol) in DCM (12 ml) was stirred at 0° C. Phenyl isocyanate (0.781 g, 0.0065 mol) was added and the resulting reaction mixture was allowed to reach 25° C. and stirred for 16 h. The solvent was removed under reduced pressure and the reaction mixture was quenched with ice-water (30 ml). The resulting solution was extracted with Ethyl Acetate (3×40 ml) and the combined organic layer was washed with brine (30 ml). The organic layer was dried over sodium sulfate and evaporated under reduced pressure to obtain the crude product. The crude product was purified by column chromatography on silica gel (100-200 mesh) using 40% ethyl acetate in hexanes as an eluent to obtain 1.19 g (64%) of the title compound. $^1$H NMR (400 MHz, DMSO-d6) δ ppm 6.86-6.97 (m, 2H) 6.99 (t, J=7.6 Hz, 1H) 7.04-7.16 (m, 2H) 7.24-7.41 (m, 5H) 7.42-7.50 (m, 2H) 7.86 (d, J=2.6 Hz, 1H) 8.76 (s, 1H) 8.90 (s, 1H); MS (ES+) m/z 339 [M+H]+

Intermediate 64

1-(3-methyl-4-phenoxyphenyl)-3-(5-methylthiophen-2-yl)urea

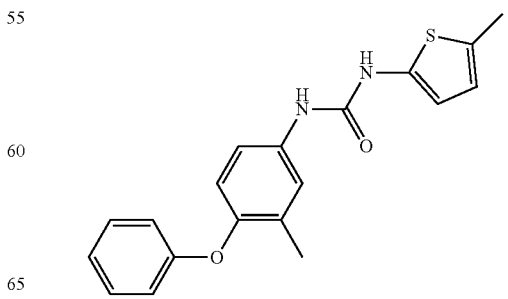

A solution of 5-methyl-2-thiophenamine (0.670 g, 0.0045 mol), NaHCO$_3$(0.984 g, 0.0112 mol) in DCM (7.5 mL) was stirred at 0° C. To the reaction mixture, Triphosgene (0.722 g, 0.0024 mol) was added and the resulting reaction mixture was stirred at 0° C. for 4 hours. To the reaction mixture 3-methyl-4-phenoxyaniline (0.750 g, 0.0037 mol) and NaHCO$_3$ (0.984 g, 0.0112 mol) were added and the mixture was allowed to reach 25° C. and stirred for 16 hours. The solvent was evaporated and the reaction mixture was diluted with water (30 ml) and the product was extracted with ethyl acetate (3×40 m). The combined organic layer was washed with brine (30 ml) and dried over sodium sulphate and evaporated under reduced pressure to obtain the crude product. The crude product was purified on combi-flash chromatography using 50% ethyl acetate in hexanes as an eluent to obtain 1.07 g (84% yield) of the title compound. $^1$H NMR (400 MHz, DMSO-d6) δ ppm 2.11 (s, 3H), 2.33 (S, 3H), 6.33 (d, J=3.6 Hz, 1H), 6.48 (d, J=3.5, 1.4 Hz, 1H), 6.93-6.81 (m, 3H), 7.04 (t, J=7.3 Hz, 1H), 7.31 (m, 3H), 7.41 (d, J=2.6 Hz, 1H), 8.67 (s, 1H), 9.43 (s, 1H); MS (ES+) m/z 339 [M+H]+

Intermediate 65

1-(4-fluorophenyl)-3-(3-methyl-4-phenoxyphenyl) urea

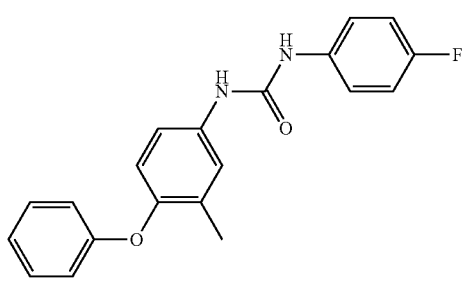 [SMILES: Cc1cc(NC(=O)Nc2ccc(F)cc2)ccc1Oc1ccccc1]

A mixture of 3-methyl-4-phenoxyaniline (0.375 g, 0.0018 mol), NaHCO$_3$ (0.474 g, 0.0056 mol) in DCM (3.75 ml) was stirred and cooled to 0° C. Triphosgene (0.368 g, 0.0012 mol) was added and the resulting reaction mixture was stirred at 0° C. for 4 h. 4-fluro-aniline (0.209 g, 0.0018 mol) and NaHCO$_3$ (0.474 g, 0.0056 mol) were added to the reaction mixture and stirred at 25° C. for 16 h. The solvent was evaporated, and the reaction mixture was quenched with water (20 ml) and the product was extracted with EtOAc (3×30 ml). The combined organic layer was washed with brine (20 ml) and dried over sodium sulphate. The solvent was evaporated under reduced pressure to obtain crude product. The crude product was purified by Combi-flash chromatography using 40% ethyl acetate in hexanes as an eluent to obtain 0.110 g (17% yield) of the title compound. $^1$H NMR (400 MHz, DMSO-d6) δ ppm 2.11 (s, 3H), 6.81-6.93 (m, 3H), 6.99-7.13 (m, 1H), 7.14 (d, J=8.9 Hz, 2H), 7.25-7.38 (m, 4H), 7.39-7.52 (m, 2H), 8.63 (s, 1H), 8.69 (s, 1H); MS (ES+) m/z 337 [M+H]+

Intermediate 66

1-(benzofuran-5-yl)-3-(3-methyl-4-phenoxyphenyl) urea

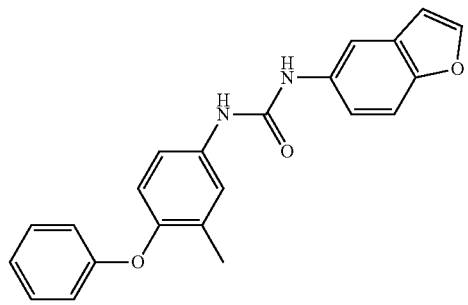 [SMILES: Cc1cc(NC(=O)Nc2ccc3occc3c2)ccc1Oc1ccccc1]

Benzofuran-5-amine (10 mg, 0.08 mmol) and triphosgene (7.5 mg, 0.02 mmol) were dissolved in 2 ml DCM and the solution was cooled to 0° C. Triethylamine (21 µl, 0.15 mmol) was added and the solution was stirred at 0° C. for 1 h. A solution of 3-methyl-4-phenoxy-aniline (16.5 mg, 0.08 mmol) and trimethylamine (21 µl, 0.15 mmol) in DCM (0.25 ml) was added. The reaction mixture was allowed to reach RT and the reaction was left to stir overnight. The reaction was quenched with 0.5 ml of H$_2$O. NH4Cl (aq. sat) and DCM were added and the water phase was extracted further with DCM (×3). The solid present in the combined organic phases was filtered off. The solution was dried over MgSO$_4$ and concentrated at reduced pressure to yield 0.026 g (96% yield) of the title compound that was used without further purification in the next step. MS (ESI+) m/z 359 (M+H)+

Intermediate 67

1-(1H-indol-5-yl)-3-(3-methyl-4-phenoxyphenyl) urea

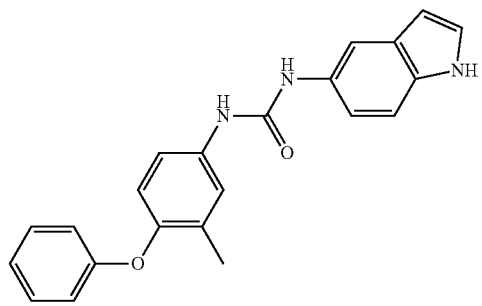 [SMILES: Cc1cc(NC(=O)Nc2ccc3[nH]ccc3c2)ccc1Oc1ccccc1]

1H-indol-5-amine (50 mg, 0.38 mmol) and triphosgene (37 mg, 0.12 mmol) were dispersed in 5 ml DCM and the solution was cooled to 0° C. Triethylamine (105 µl, 0.76 mmol) was added and the mixture was stirred at 0° C. for 1.5 h. A solution of 3-methyl-4-phenoxy-aniline (83 mg, 0.42 mmol) and trimethylamine (105 µl, 0.76 mmol) in 0.5 ml DCM was then added. The reaction mixture was allowed to reach room temperature and was stirred for 4 h. The reaction was quenched with 0.5 ml of H$_2$O. NH4Cl (aq sat.) and DCM were added and the water phase was extracted further with DCM (×3). The combined organic phases were concentrated at reduced pressure and dried at 35° C. under vacuum overnight. The product was dissolved in DCM/MeOH solvent mix and was concentrated onto silica. It was purified by column chromatography (Isolera, Biotage silica column 25 g) eluting with gradients of MeOH in DCM (0-4.5%) to yield 69 mg (51% yield) of title compound. 1H NMR (400 MHz, DMSO-d6) δ 10.93 (s, 1H), 8.51 (s, 1H), 8.37 (s, 1H), 7.68 (d, J=1.9 Hz, 1H), 7.43 (d, J=2.4 Hz, 1H), 7.37-7.25 (m, 5H), 7.07 (dd, J=8.7, 2.0 Hz, 1H), 7.03 (t, J=7.4 Hz, 1H), 6.88 (d, J=8.7 Hz, 1H), 6.86-6.81 (m, 2H), 6.38-6.32 (m, 1H), 2.11 (s, 3H). MS (ESI+) m/z 358 (M+H)+

Intermediate 68

1-(1,3-benzodioxol-5-yl)-3-(3-methyl-4-phenoxyphenyl)urea

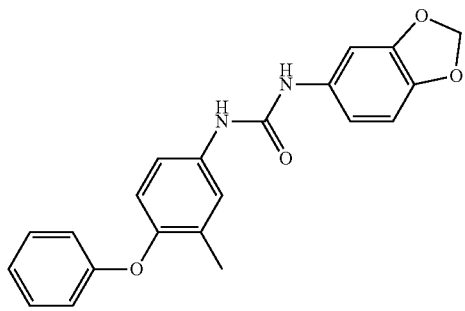 [SMILES: Cc1cc(NC(=O)Nc2ccc3c(c2)OCO3)ccc1Oc1ccccc1]

1,3-benzodioxol-5-amine (83 mg, 0.61 mmol) and triphosgene (54 mg, 0.18 mmol) were dispersed in 10 ml DCM and the solution was cooled to 0° C. Triethylamine (0.15 ml, 1.1 mmol) was added and the mixture was stirred at 0° C. for 1.5 h. A solution of 3-methyl-4-phenoxy-aniline (110 mg, 0.55 mmol) and triethylamine (0.15 ml, 1.1 mmol) in 1 ml DCM was added. The reaction mixture was allowed to reach room temperature and stirred for 2 h. The reaction was quenched with H₂O. NH4Cl (aq. sat.) and DCM were added and the phases were separated. The organic phase was concentrated at reduced pressure and further dried under vacuum at 40° C. for 3 h to yield 215 mg of the crude title compound that was used without further purification the next step. MS(ESI+) m/z 363 (M+H)+

Intermediate 69

1-(1H-indol-4-yl)-3-(3-methyl-4-phenoxyphenyl)urea

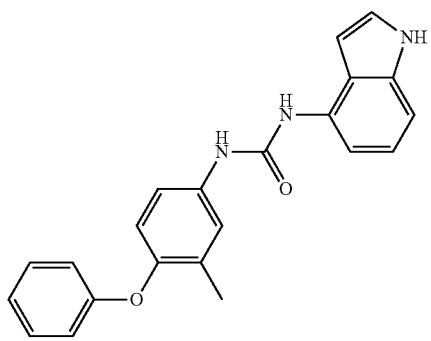 [SMILES: Cc1cc(NC(=O)Nc2cccc3[nH]ccc23)ccc1Oc1ccccc1]

1H-indol-4-amine (50 mg, 0.38 mmol) and triphosgene (37 mg, 0.12 mmol) were dispersed in 5 ml DCM and the solution was cooled to 0° C. Triethylamine (105 μl, 0.76 mmol) was added and the mixture was stirred at 0° C. for 1.5 h. A solution of 3-methyl-4-phenoxy-aniline (83 mg, 0.42 mmol) and triethylamine (105 μl, 0.76 mmol) in 0.5 ml DCM was added. The reaction mixture was allowed to reach room temperature and stirred for 2 h. The reaction was quenched with H2O. NH4Cl (aq. sat.) and DCM were added and the phases were separated. The organic phase was concentrated at reduced pressure. The solid was washed with pentane and dried under vacuum at 35° C. to yield 118 mg of the crude title compound that was used without further purification in the next step. MS(ESI+) m/z 358 (M+H)+

Intermediate 70

1-(3-methoxyphenyl)-3-(3-methyl-4-phenoxyphenyl)urea

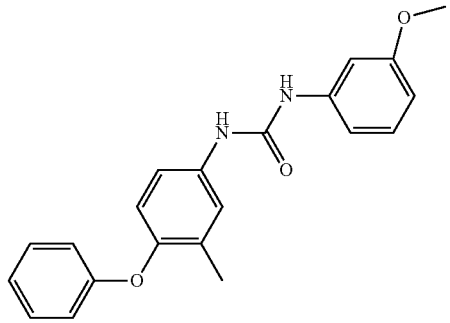 [SMILES: COc1cccc(NC(=O)Nc2ccc(Oc3ccccc3)c(C)c2)c1]

3-methoxyaniline (90 μl, 0.80 mmol) and triphosgene (79 mg, 0.26 mmol) were dispersed in 10 ml DCM and the solution was cooled to 0° C. Triethylamine (223 μl, 1.61 mmol) was added and the mixture was stirred at 0° C. After stirring the reaction mixture for a total of 1.5 h, a solution of 3-methyl-4-phenoxy-aniline (176 mg, 0.88 mmol) and triethylamine (223 μl, 1.61 mmol) in 1 ml DCM was added. The solution was allowed to reach room temperature and the reaction mixture was left at RT overnight. The reaction was quenched with H2O. NH4Cl (aq. sat.) and DCM were added and the phases were separated, the organic phase was dried over MgSO4. The solution was thereafter divided in half and was concentrated at reduced pressure, dried under vacuum at 30° C. overnight and further purified by column chromatography (Grace 40 g column, Biotage Isolera) eluting with gradients of MeOH in DCM (0-5%) to yield 115 mg (36% yield) of the title compound. MS(ESI+) m/z 349 (M+H)+

Intermediate 71

1-(2-methoxyphenyl)-3-(3-methyl-4-phenoxyphenyl)urea

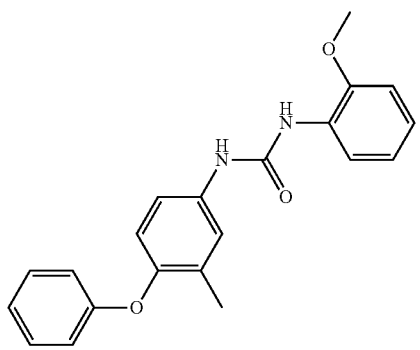 [SMILES: COc1ccccc1NC(=O)Nc1ccc(Oc2ccccc2)c(C)c1]

2-methoxyaniline (99 µl, 0.88 mmol) and triphosgene (87 mg, 0.29 mmol) were dispersed in 10 ml DCM and the solution was cooled to 0° C. Triethylamine (243 µl, 1.75 mmol) was added and the mixture was stirred at 0° C. After stirring the reaction mixture for a total of 1.5 h, a solution of 3-methyl-4-phenoxy-aniline (192 mg, 0.96 mmol) and triethylamine (243 µl, 1.75 mmol) in 1 ml DCM was added. The solution was allowed to reach room temperature and was left to stir a RT overnight. The reaction was quenched with H₂O. NH4Cl (aq. sat.) and DCM were added and the phases were separated, the organic phase was dried over MgSO₄. The solution was thereafter divided equally into 2 vials and was concentrated at reduced pressure. Half of the material taken out, concentrated at reduced pressure and dried under vacuum at 30° C. overnight and further purified by column chromatography (Grace 40 g column, Biotage Isolera) eluting with gradients of MeOH in DCM (0-5%) to yield 119 mg (35% yield) of the title compound. MS(ESI+) m/z 349 (M+H)+

Intermediate 72

1-(3-methoxy-4-phenoxyphenyl)-3-(3-methoxyphenyl)urea

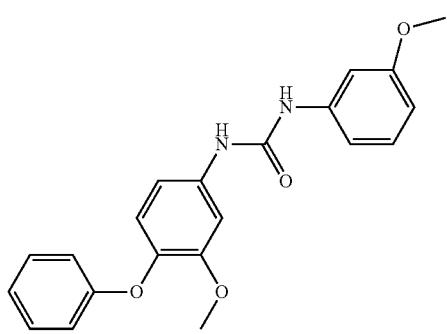 [SMILES: COc1cccc(NC(=O)Nc2ccc(Oc3ccccc3)c(OC)c2)c1]

3-methoxyaniline (108 mg, 0.88 mmol) and triphosgene (87 mg, 0.29 mmol) were dispersed in 10 ml DCM and the solution was cooled to 0° C. Triethylamine (243 µl, 1.75 mmol) was added and the mixture was stirred at 0° C. for 1.5 h. 3-Methoxy-4-phenoxy-aniline (207 mg, 0.96 mmol) and triethylamine (243 µl, 1.75 mmol) were dissolved in DCM (1 ml) and was added to the mixture. The mixture was stirred at RT over night. The reaction mixture was quenched with H₂O. NH4Cl (aq. sat.) and DCM were added and the phases were separated, the organic phase was dried over MgSO4. The solution was concentrated at reduced pressure and the product was purified by column chromatography (Biotage Isolera, 80 g silica column) eluting with gradients of MeOH in DCM (0 to 5%) to yield 225 mg (70% yield) of the title compound. MS(ESI+) m/z 365 (M+H)+

Intermediate 73

1-(3-methoxy-4-phenoxyphenyl)-3-(4-methoxyphenyl)urea

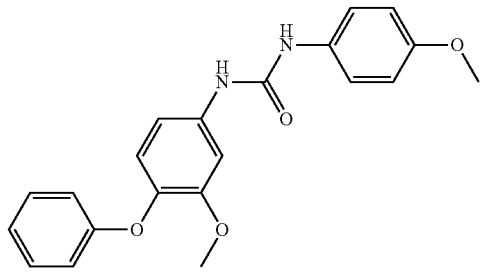 [SMILES: COc1ccc(NC(=O)Nc2ccc(Oc3ccccc3)c(OC)c2)cc1]

4-Methoxyaniline (108 mg, 0.88 mmol) and triphosgene (87 mg, 0.29 mmol) were dispersed in 10 ml DCM and the solution was cooled to 0° C. Triethylamine (243 µl, 1.75 mmol) was added and the mixture was stirred at 0° C. for 1.5 h. 3-methoxy-4-phenoxy-aniline (207 mg, 0.96 mmol) and triethylamine (243 µl, 1.75 mmol) were dissolved in DCM (1 ml) and was added to the mixture. The mixture was stirred at RT over night. The reaction mixture was quenched with H2O. NH4Cl (aq. sat.) and DCM were added and the phases were separated. The organic phase was dried over MgSO4 and concentrated at reduced pressure. The crude was dissolved in DCM/MeOH and was evaporated onto silica. The product/silica mix was applied to a silica column and the product was purified by column chromatography (Biotage Isolera, 80 g silica column) eluting with gradients of MeOH in DCM (0 to 5%) to yield 288 mg (90% yield) of the title compound. MS(ESI+) m/z 365 (M+H)+

Intermediate 74

1-(4-benzyl-3-methylphenyl)-3-phenylurea

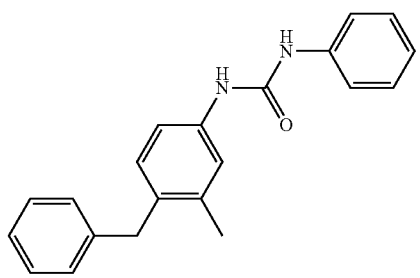 [SMILES: Cc1cc(NC(=O)Nc2ccccc2)ccc1Cc1ccccc1]

4-benzyl-3-methylaniline (0.70 g, 0.0035 mol) and TEA (0.99 ml) in DCM (7.0 ml) was stirred at 0° C. To the mixture, Phenyl isocyanate (0.63 g, 0.0053 mol) was added and the resulting reaction mixture was allowed to reach 25° C. and stirred for 16 h. The reaction was quenched with mixture of ice-water (20 ml). Product was extracted with DCM (3×30 ml) and the combined organic layer was washed with brine (20 ml). The organic layer was dried over sodium sulphate and evaporated under reduced pressure to obtain the crude product. The crude product was purified by column chromatography on silica gel (100-200 mesh) using 20% ethyl acetate in hexanes as an eluent to obtain 0.6 g (53% yield) of the title compound. MS(ESI+) m/z 317 (M+H)+

Intermediate 75

1-(3-chlorophenyl)-3-(3-methyl-4-phenoxyphenyl) urea

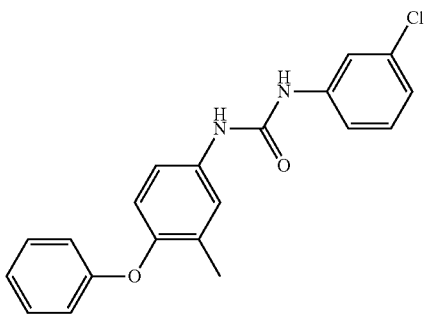 [SMILES: Cc1cc(NC(=O)Nc2cccc(Cl)c2)ccc1Oc1ccccc1]

3-methyl-4-phenoxy-aniline (0.50 g, 0.0025 mol) NaHCO$_3$ (0.63 g, 0.0075 mol) in DCM (5.0 ml) was stirred and cooled to 0° C. Triphosgene (0.29 g, 0.0010 mol) was added to the mixture and it was stirred for 4 h. 3-Chloro aniline and NaHCO$_3$ ((0.63 g, 0.0075 mol)) were added. The resulting reaction mixture was stirred at 25° C. for 16 h. The solvent was evaporated under reduced pressure and the reaction mixture was quenched with water (30 ml) and product was extracted with EtOAc (3×40 ml). The combined organic layer was washed with brine (30 ml) and dried over sodium sulphate and evaporated under reduced pressure to obtain crude product. The crude product was purified by Combi-flash chromatography using 20% ethyl acetate in hexanes as an eluent to yield 0.470 g (53% yield) of the title compound. $^1$H NMR (400 MHz, DMSO-d6) δ ppm 8.88 (s, 1H), 8.72 (s, 1H), 7.77-7.68 (m, 1H), 7.44 (d, J=2.6 Hz, 1H), 7.38-7.23 (m, 5H), 7.08-6.98 (m, 2H), 6.88 (dd, J=20.6, 8.3 Hz, 3H), 2.12 (s, 3H); MS(ESI+) m/z 353 (M+H)+

Intermediate 76

1-(3-methyl-4-phenoxyphenyl)-3-[3-(trifluoromethoxy)phenyl]urea

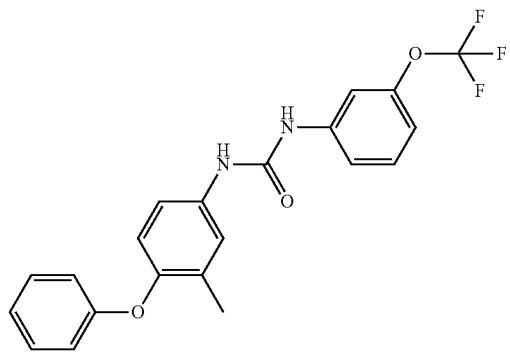 [SMILES: Cc1cc(NC(=O)Nc2cccc(OC(F)(F)F)c2)ccc1Oc1ccccc1]

3-methyl-4-phenoxy-aniline (0.5 g, 0.0025 mol) and NaHCO$_3$ (0.63 g, 0.0075 mol) was added to DCM (5.0 ml) and stirred at 0° C. Triphosgene (0.29 g, 0.0010 mol) was added and the resulting reaction mixture was stirred at 0° C. for 4 h. 3-(trifluromethoxy)-aniline (0.44 g, 0.0025 mol) and NaHCO$_3$ (0.63 g, 0.0075 mol) were added. The resulting reaction mixture was stirred at 25° C. for 16 h. The solvent was evaporated and the reaction mixture was quenched with water (25 ml) and product was extracted with EtOAc (3×30 ml). The combined organic layer was washed with brine (25 ml). The combined organic layer was dried over sodium sulphate and evaporated under reduced pressure to obtain crude product. The crude product was purified by Combi-flash chromatography using 30% ethyl acetate in hexanes as an eluent to obtain 0.450 g (44% yield) of the title compound. $^1$H NMR (400 MHz, DMSO-d6) δ ppm 9.00 (s, 1H), 8.73 (s, 1H), 7.72 (s, 1H), 7.47-7.36 (m, 2H), 7.39-7.26 (m, 4H), 7.04 (t, J=7.3 Hz, 1H), 6.92 (dd, J=16.7, 8.5 Hz, 2H), 6.85 (d, J=8.0 Hz, 2H), 2.13 (s, 3H); MS(ESI+) m/z 403 (M+H)+

Intermediate 77

1-(3-methyl-4-phenoxyphenyl)-3-(4-methylphenyl) urea

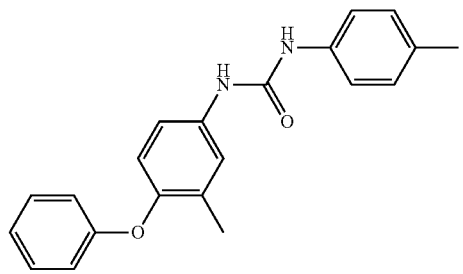 [SMILES: Cc1ccc(NC(=O)Nc2ccc(Oc3ccccc3)c(C)c2)cc1]

3-methyl-4-phenoxy-aniline (0.50 g, 0.0025 mol) NaHCO$_3$ (0.63 g, 0.0075 mol) was added to DCM (5.0 ml) and the mixture was cooled to 0° C. Triphosgene (0.49 g, 0.0016 mol) was added and the resulting reaction mixture was stirred at 0° C. for 4 h. p-Toluidine (0.26 g, 0.0025 mol) and NaHCO$_3$ (0.63 g, 0.0075 mol) were added and resulting reaction mixture was stirred at 25° C. for 16 h. The solvent was evaporated under reduced pressure and the reaction mixture was quenched with water (20 ml) and product was extracted with EtOAc (3×30 ml). The combined organic layer was washed with brine (20 ml) and dried over sodium sulphate and the solvent evaporated under reduced pressure to obtain crude product that was purified by Combi-flash chromatography using 30% ethyl acetate in hexanes as an eluent to yield 0.240 (28% yield) of the title compound. $^1$H NMR (400 MHz, DMSO-d6) δ ppm 8.61-8.47 (m, 2H), 7.37-7.25 (m, 6H), 7.12-6.99 (m, 4H), 6.93-6.81 (m, 2H), 2.24 (s, 3H), 2.11 (s, 3H); MS(ESI+) m/z 333 (M+H)+

Intermediate 78

1-methyl-3-(3-methyl-4-phenoxyphenyl)urea

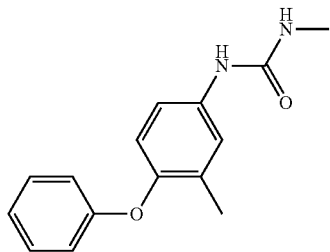 [SMILES: CNC(=O)Nc1ccc(Oc2ccccc2)c(C)c1]

3-methyl-4-phenoxy-aniline (0.5 g, 0.0025 mol) and NaHCO$_3$ (0.63 g, 0.0075 mol) was added to DCM (5.0 ml) and stirred at 0° C. Triphosgene (0.49 g, 0.0016 mol) was added and the reaction mixture was stirred at 0° C. for 4 h. Methyl amine (33% in ethanol, 0.25 ml, 0.0025 mol) and NaHCO$_3$ (0.63 g, 0.0075 mol) were added and reaction mixture was stirred at 25° C. for 16 h. The reaction mixture was quenched with water (20 ml) and extracted with DCM (3×35 ml). The combined organic layer was washed with brine (20 ml) and dried over sodium sulfate and the solvent evaporated under reduced pressure. The crude product was purified by column chromatography on silica gel (100-200 mesh) using 30% ethyl acetate in hexanes as an eluent to yield 0.350 g (54% yield) of the title compound. $^1$H NMR (400 MHz, DMSO-d6) δ ppm 8.46 (s, 1H), 7.33-7.24 (m, 4H), 7.03 (t, J=7.3 Hz, 1H), 6.84 (t, J=8.1 Hz, 3H), 5.99 (q, J=4.6 Hz, 1H), 2.65 (d, J=4.6 Hz, 3H), 2.08 (s, 3H); MS(ESI+) m/z 257 (M+H)+

Intermediate 79

1-(2,5-dimethyl-4-phenoxyphenyl)-3-phenylurea

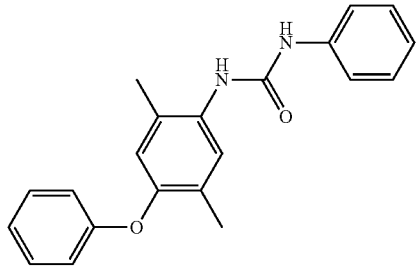 [SMILES: Cc1cc(Oc2ccccc2)c(C)cc1NC(=O)Nc1ccccc1]

A solution of 2,5-dimethyl-4-phenoxyaniline (commercially available, 1.40 g, 0.0065 mol) in DCM (14.0 ml) and TEA (1.84 ml, 0.0131 mol) was stirred and cooled to 0° C. Phenyl Isocyanate (0.93 g, 0.0078 mol) was added and the reaction mixture was allowed to reach 25° C. and stirred for 16 h. The obtained solid precipitates were filtered out and washed with n-pentane (20 ml) to yield 1.3 g (59% yield) of the title compound. $^1$H NMR (400 MHz, DMSO-d6) δ ppm 8.97 (s, 1H), 7.89 (s, 1H), 7.74 (s, 1H), 7.40-7.52 (m, 2H), 7.22-7.38 (m, 4H), 7.04 (t, J=7.4 Hz, 1H), 6.97 (t, J=7.3 Hz, 1H), 6.89-6.79 (m, 3H), 2.19 (s, 3H), 2.09 (s, 3H); MS(ESI+) m/z 333 (M+H)+

Intermediate 80

1-[3-(2-methoxyethoxy)-4-phenoxyphenyl]-3-(4-methylphenyl)urea

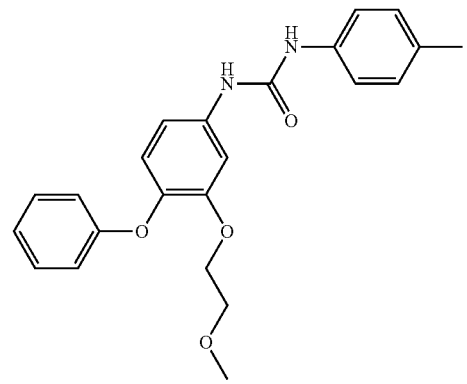 [SMILES: COCCOc1cc(NC(=O)Nc2ccc(C)cc2)ccc1Oc1ccccc1]

A solution of 3-(2-methoxyethoxy)-4-phenoxyaniline (Intermediate 43, 0.30 g, 0.0011 mol) and NaHCO$_3$ (0.29 g, 0.0035 mol) in DCM (3.0 ml) was stirred and cooled to 0° C. Triphosgene (0.22 g, 0.0007 mol) was added and the reaction mixture was stirred at 0° C. for 4 h. 4-methylaniline (0.16 g, 0.0015 mol) and NaHCO$_3$ (0.29 g, 0.0035 mol) were added and the reaction mixture was stirred at 25° C. for 16 h. The solvent was evaporated under reduced pressure and the reaction mixture was quenched with water (30 ml) and extracted with DCM (3×40 ml). The combined organic layer was washed with brine (30 ml) and dried over sodium sulphate and evaporated under reduced pressure. The crude product was purified by Combi-flash chromatography using 20% ethyl acetate in hexanes as an eluent to yield 0.210 g (46% yield) of the title compound. $^1$H NMR (400 MHz, DMSO-d6) δ ppm 8.67 (s, 1H), 8.56 (s, 1H), 7.41 (d, J=2.2 Hz, 1H), 7.38-7.24 (m, 4H), 7.09-7.12 (m, 2H), 6.97 (m, 3H), 6.82-6.89 (m, 2H), 4.04 (t, J=4.6 Hz, 2H), 3.49 (t, J=4.6 Hz, 2H), 3.16 (s, 3H), 2.25 (s, 3H); MS(ESI+) m/z 393 (M+H)+

Intermediate 81

1-[3-(2-methoxyethoxy)-4-phenoxyphenyl]-3-(3-methylphenyl)urea

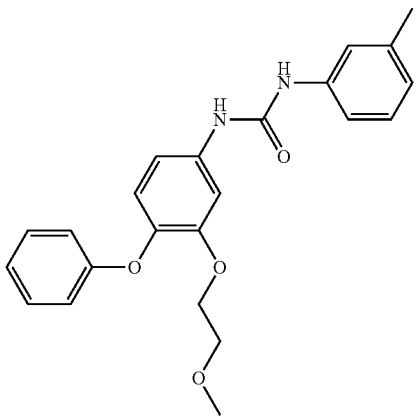 [SMILES: COCCOc1cc(NC(=O)Nc2cccc(C)c2)ccc1Oc1ccccc1]

A solution of 3-(2-methoxyethoxy)-4-phenoxyaniline (Intermediate 43, 0.50 g, 0.0019 mol) and NaHCO$_3$ (0.48 g, 0.0057 mol) in DCM (5.0 ml) was stirred and cooled to 0° C. Triphosgene (0.37 g, 0.0012 mol) was added and the reaction mixture was stirred at 0° C. for 4 h. 3-methylaniline (0.20 g, 0.0019 mol) and NaHCO$_3$ (0.48 g, 0.0057 mol) were added and the reaction mixture was stirred at 25° C. for 16 h. The solvent was removed under reduced pressure and the reaction mixture was quenched with water (40 ml) and the product was extracted with EtOAc (3×50 ml). The combined organic layer was washed with brine (40 ml) and dried over sodium sulfate and evaporated under reduced pressure. The crude product was purified by Combi-flash chromatography using 40% ethyl acetate in hexanes as an eluent to yield 0.30 g (39%) of the title compound. H NMR (400 MHz, DMSO-d6) δ ppm 8.71 (s, 1H), 8.60 (s, 1H), 7.44 (d, J=2.2 Hz, 1H), 7.36-7.22 (m, 4H), 7.26-7.13 (m, 1H), 7.06-6.92 (m, 3H), 6.89-6.77 (m, 3H), 4.06 (t, J=4.4 Hz, 2H), 3.51 (t, J=4.8 Hz, 2H), 3.17 (s, 3H), 2.29 (s, 3H); MS(ESI+) m/z 393 (M+H)+

Intermediate 82

1-[3-(2-methoxyethoxy)-4-phenoxyphenyl]-3-(3-chlorophenyl)urea

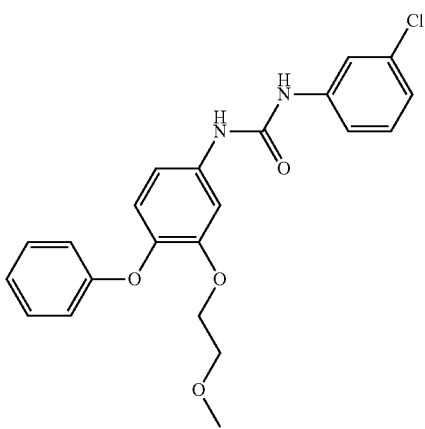 [SMILES: COCCOc1cc(NC(=O)Nc2cccc(Cl)c2)ccc1Oc1ccccc1]

A solution of 3-(2-methoxyethoxy)-4-phenoxyaniline (Intermediate 43, 0.30 g, 0.0011 mol) and NaHCO$_3$ (0.29 g, 0.0034 mol) in DCM (3.0 ml) was stirred and cooled to 0° C. Triphosgene (0.22 g, 0.0007 mol) was added and the reaction mixture was stirred at 0° C. for 4 h. 3-chloroaniline (0.11 g, 0.0008 mol) and NaHCO$_3$ (0.29 g, 0.0034 mol) were added and the reaction mixture was stirred at 25° C. for 16 h. The solvent was removed under reduced pressure and the reaction mixture was quenched with water (100 ml) and extracted with EtOAc (3×50 ml). The combined organic layer was washed with brine (50 ml) and dried over sodium sulfate and the solvent evaporated under reduced pressure. The crude product was purified by Combi-flash chromatography using 40% ethyl acetate in hexanes as an eluent to yield 0.120 g (25% yield) of the title compound. $^1$H NMR (400 MHz, DMSO-d6) δ ppm 8.90 (s, 1H), 8.81 (s, 1H), 7.73 (s, 1H), 7.42 (s, 1H), 7.36-7.23 (m, 4H), 7.06-6.92 (m, 4H), 6.81-6.90 (m, 2H), 4.05 (t, J=4.6 Hz, 2H), 3.50 (t, J=4.6 Hz, 2H), 3.16 (s, 3H); MS(ESI+) m/z 413 (M+H)+

Intermediate 83

1-[3-(2-methoxyethoxy)-4-phenoxyphenyl]-3-(4-chlorophenyl)urea

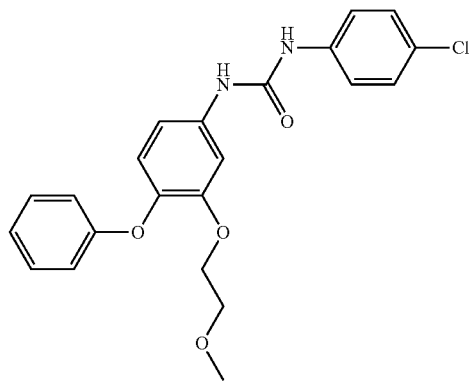 [SMILES: COCCOc1cc(NC(=O)Nc2ccc(Cl)cc2)ccc1Oc1ccccc1]

3-(2-methoxyethoxy)-4-phenoxyaniline (Intermediate 43, 0.30 g, 0.0011 mol) and NaHCO$_3$ (0.29 g, 0.0034 mol) in DCM (3.0 m) was cooled under stirring to 0° C. Triphosgene (0.22 g, 0.0007 mol) was added and the resulting reaction mixture was stirred at 0° C. for 4 h. 4-Chloroaniline (0.19 g, 0.0015 mol) and NaHCO$_3$ (0.29 g, 0.0034 mol) were added and the reaction mixture was stirred at 25° C. for 16 h. The solvent was evaporated under reduced pressure and the reaction mixture was quenched with water (30 ml) and extracted with DCM (3×45 ml). The combined organic layer was washed with brine (30 ml) and dried over sodium sulfate and the solvent removed under reduced pressure. The crude product was purified by Combi-flash chromatography using 22% ethyl acetate in hexanes as an eluent to yield 0.230 g (48% yield) of the title compound. $^1$H NMR (400 MHz, DMSO-d6) δ ppm 8.84 (s, 1H), 8.77 (s, 1H), 7.54-7.47 (m, 2H), 7.42 (d, J=2.1 Hz, 1H), 7.39-7.26 (m, 4H), 7.06-6.93 (m, 3H), 6.80-6.90 (m, 2H), 4.05 (t, J=4.7 Hz, 2H), 3.51 (t, J=4.7 Hz, 2H), 3.17 (s, 3H); MS(ESI+) m/z 413 (M+H)+

Intermediate 84

1-[3-(2-methoxyethoxy)-4-phenoxyphenyl]-3-(4-methoxyphenyl)urea

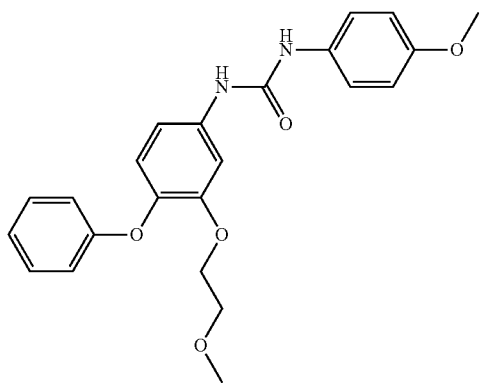 [SMILES: COCCOc1cc(NC(=O)Nc2ccc(OC)cc2)ccc1Oc1ccccc1]

3-(2-methoxyethoxy)-4-phenoxyaniline (Intermediate 43, 0.50 g, 0.0019 mol) and NaHCO$_3$ (0.48 g, 0.0057 mol) were added to DCM (5.0 ml) and the mixture was stirred and cooled to 0° C. Triphosgene (0.37 g, 0.0012 mol) was added and the reaction mixture was stirred at 0° C. for 4 h. 4-methoxyaniline (0.30 g, 0.0025 mol) and NaHCO$_3$ (0.48 g, 0.0057 mol) were added and the reaction mixture was stirred at 25° C. for 16 h. The solvent was evaporated and the reaction mixture was quenched with water (30 ml) and extracted with DCM (3×50 ml). The combined organic layer was washed with brine (30 ml) and dried over sodium sulfate and concentrated under reduced pressure. The crude product was purified by the Combi-flash chromatography using 30% ethyl acetate in hexanes as an eluent to yield 0.250 g (31% yield) of the title compound. $^1$H NMR (400 MHz, DMSO-d6) δ ppm 8.64 (s, 1H), 8.49 (s, 1H), 7.44-7.25 (m, 6H), 7.05-6.81 (m, 8H), 4.05 (t, J=4.6 Hz, 2H), 3.73 (s, 3H), 3.50 (t, J=4.7 Hz, 2H), 3.17 (s, 3H). MS(ESI+) m/z 409 (M+H)+

Intermediate 85

1-[3-(2-methoxyethoxy)-4-phenoxyphenyl]-3-(3-methoxyphenyl)urea

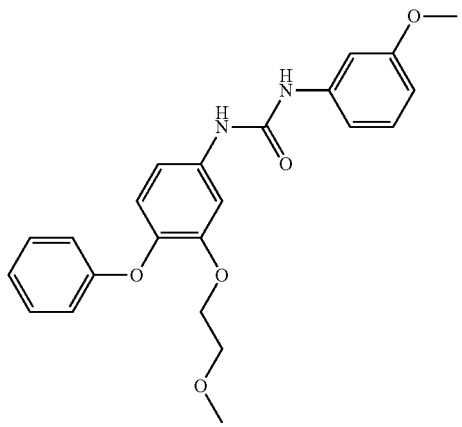 [SMILES: COCCOc1cc(NC(=O)Nc2cccc(OC)c2)ccc1Oc1ccccc1]

3-(2-methoxyethoxy)-4-phenoxyaniline (Intermediate 43, 0.50 g, 0.0019 mol) and NaHCO$_3$ (0.48 g, 0.0057 mol) in DCM (5.0 ml) was stirred and cooled to 0° C. Triphosgene (0.37 g, 0.0012 mol) was added and the reaction mixture was stirred at 0° C. for 4 h. 3-methoxyaniline (0.23 g, 0.0019 mol) and NaHCO$_3$ (0.48 g, 0.0057 mol) were added and the reaction mixture was stirred at 25° C. for 16 h. The solvent was evaporated and the reaction mixture was quenched with water (100 ml) and extracted with EtOAc (3×50 ml). The combined organic layer was washed with brine (50 ml) and dried over sodium sulfate and concentrated under reduced. The crude product was purified by Combi-flash chromatography using 40% ethyl acetate in hexanes as an eluent to yield 0.35 g (44% yield) of the title compound. $^1$H NMR (400 MHz, DMSO-d6) δ ppm 8.70 (s, 1H), 8.69 (s, 1H), 7.40 (d, J=2.1 Hz, 1H), 7.35-7.28 (m, 2H), 7.21-7.15 (m, 2H), 7.06-6.92 (m, 4H), 6.85-6.80 (m, 2H), 6.57 (dd, J=8.2, 2.5 Hz, 1H), 4.06 (t, J=4.7 Hz, 2H), 3.75 (s, 3H), 3.51 (t, J=4.6 Hz, 2H), 3.17 (s, 3H); MS(ESI+) m/z 409 (M+H)+

Intermediate 86

1-[3-methyl-4-(2-methylphenoxy)phenyl]-3-phenylurea

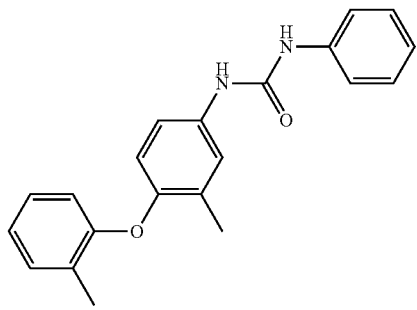 [SMILES: Cc1ccccc1Oc1ccc(NC(=O)Nc2ccccc2)cc1C]

3-methyl-4-(2-methylphenoxy)aniline (commercially available, 0.25 g, 0.0011 mol) was dissolved in DCM (2.5 ml) under stirring. TEA (0.32 ml, 0.0023 mol) was added at 0° C. followed by the addition of phenyl isocyanate (0.15 g, 0.0012 mol). Reaction mixture was allowed to reach 25° C. and stirred for 16 h. The obtained solid precipitates were filtered out and washed with n-pentane (15 ml) to yield 0.25 g (64%) of the title compound that was used in the next step without further purification. $^1$H NMR (400 MHz, DMSO-d6) δ ppm 8.69-8.57 (m, 2H), 7.50-7.39 (m, 3H), 7.28 (m, 4H), 7.13 (t, J=3.2 Hz, 1H), 7.04-6.93 (m, 2H), 6.75 (d, J=8.7 Hz, 1H), 6.59 (d, J=8.0 Hz, 1H), 2.27 (s, 3H), 2.16 (s, 3H); MS(ESI+) m/z 333 (M+H)+

Intermediate 87

1-(3-methyl-4-phenoxyphenyl)-3-(1,3-thiazol-4-yl)urea

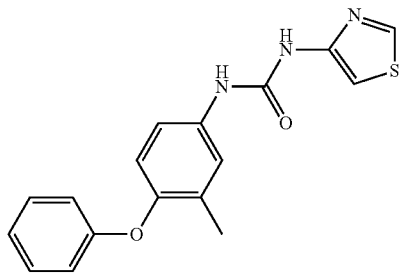 [SMILES: Cc1cc(NC(=O)Nc2cscn2)ccc1Oc1ccccc1]

A solution of 1,3-Thiazole-4-carboxylic acid (0.50 g, 0.0038 mol) in toluene (5.0 ml) was stirred and cooled to 0° C. and TEA (1.63 ml, 0.0116 mol) was added drop wise. To the resulting mixture diphenyl phosphoryl azide (DPPA, 1.17 g, 0.0042 mol) was added dropwise and stirred at 0° C. for 1 h. 3-methyl-4-phenoxy-aniline (0.50 g, 0.0025 mol) in toluene was added dropwise and resulting reaction mixture was stirred at 110° C. for 16 h. The solvent was evaporated and the reaction mixture was quenched with water (40 ml) and extracted with EtOAc (3×50 ml). The combined organic layer was washed with brine (40 ml) and dried over sodium sulfate and concentrated under reduced pressure. The crude product was purified by Combi-flash chromatography using 30% ethyl acetate in hexanes as an eluent to yield 0.400 g (49% yield) the title compound. $^1$H NMR (400 MHz, DMSO-d6) δ ppm 9.47 (s, 1H), 8.95 (d, J=2.2 Hz, 1H), 8.78 (s, 1H), 7.43 (d, J=2.6 Hz, 1H), 7.38-7.27 (m, 4H), 7.04 (t, J=7.4 Hz, 1H), 6.90 (d, J=8.8 Hz, 1H), 6.89-6.79 (m, 2H), 2.12 (s, 3H). MS(ESI+) m/z 326 (M+H)+

Intermediate 88

1-[4-(4-chlorophenoxy)phenyl]-3-methylurea

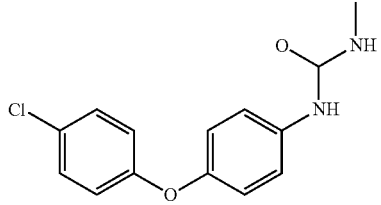 [SMILES: CNC(O)Nc1ccc(Oc2ccc(Cl)cc2)cc1]

In a microwave vial previously equipped with a magnetic stirrer and nitrogen balloon, triethylamine (0.383 g, 0.0027 mol) was added drop wise to a solution of 4-(4-chlorophenoxy)aniline (0.300 g, 0.0045 mol) and N-methyl formyl chloride (0.125 g, 0.0045 mol) in DCM (3.0 ml) at 0° C. The reaction mixture was allowed to reach 25° C. and stirred for 16 h. The reaction mixture was quenched with ice-water (50 ml) and extracted with ethyl acetate (3×40 ml). The combined organic layer was washed with brine (30 ml), dried over sodium sulfate and the solvent removed under reduced pressure. The crude product was purified on silica gel (60-120 mesh) using 10% methanol in dichloromethane as an eluent to yield 0.130 g (34% yield) of the title compound.

Intermediate 89

1-(3-Chloro-4-phenoxyphenyl)-3-methylurea

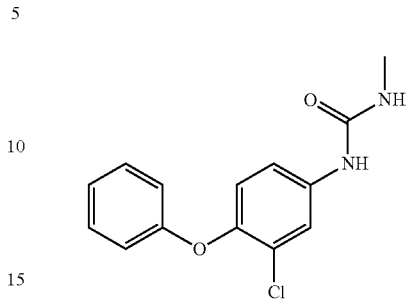

3-Chloro-4-phenoxyaniline (commercially available, 0.340 g, 0.0015 mol) dissolved in DCM (3.4 ml) was stirred and cooled to 0° C. Triethylamine (0.435 ml, 0.0030 mol) followed by N-methyl formyl chloride (0.144 g, 0.0015 mol) were added at 0° C. under nitrogen atmosphere. The reaction mixture was allowed reach 25° C. and stirred for 16 h. The solvent was removed under reduced pressure and the mixture was diluted with water (20 ml). The aqueous layer was extracted with EtOAc (3×25 ml). The combined organic layer was washed with brine (20 ml) and dried over sodium sulfate. The solvent was removed under reduced pressure and the crude product was purified on combi-flash chromatography using 50% Ethyl acetate in hexanes as an eluent to yield 0.150 g (35% yield) of the title compound. MS(ESI+) m/z 277 (M+H)+

Intermediate 90

1-[3-(2-methoxyethoxy)-4-phenoxyphenyl]-3-(5-methylthiophen-2-yl)urea

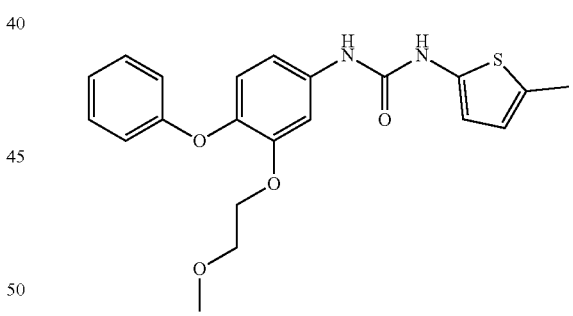

In a microwave vial, previously equipped magnetic stirrer, was added 5-methylthiophene-2-carboxylic acid (0.30 g, 0.0021 mol) and Toluene (10 ml). This solution was cooled to 0° C. and triethylamine (0.59 ml, 0.0042 mol) was added drop wise. Diphenyl phosphoryl azide (DPPA, 0.63 g, 0.0023 mol) was added drop wise to the resulting mixture and stirred at 0° C. for 1 h. 3-(2-methoxyethoxy)-4-phenoxyaniline (Intermediate 43, 0.32 g, 0.0012 mol) was added drop wise in Toluene (8 ml). The resulting reaction mixture was stirred at 110° C. for 16 h. The solvent was evaporated, and the reaction mixture was quenched with water (40 ml). The product was extracted with Ethyl acetate (3×50 ml). The combined organic layer was washed with brine (40 ml) and dried over sodium sulphate and the solvent evaporated under reduced pressure. The crude product was purified by Combi-flash chromatography using 30% ethyl acetate in hexanes as an eluent to obtain 0.32 g of the title compound. $^1$H NMR (400 MHz, DMSO-d6) δ ppm 9.41 (s, 1H), 8.71 (s, 1H), 7.38 (s, 1H), 7.29 (t, J=7.6 Hz, 2H), 7.02-6.95 (m, 3H), 6.83 (d, J=7.6, 2H), 6.48 (d, J=2.4 Hz, 1H), 6.35 (d, J=3.6 Hz, 1H), 4.04 (t, J=4.4 Hz, 2H), 3.49 (t, J=4.8 Hz, 2H), 3.15 (s, 3H), 2.33 (s, 3H). MS(ESI+) m/z 399 (M+H)+

Intermediate 91

1,3-bis(3-methyl-4-phenoxyphenyl)urea

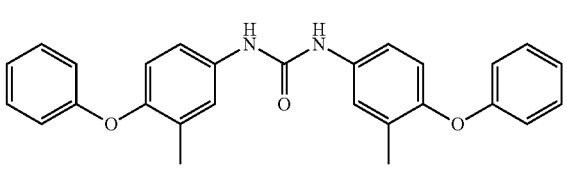 [SMILES: Cc1cc(NC(=O)Nc2ccc(Oc3ccccc3)c(C)c2)ccc1Oc1ccccc1]

In a RBF previously equipped with a magnetic stirrer was added 3-methyl-4-phenoxyaniline (commercially available, 0.3 g, 0.0015 mol), NaHCO$_3$ (0.75 g, 0.009 mol) and DCM (6 ml). The mixture was cooled to 0° C., and triphosgene (0.589 g, 0.0019 mol) was added and reaction mixture was stirred for 4 h. 3-methyl-4-phenoxyaniline (commercially available, 0.3 g, 0.0015 mol) and NaHCO$_3$(0.75 g, 0.009 mol) were added. The resulting reaction mixture was stirred at 25° C. for 16 h. The solvent was evaporated and the reaction mixture was quenched with water (30 ml) and product was extracted with EtOAc (3×40 ml). The combined organic layer was washed with brine (30 ml) and the organic layer was dried over sodium sulphate and the solvent evaporated under reduced pressure to obtain crude product. The crude product was purified by Combi-flash chromatography using 20% ethyl acetate in hexanes as an eluent to yield 0.30 g (46% yield) of the title compound. $^1$H NMR (400 MHz, DMSO-d6) δ ppm 8.68 (s, 2H), 7.44 (d, J=2.0 Hz, 2H), 7.38-7.26 (m, 6H), 7.04 (t, J=7.2 Hz, 2H), 6.93-6.81 (m, 6H), 2.12 (s, 6H). MS (ES+) m/z 425 [M+H]$^+$ Intermediate 92

Phenyl (3-methyl-4-phenoxyphenyl)carbamate

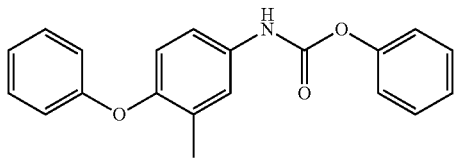 [SMILES: Cc1cc(NC(=O)Oc2ccccc2)ccc1Oc1ccccc1]

In a RBF previously equipped with a magnetic stirrer was added 3-methyl-4-phenoxyaniline (commercially available, 1.00 g, 0.005 mol) in DCM (10 ml) and the mixture was cooled to 0° C. Triethylamine (1.41 ml, 0.010 mol) was added and then phenyl chloroformate (0.67 ml, 0.0055 mol) was added drop wise. The reaction mixture was allowed to reach room temperature and stirred at 25° C. for 2 h. The reaction mixture was quenched with water (50 ml) and product was extracted with DCM (3×50 ml). The combined organic layer was washed with brine (50 ml) dried over sodium sulphate and the solvent evaporated under reduced pressure. The crude product was purified by Combi-flash chromatography using 30% ethyl acetate in hexanes as an eluent to yield 1.0 g (62% yield) of the title compound. MS (ES+) m/z 320 [M+H]$^+$ Intermediate 93

1-(3-methyl-4-phenoxyphenyl)-3-(1-phenyl-1H-pyrazol-4-yl)urea

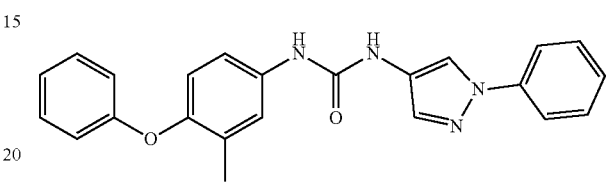

In a RBF previously equipped with a magnetic stirrer phenyl (3-methyl-4-phenoxyphenyl)carbamate (Intermediate 92, 1.0 g, 0.0031 mol) in DMF (7 ml) was added and the mixture cooled to 0° C. Triethylamine (0.88 ml, 0.0063 mol) was added drop wise followed drop-wise addition of 1-Phenyl-1H-pyrazol-4-ylamine (0.335 g, 0.0031 mol) in DMF (3 ml). The resulting reaction mixture was allowed to reach room temperature and stirred at 90° C. for 16 h. The reaction mixture was allowed cool at room temperature and n-hexane was added. The solid product precipitated and filtered through Buchner funnel to get crude product. The crude product was purified by Combi-flash chromatography using 30% ethyl acetate in hexanes as an eluent to yield 0.23 g (19% yield of the title compound. MS (ES+) m/z 385 [M+H]$^+$ Intermediate 94

1-(3-bromo-4-phenoxyphenyl)-3-phenylurea

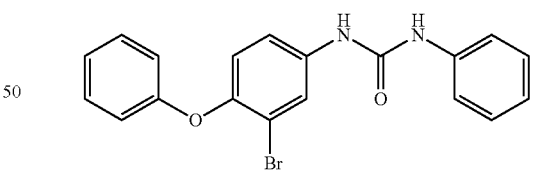

In a RBF previously equipped with a magnetic stirrer 3-bromo-4-phenoxyaniline (commercially available, 1.00 g, 0.0038 mol) and DCM (10 ml) was added. Triethylamine (1.06 ml, 0.0076 mol) was added at 0° C. followed by the addition of phenyl isocyanate (0.45 g, 0.0038 mol). The reaction mixture was allowed to reach 25° C. and stirred for 2 h. The obtained solid precipitates were filtered out and washed with n-pentane (15 ml) to yield 0.90 (62% yield) of the title compound. $^1$H NMR (400 MHz, DMSO-d6) δ ppm 8.91 (s, 1H), 8.78 (s, 1H), 8.02 (d, J=2.4 Hz, 1H), 7.48 (app d, 2H), 7.39-7.28 (m, 5H), 7.11-7.07 (m, 2H), 7.00 (t, J=7.2 Hz, 1H), 6.90 (app d, 2H). MS(ESI+) m/z 383 (M+H)$^+$

Intermediate 95

1-(2-methyl-4-phenoxyphenyl)-3-phenylurea

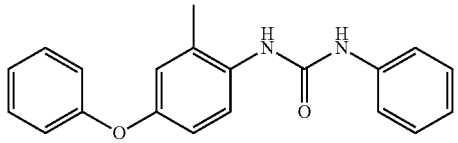 [SMILES: Cc1cc(Oc2ccccc2)ccc1NC(=O)Nc1ccccc1]

In a RBF previously equipped with a magnetic stirrer was added 2-methyl-4-phenoxyaniline (commercially available, 0.35 g, 0.0017 mol) and triethylamine (0.49 ml, 0.0035 ml) in DCM (3.5 ml) and the mixture was cooled to 0° C. Phenyl isocyanate (0.20 g, 0.0017 mol) was added and the reaction mixture was allowed to reach 25° C. and stirred for 3 h. The solid product was filtered off and washed with n-pentane and dried under vacuum to yield 0.370 g (66% yield) of the title compound. MS(ESI+) m/z 319 (M+H)+

Intermediate 96

Phenyl (2-methyl-4-phenoxyphenyl)carbamate

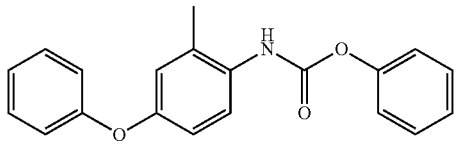 [SMILES: Cc1cc(Oc2ccccc2)ccc1NC(=O)Oc1ccccc1]

In a RBF previously equipped with a magnetic stirrer was taken 2-methyl-4-phenoxyaniline (commercially available, 0.90 g, 0.0045 mol) in DCM (9.0 ml) and the mixture was cooled to 0° C. Triethylamine (1.90 ml, 0.0135 mol) was added followed by drop wise addition of phenyl chloroformate (1.65 ml, 0.0135 mol). The reaction mixture was allowed to reach 25° C. and stirred for 2 h. The reaction mixture was quenched with water (50 ml) and the product was extracted with DCM (3×50 m). The combined organic layer was washed with brine (50 ml). The organic layer was dried over sodium sulphate and the solvent removed under reduced pressure to obtain 2.0 g crude title compound that was used in next step. MS(ESI+) m/z 320(M+H)+

Intermediate 97

1-(2-methyl-4-phenoxyphenyl)-3-(4-methylphenyl)urea

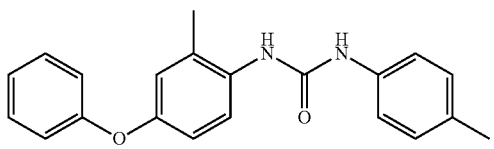 [SMILES: Cc1ccc(NC(=O)Nc2ccc(Oc3ccccc3)cc2C)cc1]

In a RBF previously equipped with a magnetic stirrer was taken phenyl (2-methyl-4-phenoxyphenyl)carbamate (Intermediate 96, 1.00 g, 0.0031 mol) in DMF (7 ml) and the mixture was cooled to 0° C. Triethylamine (0.88 ml, 0.0063 mol) was added drop wise followed by 4-methyl-aniline (0.335 g, 0.0031 mol) in DMF (8 ml). The reaction mixture allowed to reach room temperature and then stirred at 100° C. for 16 h. The reaction mixture was allowed to cool to room temperature and n-hexane was added. The solid product precipitated and was filtered through Buchner funnel to get 0.50 g crude title compound that was used in next step without further purification. MS(ESI+) m/z 320 (M+H)+

Intermediate 98

1-(1-benzofuran-4-yl)-3-(3-methyl-4-phenoxyphenyl)urea

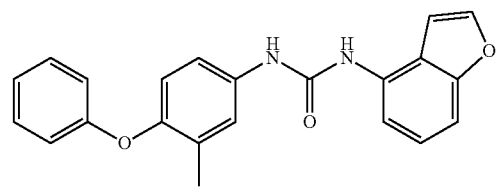 [SMILES: Cc1cc(NC(=O)Nc2cccc3occc23)ccc1Oc1ccccc1]

In a RBF previously equipped with a magnetic stirrer was added phenyl (3-methyl-4-phenoxyphenyl)carbamate (Intermediate 92, 0.50 g, 0.00156 mol) in DMF (3 ml) and the mixture was cooled to 0° C. Triethylamine (0.44 ml, 0.00313 mol) was added drop wise and followed by drop wise addition of 4-amino-benzofuran (0.208 g, 0.00156 mol) in DMF (2 ml). The reaction mixture was stirred at 100° C. for 16 h. The reaction mixture was allowed cool at room temperature and n-hexane was added and stirred for 5 min. The obtained solid was collected by filtration to yield 0.25 g of crude title compound that was used in the next step without further purification. MS(ESI+) m/z 359 (M+H)+

Intermediate 99

1-(1-benzofuran-7-yl)-3-(3-methyl-4-phenoxyphenyl)urea

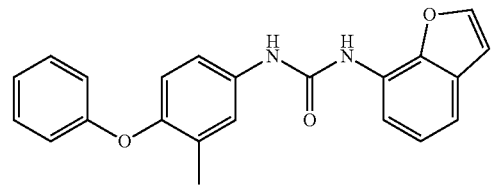 [SMILES: Cc1cc(NC(=O)Nc2cccc3ccoc23)ccc1Oc1ccccc1]

In a RBF previously equipped with a magnetic stirrer was taken phenyl (3-methyl-4-phenoxyphenyl)carbamate (Intermediate 92, 1.0 g, 0.00313 mol) in DMF (7 ml) and the mixture was cooled to 0° C. Triethylamine (0.88 ml, 0.0063 mol) was added followed by drop wise addition of 7-amino-benzofuran (0.417, 0.00313 mol) in DMF (3 ml). The reaction mixture was stirred at 100° C. for 16 h. The reaction mixture was allowed to cool to room temperature and n-hexanes was added. After stirring for 5 min the obtained solid was collected by filtration to yield 0.60 g of the crude title compound that was used without further purification in the next step. MS(ESI+) m/z 359 (M+H)+

Intermediate 100

2-(2-fluoro-5-nitrophenyl)-N,N-dimethylacetamide

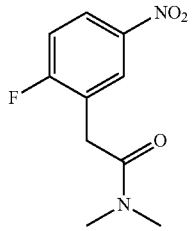 [SMILES: CN(C)C(=O)Cc1cc([N+](=O)[O-])ccc1F]

2-Fluoro-5-nitrophenyl)acetic acid (commercially available, 3.0 g, 15 mmol), dimethyl amine (10% in THF, 10.1 g, 22.6 mmol) and HATU (11.45 g, 30.1 mmol) in DMF (30 ml) was added to a RBF previously equipped with a magnetic stirrer and nitrogen balloon and the mixture was cooled to 0° C. After 30 minutes, N,N-Diisopropylethylamine (5.20 ml) was added drop wise and the reaction mixture was stirred at room temperature for 3 h. The reaction mixture was quenched with water (150 ml). The product was extracted with ethyl acetate (3×100 ml) and the combined organic layer was washed with brine (100 ml). The organic layer was dried over sodium sulphate and the solvent evaporated under reduced pressure. The crude product was purified by combi flash chromatography using 2% Methanol in DCM as an eluent to obtain 3.6 g of the title compound. $^1$H NMR (400 MHz, DMSO-$d_6$) δ 8.27-8.20 (m, 2H), 7.48 (t, J=9.0 Hz, 1H), 3.92 (s, 2H), 3.10 (s, 3H), 2.87 (s, 3H); MS (ES+) m/z 227 [M+H]$^+$

Intermediate 101

N,N-dimethyl-2-(5-nitro-2-phenoxyphenyl)acetamide

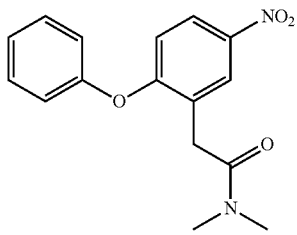 [SMILES: CN(C)C(=O)Cc1cc([N+](=O)[O-])ccc1Oc1ccccc1]

Phenol (1.79 g, 19.0 mmol) and NMP (20 ml) was added to a RBF previously equipped with a magnetic stirrer and nitrogen balloon, and K$_2$CO$_3$ (6.60 g, 47.7 mmol) was added at RT. After stirring for 1 h, 2-(2-fluoro-5-nitrophenyl)-N,N-dimethylacetamide (Intermediate 90, 3.6 g, 15.9 mmol) in NMP (16 ml) was added to mixture and the reaction mixture was stirred at RT for 16 h. The reaction mixture was quenched with water (150 ml) and extracted with Ethyl acetate (3×100 ml). The combined organic layer was washed with brine (100 ml). The organic layer was dried over sodium sulphate and the solvent removed under reduced pressure. The crude product was purified by combi flash chromatography using 30% Ethyl acetate in hexane as an eluent to obtain 3.6 g (75% yield) of the title compound. $^1$H NMR (400 MHz, DMSO-$d_6$): δ 8.24 (d, J=2.4 Hz, 1H), 8.12 (dd, J=9.2, 2.8 Hz, 1H), 7.49 (t, J=7.6 Hz, 2H), 7.29 (t, J=7.4 Hz, 1H), 7.14 (d, J=7.6 Hz, 2H), 6.83 (d, J=9.2 Hz, 1H), 3.92 (s, 2H), 3.07 (s, 3H), 2.85 (s, 3H); MS (ES+) m/z 301 [M+H]$^+$

Intermediate 102

2-(5-amino-2-phenoxyphenyl)-N,N-dimethylacetamide

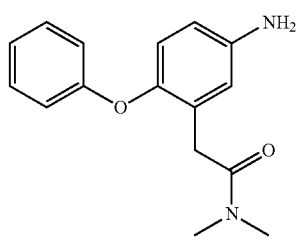 [SMILES: CN(C)C(=O)Cc1cc(N)ccc1Oc1ccccc1]

N,N-Dimethyl-2-(5-nitro-2-phenoxyphenyl)acetamide (Intermediate 101, 3.50 g, 11.6 mmol) in Methanol (70 ml) was added to a RBF previously equipped with a magnetic stirrer and nitrogen balloon. 10% Pd/C (50% wet, 0.35 g) was added to the stirred solution under N$_2$ atmosphere. The reaction mixture was stirred for 1 hours under H$_2$ (gas). The reaction mixture was filtered through a celite bed, washed with methanol and the solvent was removed under reduced pressure to obtain 3.2 g of the title compound. $^1$H NMR (400 MHz, DMSO-$d_6$): δ 7.34-7.24 (m, 2H), 6.99 (t, J=7.2 Hz, 1H), 6.82 (d, J=7.6 Hz, 2H), 6.67 (d, J=8.0 Hz, 1H), 6.50-6.46 (m, 2H), 5.01 (s, 2H), 3.40 (s, 2H), 2.87 (s, 3H), 2.75 (s, 3H); MS (ES+) m/z 271 [M+H]$^+$

Intermediate 103

1-(Dimethylamino)-2-[2-phenoxy-5-(3-phenylureido)phenyl]-1-ethanone

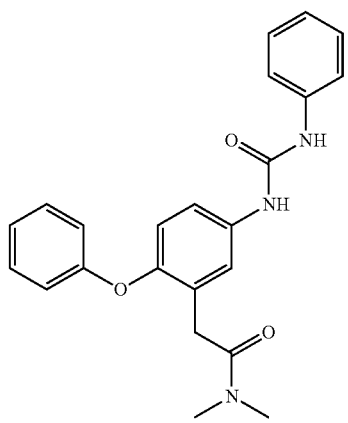 [SMILES: CN(C)C(=O)Cc1cc(NC(=O)Nc2ccccc2)ccc1Oc1ccccc1]

2-(5-Amino-2-phenoxyphenyl)-N,N-dimethylacetamide (Intermediate 102, 1.00 g, 3.6 mmol) and triethylamine (0.50 ml, 3.6 mmol) in DCM (10 ml) was added to a RBF previously equipped with a magnetic stirrer and nitrogen balloon, and the mixture was cooled to 0° C. Phenyl isocyanate (0.44 g, 3.6 mmol) was added, and the reaction mixture was allowed to reach 25° C. and stirred for 3 h. The reaction mixture was quenched with water (50 ml) and extracted with ethyl acetate (3×50 ml). The combined organic layer was washed with brine (50 ml). The organic layer was dried over sodium sulphate and the solvent removed under reduced pressure to obtain 0.80 g (55% yield) of the title compound. $^1$H NMR (400 MHz, DMSO-$d_6$): δ 8.69 (s, 1H), 8.61 (s, 1H), 7.45 (d, J=8.0 Hz, 2H), 7.41-7.26 (m, 6H), 7.06 (t, J=7.0 Hz, 1H), 6.96 (t, J=7.2 Hz, 1H), 6.90 (d, J=7.6 Hz, 2H), 6.85 (d, J=9.2 Hz, 1H), 3.59 (s, 2H), 2.93 (s, 3H), 2.77 (s, 3H); MS (ES+) m/z 388 [M+H]$^+$ Intermediate 104

2-(2-fluoro-5-nitrophenoxy)-N,N-dimethylacetamide

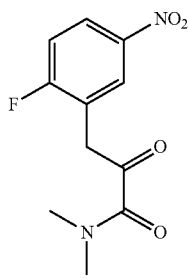 [SMILES: CN(C)C(=O)C(=O)Cc1cc([N+](=O)[O-])ccc1F]

2-Fluoro-5-nitrophenol (commercially available, 5.00 g, 31.8 mmol) in acetonitrile (30 ml) was added to a RBF previously equipped with a magnetic stirrer and nitrogen balloon. $K_2CO_3$ (13.19 g, 95.4 mmol) was added at room temperature. After 15 min, 2-chloro-N,N-dimethylacetamide (3.87 g, 31.8 mmol) in acetonitrile (20 ml) was added to the mixture and the reaction mixture was heated at 80° C. for 16 h. The reaction mixture was filtered through celite bed, the bed washed with acetonitrile and the solvent was removed under reduced pressure to obtain 6.10 g (79% yield) the title compound which used in next step without any further purification. MS (ES+) m/z 243 [M+H]$^+$ Intermediate 105

N,N-dimethyl-2-(5-nitro-2-phenoxyphenoxy)acetamide

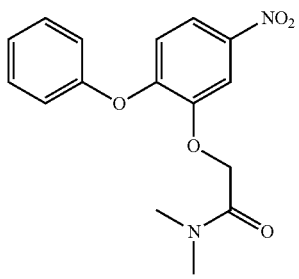

Phenol (2.84 g, 30.2 mmol) in NMP (41 ml) and $K_2CO_3$ (13.91 g, 100 mmol) was added to a RBF previously equipped with a magnetic stirrer and nitrogen balloon, and stirred at room temperature. After 1 h, 2-(2-fluoro-5-nitrophenoxy)-N,N-dimethylacetamide (Intermediate 104, 6.10 g, 25.1 mmol) in NMP (20 ml) was added and the reaction mixture was heated at 85° C. for 16 h. The reaction mixture was quenched with water (150 ml) and extracted with Ethyl acetate (3×100 ml). The combined organic layer was washed with brine (100 ml). The organic layer was dried over sodium sulphate and the solvent removed under reduced pressure to obtain 7.20 g (90% yield) of the title compound that used in next step without any further purification. MS (ES+) m/z 317 [M+H]$^+$ Intermediate 106

2-(5-amino-2-phenoxyphenoxy)-N,N-dimethylacetamide

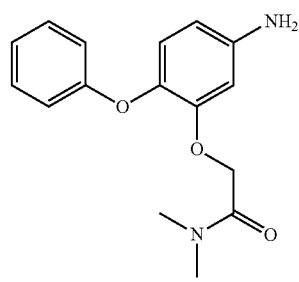 [SMILES: CN(C)C(=O)COc1cc(N)ccc1Oc1ccccc1]

N,N-Dimethyl-2-(5-nitro-2-phenoxyphenoxy)acetamide (Intermediate 105, 7.20 g, 22.7 mmol) in methanol (72 ml) was added to a RBF previously equipped with a magnetic stirrer and nitrogen balloon. 10% Pd/C (50% wet, 0.72 g) was added to the stirred mixture under $N_2$ atmosphere. The reaction mixture was stirred for 2 hours under $H_2$ (gas). The reaction mixture was filtered through a celite bed, the bed was washed with methanol and the solvent was removed under reduced pressure to obtain 3.0 g (46% yield) of the title compound. MS (ES+) m/z 287 [M+H]$^+$ Intermediate 107

1-(Dimethylamino)-2-[2-phenoxy-5-(3-phenylureido)phenoxy]-1-ethanone

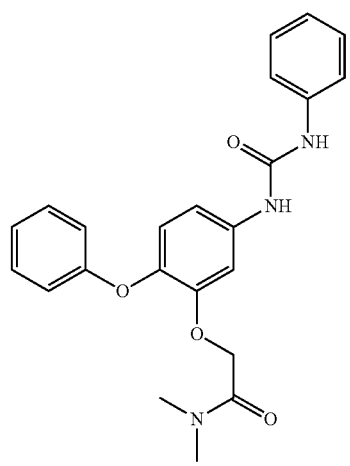 [SMILES: CN(C)C(=O)COc1cc(NC(=O)Nc2ccccc2)ccc1Oc1ccccc1]

2-(5-amino-2-phenoxyphenoxy)-N,N-dimethylacetamide (Intermediate 106, 1.50 g, 5.2 mmol) and triethylamine (0.73 ml, 5.2 mmol) in DCM (15 ml) was added to a RBF previously equipped with a magnetic stirrer and nitrogen balloon, and stirred at 0° C. Phenyl isocyanate (0.62 g, 5.2 mmol) was added and the reaction mixture was allowed to reach 25° C. and stirred for 3 h. The reaction mixture was quenched with water (30 ml) and product was extracted with DCM (3×50 m). The combined organic layer was washed with brine (30 ml) and dried over sodium sulphate. The solvent was removed under reduced pressure. The crude product was purified by combi flash chromatography using 80% ethyl acetate in hexanes as an eluent to yield 0.720 g (33% yield) of the title compound. MS (ES+) m/z 406 [M+H]+

Intermediate 108

3-Methyl-2-phenoxy-5-(phenoxycarbonylamino) pyridine

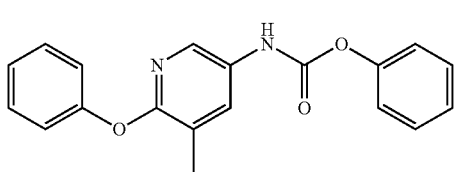 [SMILES: Cc1cc(NC(=O)Oc2ccccc2)cnc1Oc1ccccc1]

In a RBF previously equipped with a magnetic stirrer was taken 5-Methyl-6-phenoxy-3-pyridylamine (commercially available, 0.5 g, 0.0025 mol) in DCM and the mixture was cooled to 0° C. TEA (0.35 ml, 0.0025 mol) was added followed by drop wise addition of Phenyl Chloroformate (0.39 ml, 0.0025 mol). The reaction mixture was allowed to reach 25° C. and stirred for 2 h. The reaction mixture was quenched with water (50 ml) and both the layers were separated. The aqueous layer was extracted with DCM (2×50 ml). The combined organic layer was washed with brine (50 ml), dried over sodium sulphate and the solvent removed under reduced pressure to obtain crude product. The crude product was purified by Combi-flash chromatography using 15% ethyl acetate in hexanes as an eluent to yield 0.5 g (62% yield) of the title compound. MS (ES+) m/z 321 [M−H]+.

Intermediate 109

3-(5-Methyl-6-phenoxy-3-pyridyl)-1-(4-methylphenyl)urea

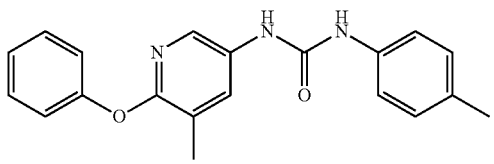 [SMILES: Cc1ccc(NC(=O)Nc2cnc(Oc3ccccc3)c(C)c2)cc1]

In a RBF previously equipped with a magnetic stirrer was taken 3-Methyl-2-phenoxy-5-(phenoxycarbonylamino)pyridine (Intermediate 108, 0.5 g, 0.0015 mol) in DMF (2 ml) and the mixture was cooled to 0° C. To the reaction mixture TEA (0.21 ml, 0.0031 mol) was added followed by drop wise addition of 4-methyl-aniline (0.16 g, 0.0015 mol) in DMF (3 ml. The reaction mixture was allowed to reach room temperature and then heated to 100° C. and stirred for 2 h. The reaction mixture was quenched with water (50 ml) and product was extracted with DCM (3×30 ml). The combined organic layer was washed with brine (25 ml), dried over sodium sulphate and the solvent removed under reduced pressure to obtain 0.30 g (57% yield) of the title compound which was used in the next step without further purification. 1H NMR (400 MHz, DMSO-d6): δ 8.66 (s, 2H), 7.99 (s, 1H), 7.91 (s, 1H), 7.40-7.33 (m, 4H), 7.15 (t, J=7.2 Hz, 1H), 7.10 (app d, 2H), 7.05 (app d, 2H), 2.28 (s, 3H), 2.25 (s, 3H). MS (ES+) m/z 334 [M−H]+.

EXAMPLES

Example 1

1-(4-phenoxyphenyl)-3-phenyl-1,3,5-triazinane-2,4, 6-trione

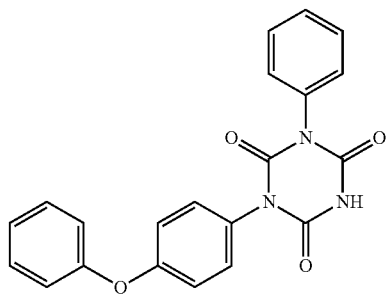 [SMILES: O=c1[nH]c(=O)n(-c2ccc(Oc3ccccc3)cc2)c(=O)n1-c1ccccc1]

In a microwave tube 1-(4-phenoxyphenyl)-3-phenylurea (Intermediate 1, 0.110 g, 0.00082 mol) and ethoxycarbonyl isocyanate (0.042 g, 0.00036 mol) were taken in bromo benzene (1.10 mL) and heated in a microwave reactor at 150° C. for 1 h. The reaction mixture was diluted with water (50 ml) and extracted with ethyl acetate (3×40 ml). The combine organic layers were washed with brine (30 ml), dried over sodium sulfate and evaporated under reduced pressure to obtain a crude product. The crude product was purified by combi flash chromatography using 0-100% ethyl acetate in hexanes as a mobile phase and 60-120 silica as stationary phase. The obtained product was further purified using 5 mM ammonia acetate as a modifier and water: Acetonitrile (0-100% gradient system) as a mobile phase using prep HPLC purification to obtain 0.033 g (24% yield) of the title compound. $^1$H NMR (400 MHz, CDCl$_3$) δ ppm 7.07-7.12 (m, 4H) 7.19 (br. t, 1H) 7.31 (m, 2H) 7.34-7.42 (m, 4H) 7.47-7.56 (m, 3H) 8.24 (s, 1H); MS (ES−) m/z 372 [M−H]−

Example 2

1-(4-methoxyphenyl)-3-(4-phenoxyphenyl)-1,3,5-triazinane-2,4,6-trione

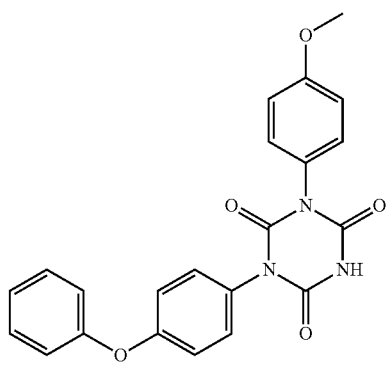 [SMILES: COc1ccc(-n2c(=O)[nH]c(=O)n(-c3ccc(Oc4ccccc4)cc3)c2=O)cc1]

Ethoxycarbonyl isocyanate (0.103 g, 0.00089 mol) was added to a solution of 1-(4-methoxyphenyl)-3-(4-phenoxyphenyl)urea (Intermediate 2, 0.200 g, 0.00059 mol) under stirring in toluene (2.0 mL) at 0° C. The reaction mixture was stirred at 110° C. for 16.0 hrs in a sealed tube. The reaction mixture was quenched with ice-water (30 ml) and extracted with Ethyl Acetate (3×30 ml). The combined organic layers were washed with brine (30 ml). The organic layer was dried over sodium sulfate and evaporated under reduced pressure to obtain crude product. The crude product was purified by preparative HPLC using 0.1% ammonia as a modifier and water:Acetonitrile (0-100% gradient system) as a mobile phase to yield 0.018 g (9% yield) of the title compound. $^1$H NMR (400 MHz, DMSO-d6) δ ppm 3.79 (s, 3H) 6.98-7.12 (m, 6H) 7.17-7.23 (m, 1H) 7.26-7.31 (m, 2H) 7.34-7.39 (m, 2H) 7.42-7.48 (m, 2H) 11.92 (s, 1H); MS (ES+) m/z 404 [M+H]$^+$ Example 3

3-[2,4,6-trioxo-3-(4-phenoxyphenyl)-1,3,5-triazinan-1-yl]benzonitrile

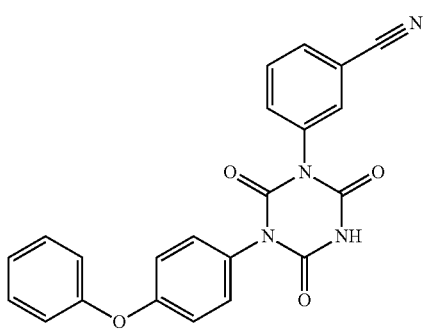 [SMILES: N#Cc1cccc(-n2c(=O)[nH]c(=O)n(-c3ccc(Oc4ccccc4)cc3)c2=O)c1]

Ethoxycarbonyl isocyanate (0.083 g, 0.00072 mol) was added to a solution of (Intermediate 3, 0.160 g, 0.00048 mol) in toluene (1.60 mL) at 0° C. The reaction mixture was stirred at 110° C. for 16 h in a sealed tube. The reaction mixture was quenched with ice-water (50 ml) and product was extracted with Ethyl Acetate (3×40 ml). The combined organic layers were washed with brine (30 ml), dried over sodium sulfate and evaporated under reduce pressure to obtain crude product. The crude product was purified on column chromatography by 70% ethyl acetate in hexane as a mobile phase and 60-120 silica as stationary phase. The obtained product was further purified on preparative HPLC using 5 mM ammonium acetate as a modifier and water:Acetonitrile (0-100% gradient system) as a mobile phase to yield 0.020 g (10% yield) of the title compound. $^1$H NMR (400 MHz, DMSO-d6) δ ppm 7.04-7.12 (m, 4H) 7.18-7.24 (m, 1H) 7.33-7.38 (m, 2H) 7.42-7.48 (m, 2H) 7.60-7.80 (m, 2H) 7.89-8.01 (m, 2H) 12.18 (s, 1H); MS (ES−) m/z 397 [M−H]−

Example 4

1-(3-methoxyphenyl)-3-(4-phenoxyphenyl)-1,3,5-triazinane-2,4,6-trione

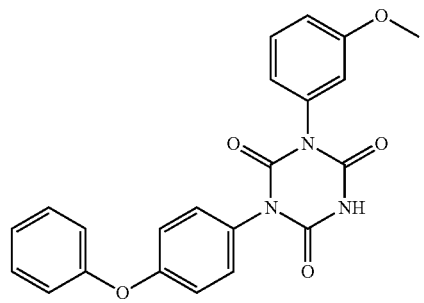 [SMILES: COc1cccc(-n2c(=O)[nH]c(=O)n(-c3ccc(Oc4ccccc4)cc3)c2=O)c1]

Ethoxycarbonyl isocyanate (0.077 g, 0.00044 mol) was added to the solution of 1-(3-methoxyphenyl)-3-(4-phenoxyphenyl)urea (Intermediate 4, 0.150 g, 0.00029 mol) in toluene (1.5 mL) at 0° C. The reaction mixture was stirred at 110° C. for 16 h in a sealed tube. The reaction mixture was quenched with ice-water (50 ml) and extracted with ethyl acetate (3×40 ml). The combined organic layers were washed with brine (30 ml), dried over sodium sulfate and evaporated under reduced pressure to obtain a crude product. The crude product was purified by ethyl acetate as a mobile phase and 60-120 silica as stationary phase on column chromatography. The obtained product was further purified using preparative HPLC purification using 5 mM ammonium acetate as a modifier and water:Acetonitrile (0-100% gradient system) as a mobile phase to yield 0.012 g (6.7% yield) of the title compound. $^1$H NMR (400 MHz, DMSO-d6) δ ppm 3.77 (s, 3H) 6.93-7.03 (m, 3H) 7.04-7.12 (m, 4H) 7.17-7.24 (m, 1H) 7.34-7.48 (m, 5H) 11.99 (s, 1H); MS (ES+) m/z 404 [M+H]$^+$ Example 5

1-(3-methyl-4-phenoxyphenyl)-3-phenyl-1,3,5-triazinane-2,4,6-trione

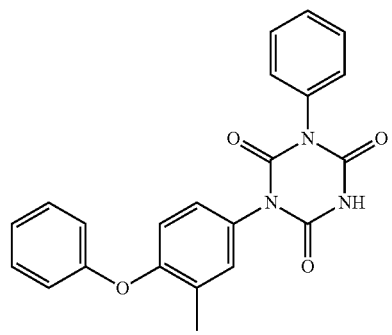 [SMILES: Cc1cc(-n2c(=O)[nH]c(=O)n(-c3ccccc3)c2=O)ccc1Oc1ccccc1]

Ethoxycarbonyl isocyanate (0.108 g, 0.00094 mol) was added to the solution of 1-(3-methyl-4-phenoxyphenyl)-3-phenylurea (Intermediate 5, 0.200 g, 0.00062 mol) in Toluene (2.0 mL) at 0° C. The resulting reaction mixture was stirred at 110° C. for 16 h in a microwave vial. Reaction mixture was quenched with ice-water (50 ml) and extracted with Ethyl Acetate (3×40 ml). The combine organic layers were washed with brine (30 ml). The organic layer was dried over sodium sulfate and evaporated under reduced pressure to obtain crude product. The crude product was purified on combi flash chromatography using 30% ethyl acetate in hexane as a mobile phase and 60-120 silica as stationary phase. The obtained product was further purified using preparative HPLC purification using 5 mM ammonium acetate as a modifier and water:acetonitrile (0-100% gradient system) as a mobile phase to yield 0.050 g (20% yield) of the title compound. $^1$H NMR (400 MHz, DMSO-d6) δ ppm 2.20 (s, 3H) 6.88-7.01 (m, 3H) 7.11-7.24 (m, 2H) 7.30-7.53 (m, 8H) 12.02 (s, 1H); MS (ES+) m/z 388 [M+H]$^+$ Example 6

1-[4-(benzyloxy)phenyl]-3-phenyl-1,3,5-triazinane-2,4,6-trione

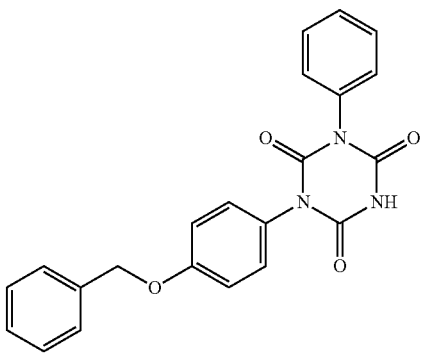 [SMILES: O=c1[nH]c(=O)n(-c2ccc(OCc3ccccc3)cc2)c(=O)n1-c1ccccc1]

In a 30 ml seal tube previously equipped with a magnetic stirrer, ethoxycarbonyl isocyanate (0.181 g, 0.0015 mol) was added to a solution of 1-[4-(benzyloxy)phenyl]-3-phenylurea (Intermediate 7, 0.250 g, 0.0007) in toluene (2.5 mL) at 0° C. The reaction mixture was allowed to come to 25° C. and then heated at 110° C. for 16 h. The reaction mixture was quenched with ice-water (50 ml) and product extracted with ethyl acetate (3×40 ml). The combined organic layers washed with brine (30 ml), dried over sodium sulfate and evaporated under reduce pressure to obtain crude product. The crude product was purified on silica gel (60-120 mesh) using 30% ethyl acetate in hexane as an eluent to obtained 0.030 g (10% yield) the title compound. $^1$H NMR (400 MHz, DMSO-d6) δ ppm 5.14 (s, 2H) 7.04-7.12 (m, 2H) 7.26-7.52 (m, 12H) 11.97 (s, 1H); MS (ES−) m/z 386 [M−H]$^−$ Example 7

1-[4-(4-chlorophenoxy)phenyl]-3-phenyl-1,3,5-triazinane-2,4,6-trione

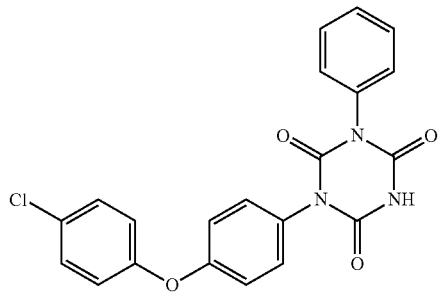 [SMILES: O=c1[nH]c(=O)n(-c2ccc(Oc3ccc(Cl)cc3)cc2)c(=O)n1-c1ccccc1]

In a 30 ml seal tube previously equipped with a magnetic stirrer ethoxycarbonyl isocyanate (0.135 g, 0.00110 mol) was added to a solution of 1-[4-(4-chlorophenoxy)phenyl]-3-phenylurea (Intermediate 8, 0.265 g, 0.00078) in toluene (2.60 mL) at 0° C. The reaction mixture was allowed to come at 25° C. and heated at 110° C. for 16 h. The reaction mixture was quenched with NaHCO$_3$ (50 ml) and product extracted with ethyl acetate (3×40 ml). The combine organic layers were washed with brine (30 ml), dried over sodium sulfate and evaporated under reduced pressure to obtain crude product. The crude product was purified on silica gel (60-120 mesh) using 40% ethyl acetate in hexane as an eluent to yield 0.010 g (3% yield) of the title compound. $^1$H NMR (400 MHz, DMSO-d6) δ ppm 7.07 (m, 4H) 7.35-7.52 (m, 9H) 12.02 (s, 1H); MS (ES−) m/z 406 [M−H]−

Example 8

4-[4-(2,4,6-trioxo-3-phenyl-1,3,5-triazinan-1-yl)phenoxy]benzonitrile

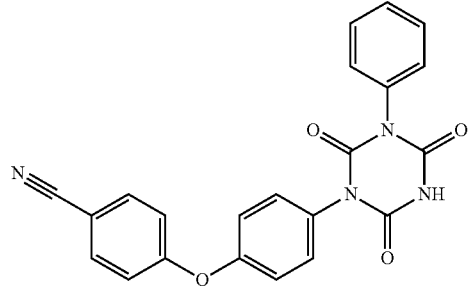 [SMILES: N#Cc1ccc(Oc2ccc(-n3c(=O)[nH]c(=O)n(-c4ccccc4)c3=O)cc2)cc1]

In a 30 ml seal tube previously equipped with a magnetic stirrer, ethoxycarbonyl isocyanate (0.130 g, 0.0011 mol) was added to the solution of 1-[4-(4-cyanophenoxy)phenyl]-3-phenylurea (Intermediate 10, 0.250 g, 0.00076 mol) in toluene (3.00 mL) at 0° C. The reaction mixture was stirred at 110° C. for 16 h. The solvent was evaporated under reduced pressure to obtain crude product. The crude product was purified by 0-30% Ethyl acetate in Hexane as a mobile phase and 60-120 silica as stationary phase on Combi flash chromatography. The obtained material was further purified by preparative HPLC purification using 0.1% ammonia in water and acetonitrile as mobile phases ((0-100% gradient system) to yield 0.007 g (2% yield) of the title compound. ¹H NMR (400 MHz, DMSO-d6) δ ppm 7.14-7.27 (m, 4H) 7.36-7.40 (m, 2H) 7.42-7.52 (m, 5H) 7.87-7.93 (m, 2H) 12.06 (s, 1H); MS (ES−) m/z 397 [M−H]⁻

Example 9

1-(2-methoxy-4-phenoxyphenyl)-3-phenyl-1,3,5-triazinane-2,4,6-trione

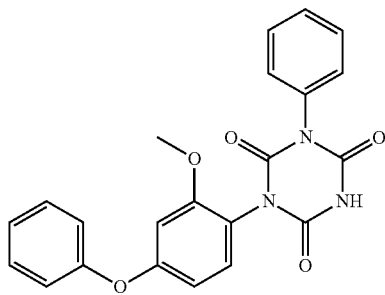 [SMILES: COc1cc(Oc2ccccc2)ccc1-n1c(=O)[nH]c(=O)n(-c2ccccc2)c1=O]

1-(2-methoxy-4-phenoxyphenyl)-3-phenylurea (Intermediate 11, 0.300 g, 0.00089 mol) in dry toluene (3.00 mL) was added to a seal tube previously equipped with a magnetic stirrer and cooled to 0° C. Ethoxycarbonyl isocynate (0.100 g, 0.00089 mol) was added and the reaction mixture was stirred at 110° C. for 16 h. The reaction mixture was quenched with ice-water (20 ml) and product extracted with ethyl acetate (3×20 ml). The combined organic layers were washed with brine (30 ml). and dried over sodium sulfate and evaporated under reduced pressure to obtain the crude product. The crude product was purified on column chromatography using 35% ethyl acetate in hexane as a mobile phase and 60-120 silica to yield 0.015 g (4% yield) of the title compound. ¹H NMR (400 MHz, DMSO-d6) δ ppm 3.76 (s, 3H) 6.50-6.58 (m, 1H) 6.85-6.89 (m, 1H) 7.08-7.15 (m, 2H) 7.18-7.24 (m, 1H) 7.29-7.34 (m, 1H) 7.35-7.40 (m, 2H) 7.41-7.52 (5H) 12.09 (s, 1H); MS (ES−) m/z 402 [M−H]⁻

Example 10

1-[4-(morpholin-4-yl)phenyl]-3-(4-phenoxyphenyl)-1,3,5-triazinane-2,4,6-trione

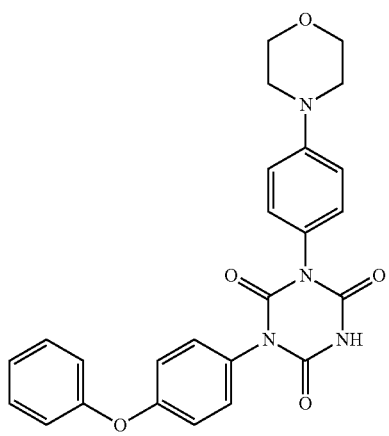 [SMILES: O=c1[nH]c(=O)n(-c2ccc(N3CCOCC3)cc2)c(=O)n1-c1ccc(Oc2ccccc2)cc1]

Ethoxycarbonyl isocyanate (0.038 g, 0.00033 mol) was added to a solution of 1-(4-Morpholinophenyl)-3-(4-phenoxyphenyl)urea (Intermediate 12, 0.130 g, 0.00033 mol)) in dry toluene (1.30 ml) at 0° C. in a 30 ml seal tube previously equipped with a magnetic stirrer. The reaction mixture was allowed to come to 25° C. and then heated at 110° C. for 16 h. The reaction mixture was quenched with ice-water (50 ml) and extracted with ethyl acetate (3×40 ml). The combined organic layers were washed with brine (30 ml), dried over sodium sulfate and evaporated under reduced pressure to obtain the crude product. The crude product was purified on silica gel (100-200 mesh) using 80% ethyl acetate in hexane as an eluent to yield 0.010 g (6.5% yield) of the title compound.

¹H NMR (400 MHz, DMSO-d6) δ ppm 3.13-3.18 (m, 4H) 3.72-3.78 (m, 4H) 6.97-7.02 (m, 2H) 7.03-7.13 (m, 4H) 7.17-7.24 (m, 3H) 7.34-7.40 (m, 2H) 7.41-7.49 (m, 2H) 11.92 (s, 1H); MS (ES+) m/z 459 [M+H]⁺

Example 11

1-(3-methoxy-4-phenoxyphenyl)-3-phenyl-1,3,5-triazinane-2,4,6-trione

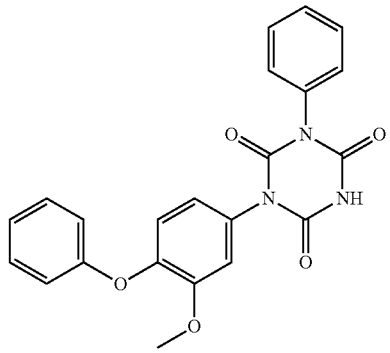 [SMILES: COc1cc(-n2c(=O)[nH]c(=O)n(-c3ccccc3)c2=O)ccc1Oc1ccccc1]

Ethoxycarbonyl isocyanate was added (0.103 g, 0.0008 mol) to the solution of 1-(3-methoxy-4-phenoxyphenyl)-3-phenylurea (Intermediate 13, 0.200 g, 0.0005 mol) in toluene (2.00 mL) at 0° C. in a 30 ml seal tube previously equipped with a magnetic stirrer. The reaction mixture was stirred and allowed to reach 25° C. and then heated at 110° C. for 16 h. The reaction mixture was quenched with water (50 ml) and extracted with ethyl acetate (3×40 ml). The combined organic layers were washed with brine (30 ml), dried over sodium sulfate and evaporated under reduced pressure to obtain the crude product. The crude product was purified on silica gel (60-120 mesh) using 60% ethyl acetate in hexane as an eluent. The compound was recrystallized in dichloromethane/hexane to yield 0.045 g (18% yield) of the title compound. ¹H NMR (400 MHz, DMSO-d6) δ ppm 3.72 (s, 3H) 6.86-6.92 (m, 2H) 6.97-7.03 (m, 1H) 7.05-7.12 (m, 2H) 7.24-7.27 (m, 1H) 7.32-7.41 (m, 4H) 7.42-7.53 (m, 3H) 12.06 (s, 1H); MS (ES−) m/z 402 [M−H]−

Example 12

2-phenoxy-5-(2,4,6-trioxo-3-phenyl-1,3,5-triazinan-1-yl)benzonitrile

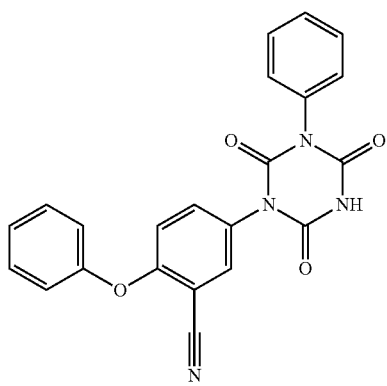 [SMILES: N#Cc1cc(-n2c(=O)[nH]c(=O)n(-c3ccccc3)c2=O)ccc1Oc1ccccc1]

Ethoxycarbonyl isocyanate (0.140 g, 0.00110 mol) was added to 1-(3-cyano-4-phenoxyphenyl)-3-phenylurea (Intermediate 14, 0.250 g, 0.00075 mol) in dry toluene (2.5 mL) at 0° C. in a 30 ml seal tube previously equipped with a magnetic stirrer. The reaction mixture was stirred at 110° C. for 16 h. The solvent was evaporated under reduced pressure to obtain the crude product. The crude product was purified by using 0.1% TFA in water and acetonitrile as a mobile phase (0-100% gradient system) in preparative HPLC purification to yield 0.034 g (11% yield) of the title compound. $^1$H NMR (400 MHz, DMSO-d6) δ ppm 7.00 (d, 1H) 7.23-7.29 (m, 2H) 7.31-7.39 (m, 3H) 7.40-7.78 (m, 5H) 7.69 (dd, 1H) 7.95 (d, 1H) 12.16 (s, 1H); MS (ES−) m/z 397 [M−H]−

Example 13

1-(2-methoxy-5-methyl-4-phenoxyphenyl)-3-phenyl-1,3,5-triazinane-2,4,6-trione

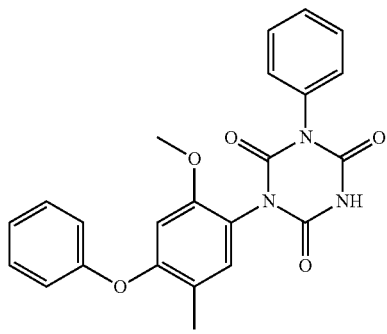 [SMILES: COc1cc(Oc2ccccc2)c(C)cc1-n1c(=O)[nH]c(=O)n(-c2ccccc2)c1=O]

1-(2-methoxy-5-methyl-4-phenoxyphenyl)-3-phenylurea (Intermediate 17, 0.260 g, 0.00074 mol) was dissolved in dry toluene (2.60 mL) in a seal tube and cooled to 0° C. Ethoxycarbonyl isocyanate (0.094 g, 0.00082 mol) was added and the reaction mixture was stirred at 110° C. for 16 h. The solvent was evaporated under reduced pressure to obtain a crude product. The crude product was purified on Combi flash chromatography by using ethyl acetate as a mobile phase and 60-120 silica as stationary phase. The obtained product was further purified by using 10 mM ammonium bicarbonate as modifier and water:acetonitrile (0-100% gradient system) as a mobile phase in preparative HPLC purification to yield 0.042 g (13% yield) of the title compound. $^1$H NMR (400 MHz, DMSO-d6) δ ppm 2.10 (s, 3H) 3.67 (s, 3H) 6.72 (s, 1H) 6.91-6.97 (m, 2H) 7.07-7.14 (m, 1H) 7.28 (s, 1H) 7.33-7.51 (m, 7H) 12.06 (s, 1H); MS (ES+) m/z 418 [M+H]+

Example 14

1-(3-methoxy-5-methyl-4-phenoxyphenyl)-3-phenyl-1,3,5-triazinane-2,4,6-trione

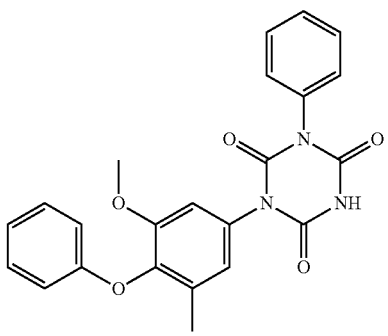 [SMILES: COc1cc(-n2c(=O)[nH]c(=O)n(-c3ccccc3)c2=O)cc(C)c1Oc1ccccc1]

In a 10 ml seal tube previously equipped with a magnetic stirrer and nitrogen balloon, ethoxycarbonyl isocyanate (0.033 g, 0.00030 mol) was added drop wise to the solution of 1-(3-methoxy-5-methyl-4-phenoxyphenyl)-3-phenylurea (Intermediate 20, 0.090 g, 0.00025 mol) in dry toluene (0.9 mL) at 25° C. The reaction mixture was heated at 110° C. for 16 h. The reaction mixture was concentrated under reduced pressure to obtain a crude product. The crude product was purified by preparative HPLC with 5 mM ammonium acetate in water:acetonitrile as mobile phase (0-100% gradient system) to yield 0.008 g (8% yield) of the title compound. $^1$H NMR (400 MHz, DMSO-d6 δ ppm 2.10 (s, 3H) 3.67 (s, 3H) 6.72-6.77 (m, 2H) 6.93-6.96 (m, 1H) 6.97-7.03 (m, 1H) 7.08-7.12 (m, 1H) 7.26-7.33 (m, 2H) 7.36-7.53 (m, 5H) 12.04 (s, 1H); MS (ES−) m/z 416 [M−H]−

Example 15

1-[3-(cyclopentyloxy)-4-phenoxyphenyl]-3-methyl-1,3,5-triazinane-2,4,6-trione

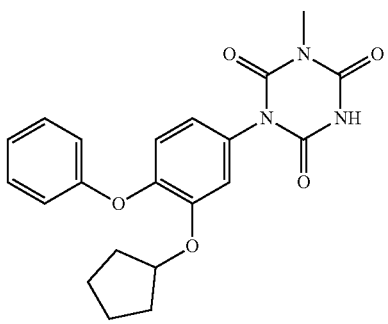 [SMILES: Cn1c(=O)[nH]c(=O)n(-c2ccc(Oc3ccccc3)c(OC3CCCC3)c2)c1=O]

1-[3-(cyclopentyloxy)-4-phenoxyphenyl]-3-methylurea (Intermediate 23, 0.180 g, 0.0005516 mol) was dissolved in toluene (1.80 mL) in a 30 ml seal tube previously equipped with a magnetic stirrer and cooled to 0° C. Ethoxycarbonyl isocyanate (0.069 g, 0.0006067 mol) was added and the reaction mixture was stirred at 110° C. for 16 h. The solvent was evaporated under reduced pressure to obtain the crude product. The crude product was purified on combi flash chromatography by using a 0-100% ethyl acetate gradient in hexane as a mobile phase and 60-120 silica as stationary phase. The product was further purified by prep HPLC purification using 3 mM ammonium acetate in water acetonitrile as a mobile phase (0-100% gradient system) to yield 0.049 g (22% yield) of the title compound. $^1$H NMR (400 MHz, DMSO-d6) δ ppm 1.30-1.48 (m, 4H) 1.49-1.60 (m, 2H) 1.67-1.80 (m, 2H) 3.16 (s, 3H) 4.69 (m, 1H) 6.84-6.93 (m, 3H) 7.02-7.08 (m, 1H) 7.10-7.18 (m, 2H) 7.30-7.37 (m, 2H) 11.84 (s, 1H); MS (ES−) m/z 394 [M−H]−

Example 16

1-(3-ethoxy-4-phenoxyphenyl)-3-phenyl-1,3,5-triazinane-2,4,6-trione

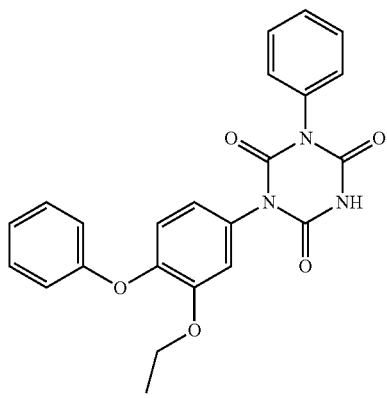 [SMILES: CCOc1cc(-n2c(=O)[nH]c(=O)n(-c3ccccc3)c2=O)ccc1Oc1ccccc1]

In a 30 ml seal tube previously equipped with a magnetic stirrer and nitrogen balloon, Ethoxycarbonyl isocyanate (0.083 ml, 0.00072 mol) was added drop wise to a solution of 1-(3-ethoxy-4-phenoxyphenyl)-3-phenylurea (Intermediate 24, 0.230 g, 0.00066 mol) in dry toluene (2.3 mL) at 0° C. The reaction mixture was allowed to reach to 25° C. and then heated at 120° C. for 12 h. The solvent was evaporated under reduced pressure to obtain the crude product. The crude product was purified by using 0.1% ammonia as a modifier and water:acetonitrile (0-100% as a gradient system) as a mobile phase in preparative HPLC purification to yield 0.0145 g (5% yield) of the title compound. $^1$H NMR (400 MHz, DMSO-d6) δ ppm 1.18 (t, 3H) 3.99 (q, 2H) 6.88-6.93 (m, 2H) 6.94-6.99 (m, 1H) 7.04-7.11 (m, 2H) 7.20-7.24 (m, 1H) 7.31-7.39 (m, 4H) 7.4.0-7.52 (m, 3H) 12.05 (s, 1H); MS (ES−) m/z 416 [M−H]−

Example 17

1-[3-(oxolan-3-yloxy-4-phenoxyphenyl]-3-phenyl-1,3,5-triazinane-2,4,6-trione

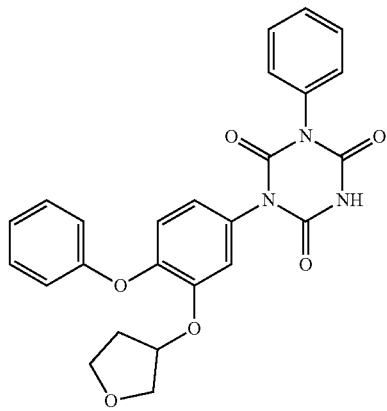 [SMILES: O=c1[nH]c(=O)n(-c2ccc(Oc3ccccc3)c(OC3CCOC3)c2)c(=O)n1-c1ccccc1]

In a 30 ml seal tube previously equipped with a magnetic stirrer Ethoxycarbonyl isocyanate (0.130 g, 0.0011 mol) was added to the solution of 1-[4-Phenoxy-3-(tetrahydrofur-3-yloxy)phenyl]-3-phenylurea (Intermediate 27, 0.400 g, 0.0010 mol) in toluene (4 mL) at 0° C. The reaction mixture was stirred at 110° C. for 16 h. The solvent was evaporated under reduced pressure to obtain crude product. The crude product was purified on combi flash chromatography using ethyl acetate as a mobile phase and 60-120 silica as stationary phase. The crude product was further purified by prep HPLC purification using using 0.1% ammonia as a modifier and water:acetonitrile (0-100% gradient system) as a mobile phase to yield 0.028 g (7% yield) of the title compound. $^1$H NMR (400 MHz, DMSO-d6) δ ppm 1.75-1.85 (m, 1H) 2.02-2.15 (m, 1H) 3.49-3.70 (m, 3H) 3.79-3.85 (m, 1H) 4.88-4.95 (m, 1H) 6.88-6.94 (m, 2H) 6.99-7.04 (m, 1H) 7.05-7.14 (m, 2H) 7.22-7.25 (m, 1H) 7.31-7.53 (m, 7H) 12.06 (s, 1H); MS (ES−) m/z 458 [M−H]−

Example 18

1-(3-methyl-4-phenoxyphenyl)-3-(pyridin-2-yl)-1,3,5-triazinane-2,4,6-trione

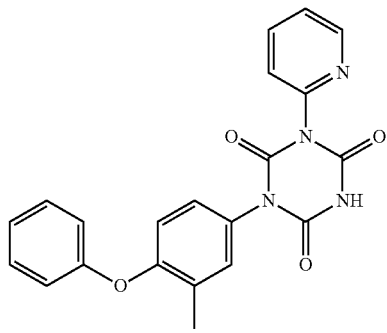

In a 30 ml seal tube previously equipped with a magnetic stirrer, 1-(3-methyl-4-phenoxyphenyl)-3-pyridin-2-ylurea (Intermediate 28, 0.250 g, 0.0007 mol) was dissolved in Bromo Benzene (2.5 mL) at 0° C. To the mixture Ethoxycarbonyl isocyanate (0.099 g, 0.0008 mol) was added. The resulting reaction mixture was stirred at 110° C. for 16 h. The solvent was evaporated under reduced pressure to obtain crude product. The crude product was purified on combi flash chromatography by using 0-100% ethyl acetate in hexane as a mobile phase and 60-120 silica as stationary phase. The obtained product was further purified using 5 mM ammonia acetate as a modifier and water:acetonitrile (0-100% gradient system) as a mobile phase using preparative HPLC purification to yield 0.036 g (12% yield) of the title compound. $^1$H NMR (400 MHz, DMSO-d6) δ ppm 2.21 (s, 3H) 6.91 (d, 1H) 6.95-7.00 (m, 2H) 7.14 (t, 1H) 7.23 (dd, 1H) 7.35 (d, 1H) 7.37-7.43 (m, 2H) 7.49-7.57 (m 2H) 8.01 (dt, 1H) 8.57-8.62 (m, 1H) 12.12 (s, 1H); MS (ES−) m/z 387 [M−H]$^-$ Example 19

1-phenyl-3-(1-phenyl-1H-indazol-5-yl)-1,3,5-triazinane-2,4,6-trione

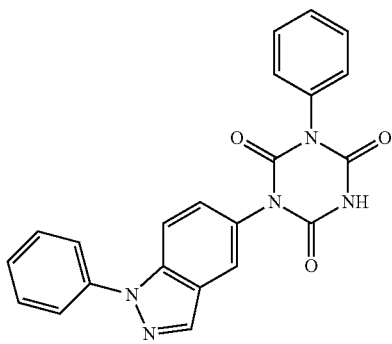 [SMILES: O=c1[nH]c(=O)n(-c2ccc3c(cnn3-c3ccccc3)c2)c(=O)n1-c1ccccc1]

In a 30 ml seal tube previously equipped with a magnetic stirrer Ethoxycarbonyl isocyanate (0.053 g, 0.0004 mol) was added to a solution of 1-phenyl-3-(1-phenyl-1H-indazol-5-yl)urea (Intermediate 29, 0.140 g, 0.0004 mol) in Toluene (1.4 mL) at 0° C. The reaction mixture was allowed to reach 25° C. and then heated at 110° C. for 16 h. The solvent was evaporated under reduced pressure to obtain the crude product. The crude product was purified by using 0.01% ammonia as a modifier and water:acetonitrile (0-100% gradient system) as a mobile phase in prep HPLC purification to yield 0.007 g (4% yield) of the title compound. $^1$H NMR (400 MHz, DMSO-d6) δ ppm 7.38-7.53 (m, 7H) 7.59-7.66 (m, 2H) 7.78-7.83 (m, 2H) 7.90-7.95 (m, 2H) 8.47-8.49 (m, 1H) 12.05 (s, 1H); MS (ES−) m/z 396 [M−H]$^-$ Example 20

1-phenyl-3-[4-(phenylamino)phenyl]-1,3,5-triazinane-2,4,6-trione

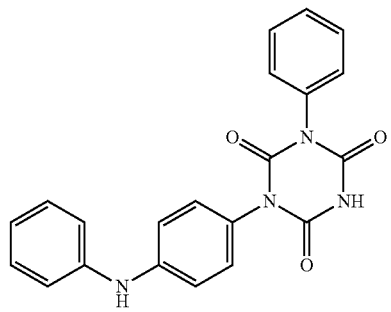 [SMILES: O=c1[nH]c(=O)n(-c2ccc(Nc3ccccc3)cc2)c(=O)n1-c1ccccc1]

In a 30 ml seal tube previously equipped with a magnetic stirrer, ethoxycarbonyl isocyanate (0.125 g, 0.0010 mol) was added to a solution of 1-phenyl-3-[4-(phenylamino)phenyl]urea (commercially available, 0.300 g, 0.0009 mol) in Bromobenzene (3.0 mL) at 0° C. The reaction mixture was stirred in a microwave reactor at 150° C. for 3 h. The solvent was evaporated under reduce pressure to obtain a crude product. The crude product was purified on combi flash chromatography by using ethyl acetate in hexane as a mobile phase and 60-120 silica as stationary phase. The obtained product was further purified by using 3 mM ammonia as modifier and water:acetonitrile (0-100% gradient system) as a mobile phase in preparative HPLC purification to yield 0.008 g (3% yield) of the title compound. $^1$H NMR (400 MHz, DMSO-d6) δ ppm 6.83-6.92 (m, 1H) 7.05-7.57 (m, 13H) 8.34 (s, 1H) 11.94 (s, 1H); MS (ES+) m/z 373 [M+H]$^+$ Example 21

1-(3-ethoxy-4-phenoxyphenyl)-3-methyl-1,3,5-triazinane-2,4,6-trione

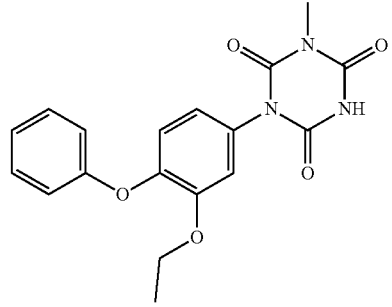 [SMILES: CCOc1cc(-n2c(=O)[nH]c(=O)n(C)c2=O)ccc1Oc1ccccc1]

In a 30 ml seal tube previously equipped with a magnetic stirrer and nitrogen balloon, ethoxycarbonyl isocyanate (0.083 mL, 0.00035 mol) was added drop wise to a solution of (Intermediate 30, 0.093 g, 0.00032 mol) in dry toluene (2.3 mL) at 0° C. The reaction mixture was allowed to reach 25° C. and then heated at 120° C. for 12 h. The solvent was evaporated under reduced pressure to obtain a crude product. The crude product was purified by preparative HPLC purification using 0.1% ammonia as modifier and water:acetonitrile (0-100% gradient system) as a mobile phase to yield 0.026 g (22% yield) of the title compound. $^1$H NMR (400 MHz, DMSO-d6) δ ppm 1.18 (t, 3H) 3.16 (s, 3H) 3.97 (q, 2H) 6.88-6.95 (m, 3H) 7.03-7.12 (m, 2H) 7.16-7.20 (m, 1H) 7.32-7.40 (m, 2H) 11.83 (s, 1H); MS (ES−) m/z 354 [M−H]−

Example 22

1-methyl-3-[3-(oxolan-3-yloxy)-4-phenoxyphenyl]-1,3,5-triazinane-2,4,6-trione

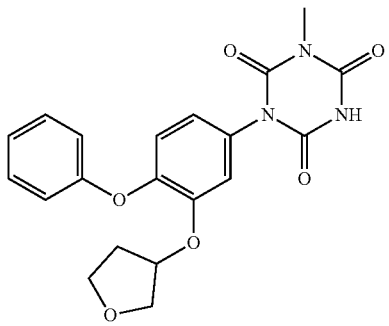 [SMILES: Cn1c(=O)[nH]c(=O)n(-c2ccc(Oc3ccccc3)c(OC3CCOC3)c2)c1=O]

In a 30 ml seal tube previously equipped with a magnetic stirrer, Ethoxycarbonyl isocyanate (0.042 g, 0.0003 mol) was added to a solution of 1-methyl-3-[4-phenoxy-3-(tetrahydrofuran-3-yloxy)phenyl]urea (Intermediate 31, 0.110 g, 0.0003 mol) in Toluene (1.10 mL) at 0° C. The resulting reaction mixture was heated at 110° C. for 16 h. The solvent was evaporated under reduced pressure to obtain crude product. The crude product was purified on silica gel (60-120 mesh) using ethyl acetate as an eluent and re-purified by preparative HPLC purification using 0.1% formic acid in water acetonitrile as a mobile phase (0-100% gradient system) to yield 0.039 g (29% yield) of the title compound. $^1$H NMR (400 MHz, DMSO-d6) δ ppm 1.76-1.84 (m, 1H) 2.02-2.14 (m, 1H) 3.16 (s, 3H) 3.49-3.70 (m, 3H) 3.78-3.85 (m, 1H) 4.85-4.91 (m, 1H) 6.88-6.98 (m, 3H) 7.05-7.14 (m, 2H) 7.19 (d, 1H) 7.32-7.39 (m, 2H) 11.87 (s, 1H); MS (ES−) m/z 396 [M−H]−

Example 23

1-[3-(cyclopentyloxy)-4-phenoxyphenyl]-3-phenyl-1,3,5-triazinane-2,4,6-trione

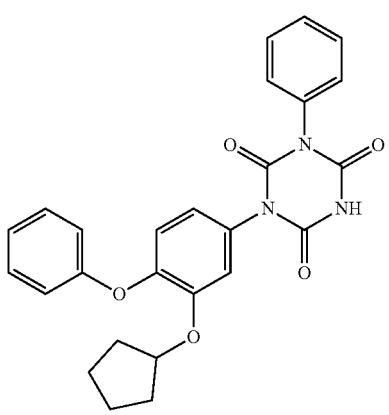 [SMILES: O=c1[nH]c(=O)n(-c2ccc(Oc3ccccc3)c(OC3CCCC3)c2)c(=O)n1-c1ccccc1]

In a 30 ml seal tube previously equipped with a magnetic stirrer, ethoxycarbonyl isocyanate (0.069 g, 0.0006 mol) was added to a solution of 1-[3-(Cyclopentyloxy)-4-phenoxyphenyl]-3-phenylurea (Intermediate 32, 0.180 g, 0.0005 mol) in bromobenzene (2.0 mL) at 0° C. The reaction mixture was stirred at 110° C. for 16 h. The solvent was evaporated under reduced pressure to obtain the crude product. The crude product was purified on combi flash chromatography by using a 0-100% ethyl acetate in hexane (gradient) as a mobile phase and 60-120 silica as stationary phase and further purified by using preparative HPLC purification using 3 mM ammonia acetate in water:acetonitrile as a mobile phase (0-100% gradient system) to yield 0.015 g (9% yield) of the title compound. $^1$H NMR (400 MHz, DMSO-d6) δ ppm 1.32-1.48 (m, 4H) 1.50-1.60 (m, 2H) 1.69-1.80 (m, 2H) 4.71 (s, 1H) 6.83-6.88 (m, 2H) 6.94-6.98 (m, 1H) 7.02-7.07 (m, 1H) 7.11-7.15 (m, 1H) 7.18-7.21 (m, 1H) 7.29-7.52 (m, 7H) 12.04 (s, 1H); MS (ES−) m/z 456 [M−H]−

Example 24

1-methyl-3-[3-(oxetan-3-ylmethoxy)-4-phenoxyphenyl]-1,3,5-triazinane-2,4,6-trione

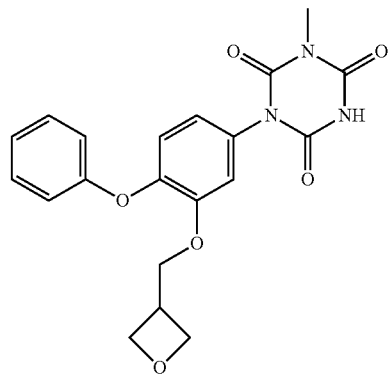 [SMILES: Cn1c(=O)[nH]c(=O)n(-c2ccc(Oc3ccccc3)c(OCC3COC3)c2)c1=O]

In a 30 ml seal tube previously equipped with a magnetic stirrer, ethoxycarbonyl isocyanate (0.042 g, 0.0003 mol) was added to a solution of 1-methyl-3-[3-(oxetan-3-ylmethoxy)-4-phenoxyphenyl]urea (Intermediate 36, 0.110 g, 0.0003 mol) in Toluene (1.10 mL) at 0° C. The reaction mixture was stirred at 110° C. for 16 h. The solvent was evaporated under reduced pressure to obtain the crude product. The crude product was purified on combi flash chromatography by using 0-5% MeOH in DCM as a mobile phase and 60-120 silica as stationary phase. The product was further purified by using 3 mM ammonia acetate as modifier and water:acetonitrile (0-100% gradient system) as a mobile phase in preparative HPLC purification to yield 0.006 g (4.5% yield) of the title compound. $^1$H NMR (400 MHz, DMSO-d6) δ ppm 3.13-3.23 (m, 1H) 3.16 (s, 3H) 4.08-4.15 (m, 4H) 4.45-4.51 (m, 2H) 6.87-6.92 (m, 2H) 6.96 (dd, 1H) 7.05-7.10 (m, 1H) 7.14 (d, 1H) 7.23 (d, 1H) 7.32-7.39 (m, 2H) 11.87 (s, 1H); MS (ES−) m/z 396 [M−H]−

Example 25

1-[3-(oxetan-3-ylmethoxy)-4-phenoxyphenyl]-3-phenyl-1,3,5-triazinane-2,4,6-trione

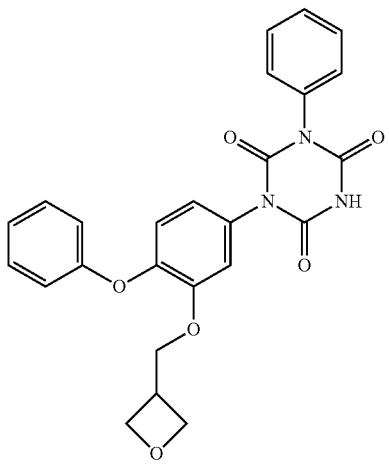 [SMILES: O=c1[nH]c(=O)n(-c2ccc(Oc3ccccc3)c(OCC3COC3)c2)c(=O)n1-c1ccccc1]

In a 30 ml seal tube previously equipped with a magnetic stirrer, ethoxycarbonyl isocyanate (0.205 g, 0.0017 mol) was added to a solution of 1-{3-[(3-Oxetanyl)methoxy]-4-phenoxyphenyl}-3-phenylurea (Intermediate 37, 0.580 g, 0.0014 mol) in toluene (5.8 mL) at 0° C. The reaction mixture was stirred at 110° C. for 16 h. The solvent was evaporated under reduced pressure to obtain the crude product. The crude product was purified using preparative HPLC purification by using 0.1% formic acid as a modifier and water:acetonitrile (0-100% gradient system) as a mobile phase to yield 0.0049 g of the title compound. $^1$H NMR (400 MHz, DMSO-d6) δ ppm 3.12-3.25 (m, 1H) 4.09-4.19 (m, 4H) 4.41-4.55 (m, 2H) 6.86-6.92 (m, 2H) 6.99-7.10 (m, 2H) 7.20-7.17 (m, 1H) 7.25-7.52 (m, 8H) 12.08 (s, 1H); MS (ES−) m/z 458 [M−H]$^-$

Example 26

1-methyl-3-[4-phenoxy-3-(propan-2-yloxy)phenyl]-1,3,5-triazinane-2,4,6-trione

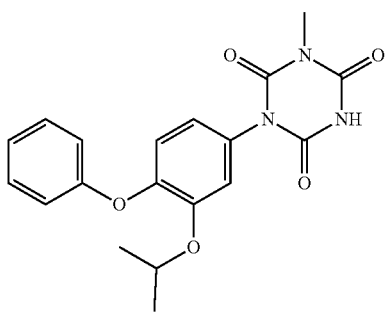 [SMILES: CC(C)Oc1cc(-n2c(=O)[nH]c(=O)n(C)c2=O)ccc1Oc1ccccc1]

In a 30 ml seal tube previously equipped with a magnetic stirrer, ethoxycarbonyl isocyanate (0.043 g, 0.37 mmol) was added to a solution of 1-methyl-3-[4-phenoxy-3-(propan-2-yloxy)phenyl]urea (Intermediate 40, 0.103 g, 0.34 mmol) in Toluene (1.3 mL) at 0° C. The reaction mixture was heated at 110° C. for 16 h. The solvent was evaporated under reduced pressure to obtain the crude product. The crude product was purified by using preparative HPLC purification with 0.1% ammonia as modifier and water:acetonitrile (0-100% gradient system) as a mobile phase to yield 0.035 g (27% yield) of the title compound. $^1$H NMR (400 MHz, DMSO-d6) δ ppm 1.13 (d, 6H) 3.16 (s, 3H) 4.40-4.52 (m, 1H) 6.88-6.93 (m, 3H) 7.04-7.11 (m, 2H) 7.16-7.21 (d, 1H) 7.32-7.38 (m, 2H) 11.75 (s, 1H); MS (ES−) m/z 368 [M−H]$^-$

Example 27

1-[4-phenoxy-3-(propan-2-yloxy)phenyl]-3-phenyl-1,3,5-triazinane-2,4,6-trione

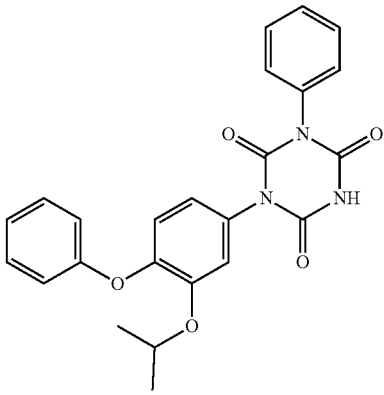 [SMILES: CC(C)Oc1cc(-n2c(=O)[nH]c(=O)n(-c3ccccc3)c2=O)ccc1Oc1ccccc1]

In a 30 ml seal tube previously equipped with a magnetic stirrer, ethoxycarbonyl isocyanate (0.115 g, 0.0010 mol) was added to the solution of 1-[4-phenoxy-3-(propan-2-yloxy)phenyl]-3-phenylurea (Intermediate 41, 0.343 g, 0.0009 mol) in toluene (3.4 mL) at 0° C. The reaction mixture was heated at 110° C. for 16 h. The solvent was evaporated under reduced pressure. The crude product was purified using preparative HPLC purification with 0.1% ammonia as modifier and water:acetonitrile (0-100% gradient system) as a mobile phase to yield 0.009 g (2% yield) of the title compound. $^1$H NMR (400 MHz, DMSO-d6) δ ppm 1.13 (d, 6H) 4.40-4.52 (m, 1H) 6.86-6.92 (m, 2H) 6.96 (dd, 1H) 7.04-7.11 (m, 2H) 7.23 (d, 1H) 7.30-7.52 (m, 7H) 12.01 (s, 1H); MS (ES−) m/z 430 [M−H]$^-$

Example 28

1-[3-(2-methoxyethoxy)-4-phenoxyphenyl]-3-methyl-1,3,5-triazinane-2,4,6-trione

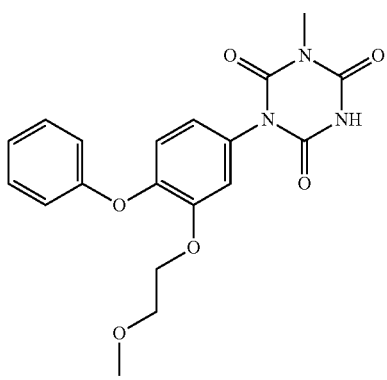 [SMILES: COCCOc1cc(-n2c(=O)[nH]c(=O)n(C)c2=O)ccc1Oc1ccccc1]

In a 30 ml seal tube previously equipped with a magnetic stirrer, ethoxycarbonyl isocyanate (0.023 g, 0.199 mmol) was added to a solution of 1-[3-(2-methoxyethoxy)-4-phenoxyphenyl]-3-methylurea (Intermediate 44, 0.062 g, 0.196 mmol) in Toluene (0.60 mL) at 0° C. The reaction mixture was heated at 110° C. for 16 h. The solvent was evaporated under reduce pressure and the crude product was purified on preparative HPLC using 0.1% ammonium acetate as modifier and water:acetonitrile (0-100% gradient system) as a mobile phase in prep HPLC purification to yield 0.027 g (36% yield) of the title compound. $^1$H NMR (400 MHz, DMSO-d6) δ ppm 3.15 (s, 3H) 3.18 (s 3H) 3.52 (t, 2H) 4.03 (t, 2H) 6.90-6.96 (m, 3H) 7.03-7.12 (m, 2H) 7.18-7.21 (m, 1H) 7.33-7.40 (m, 2H) 11.86 (s, 1H); MS (ES−) m/z 384 [M−H]$^-$

Example 29

1-[3-(2-methoxyethoxy)-4-phenoxyphenyl]-3-phenyl-1,3,5-triazinane-2,4,6-trione

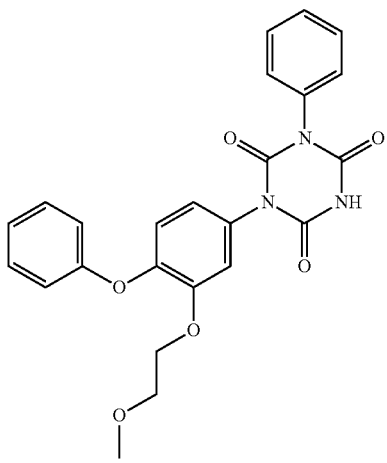 [SMILES: COCCOc1cc(-n2c(=O)[nH]c(=O)n(-c3ccccc3)c2=O)ccc1Oc1ccccc1]

In a 30 ml seal tube previously equipped with a magnetic stirrer, ethoxycarbonyl isocyanate (0.045 g, 0.0003 mol) was added to the solution of 1-[3-(2-methoxyethoxy)-4-phenoxyphenyl]-3-phenylurea (Intermediate 45, 0.135 g, 0.0003 mol) in toluene (1.30 mL) under stirring at 0° C. The reaction mixture was heated at 110° C. for 16 h. The solvent was evaporated under reduced pressure to obtain the crude product. The crude product was purified using preparative HPLC by using 0.1% ammonium acetate as a modifier and water:acetonitrile (0-100% gradient system) as a mobile phase to yield 0.012 g (7% yield) of the title compound. $^1$H NMR (400 MHz, DMSO-d6) δ ppm 3.18 (s, 3H) 3.53 (t, 2H) 4.06 (t, 2H) 6.90-6.96 (m, 2H) 6.97-7.02 (m, 1H) 7.04-7.12 (m, 2H) 7.25 (d, 1H) 7.32-7.53 (m, 7H) 12.05 (s, 1H); MS (ES−) m/z 446 [M−H]$^-$

Example 30

1-[3-(benzyloxy)-4-phenoxyphenyl]-3-methyl-1,3,5-triazinane-2,4,6-trione

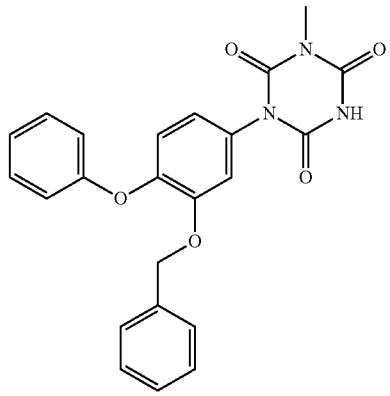 [SMILES: Cn1c(=O)[nH]c(=O)n(-c2ccc(Oc3ccccc3)c(OCc3ccccc3)c2)c1=O]

In a 30 ml seal tube previously equipped with a magnetic stirrer, ethoxycarbonyl isocyanate (0.072 g, 0.63 mmol) was added to the solution of 1-[3-(benzyloxy)-4-phenoxyphenyl]-3-methylurea (Intermediate 48, 0.200 g, 0.574 mmol) in Toluene (2.0 mL) at 0° C. The reaction mixture was heated at 110° C. for 16 h. The solvent was evaporated under reduced pressure. The crude was purified by preparative HPLC using 3 mM ammonium acetate as modifier and water:acetonitrile (0-100% gradient system) as a mobile phase to yield 0.030 g (12% yield) of the title compound. $^1$H NMR (400 MHz, DMSO-d6) δ ppm 3.15 (s, 3H) 5.01 (s, 2H) 6.90-6.97 (m, 3H) 7.06-7.20 (m, 4H) 7.25-7.32 (m, 4H) 7.33-7.40 (m, 2H) 11.87 (s, 1H); MS (ES−) m/z 416 [M−H]$^-$

Example 31

1-methyl-3-(1-phenyl-1H-indazol-5-yl)-1,3,5-triazinane-2,4,6-trione

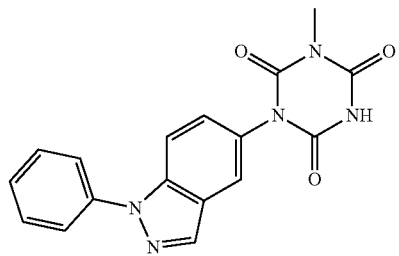 [SMILES: Cn1c(=O)[nH]c(=O)n(-c2ccc3c(cnn3-c3ccccc3)c2)c1=O]

In a 30 ml seal tube previously equipped with a magnetic stirrer, ethoxycarbonyl isocyanate (0.035 g, 0.304 mmol) was added to the solution of (Intermediate 49, 0.075 g, 0.282 mmol) in Toluene (0.75 mL) at 0° C. The reaction mixture was heated at 110° C. for 16 h. The solvent was evaporated under reduce pressure. The crude product was purified using preparative HPLC purification with 0.1% ammonia in water and 100% Acetonitrile as a mobile phase to yield 0.055 g (58% yield) of the title compound. $^1$H NMR (400 MHz, DMSO-d6) δ ppm 3.17 (s, 3H) 7.40-7.48 (m, 2H) 7.58-7.66 (m, 2H) 7.78-7.84 (m, 2H) 7.86-7.93 (m, 2H) 8.47 (d, 1H) 11.87 (s, 1H); MS (ES−) m/z 334 [M−H]−

Example 32

1-(3-methoxy-5-methyl-4-phenoxyphenyl)-3-methyl-1,3,5-triazinane-2,4,6-trione

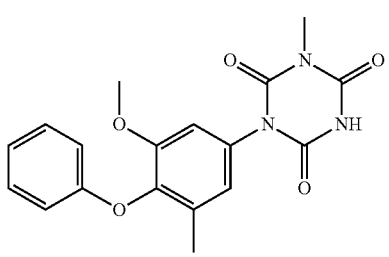 [SMILES: COc1cc(-n2c(=O)[nH]c(=O)n(C)c2=O)cc(C)c1Oc1ccccc1]

In a 10 ml seal tube flask previously equipped with a magnetic stirrer and nitrogen balloon, ethylcarbonyl isocyanate (0.033 g, 0.29 mmol) was added drop wise to a solution of 1-(3-methoxy-5-methyl-4-phenoxyphenyl)-3-methylurea (Intermediate 50, 0.070 g, 0.24 mmol) in dry toluene (0.7 mL) at 25° C. The reaction mixture was heated at 110° C. for 16 h. The reaction mixture was concentrated under reduced pressure to obtain the crude product. The crude product was purified on preparative HPLC using 0.1% ammonium acetate as a modifier and water:acetonitrile (0-100% as a gradient system) as mobile phase to yield 0.017 g (19% yield) of the title compound. $^1$H NMR (400 MHz, DMSO-d6) δ ppm 2.10 (s, 3H) 3.16 (s, 3H) 3.65 (s, 3H) 6.73-6.79 (m, 2H) 6.87-6.91 (m, 1H) 6.98-7.07 (m, 2H) 7.28-7.35 (m, 2H) 11.87 (s, 1H); MS (ES−) m/z 354 [M−H]−

Example 33

1-(2-methoxy-3-methyl-4-phenoxyphenyl)-3-phenyl-1,3,5-triazinane-2,4,6-trione

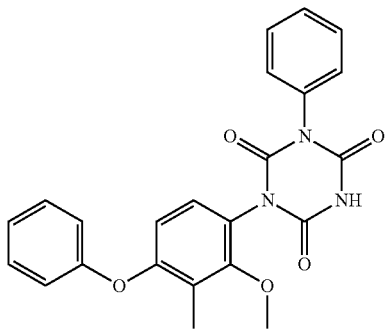 [SMILES: COc1c(-n2c(=O)[nH]c(=O)n(-c3ccccc3)c2=O)ccc(Oc2ccccc2)c1C]

In a 30 ml seal tube previously equipped with a magnetic stirrer, ethylcarbonyl isocyanate (0.138 g, 0.0011 mol) was added to a solution of 1-(2-methoxy-3-methyl-4-phenoxyphenyl)-3-phenylurea (Intermediate 53, 0.380 g, 0.0010 mol) in toluene (3.80 mL) under stirring at 0° C. The reaction mixture was heated at 110° C. for 16 h. The solvent was evaporated under reduced pressure and the crude product was purified by preparative HPLC using 0.1% ammonia as a modifier and water:acetonitrile (0-100% as a gradient system) as a mobile phase to yield 0.094 g (20% yield) of the title compound. $^1$H NMR (400 MHz, DMSO-d6) δ ppm 2.17 (s, 3H) 3.71 (s, 3H) 6.70 (d, 1H) 6.97-7.05 (m, 2H) 7.13-7.19 (m, 1H) 7.23 (d, 1H) 7.37-7.53 (m, 7H) 12.11 (s, 1H); MS (ES−) m/z 416 [M−H]−

Example 34

1-[3-methyl-4-(phenylsulfanyl)phenyl]-3-phenyl-1,3,5-triazinane-2,4,6-trione

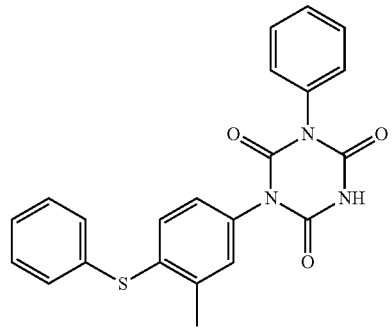 [SMILES: Cc1cc(-n2c(=O)[nH]c(=O)n(-c3ccccc3)c2=O)ccc1Sc1ccccc1]

In a 30 ml seal tube previously equipped with a magnetic stirrer, ethoxycarbonyl isocyanate (0.150 g, 0.0014 mol) was added to a solution of 1-[3-methyl-4-(phenylsulfanyl)phenyl]-3-phenylurea (Intermediate 54, 0.400 g, 0.0011 mol) in toluene (4.00 mL) stirred at 0° C. The reaction mixture was stirred at 110° C. for 16 h. The solvent was evaporated under reduced pressure to obtain the crude product. The crude product was purified on combi flash chromatography by using 100% Ethyl acetate as a mobile phase and 60-120 silica as stationary phase. The obtained product was further purified by preparative HPLC purification, using 5 mM ammonium bicarbonate as a modifier and water:Acetonitrile (0-100% gradient system) as a mobile phase to yield 0.020 g (4% yield) of the title compound. $^1$H NMR (400 MHz, DMSO-d6) δ ppm 2.34 (s, 3H) 7.15-7.25 (m, 2H) 7.30-7.53 (m, 11H) 12.01 (s, 1H); MS (ES−) m/z 402 [M−H]−

Example 35

1-(3-Methyl-1-phenyl-1H-indol-5-yl)-3-phenyl-1,3,5-triazinane-2,4,6-trione

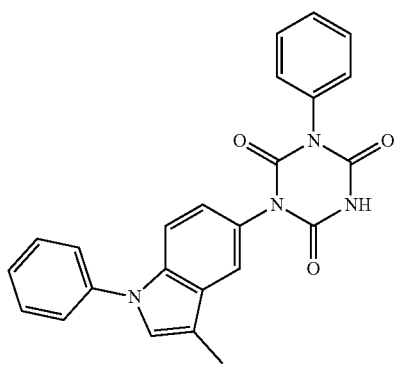 [SMILES: Cc1cn(-c2ccccc2)c2ccc(-n3c(=O)[nH]c(=O)n(-c4ccccc4)c3=O)cc12]

To a solution 1-(3-methyl-1-phenyl-1H-indol-5-yl)-3-phenylurea (Intermediate 57, 0.310 g, 0.00090 mol) in toluene (3.10 mL), was added ethoxycarbonyl isocyanate (0.209 g, 0.00180 mol) at 0° C. under nitrogen atmosphere. The resulting reaction mixture was heated at 110° C. for 16 h under nitrogen atmosphere. The reaction mixture was concentrated under reduced pressure to obtain the crude product. The crude product was purified on preparative chromatography using 0.1% ammonia as a modifier and water acetonitrile (0-100% gradient system) as mobile phases to obtain 0.015 g (4% yield) of the title compound. $^1$H NMR (400 MHz, DMSO-d6) δ ppm 2.33 (s, 3H) 7.16-7.22 (m, 1H) 7.36-7.52 (m, 6H) 7.53-7.64 (m, 7H) 11.98 (s, 1H); MS (ES-) m/z 409 [M-H]$^-$

Example 36

1-(1-Benzyl-3-methyl-1H-indol-5-yl)-3-phenyl-1,3,5-triazinane-2,4,6-trione

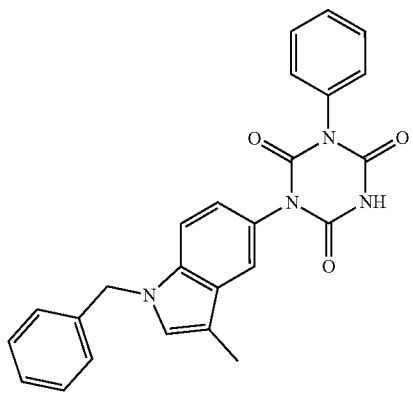 [SMILES: Cc1cn(Cc2ccccc2)c2ccc(-n3c(=O)[nH]c(=O)n(-c4ccccc4)c3=O)cc12]

To a solution of 1-(1-benzyl-3-methyl-1H-indol-5-yl)-3-phenylurea (Intermediate 60, 0.300 g, 0.0084 mol) in toluene (3.00 mL) was added ethoxycarbonyl isocyanate (0.194 g, 0.0016 mol) at 0° C. under nitrogen atmosphere. The resulting reaction mixture was heated at 110° C. for 16 h under nitrogen atmosphere. The reaction mixture was concentrated under reduce pressure to obtained the crude product. The crude product was purified on preparative chromatography using 5 mM ammonium bicarbonate+0.05% ammonia as a modifier in water acetonitrile (0-100 as a gradient system) as mobile phases to obtain 0.016 g (4% yield) of the title compound. $^1$H NMR (400 MHz, DMSO-d6) δ ppm 2.26 (s, 3H) 5.38 (s, 2H) 7.04-7.09 (m, 1H) 7.21-7.27 (m, 3H) 7.28-7.36 (m, 3H) 7.37-7.52 (m, 7H) 11.89 (s, 1H); MS (ES-) m/z 423 [M-H]$^-$

Example 37

1-methyl-3-(3-methyl-1-phenyl-1H-indol-5-yl)-1,3,5-triazinane-2,4,6-trione

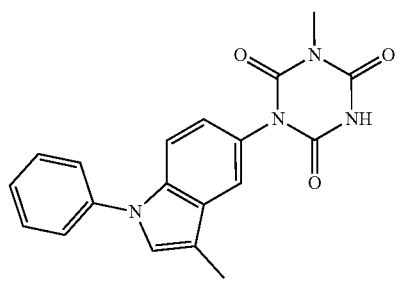 [SMILES: Cc1cn(-c2ccccc2)c2ccc(-n3c(=O)[nH]c(=O)n(C)c3=O)cc12]

To a solution of 1-methyl-3-(3-methyl-1-phenyl-1H-indol-5-yl)urea (Intermediate 61, 0.070 g, 0.00025 mol) in toluene (0.70 mL) was added ethoxycarbonyl isocyanate (0.057 g, 0.00050 mol) at 0° C. under nitrogen atmosphere. The resulting reaction mixture was heated at 110° C. for 16 h under nitrogen atmosphere. The reaction mixture was concentrated under reduced pressure to obtained the crude product. The crude product was purified on preparative chromatography using (5 mM ammonium bicarbonate+0.1% ammonia as a modifier) in water acetonitrile (0-100% gradient system) as mobile phases to obtained 0.030 g (34% yield) of the title compound. $^1$H NMR (400 MHz, DMSO-d6) δ ppm 2.32 (s, 3H) 3.17 (s, 3H) 7.08-7.13 (m, 1H) 7.35-7.44 (m, 1H) 7.52-7.64 (m, 7H) 11.75 (s, 1H); MS (ES+) m/z 349 [M+H]$^+$

Example 38

1-(1-benzyl-3-methyl-1H-indol-5-yl)-3-methyl-1,3,5-triazinane-2,4,6-trione

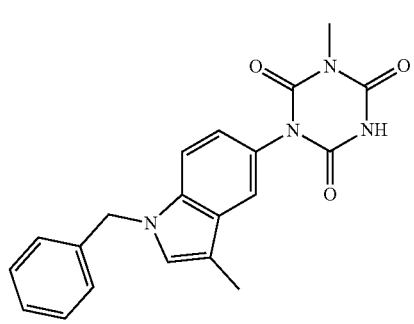 [SMILES: Cc1cn(Cc2ccccc2)c2ccc(-n3c(=O)[nH]c(=O)n(C)c3=O)cc12]

In a 10 ml seal tube previously equipped with a magnetic stirrer, ethoxycarbonyl isocyanate (0.078 g, 0.00068 mol) was added to a solution of 1-(1-benzyl-3-methyl-1H-indol- 5-yl)-3-methylurea (Intermediate 62, 0.100 g, 0.00034 mol) in toluene (1 mL) at 0° C. under N₂(g). The reaction mixture was heated at 110° C. for 16 h under N₂(g). The reaction mixture was concentrated under reduce pressure to obtained crude product. The crude product was purified by preparative HPLC purification with 5 mM ammonium bicarbonate+ 0.1% ammonia as modifier and water acetonitrile (0-100% gradient system) as a mobile phase to yield 0.067 g (54% yield) of the title compound. $^1$H NMR (400 MHz, DMSO-d6) δ ppm 2.25 (s, 3H) 3.15 (s, 3H) 5.38 (s, 2H) 6.95-7.02 (m, 1H) 7.21-7.28 (m, 3H) 7.28-7.38 (m, 3H) 7.41-7.48 (m, 2H) 11.75 (s, 1H); MS (ES+) m/z 363 [M+H]⁺

Example 39

1-(3-chloro-4-phenoxyphenyl)-3-phenyl-1,3,5-triazinane-2,4,6-trione

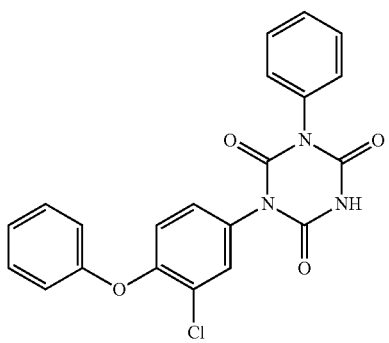 [SMILES: O=c1[nH]c(=O)n(-c2ccc(Oc3ccccc3)c(Cl)c2)c(=O)n1-c1ccccc1]

To a 10 ml microwave tube previously equipped with a magnetic stirrer, 1-(3-chloro-4-phenoxyphenyl)-3-phenylurea (Intermediate 63, 0.150 g, 0.0004 mol) and Bromobenzene (1.50 ml) was added and cooled to 0° C. Ethoxycarbonyl isocyanate (0.101 g, 0.0008 mol) was added and reaction mixture was allowed to reach to room temperature. The resulting reaction mixture was heated at 150° C. for 2 hours in a microwave oven. The solvent was evaporated under reduced pressure to obtain the crude product. The crude product was purified by preparative HPLC using 0.1% formic acid as modifier in water:acetonitrile (0-100% gradient system) as a mobile phase to yield 0.010 g (5.5% yield) of the title compound. $^1$H NMR (400 MHz, DMSO-d6) δ ppm 6.99-7.05 (m, 2H) 7.06-7.13 (m, 1H) 7.15-7.22 (m, 1H) 7.30-7.38 (m, 3H) 7.38-7.51 (m, 5H) 7.64-7.69 (m, 1H) 12.10 (s, 1H); MS (ES−) m/z 406 [M−H]⁻

Example 40

1-(3-methyl-4-phenoxyphenyl)-3-(5-methylthiophen-2-yl)-1,3,5-triazinane-2,4,6-trione

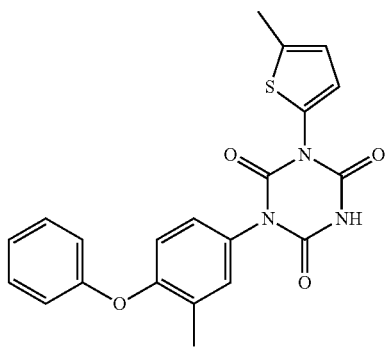 [SMILES: Cc1ccc(-n2c(=O)[nH]c(=O)n(-c3ccc(Oc4ccccc4)c(C)c3)c2=O)s1]

In a microwave tube previously equipped with a magnetic stirrer 1-(3-methyl-4-phenoxyphenyl)-3-(5-methylthiophen-2-yl)urea (Intermediate 64, 0.200 g, 0.00059 mol) was dissolved in Chlorobenzene (2.0 ml) and cooled to 0° C. Ethyoxy carbonyl isocyanate (0.136 g, 0.00118 mol) was added to the mixture and the reaction mixture was allowed to reach room temperature and then heated at 130° C. for 4 hours in a microwave oven. The solvent was evaporated under reduced pressure to obtain the crude product. The crude product was purified by preparative HPLC (55-100% Acetonitrile:Methanol (1:1) in water [0.1% Formic acid]) to yield 0.035 g (14% yield) of the title compound. $^1$H NMR (400 MHz, DMSO-d6) δ ppm 2.19 (s, 3H), 3.95 (s, 3H), 6.66-6.70 (m, 1H), 6.77-6.81 (m, 1H) 6.85-6.91 (m, 1H) 6.92-6.98 (m, 2H), 7.08-7.16 (m, 2H), 7.25 (s, 1H), 7.34-7.41 (m, 2H), 11.96 (s, 1H); MS (ES−) m/z 406 [M−H]⁻

Example 41

1-(3-methyl-4-phenoxyphenyl)-3-(4-methylphenyl)-1,3,5-triazinane-2,4,6-trione

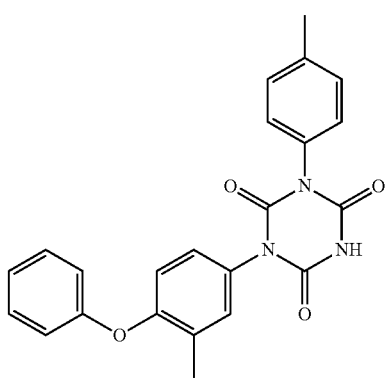 [SMILES: Cc1ccc(-n2c(=O)[nH]c(=O)n(-c3ccc(Oc4ccccc4)c(C)c3)c2=O)cc1]

In a microwave vial previously equipped with a magnetic stirrer 1-(3-methyl-4-phenoxyphenyl)-3-(4-methylphenyl)urea (Intermediate 77, 0.23 g, 0.0006 mol) and bromobenzene (2.3 ml) was added and cooled to 0° C. Ethoxy carbonyl isocyanate (0.15 g, 0.0013 mol) was added and resulting reaction mixture was allowed to reach RT and then heated at 150° C. for 2 h in a microwave synthesizer. The solvent was evaporated under reduced pressure to obtain crude product that was purified by preparative HPLC (40-100% Acetonitrile in water [0.1% Formic acid]) to yield 0.023 g (8% yield) of the title compound. ¹H NMR (400 MHz, DMSO-d6) δ ppm 11.97 (s, 1H), 7.42-7.35 (m, 2H), 7.32-7.28 (m, 1H), 7.27-7.22 (m, 3H), 7.22-7.08 (m, 3H), 6.98-6.93 (m, 2H), 6.93-6.85 (m, 1H), 2.32 (s, 3H), 2.19 (s, 3H); MS (ES−) m/z 400 [M−H]⁻

Example 42

1-(4-benzyl-3-methylphenyl)-3-phenyl-1,3,5-triazinane-2,4,6-trione

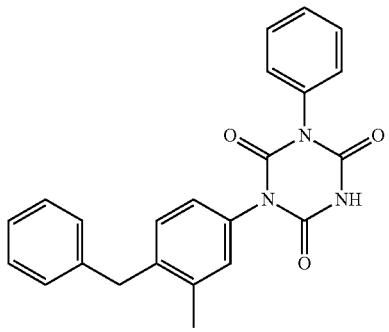 [SMILES: Cc1cc(-n2c(=O)[nH]c(=O)n(-c3ccccc3)c2=O)ccc1Cc1ccccc1]

1-(4-benzyl-3-methylphenyl)-3-phenylurea (Intermediate 74, 0.50 g, 0.0015 mol) and bromobenzene (5 ml) was added to a microwave vial with a magnetic stirrer and cooled to 0° C. Ethoxy carbonyl isocyanate (0.36 g, 0.0031 mol) was added and reaction mixture was allowed to reach RT. The resulting reaction mixture was heated at 150° C. for 2 hours in a microwave oven. The solvent was evaporated under reduced pressure and the crude product was purified by using preparative HPLC (15-100% acetonitrile in water [0.1% Formic acid]) to yield 40 mg (6% yield) of the title compound. ¹H NMR (400 MHz, DMSO-d6) δ ppm 12.00 (s, 1H), 7.53-7.29 (m, 7H), 7.26-7.11 (m, 6H), 4.00 (s, 2H), 2.25 (s, 3H); MS (ES−) m/z 384 [M−H]⁻

Example 43

1-(3-chlorophenyl)-3-(3-methyl-4-phenoxyphenyl)-1,3,5-triazinane-2,4,6-trione

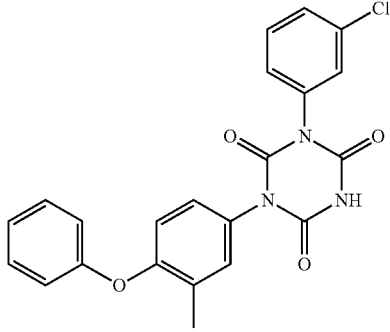 [SMILES: Cc1cc(-n2c(=O)[nH]c(=O)n(-c3cccc(Cl)c3)c2=O)ccc1Oc1ccccc1]

In a microwave vial previously equipped with a magnetic stirrer, 1-(3-chlorophenyl)-3-(3-methyl-4-phenoxyphenyl)urea (Intermediate 75, 0.30 g, 0.0008 mol) was added to bromobenzene (3.0 ml) and the mixture was cooled to 0° C. Ethoxy carbonyl isocyanate (0.19 g, 0.0017 mol) was added and resulting reaction mixture was allowed to reach RT and then heated at 150° C. for 2 h in microwave oven. The solvent was evaporated under reduce pressure to obtain crude product which was purified by preparative HPLC (20-100% Acetonitrile in water [0.1% Formic acid]) to yield 0.019 g (5% yield) of the title compound. ¹H NMR (400 MHz, DMSO-d6) δ ppm 12.12 (s, 1H), 7.57-7.51 (m, 3H), 7.46-7.37 (m, 3H), 7.32 (d, J=2.5 Hz, 1H), 7.24-7.11 (m, 2H), 7.02-6.91 (m, 3H), 2.24 (s, 3H); MS (ES−) m/z 420 [M−H]⁻

Example 44

1-(3-methyl-4-phenoxyphenyl)-3-[3-(trifluoromethoxy)phenyl]-1,3,5-triazinane-2,4,6-trione

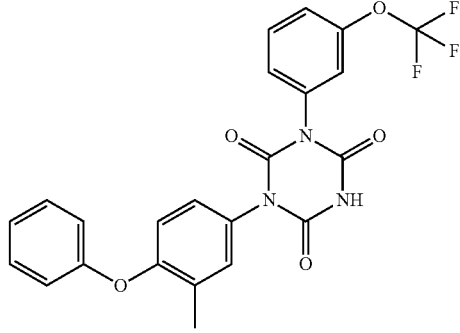 [SMILES: Cc1cc(-n2c(=O)[nH]c(=O)n(-c3cccc(OC(F)(F)F)c3)c2=O)ccc1Oc1ccccc1]

In a microwave vial previously equipped with a magnetic stirrer 1-(3-methyl-4-phenoxyphenyl)-3-[3-(trifluoromethoxy)phenyl]urea (Intermediate 76, 0.40 g, 0.0009 mol) was added to bromobenzene (4.0 ml) the mixture was cooled to 0° C. Ethoxy carbonyl isocyanate (0.22 g, 0.0019 mol) was added and reaction mixture was allowed to reach RT and then heated at 150° C. for 2 h in a microwave synthesizer. The solvent was evaporated under reduced pressure to obtain crude product which was purified by preparative HPLC (25-100% Acetonitrile in water [5 mM Ammonium bicarbonate+0.1% NH3]) to yield 0.039 g (8% yield) of the title compound. ¹H NMR (400 MHz, DMSO-d6) δ ppm 12.13 (s, 1H), 7.69-7.60 (m, 1H), 7.52-7.37 (m, 5H), 7.32 (d, J=2.5 Hz, 1H), 7.24-7.11 (m, 2H), 7.02-6.91 (m, 3H), 2.24 (s, 3H); MS (ES−) m/z 470 [M−H]⁻

Example 45

1-(4-fluorophenyl)-3-(3-methyl-4-phenoxyphenyl)-1,3,5-triazinane-2,4,6-trione

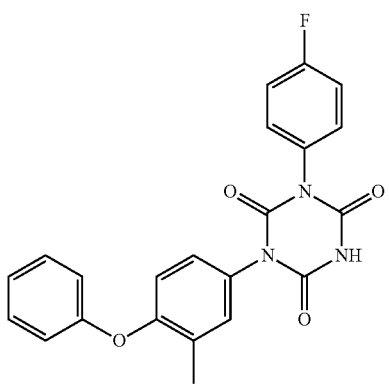 [SMILES: Cc1cc(-n2c(=O)[nH]c(=O)n(-c3ccc(F)cc3)c2=O)ccc1Oc1ccccc1]

In a microwave tube previously equipped with a magnetic stirrer 1-(4-fluorophenyl)-3-(3-methyl-4-phenoxyphenyl) urea (Intermediate 65, 0.100 g, 0.0002 mol) in bromobenzene (1.00 ml) was cooled to 0° C. Ethoxy carbonyl isocyanate was added and reaction mixture was allowed to reach RT and then heated at 150° C. for 2 h in microwave oven. The solvent was evaporated under reduced pressure and the crude product was purified by preparative HPLC (20-100% Acetonitrile in water [0.1% formic acid] to yield 0.011 g (9% yield) of the title compound. $^1$H NMR (400 MHz, DMSO-d6) δ 2.23 (s, 3H), 6.90-7.01 (m, 3H), 7.11-7.24 (m, 2H), 7.28-7.38 (m, 3H), 7.38-7.48 (m, 4H), 12.07 (s, 1H); MS (ES−) m/z 404 [M−H]⁻

Example 46

1-(1-benzofuran-5-yl)-3-(3-methyl-4-phenoxyphenyl)-1,3,5-triazinane-2,4,6-trione

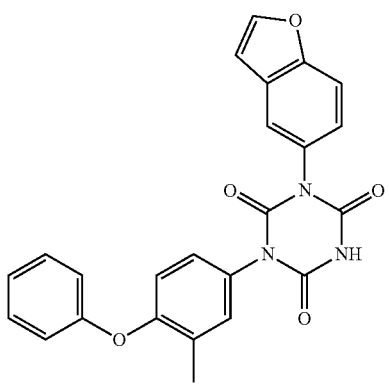 [SMILES: Cc1cc(-n2c(=O)[nH]c(=O)n(-c3ccc4occc4c3)c2=O)ccc1Oc1ccccc1]

Sodium hydride (60% in mineral oil, 7.25 mg, 0.18 mmol).) was added to a microwave vial containing a magnetic stirring bar. The vial was sealed and put under an inert atmosphere and the sodium hydride was washed with pentane. The pentane was thereafter removed, DMF (1 ml) was added and the dispersion was cooled to 0° C. 1-(benzofuran-5-yl)-3-(3-methyl-4-phenoxy-phenyl)urea (Intermediate 66, 26 mg, 0.07 mmol) was dissolved in DMF (1.5 ml) and added dropwise to the reaction vessel. The ice bath was removed and the reaction mixture was stirred for another 10 min. The solution was again cooled to 0° C. and ethoxycarbonyl isocyanate (11 μl, 0.11 mmol) was thereafter added, the ice bath was removed and the reaction mixture was stirred for 5 additional minutes before addition of water and EtOAc. The solvents were removed under reduced pressure. The crude from the water phase was purified by preparative RP-HPLC (30-90% acetonitrile in water [0.05% HCOOH]) to yield 8.8 mg (28% yield) of the title compound. $^1$H NMR (400 MHz, DMSO-d$_6$) δ ppm 12.01 (br. s, 1H), 8.08 (d, J=2.2 Hz, 1H), 7.71-7.64 (m, 2H), 7.43-7.36 (m, 2H), 7.35-7.28 (m, 2H), 7.21 (dd, J=8.5, 2.5 Hz, 1H), 7.17-7.10 (m, 1H), 7.05-7.02 (m, 1H), 7.00-6.93 (m, 2H), 6.91 (d, J=8.6 Hz, 1H), 2.22 (s, 3H); ESI+m/z 428 (M+H)+

Example 47

1-(1H-indol-5-yl)-3-(3-methyl-4-phenoxyphenyl)-1,3,5-triazinane-2,4,6-trione

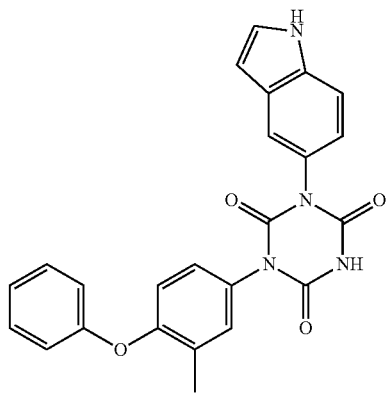 [SMILES: Cc1cc(-n2c(=O)[nH]c(=O)n(-c3ccc4[nH]ccc4c3)c2=O)ccc1Oc1ccccc1]

1-(1H-indol-5-yl)-3-(3-methyl-4-phenoxy-phenyl)urea (Intermediate 67, 21 mg, 0.06 mmol) was dispersed in toluene (0.5 ml) in a microwave vial (0.5-2 ml), ethoxycarbonyl isocyanate (6 μl, 0.06 mmol) was added and the mixture was heated at 110° C. in an oil bath for 5 h and was thereafter left at room temperature overnight. The crude was concentrated at reduced pressure and the product was purified by preparative RP-HPLC (20-80% acetonitrile in water [0.05% HCOOH]) to yield 2 mg (6% yield) of the title compound. $^1$H NMR (400 MHz, DMSO-d6) δ ppm 11.91 (br. s, 1H), 11.25 (s, 1H), 7.51 (d, J=1.9 Hz, 1H), 7.45-7.36 (m, 4H), 7.36-7.32 (m, 1H), 7.22 (dd, J=8.6, 2.4 Hz, 1H), 7.13 (t, J=7.4 Hz, 1H), 7.04 (dd, J=8.6, 1.8 Hz, 1H), 6.99-6.94 (m, 2H), 6.91 (d, J=8.6 Hz, 1H), 6.50-6.45 (m, 1H), 2.21 (s, 3H); MS(ESI+) m/z 427 (M+H)+

Example 48

1-(2H-1,3-benzodioxol-5-yl)-3-(3-methyl-4-phenoxyphenyl)-1,3,5-triazinane-2,4,6-trione

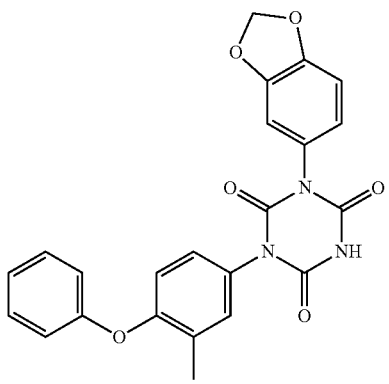 [SMILES: Cc1cc(-n2c(=O)[nH]c(=O)n(-c3ccc4c(c3)OCO4)c2=O)ccc1Oc1ccccc1]

Sodium hydride (60% in mineral oil, 33 mg, 0.82 mmol) was added to a microwave vial containing a magnetic stirring bar. The vial was sealed and put under an inert atmosphere and the sodium hydride was washed with pentane. The pentane was thereafter removed, DMF (1 ml) was added and the dispersion was cooled to 0° C. 1-(1,3-benzodioxol-5-yl)-3-(3-methyl-4-phenoxy-phenyl)urea (Intermediate 68, 119 mg, 0.33 mmol) was dissolved in DMF (2 ml) and added dropwise to the reaction vessel. The ice bath was removed and the reaction mixture was stirred for another 10 min. The solution was again cooled to 0° C. and ethoxycarbonyl isocyanate (51 µl, 0.49 mmol) was thereafter added, the ice bath was removed and the reaction mixture was stirred for 5 additional minutes before addition of water and EtOAc. The phases were separated and concentrated under reduced pressure. The crude product originating from the water phase was purified by preparative RP-HPLC (20-80% acetonitrile in water [0.05% HCOOH]) to yield 10 mg (7% yield) of the title compound. $^1$H NMR (400 MHz, DMSO-d6) δ ppm 11.97 (s, 1H), 7.44-7.36 (m, 2H), 7.30 (d, J=1.9 Hz, 1H), 7.18 (dd, J=8.8, 2.3 Hz, 1H), 7.14 (t, J=7.4 Hz, 1H), 7.01-6.94 (m, 4H), 6.91 (d, J=8.6 Hz, 1H), 6.85 (dd, J=8.2, 2.0 Hz, 1H), 6.09 (s, 2H), 2.22 (s, 3H). MS(ESI+) m/z 432 (M+H)+

Example 49

1-(1H-indol-4-yl)-3-(3-methyl-4-phenoxyphenyl)-1,3,5-triazinane-2,4,6-trione

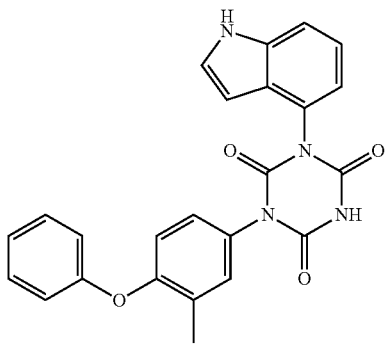 [SMILES: Cc1cc(-n2c(=O)[nH]c(=O)n(-c3cccc4[nH]ccc34)c2=O)ccc1Oc1ccccc1]

1-(1H-indol-4-yl)-3-(3-methyl-4-phenoxy-phenyl)urea (Intermediate 69, 118 mg, 0.33 mmol) was dispersed in toluene (2.5 ml) in a microwave vial, ethoxycarbonyl isocyanate (34 µl, 0.33 mmol) was added and the mixture was heated at 110° C. for 5 h and was thereafter left at room temperature overnight. The crude was concentrated at reduced pressure and the product was purified by preparative RP-HPLC (40-80% acetonitrile in water [0.05% HCOOH]) to yield 5 mg (3.5% yield) of the title compound. $^1$H NMR (400 MHz, DMSO-d6) δ ppm 11.96 (s, 1H), 11.26 (s, 1H), 7.45 (d, J=8.1 Hz, 1H), 7.42-7.35 (m, 4H), 7.26 (dd, J=8.6, 2.4 Hz, 1H), 7.17-7.10 (m, 2H), 7.01 (d, J=7.5 Hz, 1H), 6.98-6.93 (m, 2H), 6.91 (d, J=8.6 Hz, 1H), 6.59-6.54 (m, 1H), 2.21 (s, 3H); MS(ESI+) m/z 427 (M+H)+

Example 50

1-(3-methoxyphenyl)-3-(3-methyl-4-phenoxyphenyl)-1,3,5-triazinane-2,4,6-trione

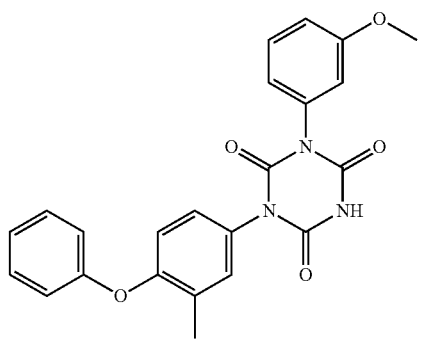 [SMILES: COc1cccc(-n2c(=O)[nH]c(=O)n(-c3ccc(Oc4ccccc4)c(C)c3)c2=O)c1]

Sodium hydride (60% in mineral oil, 33 mg, 0.83 mmol) was weighed up in a microwave vial and a stirring bar was added. was added to a microwave vial containing a magnetic stirring bar. The vial was sealed and put under an inert atmosphere and the sodium hydride was washed with pentane. The pentane was thereafter removed, DMF (2 ml) was added and the dispersion was cooled to 0° C. 1-(3-methoxyphenyl)-3-(3-methyl-4-phenoxy-phenyl)urea (Intermediate 70,115 mg, 0.33 mmol) was dissolved in DMF (2 ml) and added dropwise to the reaction vessel. The ice bath was removed and the reaction mixture was stirred for another 10 min. The solution was again cooled to 0° C. and ethoxycarbonyl isocyanate (51 µl, 0.50 mmol) was added, the ice bath was removed and the reaction mixture was stirred for 5 additional minutes before addition of water and EtOAc. The phases were separated and concentrated under reduced pressure. The product in the concentrated water phase was purified by preparative RP-HPLC (40-80% acetonitrile in water [0.05% HCOOH]) to yield 40 mg (29% yield) of the title compound. $^1$H NMR (400 MHz, DMSO-d6) δ ppm 12.00 (s, 1H), 7.44-7.34 (m, 3H), 7.32 (d, J=2.2 Hz, 1H), 7.22-7.17 (m, 1H), 7.17-7.10 (m, 1H), 7.03-6.94 (m, 5H), 6.92 (d, J=8.6 Hz, 1H), 3.77 (s, 3H), 2.22 (s, 3H); MS(ESI+) m/z 418 (M+H)+

Example 51

1-(2-methoxyphenyl)-3-(3-methyl-4-phenoxyphenyl)-1,3,5-triazinane-2,4,6-trione

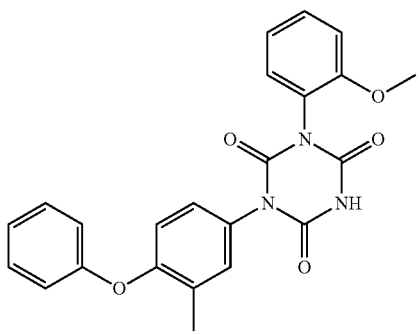 [SMILES: COc1ccccc1-n1c(=O)[nH]c(=O)n(-c2ccc(Oc3ccccc3)c(C)c2)c1=O]

Sodium hydride (60% in mineral oil, 34 mg, 0.85 mmol) was added to a microwave vial containing a magnetic stirring bar. The vial was sealed and put under an inert atmosphere and the sodium hydride was washed with pentane. The pentane was thereafter removed, DMF (2 ml) was added and the dispersion was cooled to 0° C. 1-(2-methoxyphenyl)-3-(3-methyl-4-phenoxy-phenyl)urea (Intermediate 71, 119 mg, 0.34 mmol) was dissolved in DMF solution (2 ml) and was added dropwise to the reaction vessel. The ice bath was removed and the reaction mixture was stirred for another 10 min. The solution was again cooled to 0° C. and ethoxycarbonyl isocyanate (53 µl, 0.51 mmol) was added, the ice bath was removed and the reaction mixture was stirred for 5 additional minutes before addition of water and EtOAc. The phases were separated and concentrated by reduced pressure. The crude product originating from the water phase was purified by preparative RP-HPLC (40-80% acetonitrile in water [0.05% HCOOH]) to yield 54 mg (37% yield) of the title compound. $^1$H NMR (400 MHz, DMSO-d6) δ ppm 12.07 (br. s, 1H), 7.46-7.30 (m, 5H), 7.20 (dd, J=8.6, 2.5 Hz, 1H), 7.18-7.10 (m, 2H), 7.03 (td, J=7.6, 1.2 Hz, 1H), 6.99-6.93 (m, 2H), 6.91 (d, J=8.6 Hz, 1H), 3.79 (s, 3H), 2.22 (s, 3H); MS(ESI+) m/z 418 (M+H)+

Example 52

1-(3-methoxy-4-phenoxyphenyl)-3-(3-methoxyphenyl)-1,3,5-triazinane-2,4,6-trione

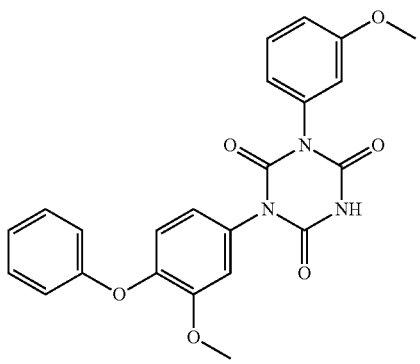 [SMILES: COc1cccc(-n2c(=O)[nH]c(=O)n(-c3ccc(Oc4ccccc4)c(OC)c3)c2=O)c1]

Sodium hydride (60% in mineral oil, 62 mg, 1.5 mmol) was added to a microwave vial containing a magnetic stirring bar. The vial was sealed and put under an inert atmosphere and the sodium hydride was washed with pentane. The pentane was thereafter removed, and the vessel was cooled to 0° C. 1-(3-methoxy-4-phenoxy-phenyl)-3-(3-methoxyphenyl)urea (Intermediate 72, 225 mg, 0.617 mmol) was dissolved in DMF (2 ml) and added dropwise to the reaction vessel containing the sodium hydride. The ice bath was removed and the reaction mixture was stirred for another 10 min. The solution was again cooled to 0° C. and ethoxycarbonyl isocyanate (96 µl, 0.93 mmol) was added, the ice bath was removed and the reaction mixture was stirred for 5 additional minutes before addition of water and EtOAc. The phases were separated and concentrated under reduced pressure. The crude product from the water phase was purified by preparative RP-HPLC (30-80% acetonitrile in water [0.05% HCOOH]) to yield 77 mg (28%) of the title compound. $^1$H NMR (400 MHz, DMSO-d6) δ ppm 12.02 (br. s, 1H), 7.42-7.31 (m, 3H), 7.23 (d, J=2.3 Hz, 1H), 7.10-6.93 (m, 6H), 6.92-6.86 (m, 2H), 3.77 (s, 3H), 3.73 (s, 3H) MS(ESI+) m/z 434 (M+H)+

Example 53

1-(3-methoxy-4-phenoxyphenyl)-3-(4-methoxyphenyl)-1,3,5-triazinane-2,4,6-trione

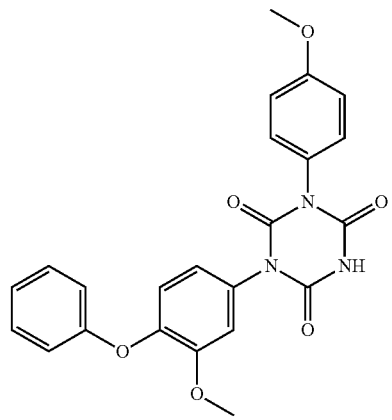 [SMILES: COc1ccc(-n2c(=O)[nH]c(=O)n(-c3ccc(Oc4ccccc4)c(OC)c3)c2=O)cc1]

Sodium hydride (60% in mineral oil, 36 mg, 0.90 mmol) was added to a microwave vial containing a magnetic stirring bar. The vial was sealed and put under an inert atmosphere and the sodium hydride was washed with pentane. The pentane was removed and the vial cooled to 0° C. 1-(3-methoxy-4-phenoxy-phenyl)-3-(4-methoxyphenyl)urea (Intermediate 73, 131 mg, 0.359 mmol) was dissolved in DMF solution (2 ml) and was added dropwise to the reaction vessel containing the sodium hydride. The ice bath was removed and the reaction mixture was stirred for another 10 min. The solution was again cooled to 0° C. and ethoxycarbonyl isocyanate (56 µl, 0.54 mmol) was added, the ice bath was removed and the reaction mixture was stirred for 5 additional minutes before addition of water and EtOAc. The phases were separated and concentrated under reduced pressure. The crude product from the water phase was purified by preparative RP-HPLC (30-80% acetonitrile in water [0.05% HCOOH]) to yield 11 mg (7% yield) of the title compound. $^1$H NMR (400 MHz, DMSO-d6) δ ppm 11.98 (br. s, 1H), 7.38-7.32 (m, 2H), 7.31-7.25 (m, 2H), 7.24

(d, J=2.3 Hz, 1H), 7.10-7.04 (m, 2H), 7.04-6.99 (m, 2H), 6.99-6.96 (m, 1H), 6.92-6.86 (m, 2H), 3.79 (s, 3H), 3.73 (s, 3H); MS(ESI+) m/z 434 (M+H)+

Example 54

1-(2,5-dimethyl-4-phenoxyphenyl)-3-phenyl-1,3,5-triazinane-2,4,6-trione

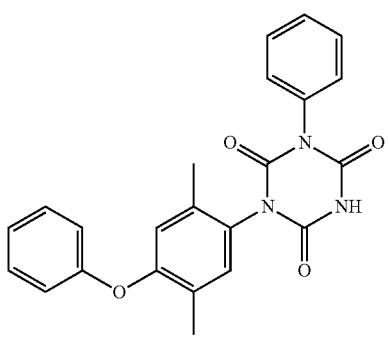 [SMILES: Cc1cc(-n2c(=O)[nH]c(=O)n(-c3ccccc3)c2=O)c(C)cc1Oc1ccccc1]

In a microwave vial previously equipped with a magnetic stirrer 1-(2,5-dimethyl-4-phenoxyphenyl)-3-phenylurea (Intermediate 79, 0.20 g, 0.0006 mol) and chlorobenzene (2.0 ml) was added. The solution was cooled to 0° C. and Ethoxy carbonyl isocyanate (0.20 g, 0.0018 mol) was added and reaction mixture was allowed to reach RT and then heated at 130° C. for 2 hours in a microwave synthesizer. The solvent was evaporated under reduced pressure and the crude product was purified by preparative HPLC (45-100% Acetonitrile in water [0.1% Formic acid]) to yield 0.093 g (38%) of the title compound. $^1$H NMR (400 MHz, DMSO-d6) δ ppm 12.07 (s, 1H), 7.54-7.45 (m, 3H), 7.45-7.37 (m, 4H), 7.30 (s, 1H), 7.18-7.10 (m, 1H), 6.99-6.92 (m, 2H), 6.82 (s, 1H), 2.17 (s, 3H), 2.10 (s, 3H); MS(ESI-) m/z 400 (M-H)-

Example 55

1-methyl-3-(3-methyl-4-phenoxyphenyl)-1,3,5-triazinane-2,4,6-trione

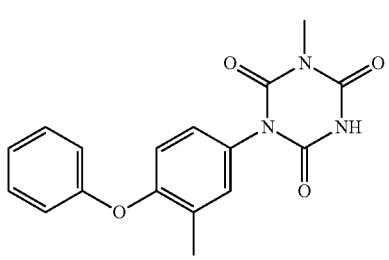 [SMILES: Cc1cc(-n2c(=O)[nH]c(=O)n(C)c2=O)ccc1Oc1ccccc1]

In a microwave vial previously equipped with a magnetic stirrer 1-methyl-3-(3-methyl-4-phenoxyphenyl)urea (Intermediate 78, 0.35 g, 0.0013 mol) and bromobenzene (3.5 ml) was added and the solution cooled to 0° C. Ethoxy carbonyl isocyanate (0.31 g, 0.0027 mol) was added and reaction mixture was allowed to reach RT and then heated at 150° C. for 2 h in a microwave synthesizer. The solvent was evaporated under reduced pressure and the crude product was purified by preparative HPLC (30-100% Acetonitrile in water [0.1% Formic acid]) to yield 0.070 g (15% yield) of the title compound. $^1$H NMR (400 MHz, DMSO-d6) δ ppm 11.84 (s, 1H), 7.47-7.37 (m, 2H), 7.30-7.27 (m, 1H), 7.21-7.11 (m, 2H), 7.04-6.96 (m, 2H), 6.95-6.88 (m, 1H), 3.16 (s, 3H), 2.22 (s, 3H); MS(ESI-) m/z 324 (M-H)-

Example 56

1-[3-(2-methoxyethoxy)-4-phenoxyphenyl]-3-(4-methylphenyl)-1,3,5-triazinane-2,4,6-trione

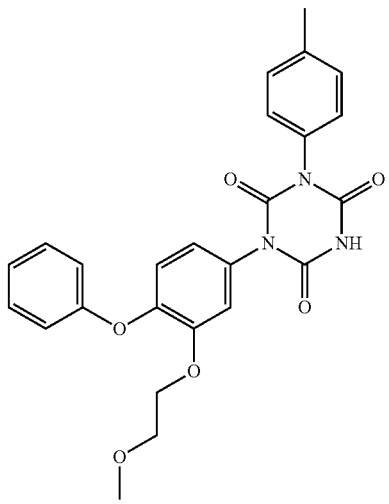 [SMILES: COCCOc1cc(-n2c(=O)[nH]c(=O)n(-c3ccc(C)cc3)c2=O)ccc1Oc1ccccc1]

In a microwave vial previously equipped with a magnetic stirrer 1-[3-(2-methoxyethoxy)-4-phenoxyphenyl]-3-(4-methylphenyl)urea (Intermediate 80, 0.20 g, 0.0005 mol) and bromobenzene (2.0 ml) was added and the solution cooled to 0° C., Ethoxy carbonyl isocyanate (0.17 g, 0.0015 mol) was added and reaction mixture was heated at 150° C. for 3 h in a microwave synthesizer. The solvent was evaporated under reduced pressure and the crude product was purified by preparative HPLC (40-100% Acetonitrile in water [0.1% Formic acid]) to yield 0.032 g (13% yield) of the title compound. $^1$H NMR (400 MHz, DMSO-d6) δ ppm 12.02 (s, 1H), δ 7.42-7.33 (m, 2H), 7.33-7.19 (m, 5H), 7.13-7.03 (m, 2H), 7.02-6.90 (m, 3H), 4.06 (t, J=4.6 Hz, 2H), 3.53 (t, J=4.5 Hz, 2H), 3.19 (s, 3H), 2.36 (s, 3H); MS(ESI-) m/z 460 (M-H)-

Example 57

1-[3-(2-methoxyethoxy)-4-phenoxyphenyl]-3-(3-methylphenyl)-1,3,5-triazinane-2,4,6-trione

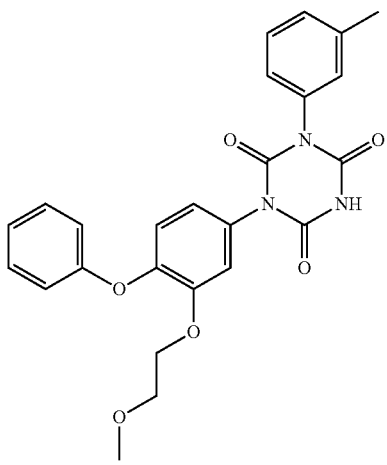 [SMILES: COCCOc1cc(-n2c(=O)[nH]c(=O)n(-c3cccc(C)c3)c2=O)ccc1Oc1ccccc1]

In a microwave vial previously equipped with a magnetic stirrer 1-[3-(2-methoxyethoxy)-4-phenoxyphenyl]-3-(3-methylphenyl)urea (Intermediate 81, 0.29 g, 0.0007 mol) and bromobenzene (2.90 ml) was added and cooled to 0° C. Ethoxy carbonyl isocyanate (0.25 g, 0.0022 mol) was added and the reaction mixture was heated at 150° C. for 2 h. The solvent was evaporated under reduced and the crude product was purified by preparative HPLC (30-100% Acetonitrile in water [0.1% Formic acid]) to yield 0.030 g (8% yield) of the title compound. $^1$H NMR (400 MHz, DMSO-d6) δ ppm 12.04 (s, 1H), 7.42-7.33 (m, 3H), 7.30-7.22 (m, 2H), 7.21-7.15 (m, 2H), 7.14-7.06 (m, 2H), 7.04-6.97 (m, 1H), 6.97-6.91 (m, 2H), 4.06 (t, J=4.5 Hz, 2H), 3.54 (t, J=4.4 Hz, 2H), 3.19 (s, 3H), 2.36 (s, 3H); MS(ESI-) m/z 460 (M-H)-

Example 58

1-(3-chlorophenyl)-3-[3-(2-methoxyethoxy)-4-phenoxyphenyl]-1,3,5-triazinane-2,4,6-trione

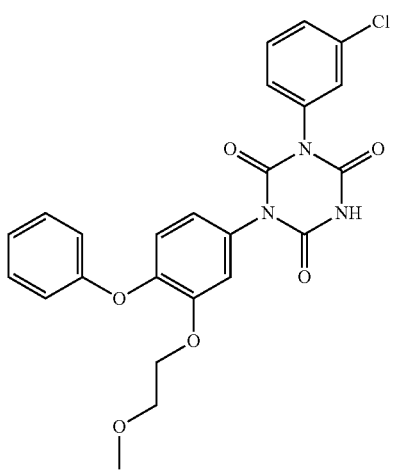 [SMILES: COCCOc1cc(-n2c(=O)[nH]c(=O)n(-c3cccc(Cl)c3)c2=O)ccc1Oc1ccccc1]

In a microwave vial previously equipped with a magnetic stirrer 1-[3-(2-methoxyethoxy)-4-phenoxyphenyl]-3-(3-chlorophenyl)urea (Intermediate 82, 0.12 g, 0.0002 mol) and bromobenzene (1.2 ml) was added and cooled to 0° C., Ethoxy carbonyl isocyanate (0.060 g, 0.0005 mol) was added and the reaction mixture was heated to 150° C. for 2 h. The solvent was evaporated under reduced pressure and the crude product was purified by preparative HPLC (15-100% Acetonitrile in water [5 mM Ammonium bicarbonate+ 0.1% NH3]) to yield 8.5 mg (6% yield) of the title compound. $^1$H NMR (400 MHz, DMSO-d6) δ ppm 12.14 (s, 1H), 7.60-7.50 (m, 3H), 7.42-7.32 (m, 3H), 7.20 (d, J=2.3 Hz, 1H), 7.12-7.05 (m, 2H), 7.00-6.90 (m, 3H), 4.06 (t, J=4.6 Hz, 2H), 3.53 (t, J=4.5 Hz, 2H), 3.18 (s, 3H); MS(ESI-) m/z 480 (M-H)-

Example 59

1-(4-chlorophenyl)-3-[3-(2-methoxyethoxy)-4-phenoxyphenyl]-1,3,5-triazinane-2,4,6-trione

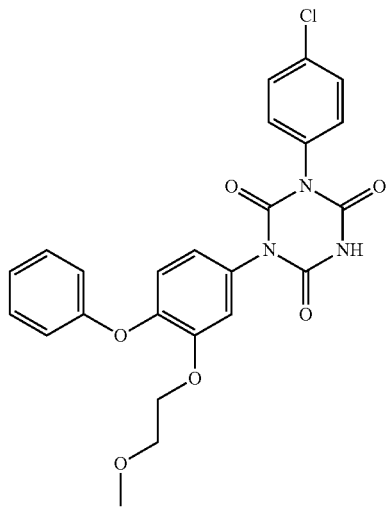 [SMILES: COCCOc1cc(-n2c(=O)[nH]c(=O)n(-c3ccc(Cl)cc3)c2=O)ccc1Oc1ccccc1]

In a microwave vial previously equipped with a magnetic stirrer, 1-[3-(2-methoxyethoxy)-4-phenoxyphenyl]-3-(4-chlorophenyl)urea (Intermediate 83, 0.22 g, 0.0005 mol) and bromobenzene (2.20 ml) was added and the solution was cooled to 0° C. Ethoxy carbonyl isocyanate (0.18 g, 0.00159 mol) was added and the reaction mixture was heated at 150° C. in a microwave synthesizer for 3 h. The solvent was evaporated under reduced pressure to obtain crude product that was purified by preparative HPLC (40-100% Acetonitrile:Methanol (1:1) in water [0.1% Formic acid]) to yield 10 mg (3.8% yield) of the title compound. $^1$H NMR (400 MHz, DMSO-d6) δ ppm 12.14 (s, 1H), 7.60-7.54 (m, 2H), 7.46-7.33 (m, 4H), 7.22 (d, J=2.3 Hz, 1H), 7.13-7.05 (m, 2H), 7.00-6.91 (m, 3H), 4.06 (t, J=4.6 Hz, 2H), 3.54 (t, J=4.5 Hz, 2H), 3.19 (s, 3H); MS(ESI-) m/z 480 (M-H)-

Example 60

1-[3-(2-methoxyethoxy)-4-phenoxyphenyl]-3-(4-methoxyphenyl)-1,3,5-triazinane-2,4,6-trione

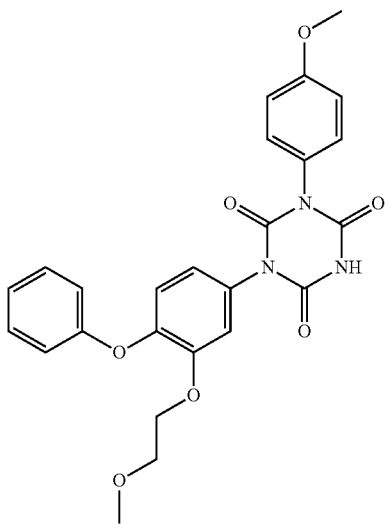 [SMILES: COCCOc1cc(-n2c(=O)[nH]c(=O)n(-c3ccc(OC)cc3)c2=O)ccc1Oc1ccccc1]

In a microwave vial previously equipped with a magnetic stirrer 1-[3-(2-methoxyethoxy)-4-phenoxyphenyl]-3-(4-methoxyphenyl)urea (Intermediate 84, 0.24 g, 0.0005 mol) and bromobenzene (2.4 ml) was added and the solution was cooled to 0° C. Ethoxy carbonyl isocyanate (0.27 g, 0.0023 mol) was added to the reaction mixture and it was heated at 150° C. in a microwave synthesizer for 3 h. The solvent was evaporated under reduced pressure to obtain crude product that was purified by preparative HPLC (30-100% Acetonitrile in water [0.1% Formic acid]) to yield 16 mg (5% yield) of the title compound. $^1$H NMR (400 MHz, DMSO-d6) δ ppm 12.01 (s, 1H), 7.42-7.32 (m, 2H), 7.32-7.22 (m, 3H), 7.15-6.91 (m, 7H), 4.07 (t, J=4.5 Hz, 2H), 3.81 (s, 3H), 3.54 (t, J=4.6 Hz, 2H), 3.19 (s, 3H); MS(ESI−) m/z 476 (M−H)−

Example 61

1-[3-(2-methoxyethoxy)-4-phenoxyphenyl]-3-(3-methoxyphenyl)-1,3,5-triazinane-2,4,6-trione

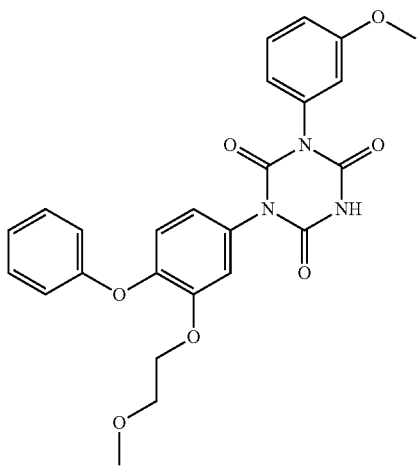 [SMILES: COCCOc1cc(-n2c(=O)[nH]c(=O)n(-c3cccc(OC)c3)c2=O)ccc1Oc1ccccc1]

In a microwave vial, previously equipped with a magnetic stirrer, 1-[3-(2-methoxyethoxy)-4-phenoxyphenyl]-3-(3-methoxyphenyl)urea (Intermediate 85, 0.25 g, 0.0006 mol) and bromobenzene (2.5 ml) was added and the solution was cooled to 0° C. Ethoxy carbonyl isocyanate (0.28 g, 0.0024 mol) was slowly added and reaction mixture was heated at 150° C. for 3 h. The solvent was evaporated under reduced pressure and the crude product was purified by preparative HPLC (45-100% Acetonitrile in water [0.1% Formic acid]) to yield 0.025 g (8% yield) of the title compound. $^1$H NMR (400 MHz, DMSO-d6) δ ppm 12.04 (s, 1H), 7.45-7.33 (m, 3H), 7.25 (d, J=2.3 Hz, 1H), 7.15-7.01 (m, 2H), 7.05-6.91 (m, 6H), 4.07 (t, J=4.6 Hz, 2H), 3.79 (s, 3H), 3.54 (t, J=4.6 Hz, 2H), 3.19 (s, 3H); MS(ESI−) m/z 476 (M−H)−

Example 62

1-[3-methyl-4-(2-methylphenoxy)phenyl]-3-phenyl-1,3,5-triazinane-2,4,6-trione

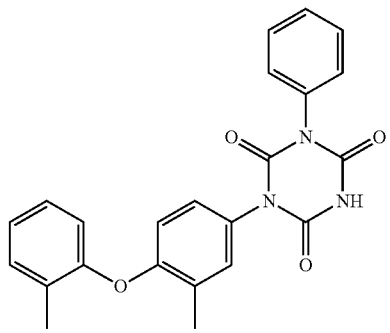 [SMILES: Cc1ccccc1Oc1ccc(-n2c(=O)[nH]c(=O)n(-c3ccccc3)c2=O)cc1C]

n a microwave vial previously equipped with a magnetic stirrer, 1-[3-methyl-4-(2-methylphenoxy)phenyl]-3-phenylurea (Intermediate 86, 0.23 g, 0.0006 mol) in chlorobenzene (2.30 ml) was added and cooled to 0° C. Ethoxy carbonyl isocyanate (0.23 g, 0.0020 mol) was added and reaction mixture was heated at 130° C. for 2 h. The solvent was evaporated under reduced pressure and the crude product was purified by the preparative HPLC (55-100% Acetonitrile:Methanol (1:1) in water [0.1% Formic acid]) to yield 9 mg (3% yield) of the title compound. $^1$H NMR (400 MHz, DMSO-d6) δ ppm 11.93 (s, 1H), 7.52-7.40 (m, 3H), 7.40-7.32 (m, 3H), 7.31-7.27 (m, 1H), 7.25-7.18 (m, 1H), 7.17-7.06 (m, 2H), 6.82 (d, J=7.9 Hz, 1H), 6.66 (d, J=8.6 Hz, 1H), 2.27 (s, 3H), 2.21 (s, 3H); MS(ESI−) m/z 400 (M−H)−

Example 63

1-(3-methyl-4-phenoxyphenyl)-3-(1,3-thiazol-4-yl)-1,3,5-triazinane-2,4,6-trione

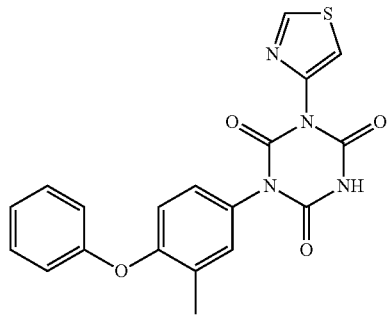 [SMILES: Cc1cc(-n2c(=O)[nH]c(=O)n(-c3cscn3)c2=O)ccc1Oc1ccccc1]

In a microwave vial previously equipped with a magnetic stirrer, 1-(3-methyl-4-phenoxyphenyl)-3-(1,3-thiazol-4-yl) urea (Intermediate 87, 0.30 g, 0.0009 mol) in bromobenzene (3.0 ml) was added and cooled to 0° C. Ethoxy carbonyl isocyanate (0.42 g, 0.0036 mol) was added at 0° C. and the reaction mixture was allowed to reach RT and then heated at 150° C. for 3 h in a microwave synthesizer. The solvent was evaporated under reduced pressure and the crude product was purified by Combi-flash chromatography using 45% ethyl acetate in hexanes as an eluent to yield 16 mg (4% yield) of the title compound. $^1$H NMR (400 MHz, DMSO-d6) δ ppm 12.13 (s, 1H), 9.14 (d, J=2.2 Hz, 1H), 7.82 (d, J=2.2 Hz, 1H), 7.45-7.32 (m, 3H), 7.23 (dd, J=8.5, 2.6 Hz, 1H), 7.14 (t, J=7.4 Hz, 1H), 7.01-6.95 (m, 2H), 6.93-6.88 (m, 1H), 2.22 (s, 3H); MS(ESI−) m/z 393 (M−H)−

Example 64

1-[4-(4-chlorophenoxy)phenyl]-3-methyl-1,3,5-triazinane-2,4,6-trione

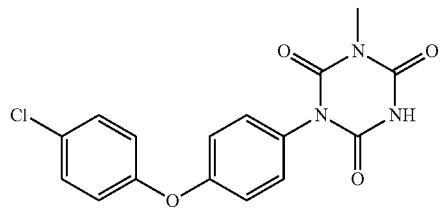 [SMILES: Cn1c(=O)[nH]c(=O)n(-c2ccc(Oc3ccc(Cl)cc3)cc2)c1=O]

In a microwave vial previously equipped with a magnetic stirrer, Ethoxy carbonyl isocyanate (0.074 g, 0.00065 mol) was added to a solution of 1-[4-(4-chlorophenoxy)phenyl]-3-methylurea (Intermediate 88, 0.120 g, 0.00043 mol) in Toluene (1.20 ml) at 0° C. The reaction mixture was heated at 110° C. for 16 h and quenched with ice-water (50 ml) and extracted with ethyl acetate (3×40 ml). The combined organic layer was washed with brine (30 ml), dried over sodium sulfate and the solvent removed under reduced pressure to obtain 0.140 g (93% yield) of the title compound. $^1$H NMR (400 MHz, DMSO-d6) δ ppm 3.15 (s, 3H) 7.06-7.15 (m, 4H) 7.31-7.37 (m, 2H) 7.46-7.52 (m, 2H) 11.82 (s, 1H); MS (ES−) m/z 344 [M−H]−

Example 65

1(3-chloro-4-phenoxyl)enyl)-3-methyl-1,3,5-triazinane-2,4,6-trione

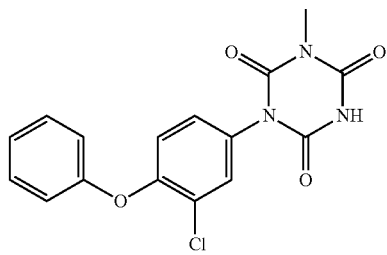 [SMILES: Cn1c(=O)[nH]c(=O)n(-c2ccc(Oc3ccccc3)c(Cl)c2)c1=O]

1-(3-Chloro-4-phenoxyphenyl)-3-methylurea (Intermediate 89, 0.145 g, 0.00052 mol) in bromobenzene (1.45 ml) was added to a microwave tube previously equipped with a magnetic stirrer and cooled to 0° C. Ethoxy carbonyl isocyanate (0.120 g, 0.00104 mol) was added and reaction mixture was heated at 150° C. for 2 h. The solvent was removed under reduced pressure and the crude product was purified by preparative HPLC (30-100% Acetonitrile in water [5 mM ammonium bicarbonate and 0.1% ammonia]) to yield 0.020 g (11% yield) of the title compound. $^1$H NMR (400 MHz, DMSO-d6): δ11.86 (s, 1H), δ 7.64 (d, J=2.4 Hz, 1H), 7.45 (t, J=7.9 Hz, 2H), 7.32 (dd, J=8.7, 2.5 Hz, 1H), 7.21 (t, J=7.4 Hz, 1H), 7.11 (d, J=8.7 Hz, 1H), 7.05 (d, J=8.1 Hz, 2H), 3.15 (s, 3H). MS(ESI−) m/z 344.49 (M−H)−

Example 66

1-[3-(2-methoxyethoxy)-4-phenoxyphenyl]-3-(5-methylthiophen-2-yl)-1,3,5-triazinane-2,4,6-trione

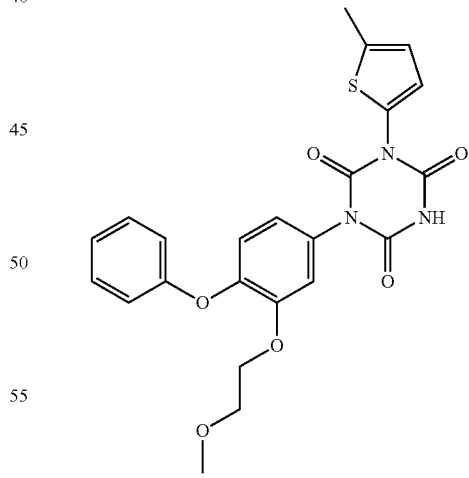

In a microwave vial previously equipped with a magnetic stirrer was taken 1-[3-(2-methoxyethoxy)-4-phenoxyphenyl]-3-(5-methylthiophen-2-yl)urea (Intermediate 90, 0.32 g, 0.0008 mol) and chlorobenzene (6.4 ml). The solution was cooled to 0° C. and Ethoxy carbonyl isocyanate (0.37 g, 0.0032 mol) was added. The reaction mixture was allowed to reach room temperature and then heated at 130° C. for 3 h in an Anton paar microwave synthesizer-300. The solvent was evaporated under reduced pressure and the crude product was purified by preparative RP-HPLC (15-100% acetonitrile in water [10 mM Ammonium acetate]) to yield 5 mg (1.3% yield) of the title compound. $^1$H NMR (400 MHz, DMSO-d6) δ ppm 12.10 (s, 1H), 7.42-7.33 (m, 2H), 7.24 (d, J=2.0 Hz, 1H), 7.12-7.06 (m, 2H), 6.99-6.93 (m, 3H), 6.87 (d, J=3.6 Hz, 1H), 6.74 (m, 1H), 4.06 (t, J=4.0 Hz, 2H), 3.53 (t, J=4.4 Hz, 2H), 3.19 (s, 3H), 2.46 (s, 3H). MS (ES−) m/z 466 [M−H]−

Example 67

1,3-bis(3-methyl-4-phenoxyphenyl)-1,3,5-triazinane-2,4,6-trione

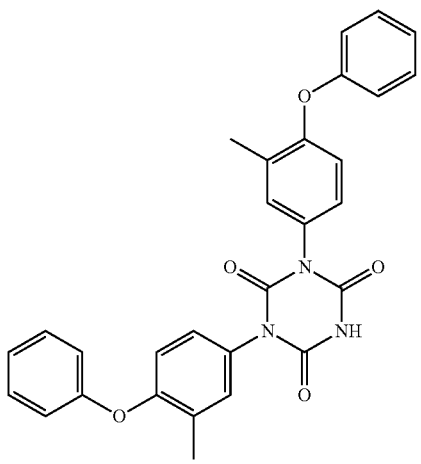 [SMILES: Cc1cc(-n2c(=O)[nH]c(=O)n(-c3ccc(Oc4ccccc4)c(C)c3)c2=O)ccc1Oc1ccccc1]

In a microwave vial previously equipped with a magnetic stirrer, 1,3-bis(3-methyl-4-phenoxyphenyl)urea (Intermediate 91, 0.30 g, 0.0007 mol) in Bromobenzene (3 ml) was added and the mixture was cooled to 0° C. Ethoxy carbonyl isocyanate (0.32 g, 0.0028 mol) was added and the resulting reaction mixture was allowed to reach room temperature and then heated at 150° C. for 3 h in an Anton paar microwave synthesizer-300. The solvent was evaporated under reduce pressure to obtain crude product. The crude product was purified by preparative RP-HPLC (40-100% acetonitrile in water [0.1% formic acid]) to yield 52 mg (14% yield) of the title compound. $^1$H NMR (400 MHz, DMSO-d6) δ ppm 12.05 (s, 1H), 7.46-7.37 (m, 4H), 7.33 (d, J=2.5 Hz, 2H), 7.21 (dd, J=8.8, 2.4 Hz, 2H), 7.15 (t, J=7.6 Hz, 2H), 7.02-6.90 (m, 6H), 2.11 (s, 6H). MS(ESI−) m/z 492 [M−H]−

Example 68

1-(3-methyl-4-phenoxyphenyl)-3-(1-phenyl-1H-pyrazol-4-yl)-1,3,5-triazinane-2,4,6-trione

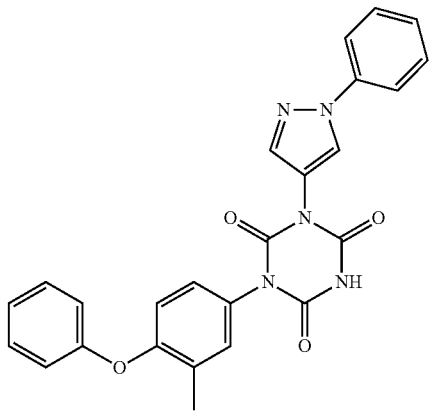 [SMILES: Cc1cc(-n2c(=O)[nH]c(=O)n(-c3cnn(-c4ccccc4)c3)c2=O)ccc1Oc1ccccc1]

In a microwave tube previously equipped with a magnetic stirrer 1-(3-methyl-4-phenoxyphenyl)-3-(1-phenyl-1H-pyrazol-4-yl)urea (Intermediate 93, 0.23 g, 0.0008 mol) in Bromobenzene (3.0 ml) was added and the mixture was cooled to 0° C. Ethoxy carbonyl isocyanate (0.19 g, 0.0017 mol) was added and the reaction mixture was allowed to reach room temperature and heated at 150° C. for 2 h in an Anton paar microwave synthesizer-300. The solvent was evaporated under reduce pressure and the crude product was purified by preparative RP-HPLC (25-100% acetonitrile in water [5 mM ammonium bicarbonate+0.1% NH$_3$]) to yield 52 mg (19% yield) of the title compound. $^1$H NMR (400 MHz, DMSO-d6) δ ppm 12.15 (s, 1H), 8.67 (s, 1H), 7.88-7.83 (m, 3H), 7.62-7.50 (m, 2H), 7.45-7.33 (m, 4H), 7.23 (d, J=8.4, 1H), 7.15 (t, J=7.2 Hz, 1H), 7.03-6.91 (m, 3H), 2.24 (s, 3H). MS (ES−) m/z 452 [M−H]−

Example 69

1-(3-bromo-4-phenoxyphenyl)-3-phenyl-1,3,5-triazinane-2,4,6-trione

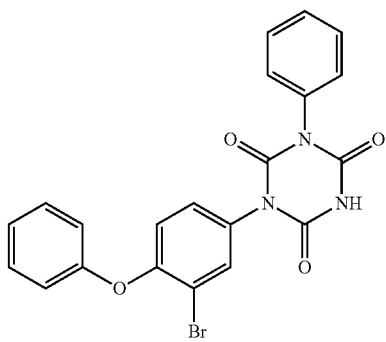 [SMILES: O=c1[nH]c(=O)n(-c2ccc(Oc3ccccc3)c(Br)c2)c(=O)n1-c1ccccc1]

In a microwave vial previously equipped with a magnetic stirrer 1-(3-bromo-4-phenoxyphenyl)-3-phenylurea (Intermediate 94, 0.50 g, 0.0013 mol) in bromobenzene (5.0 ml) was added and the mixture was cooled to 0° C. Ethoxy carbonyl Isocyanate (0.60 g, 0.0052 mol) was added at 0° C.

and the resulting reaction mixture was allowed to reach room temperature and heated at 150° C. for 3 h in an Anton paar microwave synthesizer-300. The solvent was evaporated under reduced pressure and the crude product was purified by using preparative RP-HPLC (50-100% acetonitrile in water [0.1% formic acid]) to yield 5 mg (0.85% yield) of the title compound. $^1$H NMR (400 MHz, DMSO-d6) δ ppm 12.11 (s, 1H), 7.84 (d, J=2.4 Hz, 1H), 7.52-7.36 (m, 8H), 7.22 (app t, J=7.2 Hz, 1H), 7.13-7.02 (m, 3H). MS (ES−) m/z 452 [M−H]−

Example 70

1-(2-methyl-4-phenoxyphenyl)-3-phenyl-1,3,5-triazinane-2,4,6-trione

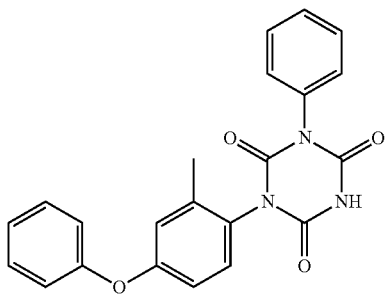 [SMILES: Cc1cc(Oc2ccccc2)ccc1-n1c(=O)[nH]c(=O)n(-c2ccccc2)c1=O]

In a microwave vial previously equipped with a magnetic stirrer 1-(2-methyl-4-phenoxyphenyl)-3-phenylurea (Intermediate 95, 0.20 g, 0.0006 mol) in bromobenzene (2.0 ml) was added and the mixture was cooled to 0° C. Ethoxy carbonyl isocyanate (0.28 g, 0.0025 mol) was added and the reaction mixture was allowed to reach room temperature and heated at 150° C. for 3 h in an Anton paar microwave synthesizer-300. The solvent was evaporated under reduced pressure and the crude product was purified by preparative RP-HPLC (40-100% acetonitrile in water [0.1% formic acid]) to yield 30 mg (yield 12%) of the title compound. $^1$H NMR (400 MHz, DMSO-d6) δ ppm 12.06 (s, 1H), 7.53-7.31 (m, 8H), 7.19 (t, J=7.2 Hz, 1H), 7.12-7.05 (m, 2H), 6.98-6.83 (m, 2H), 2.15 (s, 3H). MS (ES−) m/z 386 [M−H]−

Example 71

1-(2-methyl-4-phenoxyphenyl)-3-(4-methylphenyl)-1,3,5-triazinane-2,4,6-trione

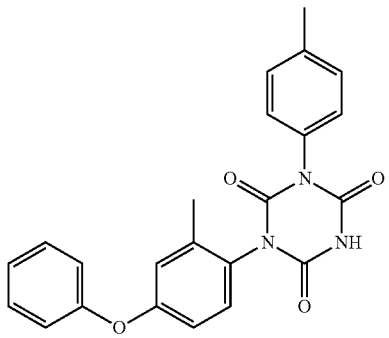 [SMILES: Cc1ccc(-n2c(=O)[nH]c(=O)n(-c3ccc(Oc4ccccc4)cc3C)c2=O)cc1]

In a microwave vial previously equipped with a magnetic stirrer 1-(2-methyl-4-phenoxyphenyl)-3-(4-methylphenyl) urea (Intermediate 97, 0.40 g, 0.0012 mol) in bromobenzene (4.0 ml) was added and the mixture was cooled to 0° C. Ethoxy carbonyl isocyanate (0.55 g, 0.0048 mol) was added and reaction mixture was allowed to reach room temperature and heated at 150° C. for 3 h in an Anton paar microwave synthesizer-300. The solvent was removed under reduced pressure to obtain crude product that was purified by preparative RP-HPLC (30-100% acetonitrile in water [0.1% formic acid]) to yield 12 mg (2% yield) of the title compound. $^1$H NMR (400 MHz, DMSO-d6) δ ppm 12.03 (s, 1H), 7.48-7.40 (m, 2H), 7.34 (d, J=8.8 Hz, 1H), 7.27 (app s, 4H), 7.20 (t, J=7.2 Hz, 1H), 7.10-7.05 (m, 2H), 6.95 (d, J=2.4 Hz, 1H), 6.88 (dd, J=8.4, 2.8 Hz, 1H), 2.35 (s, 3H), 2.14 (s, 3H). MS (ES−) m/z 400 [M−H]−

Example 72

1-(1-benzofuran-4-yl)-3-(3-methyl-4-phenoxyphenyl)-1,3,5-triazinane-2,4,6-trione

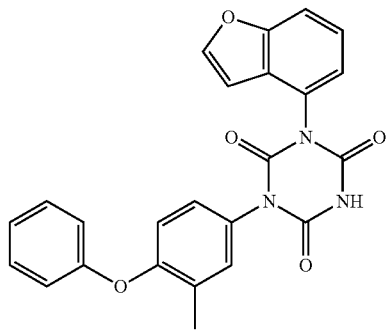 [SMILES: Cc1cc(-n2c(=O)[nH]c(=O)n(-c3cccc4occc34)c2=O)ccc1Oc1ccccc1]

In a microwave tube previously equipped with a magnetic stirrer 1-(1-benzofuran-4-yl)-3-(3-methyl-4-phenoxyphenyl)urea (Intermediate 98, 0.25 g, 0.0006 mol) in bromobenzene (2.5 ml) was added and the mixture was cooled to 0° C. Ethoxy carbonyl isocyanate (0.32 g, 0.0027 mol) was added at 0° C. and the reaction mixture was allowed to reach room temperature and heated at 150° C. for 3 h in an Anton paar microwave synthesizer-300. The solvent was removed under reduced pressure to obtain the crude product that was purified by preparative RP-HPLC (20-100% acetonitrile in water [0.1% formic acid]) to yield 16 mg (5% yield) of the title compound. $^1$H NMR (400 MHz, DMSO-d6) δ ppm 12.10 (s, 1H), 8.03 (d, J=2.0 Hz, 1H), 7.69 (d, J=8.0 Hz, 1H), 7.42-7.38 (m, 4H), 7.31-7.25 (m, 2H), 7.21-7.10 (m, 2H), 7.00-6.90 (m, 3H), 2.23 (s, 3H). MS (ES−) m/z 426 [M−H]−

Example 73

1-(1-benzofuran-7-yl)-3-(3-methyl-4-phenoxyphenyl)-1,3,5-triazinane-2,4,6-trione

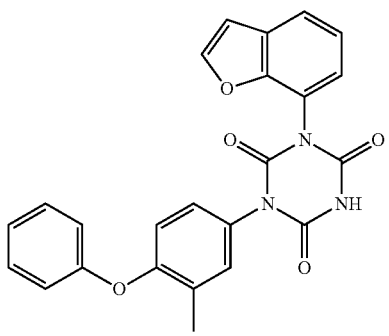 [SMILES: Cc1cc(-n2c(=O)[nH]c(=O)n(-c3cccc4ccoc34)c2=O)ccc1Oc1ccccc1]

In a microwave vial previously equipped with a magnetic stirrer, 1-(1-benzofuran-7-yl)-3-(3-methyl-4-phenoxyphenyl)urea (Intermediate 99, 0.50 g, 0.00139 mol) in bromobenzene (5.0 ml) was added and the mixture was cooled to 0° C. Ethoxy carbonyl Isocyanate (0.64 g, 0.00558 mol) was added at 0° C. and reaction mixture was allowed to reach room temperature and heated at 150° C. for 3 h in an Anton paar microwave synthesizer-300. The solvent was removed under reduced pressure to obtain crude product that was purified by preparative RP-HPLC (40-100% acetonitrile in water [0.1% formic acid]) to yield 35 mg (5% yield) of the title compound. $^1$H NMR (400 MHz, DMSO-d6) δ ppm 12.25 (s, 1H), 8.06 (d, J=2.0 Hz, 1H), 7.76 (dd, J=7.6, 1.2 Hz, 1H), 7.45-7.33 (m, 5H), 7.27 (dd, J=8.4, 2.4 Hz, 1H), 7.13 (t, J=7.2 Hz, 1H), 7.08 (d, J=2.0 Hz, 1H), 7.00-6.90 (m, 3H), 2.22 (s, 3H). MS (ES−) m/z 426 [M−H]−

Example 74

Methyl 2-phenoxy-5-(2,4,6-trioxo-3-phenyl-1,3,5-triazinan-1-yl)benzoate

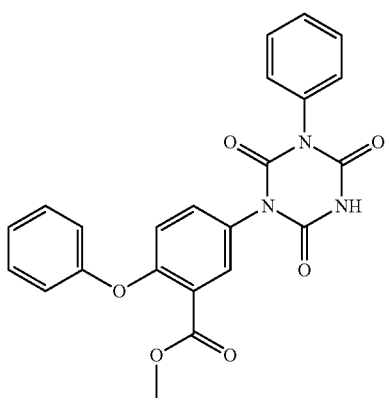 [SMILES: COC(=O)c1cc(-n2c(=O)[nH]c(=O)n(-c3ccccc3)c2=O)ccc1Oc1ccccc1]

In a microwave tube previously equipped with a magnetic stirrer and nitrogen balloon was taken methyl 2-phenoxy-5-[(phenylcarbamoyl)amino]benzoate (1.75 g, 4.8 mmol) (described in WO 2003029199) in bromobenzene (8.75 ml) and the mixture was cooled to 0° C. Ethoxy carbonyl isocyanate (2.2 g, 19.3 mmol) was added and reaction mixture was allowed to reach room temperature and heated at 150° C. for 3 h in a microwave synthesizer. The solvent was evaporated under reduced pressure the crude product was purified by column chromatography using silica gel (100-200 mesh) and 50% ethyl acetate in hexanes as an eluent to obtain 0.260 g (12% yield) of the title compound. $^1$H NMR (400 MHz, DMSO-d$_6$): δ 12.07 (s, 1H), 7.92 (d, J=2.4 Hz, 1H), 7.60 (dd, J=8.8, 2.4 Hz, 1H), 7.50-7.36 (m, 7H), 7.19 (t, J=7.2 Hz, 1H), 7.09 (d, J=8.8 Hz, 1H), 7.03 (d, J=7.6 Hz, 2H), 3.76 (s, 3H); MS (ES−) m/z 430 [M−H]−.

Example 75

1-[3-(hydroxymethyl)-4-phenoxyphenyl]-3-phenyl-1,3,5-triazinane-2,4,6-trione

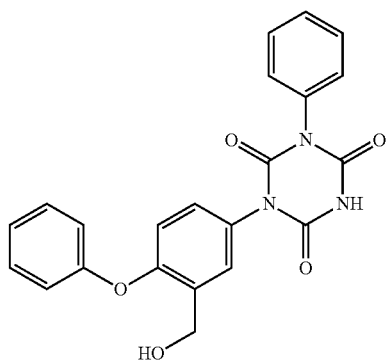 [SMILES: O=c1[nH]c(=O)n(-c2ccc(Oc3ccccc3)c(CO)c2)c(=O)n1-c1ccccc1]

In a RBF previously equipped with a magnetic stirrer and nitrogen balloon was taken methyl 2-phenoxy-5-(2,4,6-trioxo-3-phenyl-1,3,5-triazinan-1-yl)benzoate (Example 74, 0.20 g, 0.4 mmol) in THF (2.0 ml) and the solution was cooled to 0° C. A 60% Red-Al solution in Toluene (0.186 ml, 0.5 mmol) was added drop wise and the reaction mixture was stirred for 3 h at 25° C. The reaction mixture was quenched with water (15 ml) and ethyl acetate (20 ml) was added and the mixture was stirred for 10 min. The organic layer was separated and the aqueous layer was extracted with ethyl acetate (20 ml). The combined organic layer was washed with brine (20 ml), dried over sodium sulphate and the solvent removed under reduced pressure. The crude product was purified by preparative HPLC (using 25-100% acetonitrile in water [0.1% formic acid] as mobile phase) to yield 0.006 g (13% yield) of the title compound. $^1$H NMR (400 MHz, DMSO-d$_6$): δ 12.00 (s, 1H), 7.58 (d, J=2.5 Hz, 1H), 7.51-7.39 (m, 7H), 7.25 (dd, J=8.4, 2.0 Hz, 1H), 7.17 (t, J=7.2 Hz, 1H), 7.01 (d, J=7.6 Hz, 2H), 6.89 (d, J=8.4 Hz, 1H), 5.37 (t, J=5.2 Hz, 1H), 4.58 (d, J=5.2 Hz, 2H). MS (ES−) m/z 402 [M−H]−.

Example 76

1-{3-[2-(Dimethylamino)-2-oxoethyl]-4-phenoxy-phenyl}-3-phenyl-1,3,5-triazinane-2,4,6-trione

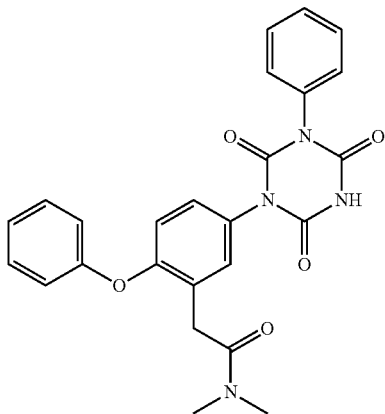 [SMILES: CN(C)C(=O)Cc1cc(-n2c(=O)[nH]c(=O)n(-c3ccccc3)c2=O)ccc1Oc1ccccc1]

1-(Dimethylamino)-2-[2-phenoxy-5-(3-phenylureido)phenyl]-1-ethanone (Intermediate 103, 0.05 g, 0.1 mmol) in Bromobenzene (0.5 ml) was added to a microwave vial previously equipped with a magnetic stirrer and nitrogen balloon and the mixture was cooled to 0° C. Ethoxy carbonyl isocyanate (0.05 g, 0.5 mmol) was added and the reaction mixture was allowed to reach room temperature and heated at 150° C. for 3 h in a microwave synthesizer. The solvent was removed under reduced pressure to give a crude product. The above steps were performed with equivalent ways in 4 parallel reaction vials, which were combined during purification. The crude product was purified by preparative RP-HPLC (using 10-100% acetonitrile in water [0.1% formic acid] as mobile phase) to yield 0.006 g (2.5% yield) of the title compound. 1H NMR (400 MHz, DMSO-d6): δ 12.02 (s, 1H), 7.49-7.36 (m, 7H), 7.28-7.13 (m, 3H), 7.04 (d, J=7.6 Hz, 2H), 6.84 (d, J=8.0 Hz, 1H), 3.72 (s, 2H), 2.99 (s, 3H), 2.80 (s, 3H); MS (ES−) m/z 457 [M−H]−.

Example 77

1-{3-[2-(Dimethylamino)-2-oxoethoxy]-4-phenoxy-phenyl}-3-phenyl-1,3,5-triazinane-2,4,6-trione

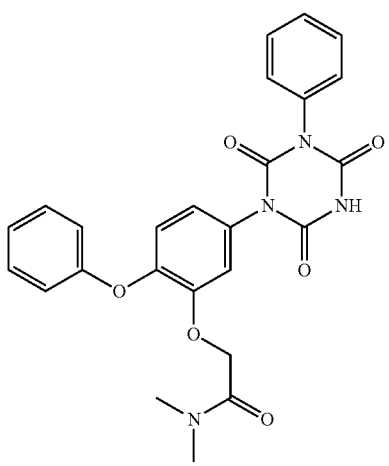 [SMILES: CN(C)C(=O)COc1cc(-n2c(=O)[nH]c(=O)n(-c3ccccc3)c2=O)ccc1Oc1ccccc1]

1-(Dimethylamino)-2-[2-phenoxy-5-(3-phenylureido)phenoxy]-1-ethanone (Intermediate 107, 0.50 g, 1.2 mmol) in Bromobenzene (5 ml) was added to a microwave tube previously equipped with a magnetic stirrer and nitrogen balloon, and the mixture was cooled to 0° C. Ethoxy carbonyl isocyanate (0.56 g, 4.9 mmol) was added and reaction mixture was allowed to reach room temperature and heated at 150° C. for 3 h in a microwave synthesizer. The solvent was removed under reduced pressure and the crude product was purified by preparative RP-HPLC (using 20-100% acetonitrile in water [0.1% formic acid] as mobile phase) to yield 0.022 g (3.7% yield) of the title compound. $^1$H NMR (400 MHz, DMSO-d$_6$): δ 12.07 (s, 1H), 7.52-7.34 (m, 7H), 7.18-7.07 (m, 3H), 7.02-6.96 (m, 3H), 4.79 (s, 2H), 2.89 (s, 3H), 2.81 (s, 3H); MS (ES−) m/z 473 [M−H]−.

The compounds below has been prepared according to analogous methods to those described above.

Example 78

1-(5-Methyl-6-phenoxypyridin-3-yl)-3-(p-tolyl)-1,3,5-triazinane-2,4,6-trione

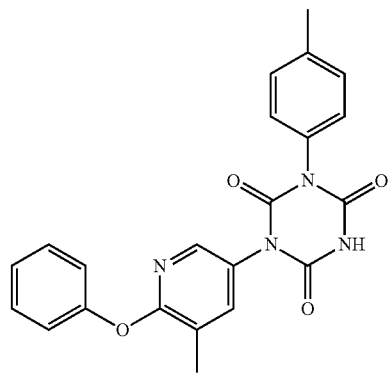 [SMILES: Cc1ccc(-n2c(=O)[nH]c(=O)n(-c3cnc(Oc4ccccc4)c(C)c3)c2=O)cc1]

In a microwave tube previously equipped with a magnetic stirrer and nitrogen balloon was taken 3-(5-Methyl-6-phenoxy-3-pyridyl)-1-(4-methylphenyl)urea (Intermediate 109, 0.3 g, 0.00089 mol) in Bromobenzene (3.0 ml). The solution was cooled to 0° C. and Ethoxy carbonyl isocyanate (0.44 g, 0.00359 mol) was added and resulting reaction mixture was allowed to reach room temperature and heated at 150° C. for 3 h in an Anton paar microwave synthesizer-300. The solvent was evaporated under reduced pressure to obtain crude product that was purified by preparative RP-HPLC (using 25-100% acetonitrile in water [0.1% formic acid] as mobile phase) to yield 0.012 g (3.3% yield) of the title compound. $^1$H NMR (400 MHz, DMSO-d$_6$): δ 12.09 (s, 1H), 7.93 (d, J=2.4 Hz, 1H), 7.75 (s, 1H), 7.49-7.41 (m, 2H), 7.29-7.23 (m, 5H), 7.20-7.13 (m, 2H), 2.35 (s, 6H). MS (ES−) m/z 401 [M−H]−.

Biological Examples

In Vitro Assay

A high throughput cell-based screen has been used to identify positive modulators of TrkA, TrkB and TrkC. The screen involves the use of cell-based assay overexpressing TrkA, TrkB or TrkC. The purpose of the assay is to identify compounds that modulate neurotrophin signalling (Forsell et al 2012). The assay can be used in inhibitor mode using a high concentration of ligand, in modulator mode using an intermediate concentration and in agonist mode using a low concentration of ligand.

The assay uses Enzyme Fragment Complementation (EFC) technique, which is a proximity-based assay. Briefly, cells used in this assay over-express two fusion proteins, i.e. the receptor, which can be either one of TrkA, TrkB, TrkC, IGF1R or FGFR1, fused to a small peptide of beta-galactosidase and an adaptor protein, i.e. SHC1 (or any other Trk-adaptor protein) fused to the major part of beta-galactosidase. Ligand binding to the receptor induces phosphorylation of the intracellular domain and hence, recruitment of the adaptor protein to the receptor. The proximity between the small activating peptide on the receptor and the major part of beta-galactosidase on the adaptor protein leads to an active beta-galactosidase enzyme. The activation of the receptor is quantified by measuring the amount of active beta-galactosidase by its conversion of a non-luminescent substrate into a luminescent product.

U2OS-cells, over-expressing TrkA or TrkB or TrkC, are plated in 96- or 384-well plates and incubated overnight. Alternatively, cryopreserved HEK293-cells expressing IGFR1 or cryopreserved U2OS-cells expressing FGFR1 were plated in 96- or 384-well plates. On the following day, test compound was pre-mixed with ligand (NGF, BDNF, NT-3, IGF-1 or basic fibroblast growth factor (bFGF (FGF-2))) and the ligand-compound mixture is then added to the cells to yield a final ligand concentration of 10 ng/mL. After 3 hours of incubation at room temperature, the incubation is stopped by the addition of a beta-galactosidase substrate mixture containing detergents. The substrate mixture is incubated for 60 minutes at ambient temperature. The luminescence is thereafter read by the use of a plate reader.

Results

Data from these assays for representative compounds is shown in the Table below. The potency is expressed as EC50 ($\mu$M) for the individual receptors. The data indicate that the compounds of the invention are expected to possess useful therapeutic properties.

Results

| Example | TrkA | TrkB | TrkC | FGFR1 | IGF1R |
|---|---|---|---|---|---|
| 1 | 1.3 | 1.4 | 1.4 | 0.89 | 1.8 |
| 2 | 1.4 | 2.4 | | | |
| 3 | 6.7 | | | | |
| 4 | 0.83 | 0.95 | | 0.58 | 0.84 |
| 5 | 0.34 | 0.39 | | 0.29 | 0.25 |
| 6 | 4.4 | | | | 4.4 |
| 7 | 3.9 | | | | 2.6 |
| 8 | 1.6 | | | | 2.2 |
| 9 | 0.23 | 0.27 | | 0.17 | 0.27 |
| 10 | 1.1 | 2.2 | | 2.8 | |
| 11 | 0.32 | 0.45 | | 0.34 | 0.22 |
| 12 | 5.9 | 2.4 | | 4.7 | |
| 13 | 0.62 | 0.45 | | | |
| 14 | 0.49 | | | | |
| 15 | 0.59 | 0.65 | 1.1 | | |
| 16 | 0.39 | 0.37 | 0.51 | | |
| 17 | 0.78 | 0.75 | 0.48 | | |
| 18 | 0.87 | 0.14 | | | |
| 19 | 0.82 | 0.88 | | | |
| 20 | 6.9 | 8.9 | 3.2 | | |
| 21 | 2.1 | 2.3 | 1.2 | | |
| 22 | 1.3 | 3.6 | 3.0 | | |
| 23 | 1.0 | 0.92 | 0.77 | | |
| 24 | 0.5 | 0.61 | 0.22 | | |
| 25 | 0.55 | 0.79 | 1.0 | | |
| 26 | 1.1 | 1.5 | 2.0 | | |
| 27 | 0.36 | 0.37 | 0.33 | | |
| 28 | 1.0 | 0.99 | 0.52 | | |
| 29 | 0.56 | 0.5 | 0.34 | | |
| 30 | 1.1 | 7.5 | 0.89 | | |
| 31 | 46 | 69 | | | |
| 32 | 0.8 | | | | |
| 33 | 0.23 | 0.1 | | | |
| 34 | 1.6 | 2.0 | 1.2 | | |
| 35 | 0.98 | 0.26 | 0.50 | | |
| 36 | 0.95 | 0.46 | 1.5 | | |
| 37 | 0.39 | | 0.04 | | |
| 38 | 4.5 | 4.2 | 2.4 | | |
| 39 | 1.4 | 0.68 | 0.88 | | |
| 40 | 0.26 | 0.28 | 0.14 | | |
| 41 | 0.25 | 0.21 | 0.14 | | |
| 42 | 0.19 | 0.28 | | | |
| 43 | 0.16 | 0.12 | | | |
| 44 | 0.33 | 0.26 | | | |
| 45 | 0.47 | 0.36 | | | |
| 46 | 0.48 | 0.24 | | | |
| 47 | 0.48 | 0.27 | | | |
| 48 | 0.5 | 0.26 | | | |
| 49 | 0.19 | 0.79 | 2.0 | | |
| 50 | 0.31 | 0.19 | | | |
| 51 | 0.18 | 0.26 | | | |
| 52 | 0.38 | 0.41 | | | |
| 53 | 0.96 | 0.78 | | | |
| 54 | 0.44 | 0.31 | | | |
| 55 | 0.39 | 1.4 | | | |
| 56 | 0.29 | 0.11 | 0.17 | | |
| 57 | 0.18 | 0.12 | 0.09 | | |
| 58 | 0.22 | 0.23 | 0.18 | | |
| 59 | 0.48 | 0.46 | 0.33 | | |
| 60 | 0.3 | 0.22 | | | |
| 61 | 0.42 | 0.38 | | | |
| 62 | 0.93 | 3.18 | | | |
| 63 | 2.38 | 0.95 | | | |
| 64 | 4.4 | 5.9 | 9.6 | | |
| 65 | 4.5 | 1.6 | 0.32 | | |
| 66 | 0.37 | 0.37 | | | |
| 67 | 3.2 | 26 | | | |
| 68 | 0.23 | 0.36 | 1.1 | | |
| 69 | 0.22 | 0.25 | 0.19 | | |
| 70 | 0.66 | 0.35 | | | |
| 71 | 1.66 | 0.61 | | | |
| 72 | 0.20 | 0.11 | | | |
| 73 | 0.14 | 0.10 | | | |
| 74 | 0.58 | 0.54 | | | |
| 75 | 1.17 | 1.8 | | | |
| 76 | 33 | 4.53 | | | |
| 77 | 0.43 | 0.36 | | | |
| 78 | 3.51 | 3.83 | | | |

In Vivo Assay

Passive Avoidance Task

Passive avoidance (PA) is an aversive learning task based on classical (Pavlovian) fear conditioning that allows for analysis of both facilitation and impairment of memory function by adjusting the unconditioned stimulus, i.e. the electrical foot shock. Commonly a cognitive-impairing agent is administered to the animals to mimic the neurochemical disturbances present in various cognitive disorders e.g. cholinergic (scopolamine) and glutamatergic (MK-801) deficits.

Prior to testing, the animals are brought to the experimental room where they are allowed to habituate for 60 min. The test is conducted using a modified shuttle box with two communicating compartments of equal size with a small sliding door built into the separating wall and a stainless-steel bar floor. One of the compartments is not illuminated and thus black whereas the other compartment (the light one) is illuminated by an electric bulb, installed on the top of a plexiglass cover. The PA training is conducted in a single session. The animals are allowed to explore the compartment for 60 sec, after which the sliding door is automatically opened and the mouse is allowed to cross over into the dark compartment. Once the mouse has entered the dark chamber with all four feet, the sliding door is automatically closed and a scrambled electrical current is delivered through the grid floor. Latency to cross over into the dark compartment (training latency) is recorded. Retention latencies as well as total time spent in bright compartment are tested 24 h later (day two). The animals are placed in the light compartment and allowed to explore for 15 sec, where upon the sliding door is opened allowing free access to the dark compartment for a period of 300 sec. The latency to cross over into the dark compartment with all four feet is measured (retention latency) as well as time in bright compartment and a number of other relevant parameters (e.g. number of visits in the dark compartment).

In in vivo study 1, vehicle (20% DMSO in 0.1M PBS) or different doses of Example 5 were administered to C57/Bl6 mice once per day (s.c. administration) for 4 days prior to PA training. PA training was then performed according to the procedure described above. On the day of PA training, scopolamine at 0.3 mg/kg, or vehicle, was administered subcutaneously 30 min prior to training. Data on retention latency shown in FIG. 1.

Abbreviations

DCM—Dichloromethane
MeOH—methanol
TEA—triethylamine
RBF—round bottom flask
EtOAC—ethyl acetate
ACN—acetonitrile
RT—room Temperature
TFA—trifluoroacetic acid
DEAD—diethyl azodicarboxylate
RB—round bottom
THF—tetrahydrofuran
Pd/C—palladium on carbon
h—hours
min—minutes
combi chromatography—combi flash chromatography
column chromatography—flash chromatography
HATU—1-[bis(dimethylamino)methylene]-1H-1,2,3-triazolo[4,5-b]pyridinium 3-oxid hexafluorophosphate
DMF—dimethylformamide
NMP—N-methyl-2-pyrrolidone
RP-HPLC—reverse phase high performance liquid chromatography

The invention claimed is:
1. A compound of formula (I), wherein the compound is 1-(3-methyl-4-phenoxyphenyl)-3-phenyl-1,3,5-triazinane-2,4,6-trione,

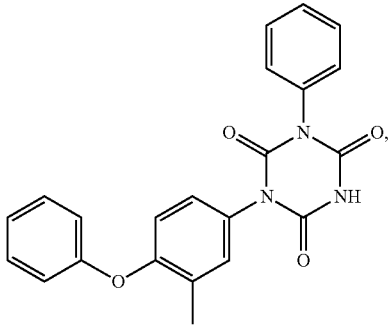

(I)

or a pharmaceutically acceptable salt thereof.

2. A pharmaceutical composition comprising the compound of claim 1, or a pharmaceutically acceptable salt thereof and a pharmaceutically acceptable excipient.

* * * * *